(12) United States Patent
Heil et al.

(10) Patent No.: US 9,107,411 B2
(45) Date of Patent: Aug. 18, 2015

(54) INDOLECARBOXAMIDES AND BENZIMIDAZOLECARBOXAMIDES AS INSECTICIDES AND ACARICIDES

(75) Inventors: Markus Heil, Leichlingen (DE); Eike Kevin Heilmann, Düsseldorf (DE); Graham Holmwood, Leverkusen (DE); Peter Jeschke, Bergisch Gladbach (DE); Michael Maue, Langenfeld (DE); Tobias Kapferer, Basel (CH); Matthias Riedrich, Köln (DE); Angela Becker, Düsseldorf (DE); Olga Malsam, Rösrath (DE); Peter Lösel, Leverkusen (DE); Arnd Voerste, Köln (DE); Ulrich Görgens, Ratingen (DE); Roland Andree, Langenfeld (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/003,778

(22) PCT Filed: Mar. 5, 2012

(86) PCT No.: PCT/EP2012/053752
§ 371 (c)(1),
(2), (4) Date: Dec. 16, 2013

(87) PCT Pub. No.: WO2012/119984
PCT Pub. Date: Sep. 13, 2012

(65) Prior Publication Data
US 2014/0088167 A1    Mar. 27, 2014

Related U.S. Application Data

(60) Provisional application No. 61/450,817, filed on Mar. 9, 2011.

(30) Foreign Application Priority Data

Mar. 9, 2011    (EP) ..................................... 11157401

(51) Int. Cl.
| | |
|---|---|
| C07D 209/42 | (2006.01) |
| C07D 235/24 | (2006.01) |
| A01N 43/52 | (2006.01) |
| A01N 43/38 | (2006.01) |
| C07D 209/24 | (2006.01) |
| C07D 235/32 | (2006.01) |

(52) U.S. Cl.
CPC ............. *A01N 43/52* (2013.01); *A01N 43/38* (2013.01); *C07D 209/24* (2013.01); *C07D 209/42* (2013.01); *C07D 235/24* (2013.01); *C07D 235/32* (2013.01)

(58) Field of Classification Search
None
See application file for complete search history.

(56) References Cited

U.S. PATENT DOCUMENTS

| | | | |
|---|---|---|---|
| 3,732,241 A | 5/1973 | Moore et al. | |
| 5,591,378 A | 1/1997 | Deline et al. | |
| 7,897,543 B2 | 3/2011 | Bretschneider et al. | |
| 8,084,452 B2 | 12/2011 | Jeschke et al. | |
| 8,106,211 B2 | 1/2012 | Jeschke et al. | |
| 8,106,212 B2 | 1/2012 | Jeschke et al. | |
| 8,138,350 B2 | 3/2012 | Jeschke et al. | |
| 8,324,390 B2 | 12/2012 | Fischer et al. | |
| 8,404,855 B2 | 3/2013 | Jeschke et al. | |
| 2006/0183753 A1 | 8/2006 | Erguden et al. | |
| 2008/0305955 A1 | 12/2008 | Bretschneider et al. | |
| 2009/0041722 A1 | 2/2009 | Liu et al. | |
| 2009/0247551 A1 | 10/2009 | Jeschke et al. | |
| 2009/0253749 A1 | 10/2009 | Jeschke et al. | |
| 2010/0048646 A1 | 2/2010 | Jeschke et al. | |
| 2010/0240705 A1 | 9/2010 | Jeschke et al. | |
| 2010/0256195 A1 | 10/2010 | Fischer et al. | |
| 2011/0105532 A1 | 5/2011 | Heil et al. | |
| 2011/0190493 A1 | 8/2011 | Bretschneider et al. | |

(Continued)

FOREIGN PATENT DOCUMENTS

| | | |
|---|---|---|
| CN | 102057925 | 5/2011 |
| DE | 2723464 | 12/1977 |

(Continued)

OTHER PUBLICATIONS

Chemical Abstracts Registry No. 1260888-45-6, indexed in the Registry file on STN CAS Online Jan. 27, 2011.*
International Search Report for PCT/EP2012/53752 Mailed Mar. 28, 2012.
Baur et al., "Polydisperse Ethoxylated Fatty Alcohol Surfactants as Accelerators of Cuticular Penetration. 1. Effects of Ethoxy Chain Length and the Size of the Penetrants," 1997, Pesticide Science, vol. 51, 131-152.

(Continued)

*Primary Examiner* — Laura L. Stockton
(74) *Attorney, Agent, or Firm* — Miles & Stockbridge P.C.

(57) ABSTRACT

The present invention relates to compounds of the general formula (I)

in which $R^1$ to $R^6$, A, Y, X, G, n and m are each as defined in the description—and to a process for preparation thereof and to the use thereof as insecticides and acaricides.

14 Claims, No Drawings

(56) References Cited

U.S. PATENT DOCUMENTS

| | | |
|---|---|---|
| 2011/0212949 A1 | 9/2011 | Bretschneider et al. |
| 2011/0306499 A1 | 12/2011 | Bretschneider et al. |
| 2012/0157498 A1 | 6/2012 | Jeschke et al. |
| 2013/0123506 A1 | 5/2013 | Jeschke et al. |
| 2013/0172390 A1 | 7/2013 | Heil et al. |

FOREIGN PATENT DOCUMENTS

| | | |
|---|---|---|
| EP | 0539588 | 5/1993 |
| EP | 0697172 | 2/1996 |
| EP | 1188745 | 3/2002 |
| EP | 1439169 | 7/2004 |
| EP | 1460064 | 9/2004 |
| JP | 2010-18586 | 1/2010 |
| WO | 0132622 | 5/2001 |
| WO | 02096882 | 12/2002 |
| WO | 03106457 | 12/2003 |
| WO | 2004032921 | 4/2004 |
| WO | 2004056768 | 7/2004 |
| WO | 2004099160 | 11/2004 |
| WO | 2005035486 | 4/2005 |
| WO | 2005063094 | 7/2005 |
| WO | 2005077934 | 8/2005 |
| WO | 2005085216 | 9/2005 |
| WO | 2006043635 | 4/2006 |
| WO | 2006089633 | 8/2006 |
| WO | 2006100288 | 9/2006 |
| WO | 2006101321 | 9/2006 |
| WO | 2007040280 | 4/2007 |
| WO | 2007057407 | 5/2007 |
| WO | 2007075459 | 7/2007 |
| WO | 2007101369 | 9/2007 |
| WO | 2007115643 | 10/2007 |
| WO | 2007115644 | 10/2007 |
| WO | 2007115646 | 10/2007 |
| WO | 2007115938 | 10/2007 |
| WO | 2007149134 | 12/2007 |
| WO | 2008009360 | 1/2008 |
| WO | 2008066153 | 6/2008 |
| WO | 2008067911 | 6/2008 |
| WO | 2008075196 | 6/2008 |
| WO | 2008104503 | 9/2008 |
| WO | 2009023179 | 2/2009 |
| WO | 2009047558 | 4/2009 |
| WO | 2009049851 | 4/2009 |
| WO | 2010005692 | 1/2010 |
| WO | 2010006713 | 1/2010 |
| WO | 2010054138 | 5/2010 |
| WO | 2010069502 | 6/2010 |
| WO | 2010074747 | 7/2010 |
| WO | 2010074751 | 7/2010 |
| WO | 2010126164 | 11/2010 |
| WO | 2011049233 | 4/2011 |
| WO | 2011054436 A2 | 5/2011 |

OTHER PUBLICATIONS

Potter et al., "Structure-guided design of [alpha]-amino acid-derived Pin1 inhibitors," Bioorganic & Medicinal Chemistry Letters, 2010, vol. 20, 586-590.

Robertson et al., "Synthesis and evaluation of a series of C5'-substituted duocarmycin SA analogs," Bioorganic & Medicinal Chemistry Letters, 2010, Vo. 20, 2722-2725.

Wolfgang Koenig, "A New Method for Synthesis of Peptides: Activation of the Carboxyl Group with Dicyclohexylcarbodiimide using 1-Hydroxybenzotriazoles as Additives," Chem. Ber. 1970, vol. 103, 788 (English abstract), pp. 788-798.

Odell et al, "Azido and Diazararinyl Analogues of Bis-Tyrphostin as Asymmetrical Inhibitors of Dynamin GTPase," Chem.Med.Chem., 2009, vol. 4(7), 1182-1188.

Alp et al., "Synthesis and antiparasitic and antifungal evaluation of 2'-arylsubstituted-1H, 1'H-[2,5']bisbenzimidazolyl-5-carboxamidines," European Journal of Medicinal Chemistry, 2009, 2002-2008, vol. 44(5).

Goldstein et al., "113. Contribution of the study of 3,4-dinitrobenzonitrile and 3,4-dinitrobenzaldehyde," Helvetica Chimica Acta (1943), vol. 26, 475, 1125, pp. 125-128 and an English translation.

Conversion of carboxylic acids, Houben-Weyl, 1952, vol. VIII, 463-485.

Anderson et al., "A Reinvestigation of the Mixed Carbonic Anhydride Method of Peptide Synthesis," J. Am. Chem. Soc.,1967, vol. 89(19), 5012-5017.

Mackman et al., "Exploiting Subsite S1 of Trypsin-Like Serine Proteases for Selectivity: Potent and Selective Inhibitors of Urokinase-Type Plasminogen Activator," Journal of Medicinal Chemistry (2001), vol. 44(23), 3856-3871.

* cited by examiner

INDOLECARBOXAMIDES AND BENZIMIDAZOLECARBOXAMIDES AS INSECTICIDES AND ACARICIDES

CROSS REFERENCE TO RELATED APPLICATIONS

This application is a §371 National Stage Application of PCT/EP2012/053752, filed Mar. 5, 2012, which claims priority to European Application No. 11157401.8, filed Mar. 9, 2011, and U.S. Provisional Application No. 61/450,817, filed Mar. 9, 2011.

BACKGROUND OF THE INVENTION

1. Field of the Invention

The present invention relates to novel pesticides, to a process for preparation thereof and to the use thereof as active ingredients, especially to the use thereof as insecticides and acaricides.

2. Description of Related Art

The literature describes indole-2-carboxamides and benzimidazole-2-carboxamides and use thereof as medicaments; see, for example, WO-A-2010/126164, WO-A-2010/054138, US 2009/0041722, WO-A-2007/115938, EP1460064, WO-A-2004-A-056768, WO-A-2004/032921, WO-A-20010/32622. It has now been found that, surprisingly, particular novel indole- and benzimidazolecarboxamides have strong insecticidal and acaricidal properties with simultaneously good plant tolerance, favorable homeotherm toxicity and good environmental compatibility. The inventive novel compounds have not been disclosed to date.

SUMMARY

The present invention therefore provides compounds of the general formula (I)

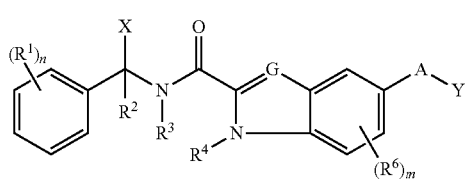

where
$R^1$ is halogen, nitro, cyano, optionally mono- or poly-halogen-substituted $C_1$-$C_6$-alkyl, $C_1$-$C_6$-alkoxy, $C_1$-$C_6$-alkylthio, $C_1$-$C_6$-alkylsulphinyl or $C_1$-$C_6$-alkylsulphonyl,
n is 1, 2, 3, 4 or 5,
or
$R^1$ is —OCF$_2$O—, —(CF$_2$)$_2$O— or —O(CF$_2$)$_2$O—, and is bonded to two adjacent carbon atoms, in which case n is 1,
$R^2$ is hydrogen, or optionally singly or multiply, identically or differently substituted $C_1$-$C_4$-alkyl,
where the substituents are each independently selected from halogen and $C_1$-$C_4$-alkyl,
$R^3$ is hydrogen, optionally singly or multiply, identically or differently substituted $C_1$-$C_4$-alkyl, $C_1$-$C_4$-alkylcarbonyl, or $C_1$-$C_4$-alkoxycarbonyl,
where the substituents are each independently selected from cyano, halogen, $C_1$-$C_4$-alkyl and $C_1$-$C_4$-alkoxy,
$R^4$ is optionally singly or multiply, identically or differently substituted $C_1$-$C_6$-alkyl, $C_2$-$C_6$-alkenyl, $C_3$-$C_6$-alkynyl, $C_3$-$C_6$-cycloalkyl, $C_3$-$C_6$-cycloalkyl-$C_1$-$C_4$-alkyl or aryl-$C_1$-$C_4$-alkyl,
where the substituents are each independently selected from halogen, cyano, $C_1$-$C_4$-alkyl and $C_1$-$C_4$-alkoxy, $C_1$-$C_4$-alkoxycarbonyl and from optionally singly or multiply, identically or differently substituted aryloxy and aryl-$C_1$-$C_3$-alkoxy,
where the substituents are each independently selected from halogen, cyano, $C_1$-$C_4$-alkyl, $C_1$-$C_4$-alkoxy,
G is C($R^5$) or N,
$R^5$ is hydrogen, halogen or cyano,
$R^6$ is halogen, nitro, cyano, or optionally mono- or poly-halogen-substituted $C_1$-$C_6$-alkyl or $C_1$-$C_6$-alkoxy,
m is 0, 1, 2, 3,
X is $C_1$-$C_6$-haloalkyl which may optionally additionally be mono- to trisubstituted, where the substituents are each independently selected from hydroxyl, cyano and $C_1$-$C_4$-alkoxy,
A is a bivalent chemical moiety which is selected from the —C($R^{11}$)($R^{12}$)NR$^{13}$C(=O)— and —C(=O)NR$^{13}$— moieties, where the first (left-hand) connection site in each case connects to the ring and the second (right-hand) connection site in each case connects to Y,
and where
$R^{11}$ and $R^{12}$ are each independently hydrogen or $C_1$-$C_4$-alkyl,
$R^{13}$ is hydrogen, $C_1$-$C_4$-alkyl, $C_3$-$C_6$-cycloalkyl, $C_1$-$C_4$-alkylcarbonyl, $C_1$-$C_4$-alkoxycarbonyl or $C_1$-$C_4$-alkenyl,
Y is optionally singly or multiply identically or differently substituted $C_1$-$C_6$-alkyl, $C_2$-$C_6$-alkenyl, $C_3$-$C_6$-alkynyl, $C_3$-$C_6$-cycloalkyl, aryl, aryl-$C_1$-$C_4$-alkyl, hetaryl or hetaryl-$C_1$-$C_4$-alkyl,
where the substituents are selected from halogen, nitro, cyano, hydroxyl, aminothiocarbonyl, aminocarbonyl, $C_1$-$C_4$-alkylaminocarbonyl, di($C_1$-$C_4$-alkyl)aminocarbonyl, hydroxycarbonyl, $C_1$-$C_4$-alkyl, $C_1$-$C_4$-haloalkyl, $C_3$-$C_6$-cycloalkyl, $C_1$-$C_4$-alkyl-$C_3$-$C_4$-cycloalkyl, $C_2$-$C_6$-alkenyl, $C_2$-$C_6$-alkynyl, $C_1$-$C_6$-alkoxy, $C_1$-$C_6$-alkoxycarbonyl, $C_1$-$C_6$-alkylcarbonyl, $C_1$-$C_4$-alkoxyimino-$C_1$-$C_4$-alkyl, $C_1$-$C_6$-alkylthio, $C_1$-$C_6$-alkylsulphinyl and $C_1$-$C_6$-alkylsulphonyl,
where
n is 2, 3, 4 or 5 when
at least one $R^1$ substituent is trifluoromethyl,
and at the same time
Y is unsubstituted $C_1$-$C_4$-alkyl, 2,2-difluoroethyl, unsubstituted $C_2$-$C_6$-alkenyl, unsubstituted $C_3$-$C_6$-alkynyl, unsubstituted $C_3$-$C_6$-cycloalkyl or unsubstituted hetaryl, and
A is —C(=O)NR$^{13}$—,
and
G is C($R^5$),
and salts and N-oxides of compounds of the formula (I), and the use thereof for control of animal pests.

The compounds of the formula (I) may possibly be present in different polymorphic forms or as a mixture of different polymorphic forms. Both the pure polymorphs and the polymorph mixtures are provided by the invention and can be used in accordance with the invention.

The compounds of the formula (I) include any E/Z isomers and diastereomers or enantiomers which exist.

DETAILED DESCRIPTION OF A PREFERRED EMBODIMENT

The substituted indole- and benzimidazolecarboxamides are defined in general terms by the formula (I). Preferred radical definitions for the formula specified above and hereinafter are given below. These definitions apply to the end products of the formula (I) and likewise to all intermediates.

The particular number of substituents n and m in the formula (I) includes only the substituents other than hydrogen. For this reason, hydrogen is also not included in the definition of $R^1$ and $R^6$. Of course, hydrogen is always present as a substituent when no $R^1$ or $R^6$ substituent is present at the particular site.

Preference, particular preference and very particular preference is given to compounds of the formula (I), and to a method for controlling pests using the compounds of the formula (I), where $R^1$ is preferably halogen, nitro, cyano, optionally mono- or poly-halogen-substituted $C_1$-$C_4$-alkyl, $C_1$-$C_4$-alkoxy, $C_1$-$C_4$-alkylthio, $C_1$-$C_4$-alkylsulphinyl or $C_1$-$C_4$-alkylsulphonyl, n is preferably 1, 2, 3, 4 or 5, or $R^1$ is —OCF$_2$O— or —O(CF$_2$)$_2$O—, and is bonded to two adjacent carbon atoms, in which case n is 1, $R^2$ is preferably hydrogen or optionally mono- to trisubstituted $C_1$-$C_4$ alkyl, where the substituents are each independently selected from halogen and $C_1$-$C_4$-alkyl, $R^3$ is preferably hydrogen, optionally singly or multiply, identically or differently substituted $C_1$-$C_4$-alkyl, $C_1$-$C_4$-alkylcarbonyl or $C_1$-$C_4$-alkoxycarbonyl, where the substituents are each independently selected from cyano, halogen and $C_1$-$C_4$-alkoxy, $R^4$ is preferably optionally singly or multiply, identically or differently substituted $C_1$-$C_4$-alkyl, $C_2$-$C_6$-alkenyl, $C_3$-$C_6$-alkynyl, $C_3$-$C_6$-cycloalkyl, $C_3$-$C_6$-cycloalkyl-$C_1$-$C_3$-alkyl or aryl-$C_1$-$C_4$-alkyl, where the substituents are each independently selected from halogen, cyano, $C_1$-$C_4$ alkyl, $C_1$-$C_4$-alkoxy, $C_1$-$C_4$-alkoxycarbonyl and from optionally singly or multiply, identically or differently substituted aryloxy and aryl-$C_1$-$C_3$-alkoxy, where the substituents are each independently selected from halogen, cyano, $C_1$-$C_4$ alkyl, $C_1$-$C_4$-alkoxy, G is preferably C($R^5$) or N, $R^5$ is preferably hydrogen, halogen or cyano, $R^6$ is preferably halogen, nitro, cyano, or optionally mono- or poly-halogen-substituted $C_1$-$C_4$-alkyl or $C_1$-$C_4$-alkoxy, m is preferably 0, 1, 2, X is preferably $C_1$-$C_4$-haloalkyl which may optionally additionally be mono- to trisubstituted by hydroxyl, cyano or $C_1$-$C_4$-alkoxy, A is preferably a bivalent chemical moiety which is selected from the —C($R^{11}$)($R^{12}$)N$R^{13}$C(=O)— or —C(=O)N$R^{13}$— moieties, where the first (left-hand) connection site in each case connects to the ring and the second (right-hand) connection site in each case connects to Y, $R^{11}$ and $R^{12}$ are preferably each independently hydrogen or $C_1$-$C_4$-alkyl, $R^{13}$ is preferably hydrogen, $C_1$-$C_4$-alkyl, $C_3$-$C_6$-cycloalkyl, $C_1$-$C_4$-alkylcarbonyl, $C_1$-$C_4$-alkoxycarbonyl or $C_2$-$C_4$-alkenyl, Y is preferably optionally singly or multiply, identically or differently substituted $C_1$-$C_4$-alkyl, $C_2$-$C_4$-alkenyl, $C_2$-$C_4$-alkynyl, $C_3$-$C_6$-cycloalkyl, phenyl, phenylmethyl, pyridinyl, pyridinylmethyl, pyrimidinyl or pyrimidinylmethyl, where the substituents are selected from halogen, nitro, cyano, hydroxyl, aminothiocarbonyl, aminocarbonyl, $C_1$-$C_4$-alkyl, $C_1$-$C_4$-haloalkyl, $C_3$-$C_5$-cycloalkyl, $C_1$-$C_4$-alkyl-$C_3$-$C_4$-cycloalkyl, $C_2$-$C_4$-alkenyl, $C_2$-$C_4$-alkynyl, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-alkoxycarbonyl, $C_1$-$C_6$-alkylcarbonyl and $C_1$-$C_4$-alkoxyimino-$C_1$-$C_4$-alkyl, where n is 2, 3, 4 or 5 when at least one $R^1$ substituent is trifluoromethyl, and at the same time Y is unsubstituted $C_1$-$C_4$-alkyl, 2,2-difluoroethyl, unsubstituted $C_2$-$C_6$-alkenyl, unsubstituted $C_3$-$C_6$-alkynyl, unsubstituted $C_3$-$C_6$-cycloalkyl or unsubstituted hetaryl, and A is —C(=O)N$R^{13}$—, and G is C($R^5$), $R^1$ is more preferably halogen, nitro, cyano, optionally mono- or poly-fluorine- or -chlorine-substituted $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, n is more preferably 1, 2, 3, 4 or 5, or $R^1$ is —OCF$_2$O—, and is bonded to two adjacent carbon atoms, in which case n is 1, $R^2$ is more preferably hydrogen or methyl, $R^3$ is more preferably hydrogen, methyl, ethyl, methylcarbonyl, ethylcarbonyl, methoxycarbonyl or ethoxycarbonyl, $R^4$ is more preferably optionally mono- to trisubstituted $C_1$-$C_4$-alkyl, $C_2$-$C_4$-alkenyl, $C_3$-$C_4$-alkynyl, $C_3$-$C_5$-cycloalkyl, $C_3$-$C_5$-cycloalkyl-$C_1$-$C_3$-alkyl or phenylalkyl, where the substituents are each independently selected from fluorine, cyano, methoxy, ethoxy, methyl, ethyl, methoxycarbonyl, ethoxycarbonyl, phenyloxy and phenyl-$C_1$-$C_3$-alkoxy, G is more preferably C($R^5$) or N, $R^5$ is more preferably hydrogen, fluorine, chlorine, bromine or cyano, $R^6$ is more preferably halogen, nitro, cyano, or optionally mono- to tri-halogen-substituted $C_1$-$C_4$-alkyl or $C_1$-$C_4$-alkoxy, m is more preferably 0, 1 or 2, X is more preferably $C_1$-$C_4$-haloalkyl, A is more preferably a bivalent chemical moiety which is selected from the —C($R^{11}$)($R^{12}$)N$R^{13}$C(=O)— and —C(=O)N$R^{13}$— moieties, where the first (left-hand) connection site in each case connects to the ring and the second (right-hand) connection site in each case connects to Y, and where $R^{11}$ and $R^{12}$ are more preferably each independently hydrogen or methyl, and where $R^{13}$ is more preferably hydrogen, methyl, ethyl, cyclopropyl, methylcarbonyl, ethylcarbonyl, methoxycarbonyl, ethoxycarbonyl or prop-2-en-1-yl, Y is more preferably optionally singly to triply, identically or differently substituted $C_1$-$C_4$-alkyl, $C_2$-$C_4$-alkenyl, $C_2$-$C_4$-alkynyl, $C_3$-$C_6$-cycloalkyl, phenyl, phenylmethyl, pyridin-2-yl, pyridin-2-ylmethyl, 1,3-pyrimidin-2-yl or 1,3-pyrimidin-2-ylmethyl, where the substituents are selected from fluorine, chlorine, nitro, cyano, $C_1$-$C_4$-alkyl, trifluoromethyl, $C_3$-$C_4$-cycloalkyl, $C_1$-$C_4$-alkyl-$C_3$-$C_4$-cycloalkyl, $C_2$-$C_4$-alkenyl, $C_3$-$C_4$-alkynyl $C_1$-$C_4$-alkoxy, $C_1$-$C_4$-alkylthio, $C_1$-$C_4$-alkylsulphinyl, $C_1$-$C_6$-alkylsulphonyl, $C_1$-$C_4$-alkoxycarbonyl and aminothiocarbonyl, where n is 2, 3, 4 or 5 when
  at least one $R^1$ substituent is trifluoromethyl,
  and at the same time
  Y is unsubstituted $C_1$-$C_4$-alkyl, 2,2-difluoroethyl, unsubstituted $C_2$-$C_6$-alkenyl, unsubstituted $C_3$-$C_6$-alkynyl, unsubstituted $C_3$-$C_6$-cycloalkyl or unsubstituted hetaryl, and
  A is —C(=O)NR$^{13}$—,
  and
  G is C(R$^5$), $R^1$ is most preferably cyano, fluorine, chlorine, bromine, iodine, difluoromethyl, dichlorofluoromethyl, chlorodifluoromethyl, trifluoromethyl, pentafluoroethyl, chlorotetrafluoroethyl, difluoromethoxy, trifluoromethoxy, trifluoromethylthio, trifluoromethylsulphinyl, trifluoromethylsulphonyl, n is most preferably 1, 2, 3, 4 or 5,
or
$R^1$ is most preferably —OCF$_2$O—, and is bonded to two adjacent carbon atoms, in which case n is 1, $R^2$ is most preferably hydrogen, $R^3$ is most preferably hydrogen, $R^4$ is most preferably methyl, ethyl, prop-1-yl, prop-2-en-1-yl, prop-2-yn-1-yl, ethenyl, but-2-yn-1-yl, cyclopropyl, cyclopropylmethyl, cyclobutyl, cyanomethyl, 2-methylprop-1-yl, ethoxymethyl, methoxycarbonylmethyl, phenylmethyl or benzyloxymethyl, G is most preferably C(R$^5$) or N, $R^5$ is most preferably hydrogen, chlorine, bromine or cyano, $R^6$ is most preferably cyano, fluorine, chlorine, bromine, methyl, ethyl, isopropyl or trifluoromethyl, m is most preferably 0 or 1, X is most preferably trifluoromethyl, A is most preferably a bivalent chemical moiety which is selected from the —CH$_2$NHC(=O)— or —C(=O)NR$^{13}$— moieties, where the first (left-hand) connection site in each case connects to the ring and the second (right-hand) connection site in each case connects to Y,
and where $R^{13}$ is most preferably hydrogen, methyl, ethyl or prop-2-en-1-yl, Y is most preferably methyl, ethyl, propan-1-yl, propan-2-yl, butan-1-yl, butan-2-yl, 2-methylpropan-1-yl, 2-methylpropan-2-yl, cyclopropyl, cyclobutyl, cyanomethyl, 1-cyanoethyl, 2-cyanoethyl, 1-cyanoprop-1-yl, 2-cyanoprop-1-yl, 3-cyanoprop-1-yl, 1-cyanoprop-2-yl, 2-cyanoprop-2-yl, 1-cyanocyclopropyl, 2-cyanoprop-2-en-1-yl, 2-cyanocyclopropyl, 1-cyanocyclobutyl, 2-cyanocyclobutyl, 3-cyanocyclobutyl, 2-fluoroethyl, 2,2-difluoroethyl, 2,2,2-trifluoroethyl, 1-fluoropropan-2-yl, 2,2-difluoroprop-1-yl, 1,3-difluoropropan-2-yl, 1-methylcyclopropyl, 2-methylcyclopropyl, 1-ethylcyclopropyl, 1-ethynylcyclopropyl, 1-ethynylcyclobutyl, 1-methoxycyclopropyl, 1-ethoxycyclopropyl, 1-methoxycarbonylcyclopropyl, 1-ethoxycarbonylcyclopropyl, 1,1'-bi(cyclopropyl)-1-yl, cyclopropylmethyl, 1-trifluoromethylcyclopropyl, pyridin-2-yl, 5-chloropyridin-2-yl, 5-fluoropyridin-2-yl, 1-cyano-1-phenylmethyl, 1,2-dimethylcyclopropyl, 1-(aminothiocarbonyl)cyclopropyl, 1-cyano-2-methylpropan-1-yl, 1-cyanobut-3-yn-1-yl, 1-cyano-2-methylpropan-1-yl, 1-cyanopropan-2-yl, 1-cyano-1-cyclopropylethyl, 1-cyano-1-ethylprop-1-yl, 1-cyano-1-methylcyclopropylmethyl, (2-R)-1-(methylsulphinyl)propan-2-yl or 1,3-dimethoxy-2-cyanopropan-2-yl when A is the —C(=O)NR$^{13}$— moiety,
or
Y is most preferably methyl, ethyl, propan-1-yl, propan-2-yl, butan-1-yl, 2-fluoroethyl, 2,2-difluoroethyl, 2,2,2-trifluoroethyl, cyclopropyl, cyclobutyl or cyclopropylmethyl when A is the —CH$_2$NHC(=O)— moiety,
where n is 2, 3, 4 or 5 when
  at least one $R^1$ substituent is trifluoromethyl,
  and at the same time
  Y is unsubstituted $C_1$-$C_4$-alkyl, 2,2-difluoroethyl, unsubstituted $C_2$-$C_6$-alkenyl, unsubstituted $C_3$-$C_6$-alkynyl, unsubstituted $C_3$-$C_6$-cycloalkyl or unsubstituted hetaryl, and
  A is —C(=O)NH—,
  and
  G is C(R$^5$).

The above-specified individual general, preferred, more preferred and most preferred definitions for the $R^1$ to $R^8$ substituents, n, m, X, G, A and Y, can be combined with one another as desired in accordance with the invention.

In the preferred definitions, unless stated otherwise, halogen is selected from the group of fluorine, chlorine, bromine and iodine, preferably in turn from the group of fluorine, chlorine and bromine.

In the more preferred definitions, unless stated otherwise, halogen is selected from the group of fluorine, chlorine, bromine and iodine, preferably in turn from the group of fluorine, chlorine and bromine.

In the most preferred definitions, unless stated otherwise, halogen is selected from the group of fluorine, chlorine, bromine and iodine, preferably in turn from the group of fluorine, chlorine and bromine.

Halogen-substituted radicals, for example haloalkyl, are mono- or polyhalogenated up to the maximum possible number of substituents. In the case of polyhalogenation, the halogen atoms may be the same or different. In this case, halogen is fluorine, chlorine, bromine or iodine, especially fluorine, chlorine or bromine.

Preference, particular preference and very particular preference is given to compounds which bear the substituents specified under preferred, particularly preferred and very particularly preferred, respectively.

Saturated or unsaturated hydrocarbyl radicals such as alkyl, alkenyl or alkynyl may each be straight-chain or branched to the extent possible, including in combination with heteroatoms, as, for example, in alkoxy.

Optionally substituted radicals may be mono- or polysubstituted, where the substituents in the case of polysubstitution may be the same or different.

The radical definitions or illustrations given above in general terms or within areas of preference apply to the end products and correspondingly to the starting materials and intermediates. These radical definitions can be combined with one another as desired, i.e. including combinations between the respective preferred ranges.

Preference is given in accordance with the invention to compounds of the formula (I) in which a combination of the definitions listed above as preferred is present.

Particular preference is given in accordance with the invention to compounds of the formula (I) in which a combination of the definitions listed above as particularly preferred is present.

In a preferred embodiment, the invention relates to the compounds of the formula (I-1)

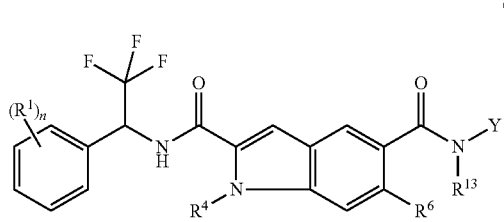
(I-1)

where $R^1$, $R^4$, $R^6$, $R^{13}$, Y and n are each as defined above.

In a further preferred embodiment, the invention relates to the compounds of the formula (I-2)

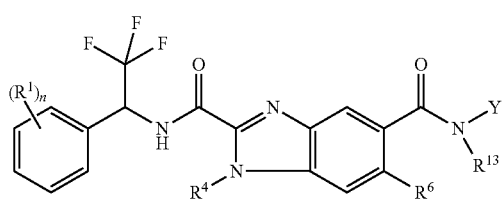
(I-2)

where $R^1$, $R^4$, $R^6$, $R^{13}$, Y and n are each as defined above.

In a further preferred embodiment, the invention relates to the compounds of the formula (I-3)

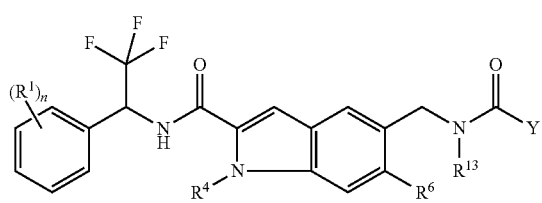
(I-3)

where $R^1$, $R^4$, $R^6$, $R^{13}$, Y and n are each as defined above.

In a further preferred embodiment, the invention relates to the compounds of the formula (I-4)

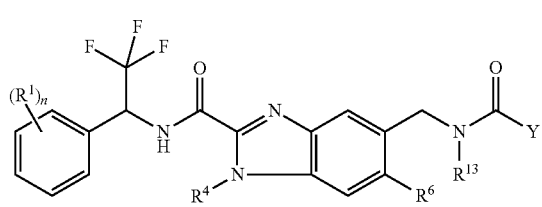
(I-4)

where $R^1$, $R^4$, $R^6$, Y, $R^{13}$ and n are each as defined above.

Likewise preferred inventive compounds are the compounds of the general formula (I) shown in Table 1.

The present compounds of the general formula (I) may optionally have a chiral carbon atom.

According to the rules of Cahn, Ingold and Prelog (CIP rules), these substituents may have either an (R) configuration or an (S) configuration.

The present invention encompasses compounds of the general formula (I) both with (S) and with (R) configuration at the particular chiral carbon atoms, i.e. the present invention encompasses the compounds of the general formula (I) in which the carbon atoms in question each independently have
(1) (R) configuration; or
(2) (S) configuration.

When more than one chiral centre is present in the compounds of the general formula (I), any desired combinations of the configurations of the chiral centres are possible, which means that
(1) one chiral centre may have (R) configuration and the other chiral centre (S) configuration;
(2) one chiral centre may have (R) configuration and the other chiral centre (R) configuration; and
(3) one chiral centre may have (S) configuration and the other chiral centre (S) configuration.

The compounds of the formula (I) likewise encompass any diastereomers or enantiomers and E/Z isomers which exist, and also salts and N-oxides of compounds of the formula (I), and the use thereof for control of animal pests.

The invention also relates to the use of the inventive compounds of the general formula (I) for production of pesticides.

The invention also relates to pesticides comprising inventive compounds of the general formula (I) and/or salts thereof in biologically effective contents of >0.00000001% by weight, preferably >0.001% by weight to 95% by weight, based on the weight of the pesticide.

The invention also relates to methods for controlling animal pests, in which inventive compounds of the general formula (I) are allowed to act on animal pests and/or their habitat. The control of the animal pests is preferably conducted in agriculture and forestry, and in material protection. Preferably excluded is the treatment, more particularly the therapeutic treatment, of the human or animal body.

The active ingredients, given good plant tolerance, favorable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection agents. They are effective against normally sensitive and resistant species and against all or some stages of development. The abovementioned pests include:

pests from the phylum of: Arthropoda, especially from the class of the Arachnida, for example, *Acarus* spp., *Aceria sheldoni*, *Aculops* spp., *Aculus* spp., *Amblyomma* spp., Amphi*tetranychus viennensis*, *Argas* spp., *Boophilus* spp., *Brevipalpus* spp., *Bryobia praetiosa*, *Centruroides* spp., *Chorioptes* spp., *Dermanyssus gallinae*, *Dermatophagoides pteronyssius*, *Dermatophagoides farinae*, *Dermacentor* spp., *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vaejovis* spp., *Vasates lycopersici*.

From the order of the Anoplura (Phthiraptera), for example, *Damalinia* spp., *Haematopinus* spp., *Linognathus* spp., *Pediculus* spp., *Ptirus pubis*, *Trichodectes* spp.

From the order of the Chilopoda, for example, *Geophilus* spp., *Scutigera* spp.

From the order of the Coleoptera, for example, *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnosterna consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sphenophorus* spp., *Stegobium paniceum*, *Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Chrysops* spp., *Cochliomyia* spp., *Contarinia* spp., *Cordylobia anthropophaga*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderma* spp., *Liriomyza* spp., *Lucilia* spp., *Lutzomia* spp., *Mansonia* spp., *Musca* spp., *Nezara* spp., *Oestrus* spp., *Oscinella fit*, *Pegomyia* spp., *Phlebotomus* spp., *Phorbia* spp., *Phormia* spp., *Prodiplosis* spp., *Psila rosae*, *Rhagoletis* spp., *Sarcophaga* spp., *Simulium* spp, *Stomoxys* spp., *Tabanus* spp., *Tannia* spp., *Tetanops* spp., *Tipula* spp.

From the order of the Heteroptera, for example, *Anasa tristis*, *Antestiopsis* spp., *Blissus* spp., *Boisea* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma pin*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Clcadulina mbila*, *Coccomytilus halli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Ferrisia* spp., *Geococcus coffeae*, *Hieroglyphus* spp., *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes* spp., *Trioza* spp., *Typhlocyba* spp., *Unaspis* spp., *Viteus vitifolii*, *Zygina* spp.

From the order of the Hymenoptera, for example, *Acromyrmex* spp., *Athalia* spp., *Atta* spp., *Diprion* spp., *Hoplocampa* spp., *Lasius* spp., *Monomorium pharaonis*, *Solenopsis invicta*, *Tapinoma* spp., *Vespa* spp.

From the order of the Isopoda, for example, *Armadillidium vulgare*, *Oniscus asellus* and *Porcellio scaber*.

From the order of the Isoptera, for example, *Coptotermes* spp., *Cornitermes cumulans*, *Cryptotermes* spp., *Incisitermes* spp., *Microtermes obesi*, *Odontotermes* spp., *Reticulitermes* spp.

From the order of the Lepidoptera, for example, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Chematobia brumata*, *Chilo* spp., *Choristoneura* spp., *Clysia ambiguella*, *Cnaphalocerus* spp., *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia* spp., *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracilaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis spp., *Lithophane antennata*, *Lobesia* spp., *Loxagrotis albicosta*, *Lymantria* spp., *Lyonetia* spp., *Malacosoma neustria*, *Maruca testulalis*, *Mamestra brassicae*, *Mocis* spp., *Mythimna separata*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plodia interpunctella*, *Plusia* spp., *Plutella xylostella*, *Prays* spp., *Prodenia* spp., *Protoparce* spp., *Pseudaletia* spp., *Pseudoplusia includens*, *Pyrausta nubilalis*, *Rachiplusia nu*, *Schoenobius* spp., *Scirpophaga* spp., *Scotia segetum*, *Sesamia* spp., *Sparganothis* spp., *Spodoptera* spp., *Stathmopoda* spp., *Stomopteryx subsecivella*, *Synanthedon* spp., *Tecia solanivora*, *Thermesia gemmatalis*, *Tinea pellionella*, *Tineola bisselliella*, *Tortrix* spp., *Trichophaga tapetzella*, *Trichoplusia* spp., *Tuta absoluta*, *Virachola* spp.

From the order of the Orthoptera, for example, *Acheta domesticus*, *Blatta orientalis*, *Blattella germanica*, *Dichroplus* spp., *Gryllotalpa* spp., *Leucophaea maderae*, *Locusta* spp., *Melanoplus* spp., *Periplaneta* spp., *Pulex irritans*, *Schistocerca gregaria*, *Supella longipalpa*.

From the order of the Siphonaptera, for example, *Ceratophyllus* spp., *Ctenocephalides* spp., *Tunga* penetrans, *Xenopsylla cheopis*.

From the order of the Symphyla, for example, *Scutigerella* spp.

From the order of the Thysanoptera, for example, *Anaphothrips obscurus*, *Baliothrips biformis*, *Drepanothris reuteri*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamoni*, *Thrips* spp.

From the order of the Zygentoma (=Thysanura), for example, *Lepisma saccharina*, *Thermobia domestica*.

Pests from the phylum of: Mollusca, especially from the class of the Bivalvia, for example *Dreissena* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

Animal parasites from the phyla of: Plathelminthes and Nematoda, especially from the class of the helminths, for example, *Ancylostoma duodenale*, *Ancylostoma ceylanicum*, *Acylostoma braziliensis*, *Ancylostoma* spp., *Ascaris* spp., *Brugia malayi*, *Brugia timori*, *Bunostomum* spp., *Chabertia* spp., *Clonorchis* spp., *Cooperia* spp., *Dicrocoelium* spp., *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., Loa Loa, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

Plant pests from the phylum of: Nematoda, i.e. phytoparasitic nematodes, especially *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis*, *Trichodorus* spp., *Tylenchulus semipenetrans*, *Xiphinema* spp.

Subphylum: Protozoa

It is also possible to control protozoa, such as *Eimeria*.

The compounds of the formula (I) can optionally, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be used as intermediates or precursors for the synthesis of other active ingredients.

The present invention further relates to formulations and use forms prepared therefrom as crop protection compositions and/or pesticides, for example drench, drip and spray liquors, comprising at least one of the inventive active ingredients. In some cases, the use forms comprise further crop protection agents and/or pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropyl guar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations optionally comprise, as well as one or more inventive active ingredients, further active agrochemical ingredients.

These are preferably formulations or use forms which comprise auxiliaries, for example extenders, solvents, spontaneity promoters, carriers, emulsifiers, dispersants, antifreezes, biocides, thickeners and/or further auxiliaries, for example adjuvants. An adjuvant in this context is a component which enhances the biological effect of the formulation, without the component itself having a biological effect. Examples of adjuvants are agents which promote retention, spreading, attachment to the leaf surface or penetration.

These formulations are produced in a known manner, for example by mixing the active ingredients with auxiliaries, for example extenders, solvents and/or solid carriers and/or further auxiliaries, for example surfactants. The formulations are produced either in suitable production plants or else before or during application.

The auxiliaries used may be substances suitable for imparting special properties, such as certain physical, technical and/or biological properties, to the formulation of the active ingredient, or to the use forms prepared from these formulations (for example ready-to-use crop protection compositions such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Examples of suitable solvents are aromatic hydrocarbons, such as xylene, toluene or alkylnaphthalenes, chlorinated aromatic or aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers include especially: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, maize cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkyl sulphonates, alkylsulphates, arylsulphonates, protein hydrolysates, lignosulphite waste liquors and methylcellulose. The presence of a surfactant is advantageous when one of the active ingredients and/or one of the inert carriers is insoluble in water and when application is effected in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability. Foam formers or antifoams may also be present.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids may also be present as additional auxiliaries in the formulations and the use forms derived therefrom. Further auxiliaries may be mineral and vegetable oils.

If appropriate, the formulations and the use forms derived therefrom may also comprise further auxiliaries. Examples of such additives include fragrances, protective colloids, binders, adhesives, thickeners, thixotropic agents, penetrants, retention promoters, stabilizers, sequestrants, complexing agents, humectants, spreaders. In general, the active ingredients can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) application liquor and/or from the spray coating into the cuticle of the plant and thereby increase the mobility of active ingredients in the cuticle. The method described in the literature (Baur et al., 1997, Pesticide Science 51, 131-152) can be used to determine this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations contain preferably between 0.00000001% and 98% by weight of active ingredient or more preferably between 0.01% and 95% by weight of active ingredient, more preferably between 0.5% and 90% by weight of active ingredient, based on the weight of the formulation.

The active ingredient content of the use forms (crop protection compositions) prepared from the formulations can vary within wide limits. The active ingredient concentration of the use forms may typically be between 0.00000001% and 95% by weight of active ingredient, preferably between 0.00001% and 1% by weight, based on the weight of the use form. The compounds are applied in a customary manner appropriate for the use forms.

The treatment of the plants and plant parts with the inventive active ingredients is effected directly or by action on their surroundings, habitat or storage space by the customary treatment methods, for example by dipping, spraying, atomizing, irrigating, evaporating, dusting, fogging, broadcasting, foaming, painting, spreading-on, injecting, watering (drenching), drip irrigating and, in the case of propagation material, especially in the case of seed, also by dry seed treatment, wet seed treatment, slurry treatment, incrustation, coating with one or more coats, etc. It is also possible to deploy the active ingredients by the ultra-low volume method or to inject the active ingredient formulation or the active ingredient itself into the soil.

A preferred direct treatment of the plants is foliar application, i.e. the inventive active ingredients are applied to the foliage, it being possible to adjust the treatment frequency and the application rate according to the level of infestation with the pest in question.

In the case of systemically active compounds, the inventive active ingredients get into the plants through the root system. In that case, the plants are treated by the action of the inventive active ingredients on the habitat of the plant. This can be done, for example, by drenching or mixing into the soil or liquid fertilizer, i.e. the site of the plant (e.g. soil or hydroponic systems) is soaked with a liquid form of the inventive active ingredients, or by soil application, i.e. the inventive active ingredients are introduced in solid form (for example in the form of granules) into the site of the plants. In the case of paddy rice crops, this can also be done by metering the inventive active ingredients in a solid application form (for example as granules) into a flooded paddy field.

The inventive active ingredients can also be used, as such or in formulations thereof, in mixtures with known fungicides, bactericides, acaricides, nematicides or insecticides, in order thus to broaden, for example, the activity spectrum or to prevent development of resistance. In many cases, synergistic effects are obtained, i.e. the efficacy of the mixtures is greater than the efficacy of the individual compounds.

Examples of useful mixing components are the following compounds:
Insecticides/Acaricides/Nematicides:

The active ingredients identified here by their common names are known and are described, for example, in the pesticide handbook ("The Pesticide Manual" 14th Ed., British Crop Protection Council 2006) or can be found on the Internet (e.g. http://www.alanwood.net/pesticides).

(1) Acetylcholinesterase (AChE) inhibitors, for example
carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or
organophosphates, for example acephate, azamethiphos, azinphos-ethyl, azinphos-methyl, cadusafos, chlorethoxyfos, chlorfenvinphos, chlormephos, chloropyrifos, chloropyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion.

(2) GABA-gated chloride channel antagonists, for example
cyclodiene organochlorines, for example chlordane and endosulfan; or
phenylpyrazoles (fiproles), for example ethiprole and fipronil.

(3) Sodium channel modulators/voltage-dependent sodium channel blockers, for example
pyrethroids, for example acrinathrin, allethrin, d-cis-trans allethrin, d-trans allethrin, bifenthrin, bioallethrin, bioallethrin S-cyclopentenyl isomer, bioresmethrin, cyprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers), esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer), pralethrin, pyrethrine (pyrethrum), resmethrin, silafluofen, tefluthrin, tetramethrin, tetramethrin [(1R) isomers)], tralomethrin and transfluthrin; or
DDT; or methoxychlor.

(4) Nicotinergic acetylcholine receptor (nAChR) agonists, for example
neonicotinoids, for example acetamiprid, clothianidin, dinotefuran, imidacloprid, nitenpyram, thiacloprid and thiamethoxam; or nicotine.

(5) Nicotinergic acetylcholine receptor (nAChR) allosteric activators, for example
spinosyns, for example spinetoram and spinosad.

(6) Chloride channel activators, for example
avermectins/milbemycins, for example abamectin, emamectin benzoate, lepimectin and milbemectin.

(7) Juvenile hormone imitators, for example
juvenile hormone analogues, for example hydroprene, kinoprene and methoprene; or fenoxycarb; or pyriproxyfen.

(8) Active ingredients with unknown or nonspecific mechanisms of action, for example
alkyl halides, e.g. methyl bromide and other alkyl halides; or chloropicrin; or sulphuryl fluoride; or borax; or tartar emetic.

(9) Selective antifeedants, for example pymetrozine; or flonicamid.

(10) Mite growth inhibitors, for example clofentezine, hexythiazox and diflovidazin; or etoxazole.

(11) Microbial disruptors of the insect gut membrane, for example *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron; or
organotin compounds, for example azocyclotin, cyhexatin and fenbutatin oxide; or
propargite; or tetradifon.

(13) Oxidative phosphorylation decouplers acting by interrupting the H proton gradient, for example chlorfenapyr, DNOC and sulfluramid.

(14) Nicotinergic acetylcholine receptor antagonists, for example bensultap, cartap hydrochloride, thiocylam, and thiosultap-sodium.

(15) Chitin biosynthesis inhibitors, type 0, for example bistrifluoron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting disruptors, dipteran, for example cyromazine.
(18) Ecdysone receptor agonists, for example chromafenozide, halofenozide, methoxyfenozide and tebufenozide.
(19) Octopaminergic agonists, for example amitraz.
(20) Complex-III electron transport inhibitors, for example hydramethylnone; or acequinocyl; or fluacrypyrim.
(21) Complex-I electron transport inhibitors, for example METI acaricides, for example fenazaquin, fenpyroximate, pyrimidifen, pyridaben, tebufenpyrad and tolfenpyrad; or rotenone (Derris).
(22) Voltage-dependent sodium channel blockers, for example indoxacarb; or metaflumizone.
(23) Inhibitors of acetyl-CoA carboxylase, for example tetronic and tetramic acid derivatives, for example spirodiclofen, spiromesifen and spirotetramat.
(24) Complex-IV electron transport inhibitors, for example phosphines, for example aluminium phosphide, calcium phosphide, phosphine and zinc phosphide; or cyanide.
(25) Complex-II electron transport inhibitors, for example cyenopyrafen.
(28) Ryanodine receptor effectors, for example diamides, for example chlorantraniliprole and flubendiamide.

Further active ingredients with unknown mechanism of action, for example amidoflumet, azadirachtin, benclothiaz, benzoximate, bifenazate, bromopropylate, chinomethionat, cryolite, cyantraniliprole (Cyazypyr), cyflumetofen, dicofol, diflovidazin, fluensulphone, flufenerim, flufiprole, fluopyram, fufenozide, imidaclothiz, iprodione, meperfluthrin, pyridalyl, pyrifluquinazon, tetramethylfluthrin and iodomethane; and additionally preparations based on *Bacillus firmus* (particularly strain CNCM I-1582, for example VOTiVO™, BioNem), and the following known active compounds:

3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934), 4-{[(6-bromopyrid-3-yl)methyl](2-fluoroethyl)amino}furan-2 (5H)-one (known from WO2007/115644), 4-{[(6-fluoropyrid-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2 (5H)-one (known from WO2007/115644), 4-{[(6-chloropyrid-3-yl)methyl](2-fluoroethyl)amino}furan-2 (5H)-one (known from WO2007/115644), flupyradifurone, 4-{[(6-chloro-5-fluoropyrid-3-yl)methyl](methyl)amino}furan-2(5H)-one (known from WO2007/115643), 4-{[(5,6-dichloropyrid-3-yl)methyl] (2-fluoroethyl)amino}furan-2(5H)-one (known from WO2007/115646), 4-{[(6-chloro-5-fluoropyrid-3-yl)methyl](cyclopropyl)amino}furan-2(5H)-one (known from WO2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), {[1-(6-chloropyridin-3-yl)ethyl](methyl)oxido-$\lambda^4$-sulphanylidene}cyanamide (known from WO2007/149134) and diastereomers thereof {[(1R)-1-(6-chloropyridin-3-yl)ethyl](methyl)oxido-$\lambda^4$-sulphanylidene}cyanamide (A) and {[(1S)-1-(6-chloropyridin-3-yl)ethyl](methyl)oxido-$\lambda^4$-sulphanylidene}cyanamide (B) (likewise known from WO2007/149134) and sulfoxaflor and diastereomers thereof [(R)-methyl(oxido){(1R)-1-[6-(trifluoromethyl)pyridin-3-yl]ethyl}-$\lambda^4$-sulphanylidene]cyanamide (A1) and [(S)-methyl(oxido){(1S)-1-[6-(trifluoromethyl)pyridin-3-yl]ethyl}-$\lambda^4$-sulphanylidene]cyanamide (A2), designated as diastereomer group A (known from WO 2010/074747, WO 2010/074751), [(R)-methyl(oxido){(1S)-1-[6-(trifluoromethyl)pyridin-3-yl]ethyl}-$\lambda^4$-sulphanylidene]cyanamide (B1) and [(S)-methyl(oxido){(1R)-1-[6-(trifluoromethyl)pyridin-3-yl]ethyl}-$\lambda^4$-sulphanylidene]cyanamide (B2), designated as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5]dec-3-en-2-one (known from WO2008/067911), 1-{2-fluoro-4-methyl-5-[(2,2,2-trifluoroethyl)sulphinyl]phenyl}-3-(trifluoromethyl)-1H-1,2,4-triazol-5-amine (known from WO2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO2008/066153), 2-cyano-3-(difluoromethoxy)-N,N-dimethylbenzenesulphonamide (known from WO2006/056433), 2-cyano-3-(difluoromethoxy)-N-methylbenzenesulphonamide (known from WO2006/100288), 2-cyano-3-(difluoromethoxy)-N-ethylbenzenesulphonamide (known from WO2005/035486), 4-(difluoromethoxy)-N-ethyl-N-methyl-1,2-benzothiazol-3-amine 1,1-dioxide (known from WO2007/057407), N-[1-(2,3-dimethylphenyl)-2-(3,5-dimethylphenyl)ethyl]-4,5-dihydro-1,3-thiazol-2-amine (known from WO2008/104503), {1'-[(2E)-3-(4-chlorophenyl)prop-2-en-1-yl]-5-fluorospiro[indole-3,4'-piperidine]-1(2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280), flometoquin, PF1364 (CAS Reg. No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2 (5H)-one (all known from WO2010/005692), NNI-0711 (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), 2-{6-[2-(5-fluoropyridin-3-yl)-1,3-thiazol-5-yl]pyridin-2-yl}pyrimidine (known from WO2010/006713), 2-{6-[2-(pyridin-3-yl)-1,3-thiazol-5-yl]pyridin-2-yl}pyrimidine (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO2010/069502), (1E)-N-[(6-chloropyridin-3-yl)methyl]-N'-cyano-N-(2,2-difluoroethyl)ethanimidamide (known from WO2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925) and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO2011/049233).

Fungicides
(1) Ergosterol biosynthesis inhibitors, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulphate, imibenconazole, ipconazole, metconazole, myclobutanil, naftifin, nuarimol, oxpoconazole, paclobutrazole, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl]1H-imidazole-1-carbothioate.

(2) Respiration inhibitors (respiratory chain inhibitors), such as, for example, bixafen, boscalid, carboxin, diflumetorim, fenfuram, fluopyram, flutolanil, fluxapyroxad, furametpyr, furmecyclox, isopyrazam mixture of the syn-epimeric racemate 1RS,4SR,9RS and of the anti-epimeric racemate 1RS,4SR,9SR, isopyrazam (anti-epimeric racemate), isopyrazam (anti-epimeric enantiomer 1R,4S,9S), isopyrazam (anti-epimeric enantiomer 1S,4R,9R), isopyrazam (syn-epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamid, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide, 5,8-difluoro-N-[2-(2-fluoro-4-{[4-(trifluoromethyl)pyridin-2-yl]oxy}phenyl)ethyl]quinazoline-4-amine, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) Respiration inhibitors (respiratory chain inhibitors) acting on complex III of the respiratory chain, for example ametoctradin, amisulbrom, azoxystrobin, cyazofamid, coumethoxystrobin, coumoxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulphanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide and (2R)-2-{2-[(2,5-dimethylphenoxy)methyl]phenyl}-2-methoxy-N-methylacetamide.

(4) Mitosis and cell division inhibitors, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine and 3-chloro-5-(6-chloropyridin-3-yl)-6-methyl-4-(2,4,6-trifluorophenyl)pyridazine.

(5) Compounds with multisite activity, for example Bordeaux mixture, captafol, captan, chlorothalonil, copper formulations such as copper hydroxide, copper naphthenate, copper oxide, copper oxychloride, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations, for example calcium polysulphide, thiram, tolylfluanid, zineb and ziram.

(6) Resistance inducers, for example acibenzolar-S-methyl, isotianil, probenazole and tiadinil.

(7) Amino acid and protein biosynthesis inhibitors, for example andoprim, blasticidin-S, cyprodinil, kasugamycin, kasugamycin hydrochloride hydrate, mepanipyrim, pyrimethanil and 3-(5-fluoro-3,3,4,4-tetramethyl-3,4-dihydroisoquinolin-1-yl)quinoline.

(8) ATP production inhibitors, for example fentin acetate, fentin chloride, fentin hydroxide and silthiofam.

(9) Cell wall synthesis inhibitors, for example benthiavalicarb, dimethomorph, flumorph, iprovalicarb, mandipropamid, polyoxins, polyoxorim, validamycin A and valifenalate.

(10) Lipid and membrane synthesis inhibitors, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Melanin biosynthesis inhibitors, for example carpropamid, diclocymet, fenoxanil, fthalide, pyroquilon, tricyclazole and 2,2,2-trifluoroethyl {3-methyl-1-[(4-methylbenzoyl)amino]butan-2-yl}carbamate.

(12) Nucleic acid synthesis inhibitors, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Signal transduction inhibitors, for example chlozolinate, fenpiclonil, fludioxonil, iprodione, procymidone, quinoxyfen and vinclozolin.

(14) Decouplers, for example binapacryl, dinocap, ferimzone, fluazinam and meptyldinocap.

(15) Further compounds, for example benthiazole, bethoxazin, capsimycin, carvone, chinomethionat, pyriofenone (chlazafenone), cufraneb, cyflufenamid, cymoxanil, cyprosulfamide, dazomet, debacarb, dichlorophen, diclomezine, difenzoquat, difenzoquat methylsulphate, diphenylamine, ecomat, fenpyrazamine, flumetover, fluoromide, flusulfamide, flutianil, fosetyl-aluminium, fosetyl-calcium, fosetyl-sodium, hexachlorobenzene, irumamycin, methasulfocarb, methyl isothiocyanate, metrafenon, mildiomycin, natamycin, nickel dimethyldithiocarbamate, nitrothal-isopropyl, octhilinone, oxamocarb, oxyfenthiin, pentachlorophenol and salts thereof, phenothrin, phosphoric acid and salts thereof, propamocarb-fosetylate, propanosine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl)prop-2-en-1-one, pyrrolnitrin, tebufloquin, tecloftalam, tolnifanid, triazoxide, trichlamide, zarilamide, (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulphonyl)pyridine, 2,3-dibutyl-6-chlorothieno[2,3-d]pyrimidin-4(3H)-one, 2,6-dimethyl-1H,5H-[1,4]dithiino[2,3-c:5,6-c']dipyrrole-1,3,5,7(2H,6H)-tetrone, 2-[5-methyl-3-(trifluoromethyl)-1H-pyrazol-1-yl]-1-(4-{[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts thereof, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulphonohydrazide, 5-fluoro-2-[(4-fluorobenzyl)oxy]pyrimidin-4-amine, 5-fluoro-2-[(4-methylbenzyl)oxy]pyrimidin-4-amine, 5-methyl-6-octyl[1,2,4]triazolo[1,5-a]pyrimidin-7-amine, ethyl (2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimidoformamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N'-{4-[(3-tert-butyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol, quinolin-8-ol sulphate (2:1) and tert-butyl {6-[({[(1-methyl-1H-tetrazol-5-yl)(phenyl)methylene]amino}oxy)methyl]pyridin-2-yl}carbamate.

(16) Further compounds, for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone, N-[2-(4-{[3-(4-chlorophenyl)prop-2-yn-1-yl]oxy}-3-methoxyphenyl)ethyl]-N2-(methylsulphonyl)valinamide, 4-oxo-4-[(2-phenylethyl)amino]butanoic acid and but-3-yn-1-yl {6-[({[(Z)-(1-methyl-1H-tetrazol-5-yl)(phenyl)methylene]amino}oxy)methyl]pyridin-2-yl}carbamate.

All mixing components mentioned in classes (1) to (16) can, if they are capable on the basis of their functional groups, optionally form salts with suitable bases or acids.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits, seeds, roots, tubers and rhizomes. Parts of plants also include harvested material and vegetative and generative propagation material, for example seedlings, tubers, rhizomes, cuttings and seeds.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The term "parts" or "parts of plants" or "plant parts" has been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They may be cultivars, varieties, bio- or genotypes.

The inventive treatment of the plants and plant parts with the active ingredients is effected directly or by allowing them to act on the surroundings, habitat or storage space thereof by the customary treatment methods, for example by dipping, spraying, evaporating, fogging, scattering, painting on, injecting, pouring on, and, in the case of propagation material, especially in the case of seeds, also by applying one or more coats.

Preferred plants are those from the group of the useful plants, ornamental plants, turfgrass types, commonly used trees which are employed as ornamentals in public and domestic areas, and forestry trees. Forestry trees include trees for the production of timber, cellulose, paper and products made from parts of the trees.

The term useful plants as used here refers to crop plants which are employed as plants for obtaining foods, animal feeds, fuels or for industrial purposes.

The useful plants which can be treated with the inventive active ingredients include, for example, the following plant species: turf, vines, cereals, for example wheat, barley, rye, oats, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao beans and peanuts; cucurbits, for example pumpkin/squash, cucumbers and melons; fibre plants, for example cotton, flax, hemp and jute; citrus fruit, for example, oranges, lemons, grapefruit and tangerines; vegetables, for example spinach, lettuce, asparagus, cabbage species, carrots, onions, tomatoes, potatoes and bell peppers; Lauraceae, for example avocado, Cinnamomum, camphor, or also plants such as tobacco, nuts, coffee, aubergine, sugarcane, tea, pepper, grapevines, hops, bananas, latex plants and ornamentals, for example flowers, shrubs, deciduous trees and coniferous trees. This enumeration does not constitute a limitation.

Particularly suitable target crops for the treatment with the inventive active ingredients are considered to be the following plants: cotton, aubergine, turf, pome fruit, stone fruit, soft fruit, maize, wheat, barley, cucumber, tobacco, vines, rice, cereals, pear, beans, soybeans, oilseed rape, tomato, bell pepper, melons, cabbage, potatoes and apples.

Examples of trees which can be improved by the method according to the invention include: *Abies* sp., *Eucalyptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved by the method according to the invention are: from the tree species *Aesculus: A. hippocastanum, A. pariflora, A. carnea*; from the tree species *Platanus: P. aceriflora, P. occidentalis, P. racemosa*; from the tree species *Picea: P. abies*; from the tree species *Pinus: P. radiate, P. ponderosa, P. contorta, P. sylvestre, P. elliottii, P. montecola, P. albicaulis, P. resinosa, P. palustris, P. taeda, P. flexilis, P. jeffregi, P. baksiana, P. strobes*; from the tree species *Eucalyptus: E. grandis, E. globulus, E. camadentis, E. nitens, E. obliqua, E. regnans, E. pilularus.*

Particularly preferred trees which can be improved by the method according to the invention are: from the tree species *Pinus: P. radiate, P. ponderosa, P. contorta, P. sylvestre, P. strobes*; from the tree species *Eucalyptus: E. grandis, E. globulus, E. camadentis.*

Very particularly preferred trees which can be improved by the method according to the invention are: horse chestnut, Platanaceae, linden tree, maple tree.

The present invention can also be applied to any turfgrass types, including cool-season turfgrasses and warm-season turfgrasses.

Depending on the plant species or plant cultivars, and the location and growth conditions (soils, climate, vegetation period, diet) thereof, the inventive treatment may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, increased flowering performance, easier harvesting, accelerated ripening, higher yields, higher quality and/or higher nutrient value of the harvested products, increased storage life and/or processibility of the harvested products, which exceed the effects actually to be expected.

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, longer storage life and/or processibility of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active ingredients. Examples of transgenic plants include the important crop plants, such as cereals (wheat, rice), maize, soya, potatoes, sugarbeet, tomatoes, peas and other vegetable types, cotton, tobacco, oilseed rape, and also fruit plants (with the fruits of apples, pears, citrus fruits and grapes), particular emphasis being given to maize, soya, potatoes, cotton, tobacco and oilseed rape. Traits that are particularly emphasized are improved defence of the plants against insects, arachnids, nematodes, slugs and snails by toxins formed in the plants, especially those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF, and also combinations thereof) (referred to hereinafter as "Bt plants"). Traits that are also particularly emphasized are the improved defence of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain active herbicidal ingredients, for example imidazolinones, sulphonylureas, glyphosate or phosphinothricin (for example the "PAT" gene). The genes which impart the desired traits in question may also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut® (for example maize), StarLink® (for example maize), Bollgard® (cotton), Nucotn® (cotton) and NewLeaf® (potato). Examples of herbicide-tolerant plants include maize varieties, cotton varieties and soya varieties which are sold under the trade names Roundup Ready® (tolerance to glyphosate, for example maize, cotton, soya), Liberty Link® (tolerance to phosphinothricin, for example oilseed rape), IMI® (tolerance to imidazolinones) and STS (tolerance to sulphonylureas, for example maize). Herbicide-resistant plants (plants bred in a conventional manner for herbicide tolerance) also include the varieties sold under the Clearfield® name (for example maize) Of course, these statements also apply to plant cultivars which have these genetic traits or genetic traits which are still to be developed and will be developed and/or marketed in the future.

The plants listed can be treated in accordance with the invention in a particularly advantageous manner with the compounds of the general formula I and/or the active ingredient mixtures according to the invention. The preferred ranges stated above for the active ingredients or mixtures also apply to the treatment of these plants. Particular emphasis is given to the treatment of plants with the compounds or mixtures specifically mentioned in the present text.

In addition, the inventive compounds can be used to control a multitude of different pests, including, for example, harmful sucking insects, biting insects and other pests which are plant parasites, stored material pests, pests which destroy industrial material, and hygiene pests including parasites in the animal health sector, and for the control thereof, for example the elimination and eradication thereof. The present invention thus also includes a method for controlling pests.

In the animal health sector, i.e. in the field of veterinary medicine, the active ingredients according to the present invention act against animal parasites, especially ectoparasites or endoparasites. The term "endoparasites" includes especially helminths such as cestodes, nematodes or trematodes, and protozoa such as coccidia. Ectoparasites are typically and preferably arthropods, especially insects such as flies (biting and licking), parasitic fly larvae, lice, hair lice, bird lice, fleas and the like; or acarids such as ticks, for example hard ticks or soft ticks, or mites such as scab mites, harvest mites, bird mites and the like.

These parasites include:

From the order of the Anoplurida, for example, *Haematopinus* spp., *Linognathus* spp., *Pediculus* spp., *Phtirus* spp. and *Solenopotes* spp.; specific examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus*

*humanus capitis, Pediculus humanus corporis, Phylloera vastatrix, Phthirus pubis, Solenopotes capillatus;*

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.; specific examples are: *Bovicola bovis, Bovicola ovis, Bovicola limbata, Damalina bovis, Trichodectes canis, Felicola subrostratus, Bovicola caprae, Lepikentron ovis, Werneckiella equi;*

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; specific examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca;*

From the order of the Siphonapterida, for example *Pulex* spp., *Ctenocephalides* spp., *Tunga* spp., *Xenopsylla* spp., *Ceratophyllus* spp.; specific examples are: *Ctenocephalides canis, Ctenocephalides felis, Pulex irritans, Tunga penetrans, Xenopsylla cheopis;*

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp. (e.g. Suppella longipalpa);

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Rhipicephalus* (*Boophilus*) spp., *Dermacentor* spp., *Haemophysalis* spp., *Hyalomma* spp., *Dermanyssus* spp., *Rhipicephalus* spp. (the original genus of multihost ticks), *Ornithonyssus* spp., *Pneumonyssus* spp., *Raillietia* spp., *Pneumonyssus* spp., *Sternostoma* spp., *Varroa* spp., *Acarapis* spp.; specific examples are: *Argas persicus, Argas reflexus, Ornithodorus moubata, Otobius megnini, Rhipicephalus* (*Boophilus*) *microplus, Rhipicephalus* (*Boophilus*) *decoloratus, Rhipicephalus* (*Boophilus*) *annulatus, Rhipicephalus* (*Boophilus*) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;*

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.; specific examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae* (=S. caprae), *Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

The inventive active ingredients are also suitable for controlling arthropods, helminths and protozoa which attack animals. The animals include agricultural livestock, for example cattle, sheep, goats, horses, pigs, donkeys, camels, buffalo, rabbits, chickens, turkeys, ducks, geese, cultured fish, honeybees. The animals also include domestic animals—also referred to as companion animals—for example dogs, cats, caged birds, aquarium fish, and what are known as test animals, for example hamsters, guinea pigs, rats and mice.

The control of these arthropods, helminths and/or protozoa should reduce cases of death and improve the performance (for meat, milk, wool, hides, eggs, honey etc.) and the health of the host animal, and so the use of the inventive active ingredients enables more economically viable and easier animal husbandry.

For example, it is desirable to prevent or to interrupt the uptake of blood from the host by the parasites (if relevant). Control of the parasites can also contribute to preventing the transmission of infectious substances.

The term "control" as used herein with regard to the field of animal health means that the active ingredients act by reducing the occurrence of the parasite in question in an animal infested with such parasites to a harmless level. More specifically, "control" as used herein means that the active ingredient kills the parasite in question, retards its growth or inhibits its proliferation.

In general, the inventive active ingredients can employed directly when they are used for the treatment of animals. They are preferably employed in the form of pharmaceutical compositions which may comprise the pharmaceutically acceptable excipients and/or auxiliaries known in the prior art.

In the sector of animal health and in animal husbandry, the active ingredients are employed (administered) in a known manner, by enteral administration in the form of, for example, tablets, capsules, potions, drenches, granules, pastes, boluses, the feed-through process and suppositories, by parenteral administration, for example by injection (intramuscular, subcutaneous, intravenous, intraperitoneal inter alia), implants, by nasal administration, by dermal administration in the form, for example, of dipping or bathing, spraying, pouring on and spotting on, washing and powdering, and also with the aid of moulded articles containing the active ingredient, such as collars, earmarks, tailmarks, limb bands, halters, marking devices, etc. The active ingredients can be formulated as a shampoo or as suitable formulations applicable in aerosols or unpressurized sprays, for example pump sprays and atomizer sprays, In the case of employment for livestock, poultry, domestic pets, etc., the inventive active ingredients can be employed as formulations (for example powders, wettable powders ["WP"], emulsions, emulsifiable concentrates ["EC"], free-flowing compositions, homogeneous solutions and suspension concentrates ["SC"]), which contain the active ingredients in an amount of 1 to 80% by weight, directly or after dilution (e.g. 100- to 10 000-fold dilution), or they can be used as a chemical bath.

In the case of use in the animal health sector, the inventive active ingredients can be used in combination with suitable synergists or other active ingredients, for example acaricides, insecticides, anthelmintics, anti-protozoal agents.

It has also been found that the inventive compounds have strong insecticidal action against insects which destroy industrial materials. Accordingly, the present invention also relates to the use of the inventive compounds for protection of industrial materials against infestation or destruction by insects.

The following insects may be mentioned as examples and as preferred—but without limitation:
beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec., *Apate monachus, Bostrychus capucins, Heterobostrychus brunneus, Sinoxylon* spec. *Dinoderus minutus;*
dermapterans, such as *Sirex juvencus, Urocerus gigas, Urocerus gigas taignus, Urocerus augur;*
termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*
bristletails such as *Lepisma saccharina.*

Industrial materials in the present context are understood to mean inanimate materials, such as preferably plastics, adhesives, sizes, papers and cards, leather, wood, processed wood products and coating compositions.

The ready-to-use compositions may optionally also comprise other insecticides, and optionally also one or more fungicides.

At the same time, the inventive compounds can be used for protection of objects which come into contact with saltwater or brackish water, especially hulls, screens, nets, buildings, moorings and signalling systems, against fouling.

In addition, the inventive compounds can be used as antifouling compositions, alone or in combinations with other active ingredients.

The active ingredients are also suitable for controlling animal pests in the domestic sector, in the hygiene sector and in the protection of stored products, especially insects, arachnids and mites, which are found in enclosed spaces, for example homes, factory halls, offices, vehicle cabins and the like. They can be used to control these pests alone or in combination with other active ingredients and auxiliaries in domestic insecticide products. They are effective against sensitive and resistant species, and against all developmental stages. These pests include:
From the order of the Scorpionidea, for example, *Buthus occitanus.*
From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*
From the order of the Araneae, for example, *Aviculariidae, Araneidae.*
From the order of the Opiliones, for example, *Pseudoscorpiones chelifer, Pseudoscorpiones cheiridium, Opiliones phalangium.*
From the order of the Isopoda, for example, *Oniscus asellus, Porcellio scaber.*
From the order of the Diplopoda, for example, *Blaniulus guttulatus, Polydesmus* spp.
From the order of the Chilopoda, for example, *Geophilus* spp.
From the order of the Zygentoma, for example, *Ctenolepisma* spp., *Lepisma saccharina, Lepismodes inquilinus.*
From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*
From the order of the Saltatoria, for example, *Acheta domesticus.*
From the order of the Dermaptera, for example, *Forficula auricularia.*
From the order of the Isoptera, for example, *Kalotermes* spp., *Reticulitermes* spp.
From the order of the Psocoptera, for example, *Lepinatus* spp., *Liposcelis* spp.
From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*
From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*
From the order of the Lepidoptera, for example, *Achroia grisella, Galleria mellonella, Plodia interpunctella, Tinea cloacella, Tinea pellionella, Tineola bisselliella.*
From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of domestic insecticides, they are used alone or in combination with other suitable active ingredients, such as phosphoric esters, carbamates, pyrethroids, neonicotinoids, growth regulators or active ingredients from other known classes of insecticides.

They are employed in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free or passive evaporation systems, moth papers, moth bags and moth gels, as granules or dusts, in baits for spreading or in bait stations.

Illustration of the Processes and Intermediates (A) the Compounds of the General Formula (I)

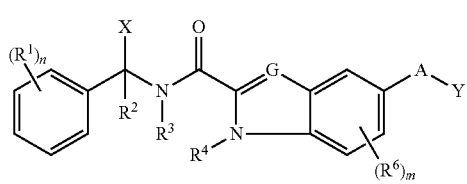
(I)

where $R^1$ bis $R^{13}$, A, X, Y, m and n are each as defined above can be obtained by first reacting carboxylic acids of the general formula (II)

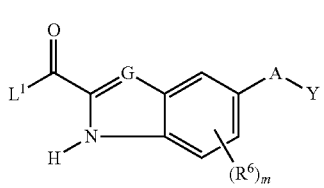
(II)

where
$L^1$ is hydroxyl or halogen,
with amines of the formula (III)

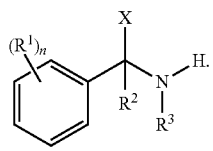
(III)

For (II), it is firstly possible to use an acid halide (e.g. $L^1$=chlorine) in the presence of a base, for example triethylamine or sodium hydroxide. Secondly, the carboxylic acid ($L^1$=OH) can, however, also be performed using coupling reagents, for example dicyclohexylcarbodiimide, and additives such as 1-hydroxybenzotriazole [Chem. Ber. 1970, 788]. It is also possible to use coupling reagents such as 1-ethyl-3-(3-dimethylaminopropyl)carbodiimide, 1,1'-carbonyl-1H-imidazole, N-[(1H-benzotriazol-1-yloxy)(dimethylamino)methylene]-N-methylmethanaminium hexafluorophosphate, and similar compounds. The coupling reagents used to perform the preparation process are all which are suitable for forming an ester or amide bond (cf. for example, Bodansky et al., Peptide Synthesis, 2nd ed., Wiley & Sons, New York, 1976; Gross, Meienhofer, The Peptide: Analysis, Synthesis, Biology, Academic Press, New York, 1979). In addition, it is also possible to use mixed anhydrides for preparation of (I). [J. Am. Chem. Soc 1967, 5012]. In this process, it is possible to use various chloroformic esters, for example isobutyl chloroformate, isopropyl chloroformate. It is likewise possible for this purpose to use diethylacetyl chloride, trimethylacetyl chloride and the like. The compounds of the formula (IVa) thus obtained

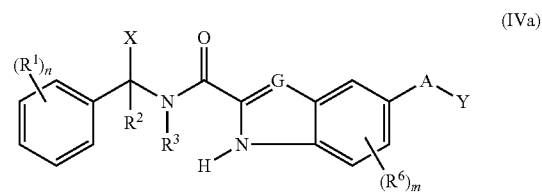
(IVa)

are then reacted with alkylating agents of the formula (V)

$R^4$-$L^2$ (V)

where
$L^2$ is halogen, the mesyl group or the tosyl group and $R^4$ is as defined above, in the presence of bases, for example sodium hydride, to give compounds of the formula (I).

(B) Compounds of the General Formula (Ia)

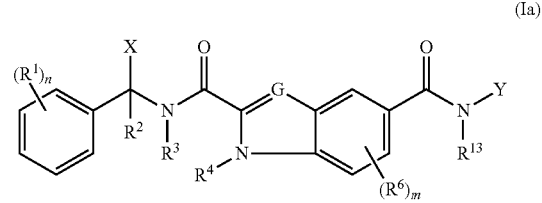
(Ia)

can be obtained by reacting carboxylic acid derivatives of the general formula (II-1b) or (II-2b)

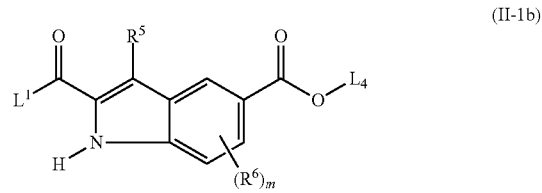
(II-1b)

-continued (II-2b)

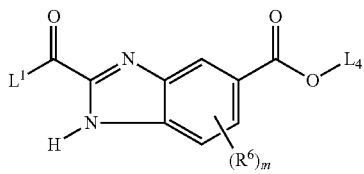

where
L¹ is hydroxyl or halogen and
L⁴ is $C_1$-$C_4$-alkyl,
first by the process described in (A) with amines of the formula (III)

(III)

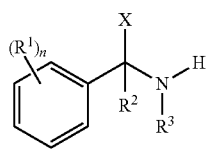

and reacting the carboxylic esters of the formula (IVb) thus obtained (IVb)

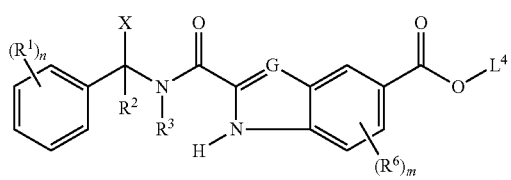

with alkylating agents of the formula (V)

R⁴-L² (V)

in the presence of bases, for example sodium hydride, to give compounds of the formula (VIa)

(VIa)

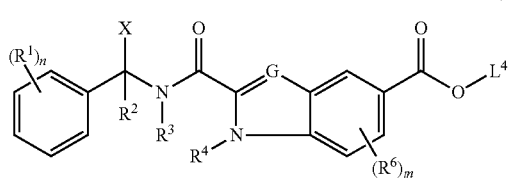

and then with amines of the general formula (VII)

(VII)

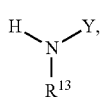

by
a) direct reaction with esters of the formula (VIa) in the presence of an activating reagent, for example trimethylaluminium, or
b) initial hydrolysis of the ester of the formula (VIa) under acidic or alkaline conditions to give carboxylic acids of the formula (VIb)

(VIb)

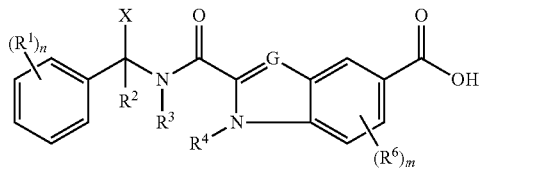

and then reaction of the latter with amines (VII) in the presence of a condensation reagent.

(C) Compounds of the General Formula (Ib)

(Ib)

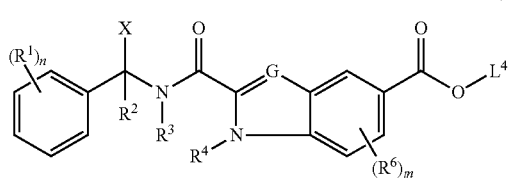

can be obtained by reacting carboxylic acids of the general formula (II-1c) or (II-2c)

(II-1c)

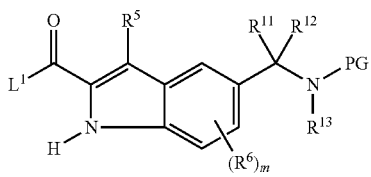

(II-2c)

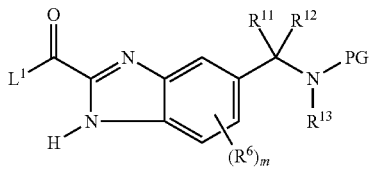

where
L¹ is halogen or a hydroxyl group and
PG is an amine protecting group, for example the tert-butyloxycarbonyl (Boc) protecting group, first by the process described in (A) with amines of the general formula (III)

(III)

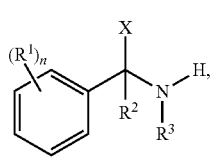

then reacting the compounds of the formula (IVc) thus obtained

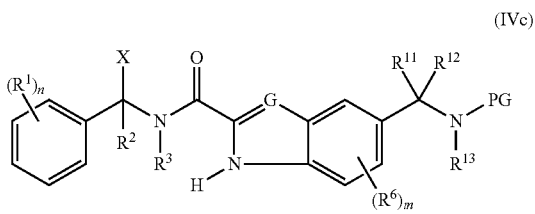
(IVc)

with alkylating agents of the formula (V)

$R^4\text{-}L^2$ (V)

in the presence of a base, for example sodium hydride, to give compounds of the formula (VIc)

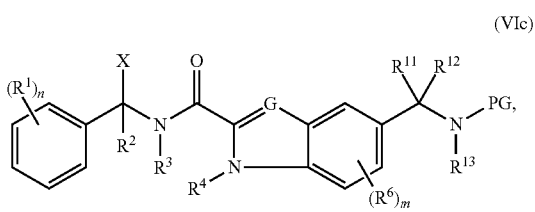
(VIc)

then removing the protecting group PG to obtain amines of the formula (VId)

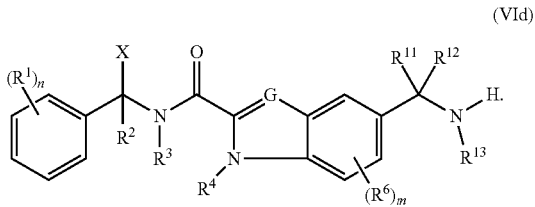
(VId)

The conversion of the compound of the formula (VIc) to the unprotected compound of the formula (VId) can be performed by commonly known methods (cf. *Greene's protective groups in organic synthesis,* 4th ed., P. G. M. Wuts, T. W. Greene, John Wiley & Sons, Inc., Hoboken, N.J., 2007); for example, (VIc, PG=Boc) can be reacted with trifluoroacetic acid in dichloromethane to give compound of the formula (VId). Compounds of the formula (VId) can finally be reacted with carboxylic acid derivatives (VIII)

(VIII)

where $L^6$ is chlorine, hydroxyl or (with formation of an anhydride) Y—C(=O)—O—, in the presence of bases ($L^6$=Cl) or condensation agents ($L^6$=OH) to give compounds of the formula (Ib).

Indolecarboxylic acids of the formula (II, $L_1$=OH) are novel. They can be obtained in analogy to known processes by the methods described in Schemes 1 to 4.

Indolecarboxylic acids of the formula (II-1a) and (II-1b) can be obtained according to Scheme 1.

Scheme 1

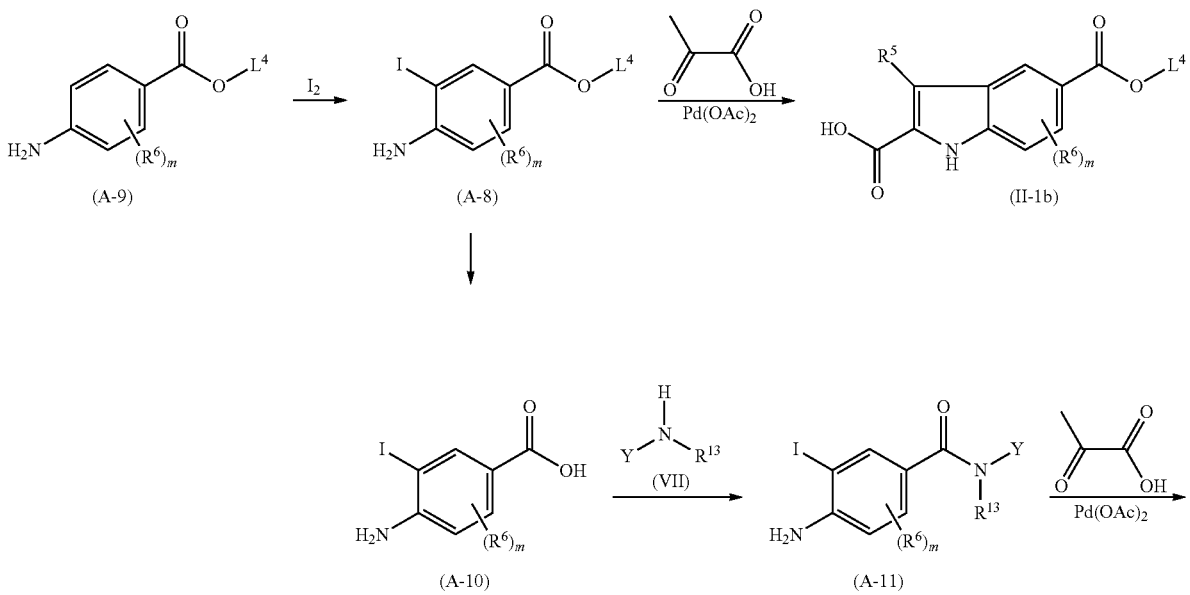

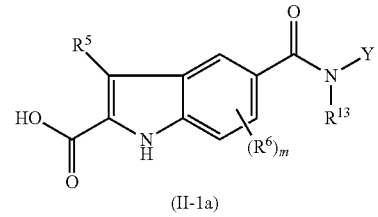

(II-1a)

Compounds of the formula (II-1b) are obtained here in analogy to known processes from compounds of the formula (A-8) by reaction with pyruvic acid in the presence of a palladium catalyst, for example palladium acetate (cf., for example, Bioorganic & Medicinal Chemistry Letters, 20(9), 2010, 2722-2725), to obtain compounds (II-1b, $R^5$=H) which can optionally be converted by reaction with a halogenating reagent, for example chloro- or bromosuccinimide, to compounds (II-1b) where $R^5$=Hal (cf., for example, WO-A-2009/023179). Compounds of the formula (A-8) are known or can be obtained by iodination from anilines of the formula (A-9) by known processes (cf., for example, Bioorganic & Medicinal Chemistry Letters, 20(9), 2010, 2722-2725) Anilines of the formula (A-9) are commercially available or can be obtained by known processes. Esters of the formula (A-8) can also be hydrolysed by commonly known methods to carboxylic acids of the formula (A-10) (cf. *Greene's protective groups in organic synthesis,* 4th ed., P. G. M. Wuts, T. W. Greene, John Wiley & Sons, Inc., Hoboken, N.J., 2007)) and then, optionally via an acid chloride formed as an intermediate, with amines of the formula (VII) to give amides of the formula (A-11) (cf., for example, the methods specified in (A) for synthesis of compounds of the formula (I)). Compounds of the formula (A11) can then be reacted as described above with pyruvic acid to give indolecarboxylic acids of the formula (II-1a).

The invention also relates to the carboxylic acids of the general formula (II-1aa)

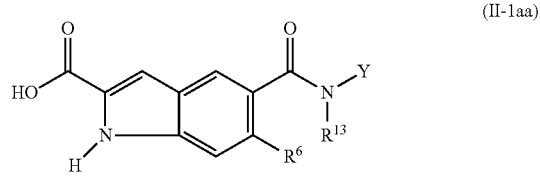

(II-1aa)

in which $R^6$, Y and $R^{13}$ are each as defined above and which can be prepared according to Scheme 1.

The invention also relates to the carboxylic acids of the general formula (II-1ba)

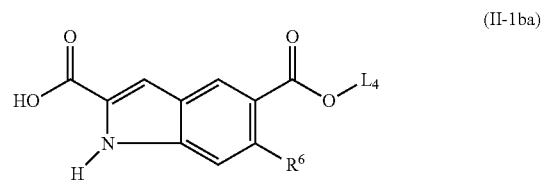

(II-1ba)

in which $L^4$ is $C_1$-$C_4$-alkyl and $R^6$ is as defined above, excluding the compound 6-chloro-5-(ethoxycarbonyl)-1H-indole-2-carboxylic acid, and which can be prepared according to Scheme 1.

Novel benzimidazolecarboxylic acids of the formula (II-2a), (II-2b) and (II-2c) can be obtained, for example, according to Scheme 2 in analogy to known processes.

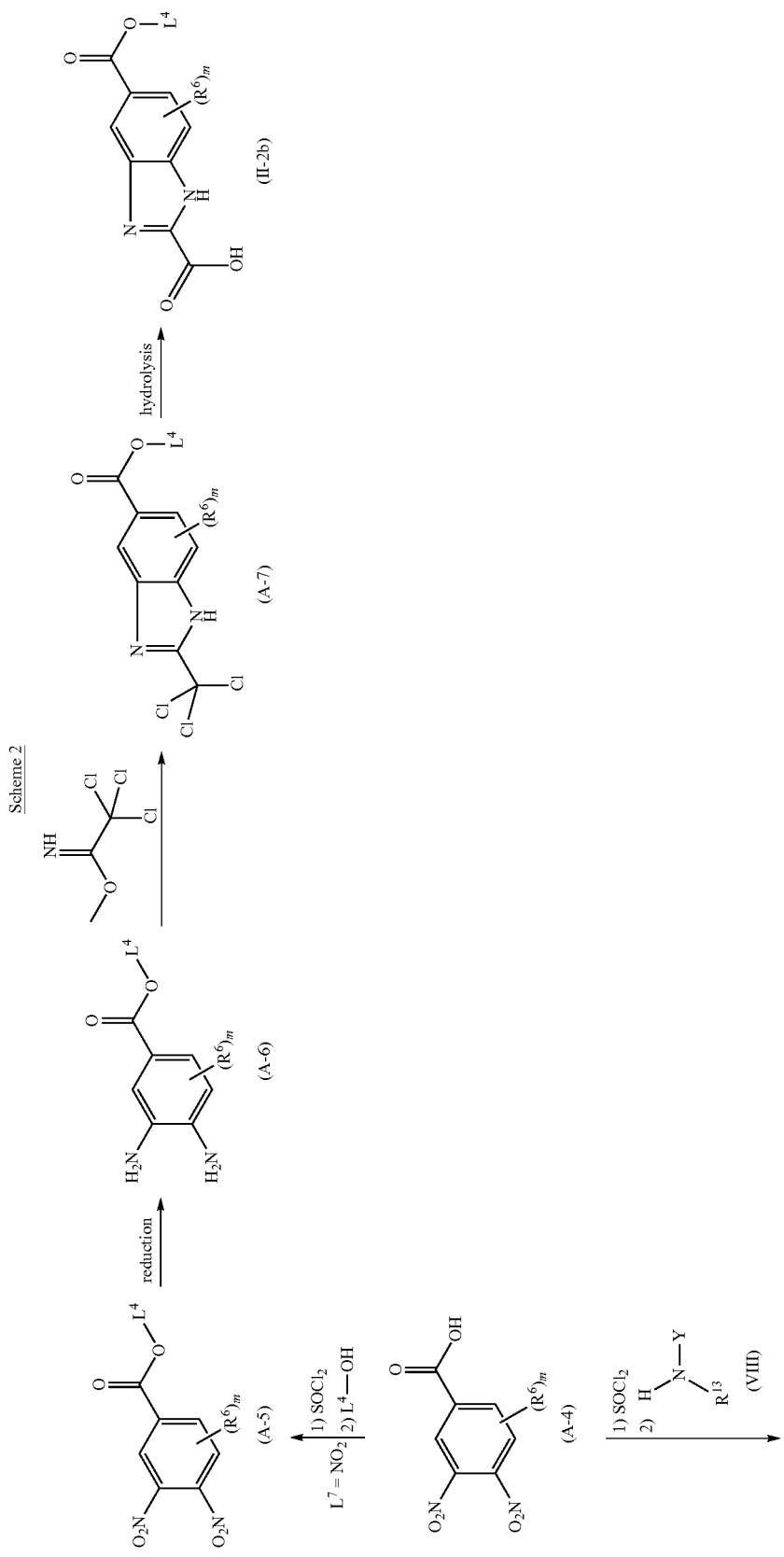

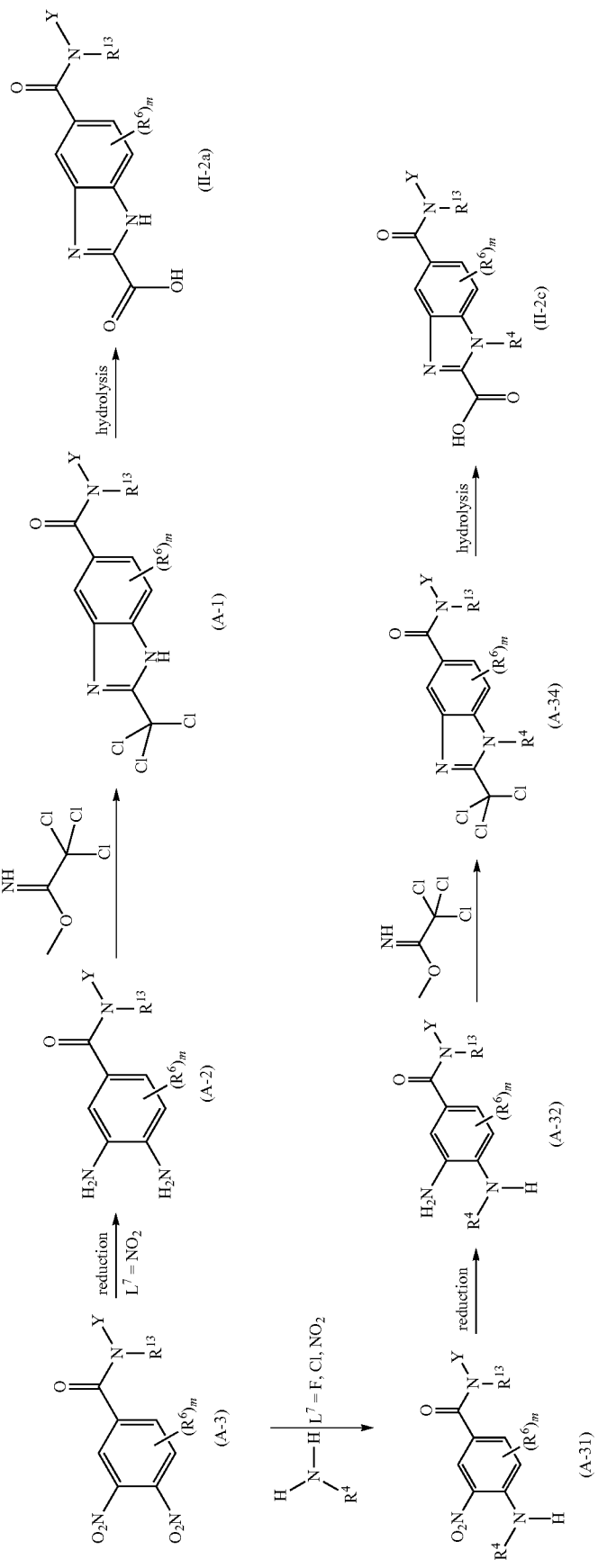

Benzimidazole derivatives of the formula (II-2a) are obtained from compounds of the formula (A-1) by hydrolysis, for example with methanol (cf., for example, Bioorganic & Medicinal Chemistry Letters, 20(2), 2010, 586-590). In the same way, it is possible to obtain compounds of the formula (II-2c) which bear an $R^4$ substituent on the imidazole nitrogen from compounds of the formula (A-34). Compounds of the formula (A-1) can be obtained by known processes, by reaction of 1,2-diaminophenyl derivatives of the formula (A-2) with 2,2,2-trichloroacetimidate (cf., for example, Bioorganic & Medicinal Chemistry Letters, 20(2), 2010, 586-590). Compounds of the formula (A-34) are likewise obtained from compounds of the formula (A-32). 1,2-Diaminophenyl derivatives of the formula (A-2) are known or can be obtained by known processes from compounds of the formula (A-3, $L^7=NO_2$) (cf., for example, European Journal of Medicinal Chemistry, 44(5), 2009, 2002-2008). The reduction of nitro derivatives of the formula (A-31) by commonly known processes gives compounds of the formula (A-32). Mononitro derivatives of the formula (A-31) can be obtained by reacting compounds of the formula (A-3, $L^7=NO_2$, F, Cl) with primary amines. Amide of the formula (A-3) can be obtained by commonly known processes, by reaction of carboxylic acids of the formula (A-4, $L^7=NO_2$, Cl, F) with amines of the formula (VII) (cf. the conditions specified for the synthesis of compounds of the formula (IVa) in (A)). Dinitrocarboxylic acids of the formula (A-4, $L^7=NO_2$) are known (see, for example, WO2009/47558A1); carboxylic acids of the formula (A-4, $L^7=F$, Cl) are commercially available.

By the process described above for compounds of the formula (II-2a), it is possible, proceeding from esters of the formula (A-5), via compounds of the formula (A-6) and (A-7), also to obtain benzimidazolecarboxylic acids of the formula (II-2b). Esters of the formula (A-5) can be obtained by commonly known processes from carboxylic acids of the formula (A-4) (cf., for example, Organikum, Wiley-VCH, 22nd edition).

The invention also relates to the carboxylic acids of the general formula (II-2aa)

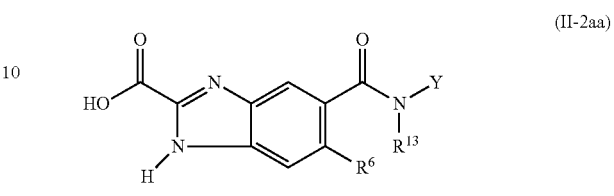

in which $R^6$, Y and $R^{13}$ are each as defined above and which can be prepared according to Scheme 2.

The invention also relates to the carboxylic acids of the general formula (II-2ba)

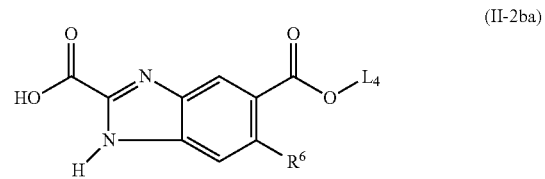

in which $L^4$ is $C_1$-$C_4$-alkyl and $R^6$ is as defined above and which can be prepared according to Scheme 2.

Novel indolecarboxylic acids of the formula (II-1c) and (II-1d) can be obtained according to Scheme 3.

Scheme 3

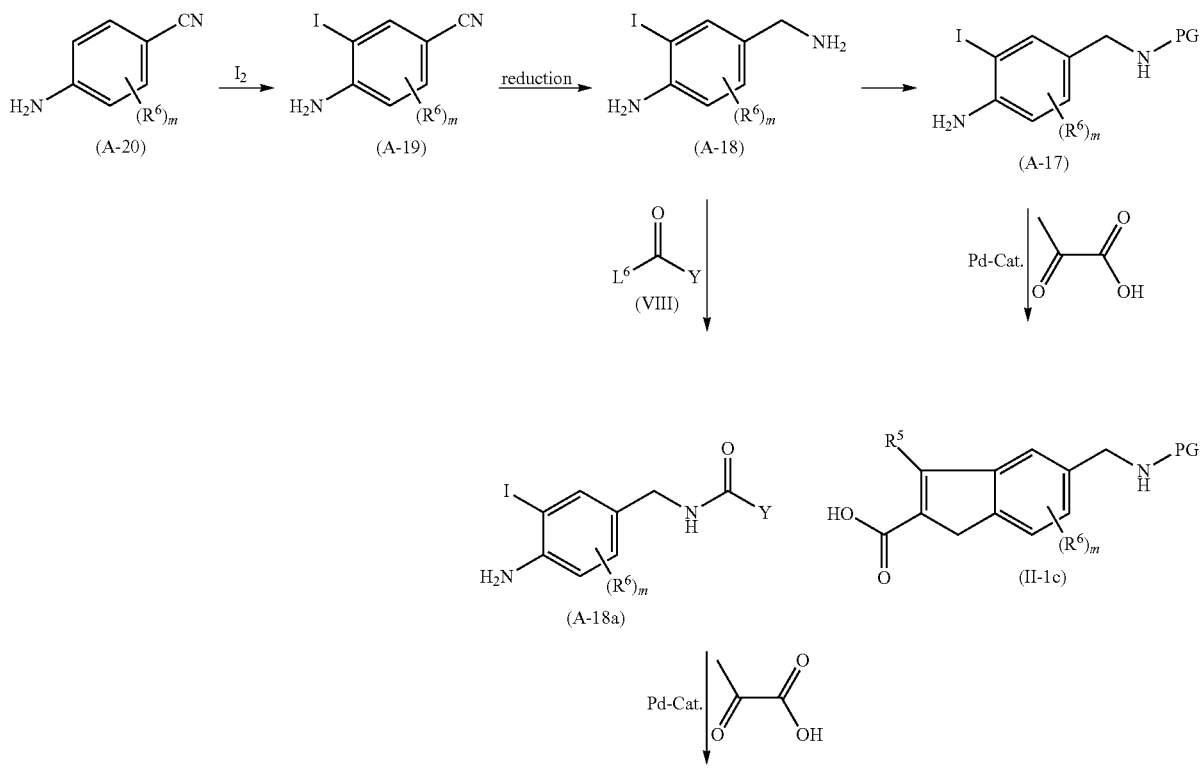

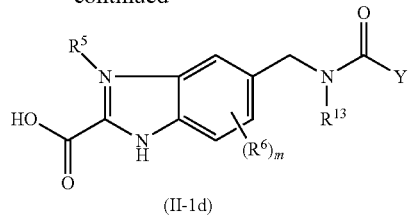

(II-1d)

It is possible here to react compounds of the formula (A-17) with pyruvic acid in the presence of a palladium catalyst, for example palladium acetate (cf., for example, Bioorganic & Medicinal Chemistry Letters, 20(9), 2010, 2722-2725), to obtain compounds (II-1c, $R^5$=H) which can optionally be converted by reaction with a halogenating reagent, for example chloro- or bromosuccinimide, to compounds (II-1c) where R5=Hal (cf., for example, WO-A-2009/023179). Compounds of the formula (A-17) are known or can be obtained in analogy to known processes from benzylamines of the formula (A-18) by reaction with reagents suitable for introduction of a protecting group (PG), for example with di-tert-butyl dicarbonate (cf., for example, WO-A-2006/101321). Benzylamines of the formula (A-18) are known or can be obtained by commonly known processes or in analogy (2001), 44(23), 3856-3871). Aminonitriles of the formula (A-20) are commercially available or can be obtained by known processes.

Compounds of the formula (II-1d) can be obtained by reacting compounds of the formula (A-18) with carboxylic acid derivatives of the formula (VIII) first to give amides (A-18a), and these are then reacted by the process described above for compounds of the formula (II-1c) with pyruvic acid to give compounds of the formula (II-1d, $R^5$=H), which can optionally be converted by reaction with a halogenating reagent, for example chloro- or bromosuccinimide, to compounds (II-1d) where $R^5$=Hal (cf., for example, WO-A-2009/023179).

Novel benzimidazolecarboxylic acids of the formula (II-2c) and (II-2d) can be obtained according to Scheme 4.

Scheme 4

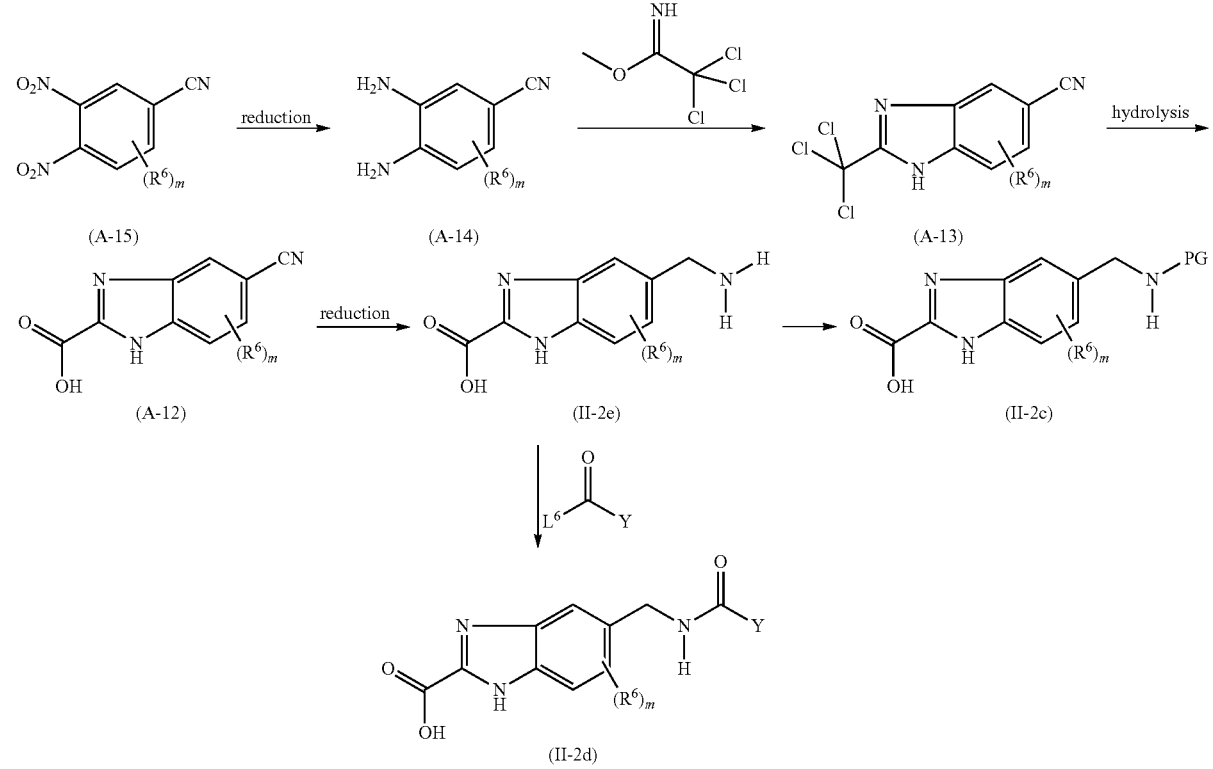

to known compounds by reduction of nitriles of the formula (A-19) (cf., for example, WO-A-2006/101321). Nitriles of the formula (A-19) are known or can be obtained in analogy to known compounds by reaction of aminobenzonitriles of the formula (A-20) with an iodinating reagent, for example iodine (cf., for example, Journal of Medicinal Chemistry Benzimidazole derivatives of the formula (II-2c) are obtained by reaction with benzylamines of the formula (II-2e), in analogy to known processes, with reagents suitable for introduction of a protecting group (PG), for example with di-tert-butyl dicarbonate (cf. *Greene's protective groups in organic synthesis,* 4th ed., P. G. M. Wuts, T. W. Greene, John Wiley &

Sons, Inc., Hoboken, N.J., 2007). Alternatively, benzylamines of the formula (A-11) can also be reacted by commonly known processes (cf., for example, the methods specified in (A) for synthesis of compounds of the formula (I)) with carboxylic acid derivatives of the formula (VIII) to obtain benzimidazoles of the formula (II-2d). Amines of the formula (II-2e) can be obtained by commonly known processes from the corresponding nitriles of the formula (A-12) (cf., for example, WO-A-2008/075196). Benzimidazole derivatives of the formula (A-12) are obtained, for example, from compounds of the formula (A-13) by hydrolysis, for example with methanol (cf., for example, Bioorganic & Medicinal Chemistry Letters, 20(2), 2010, 586-590). Compounds of the formula (A-13) can be obtained by known processes, by reaction of 1,2-diaminophenyl derivatives of the formula (A-14) with 2,2,2-trichloroacetimidate (cf., for example, Bioorganic & Medicinal Chemistry Letters, 20(2), 2010, 586-590). 1,2-Diaminophenyl derivatives of the formula (A-14) are known or can be obtained by known processes from dinitrophenyl compounds of the formula (A-15) (cf., for example, European Journal of Medicinal Chemistry, 44(5), 2009, 2002-2008). Dinitro compounds of the formula (A-15) are known or can be obtained from the corresponding carboxylic acids of the formula (A-4) by commonly known methods (see, for example, WO2009/47558A1, U.S. Pat. No. 5,591,378, Helvetica Chimica Acta (1943), 26, 1125).

Carbonyl halides, more preferably carbonyl chlorides, as likewise represented by the general structures (II) ($L^1$=halogen), can be prepared by the reaction of a carboxylic acid (L=OH) with halogenating reagents such as thionyl chloride, thionyl bromide, phosphoryl chloride, oxalyl chloride, phosphorus trichloride, etc. [Houben-Weyl, 1952, vol. VIII, p. 463 ff.].

Haloalkyl-substituted amines of the general formula (III) are commercially available or known from the literature, or can be synthesized by processes known from the literature. For example, aryl halides can be reacted in the presence of magnesium in a Grignard reaction with haloalkyl carboxylates. The ketones thus formed can then be converted by a reductive amination to the corresponding amines (cf. DE-A-2723464).

Novel haloalkyl-substituted amines of the general formula (III; $R_2$=H, $R_3$=H) can be obtained, for example, according to Scheme 5.

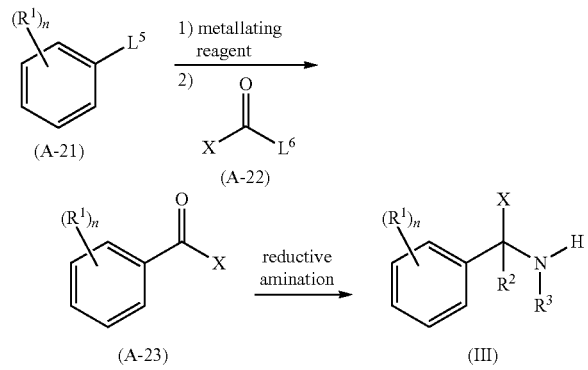

Scheme 5 where $L^6$ is —$C_1$-$C_4$-alkoxy or —N(CH$_3$)—O—$C_1$-$C_4$-alkyl, by reacting compounds of the formula (A-21) which are commercially available or known from the literature first with a metallating reagent, for example n-butyllithium, to give an organometallic intermediate, which is then reacted with a compound of the formula (A-22) to obtain ketones of the formula (A-23) (cf., for example, Chem. Med. Chem., 4(7), 2009, 1182-1188). These can then be converted in analogy to commonly known procedures by reductive amination to amines of the formula (III) (cf., for example, DE-A-2723464).

Compounds of the formula (A-21), (A-22), (V), (VII), (VIII) are substances known from the literature or are commercially available.

The processes according to the invention for preparation of the novel compounds of the formula (I) are preferably performed using a diluent. Useful diluents for performance of the processes according to the invention are, as well as water, all inert solvents. Examples include: halohydrocarbons (e.g. chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), ethers (e.g. ethyl propyl ether, methyl tert-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, 1,4-dioxane, dichlorodiethyl ether and polyethers of ethylene oxide and/or propylene oxide), amines (e.g. trimethyl-, triethyl-, tripropyl-, tributylamine, N-methylmorpholine, pyridine and tetramethylenediamine), nitrohydrocarbons (e.g. nitromethane, nitroethane, nitropropane, nitrobenzene, chloronitrobenzene, o-nitrotoluene); nitriles (for example acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (e.g. dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (e.g. pentane, hexane, heptane, octane, nonane and technical hydrocarbons), and also what are called "white spirits" with components having boiling points in the range from, for example, 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, nitrobenzene, xylene, esters (e.g. methyl, ethyl, butyl and isobutyl acetate, dimethyl, dibutyl and ethylene carbonate); amides (e.g. hexamethylenephosphoramide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-diformylpiperazine) and ketones (e.g. acetone, acetophenone, methyl ethyl ketone, methyl butyl ketone).

It is of course also possible to perform the process according to the invention in mixtures of the solvents and diluents mentioned.

When performing the process according to the invention, the reaction temperatures can be varied within a relatively wide range. In general, the temperatures employed are between −30° C. and +150° C., preferably between −10° C. and +100° C.

The process according to the invention is generally performed under atmospheric pressure. However, it is also possible to perform the process according to the invention under elevated or reduced pressure—generally at absolute pressures between 0.1 bar and 15 bar.

To perform the process according to the invention, the starting materials are generally used in approximately equimolar amounts. However, it is also possible to use one of the components in a relatively large excess. The reaction is generally performed in a suitable diluent in the presence of a reaction auxiliary, optionally under a protective gas atmosphere (for example under nitrogen, argon or helium) and the reaction mixture is generally stirred at the temperature required for several hours. The workup is performed by customary methods (cf. the Preparation Examples).

The basic reaction auxiliaries used to perform the process according to the invention may be all suitable acid binders. Examples include: alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, α-picoline, β-picoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethylenediamine).

The acidic reaction auxiliaries used to perform the process according to the invention include all mineral acids (e.g. hydrohalic acids such as hydrofluoric acid, hydrochloric acid, hydrobromic acid or hydriodic acid, and also sulphuric acid, phosphoric acid, phosphorous acid, nitric acid), Lewis acids (e.g. aluminium(III) chloride, boron trifluoride or its etherate, titanium(IV) chloride, tin(IV) chloride) and organic acids (e.g. formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesulphonic acid).

The Preparation and Use Examples which follow illustrate the invention without limiting it.

PREPARATION EXAMPLES

In the examples which follow, RT means room temperature, i.e. 20° C., and the expression "1 eq" means 1 equivalent.

Synthesis Example 1

6-chloro-$N^5$-(2,2-difluoroethyl)-1-ethyl-$N^2$-{2,2,2-trifluoro-1-[4-fluoro-3-(trifluoromethyl)phenyl]ethyl}-4H-indole-2,5-dicarboxamide (Compound No. 19 in Table 1)

Stage 1: ethyl 4-amino-2-chloro-5-iodobenzoate

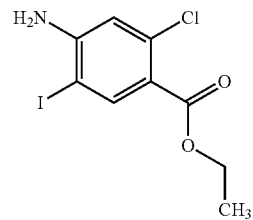

An iodine solution in ethanol was admixed with silver(I) sulphate and ethyl 4-amino-2-chlorobenzoate and then stirred at room temperature for 45 min. The reaction mixture was filtered through a frit and the filtrate was concentrated under reduced pressure. The residue was slurried in EtOAc, and dilute sodium hydrogencarbonate solution was added. Once everything had gone into solution, the aqueous phase was removed and sodium thiosulphate was dissolved therein. The organic phase was washed again with the aqueous phase and the aqueous phase was extracted with ethyl acetate. The combined organic phases were dried over sodium sulphate, filtered and concentrated under reduced pressure. Column chromatography purification on silica gel with cyclohexane/ethyl acetate as the eluent (gradient from 10% ethyl acetate to 33% ethyl acetate) gave 1.85 g (74% of theory) of ethyl 4-amino-2-chloro-5-iodobenzoate.

HPLC-MS: logP=2.95; mass (m/z): 326.0 (M+H)$^+$; $^1$H NMR (CD$_3$CN) 1.32 (t, 3H), 4.27 (q, 2H), 5.01 (br. s, 2H), 6.80 (s, 1H), 8.16 (s, 1H).

The following were obtained analogously:

methyl 4-amino-2-methyl-5-iodobenzoate from methyl 4-amino-2-methylbenzoate

HPLC-MS: logP=2.57; mass (m/z): 292.0 (M+H)$^+$; $^1$H NMR (D$_6$-DMSO) 2.37 (s, 3H), 3.72 (s, 3H), 5.91 (br. s, 2H), 6.57 (s, 1H), 8.08 (s, 1H).

ethyl 4-amino-2-ethyl-5-iodobenzoate from ethyl 4-amino-2-ethylbenzoate

HPLC-MS: logP=3.50; mass (m/z): 320.0 (M+H)$^+$; $^1$H NMR (D$_6$-DMSO) 1.10 (t, 3 H), 1.27 (t, 3H), 2.79 (q, 2H), 4.19 (q, 2H), 5.89 (br. s, 2H), 6.60 (s, 1H), 8.06 (s, 1H).

methyl 4-amino-2-isopropyl-5-iodobenzoate from methyl 4-amino-2-isopropylbenzoate HPLC-MS: logP=3.30; mass (m/z): 320.0 (M+H)$^+$; $^1$H NMR (D$_6$-DMSO) 1.34 (d, 6H), 3.70 (s, 3H), 3.80 (m, 1H), 5.87 (br. s, 2H), 6.78 (s, 1H), 8.01 (s, 1H).

Stage 2:
6-chloro-5-(ethoxycarbonyl)-1H-indole-2-carboxylic acid

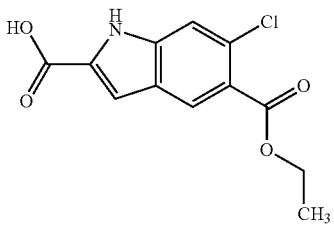 [SMILES: CCOC(=O)c1cc2cc(C(=O)O)[nH]c2cc1Cl]

A solution of ethyl 4-amino-2-chloro-5-iodobenzoate (1.82 g, 5.59 mmol) in N,N-dimethylformamide (18 ml) under argon was admixed with pyruvic acid (1.27 ml, 18.2 mmol) and 1,4-diazabicyclo[2.2.2]octane, evacuated and flushed with argon. Then argon was passed through the solution for 5 min and then palladium(II) acetate (68 mg, 0.30 mmol) was added and the mixture was heated to 100° C. for 2 h. The cooled solution was filterd through Celite and the filtercake was rinsed with ethyl acetate (100 ml). The filtrate (suspension) was washed with hydrochloric acid (2 M; 2×25 ml) and with water (2×25 ml), dried over sodium sulphate and filtered. The filtrate was concentrated to dryness under reduced pressure and gave a red-brown solid (1.93 g, approx. 51% product), which was used for the next step without further purification.

The following were obtained analogously:

6-methyl-5-(methoxycarbonyl)-1H-indole-2-carboxylic acid from methyl 4-amino-2-methyl-5-iodobenzoate HPLC-MS: logP=2.57; mass (m/z): 234.1 (M+H)$^+$; $^1$H NMR (D$_6$-DMSO) 2.37 (s, 3H), 3.2-3.4 (br. s, 1H), 3.72 (s, 3H), 7.18 (s, 1H), 7.30 (s, 1H), 8.28 (s, 1H), 11.93 (s, 1H).

6-ethyl-5-(ethoxycarbonyl)-1H-indole-2-carboxylic acid from ethyl 4-amino-2-ethyl-5-iodobenzoate HPLC-MS: logP=2.27; mass (m/z): 262.2 (M+H)$^+$; $^1$H NMR (D$_6$-DMSO) 1.19 (t, 3H), 1.34 (t, 3H), 3.00 (q, 2H) 3.2-3.4 (br. s, 1H), 4.29 (q, 2H), 7.18 (s, 1H), 7.31 (s, 1H), 8.22 (s, 1H), 11.91 (s, 1H).

6-isopropyl-5-(methoxycarbonyl)-1H-indole-2-carboxylic acid from methyl 4-amino-2-isopropyl-5-iodobenzoate HPLC-MS: logP=2.20; mass (m/z): 262.1 (M+H)$^+$; $^1$H NMR (D$_6$-DMSO) 1.18 (d, 6H), 3.2-3.4 (br. s, 1H), 3.80 (m, 1H), 7.14 (s, 1H), 7.42 (s, 1H), 8.12 (s, 1H), 11.85 (s, 1H).

Stage 3: ethyl 6-chloro-2-({2,2,2-trifluoro-1-[4-fluoro-3-(trifluoromethyl)phenyl]ethyl}carbamoyl)-1H-indole-5-carboxylate

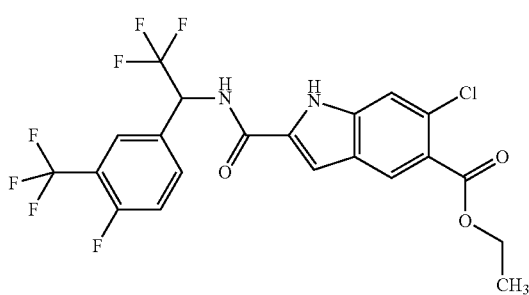 [SMILES: CCOC(=O)c1cc2cc(C(=O)NC(c3ccc(F)c(C(F)(F)F)c3)C(F)(F)F)[nH]c2cc1Cl]

2,2,2-Trifluoro-1-[4-fluoro-3-(trifluoromethyl)phenyl]ethanamine (0.82 g, 3.05 mmol) was dissolved in N,N-dimethylformamide (6 ml), and 6-chloro-5-(ethoxycarbonyl)-1H-indole-2-carboxylic acid (0.82 g, 3.05 mmol), N-[(1H-benzotriazol-1-yloxy)(dimethylamino)methylene]-N-methylmethanaminium hexafluorophosphate (1.16 g, 3.05 mmol) and 4-methylmorpholine (0.92 g, 9.10 mmol) were added. The reaction mixture was stirred at room temperature for 16 h and then water was added. The aqueous phase was extracted three times with ethyl acetate, dried over sodium sulphate, adsorbed on silica gel and chromatographed with cyclohexane/ethyl acetate (4/1). 1.29 g (65% of theory) of ethyl 6-chloro-2-({2,2,2-trifluoro-1-[4-fluoro-3-(trifluoromethyl)phenyl]ethyl}carbamoyl)-1H-indole-5-carboxylate were obtained.

HPLC-MS: logP=4.23; mass (m/z): 511.0 (M+H)$^+$; $^1$H NMR (D$_6$-DMSO): δ 1.34 (t, 3H), 4.33 (q, 2H), 6.37-6.40 (m, 1H), 7.54 (s, 1H), 7.60 (s, 1H), 7.65-7.68 (m, 1H), 8.17-8.19 (m, 1H), 8.27 (s, 1H), 8.30-8.31 (m, 1H), 9.72-9.74 (m, 1H), 12.16 (s, 1H).

The following were obtained analogously:

ethyl 6-chloro-2-({2,2,2-trifluoro-1-[3-chlorophenyl]ethyl}carbamoyl)-1H-indole-5-carboxylate HPLC-MS: logP=4.01; mass (m/z): 458.9 (M+H)$^+$; $^1$H NMR (D$_6$-DMSO): δ 1.35 (t, 3H), 4.33 (q, 2H), 6.16-6.25 (m, 1H), 7.50-7.55 (m, 3H), 7.62 (s, 1H), 7.71-7.72 (m, 1H), 7.90 (s, 1H), 8.26 (s, 1H), 9.65 (d, 1H), 12.13 (s, 1H).

ethyl 6-chloro-2-({2,2,2-trifluoro-1-[3-bromophenyl]ethyl}carbamoyl)-1H-indole-5-carboxylate HPLC-MS: logP=4.09; mass (m/z): 502.9 (M+H)$^+$; $^1$H NMR (D$_6$-DMSO): δ 1.35 (t, 3H), 4.33 (q, 2H), 6.16-6.24 (m, 1H), 7.42-7.76 (m, 5H), 8.03 (s, 1H), 8.26 (s, 1H), 9.65 (d, 1H), 12.13 (s, 1H).

ethyl 6-chloro-2-({2,2,2-trifluoro-1-[3,5-dichlorophenyl]ethyl}carbamoyl)-1H-indole-5-carboxylate HPLC-MS: logP=4.54; mass (m/z): 493.0 (M+H)$^+$; $^1$H NMR (CD$_3$CN): δ 1.38 (t, 3H), 4.36 (q, 2H), 6.03-6.06 (m, 1H), 7.35 (s, 1H), 7.55 (s, 1H), 7.59 (s, 1H), 7.62 (s, 2H), 8.00 (s, 1H), 8.26 (s, 1H), 10.22 (s, 1H).

ethyl 6-chloro-2-({2,2,2-trifluoro-1-[3-chloro-4-fluorophenyl]ethyl}carbamoyl)-1H-indole-5-carboxylate HPLC-MS: logP=4.08; mass (m/z): 477.0 (M+H)$^+$; $^1$H NMR (D$_6$-DMSO): δ 1.35 (t, 3H), 4.34 (q, 2H), 6.21-6.30 (m, 1H), 7.53-7.62 (m, 3H), 7.77-7.83 (m, 1H), 8.09 (d, 1H), 8.27 (s, 1H), 9.63 (d, 1H), 12.15 (s, 1H).

ethyl 6-chloro-2-({2,2,2-trifluoro-1-[3-bromo-4-fluorophenyl]ethyl}carbamoyl)-1H-indole-5-carboxylate HPLC-MS: logP=4.13; mass (m/z): 521.0 (M+H)$^+$; $^1$H NMR (D$_6$-DMSO): δ 1.35 (t, 3H), 4.33 (q, 2H), 6.21-6.28 (m, 1H), 7.51-7.61 (m, 3H), 7.82-7.85 (m, 1H), 8.19-8.21 (m, 1H), 8.26 (s, 1H), 9.62 (d, 1H), 12.14 (s, 1H).

ethyl 6-chloro-2-({2,2,2-trifluoro-1-[3,4-dichlorophenyl]ethyl}carbamoyl)-1H-indole-5-carboxylate HPLC-MS: logP=4.43; mass (m/z): 493.1 (M+H)+.

ethyl 6-chloro-2-({2,2,2-trifluoro-1-[3,5-dichloro-4-fluorophenyl]ethyl}carbamoyl)-1H-indole-5-carboxylate HPLC-MS: logP=4.52; mass (m/z): 511.0 (M+H)+; 1H NMR (D$_6$-DMSO): δ 1.35 (t, 3H), 4.34 (q, 2H), 6.29-6.33 (m, 1H), 7.55 (s, 1H), 7.59 (s, 1H), 8.11-8.13 (m, 2H), 8.26 (s, 1H), 9.60 (d, 1H), 12.15 (s, 1H).

ethyl 6-chloro-2-({2,2,2-trifluoro-1-[3,5-dichloro-2,4-difluorophenyl]ethyl}carbamoyl)-1H-indole-5-carboxylate HPLC-MS: logP=4.68; mass (m/z): 528.9 (M+H)+; 1H NMR (D$_6$-DMSO): δ 1.34 (t, 3H), 4.34 (q, 2H), 6.35-6.40 (m, 1H), 7.55 (s, 1H), 7.58 (s, 1H), 8.24-8.27 (m, 2H), 9.76 (d, 1H), 12.19 (s, 1H).

ethyl 6-chloro-2-({2,2,2-trifluoro-1-[3,4-difluorophenyl]ethyl}carbamoyl)-1H-indole-5-carboxylate HPLC-MS: logP=3.80; mass (m/z): 461.0 (M+H)+; 1H NMR (D$_6$-DMSO): δ 1.34 (t, 3H), 4.34 (q, 2H), 6.20-6.26 (m, 1H), 7.54-7.65 (m, 4H), 7.91-7.94 (m, 1H), 8.26 (s, 1H), 9.61 (d, 1H), 12.15 (s, 1H).

ethyl 6-chloro-2-({2,2,2-trifluoro-1-[3,4,5-trichlorophenyl]ethyl}carbamoyl)-1H-indole-5-carboxylate HPLC-MS: logP=4.85; mass (m/z): 526.9 (M+H)+; 1H NMR (D$_6$-DMSO): δ 1.34 (t, 3H), 4.33 (q, 2H), 6.29-6.38 (m, 1H), 7.54 (s, 1H), 7.59 (s, 1H), 8.16 (s, 2H), 8.26 (s, 1H), 9.63 (d, 1H), 12.15 (s, 1H).

methyl 6-methyl-2-({2,2,2-trifluoro-1-[4-fluoro-3-(trifluoromethyl)phenyl]ethyl}carbamoyl)-1H-indole-5-carboxylate HPLC-MS: logP=4.01; mass (m/z): 477.0 (M+H)+; 1H NMR (D$_6$-DMSO): δ 1.99 (s, 3H), 3.83 (s, 3H), 6.40-6.44 (m, 1H), 7.31 (s, 1H), 7.54 (s, 1H), 7.80-7.83 (m, 1H), 8.06-8.08 (m, 1H), 8.14 (s, 1H), 8.31 (s, 1H), 9.59-9.62 (m, 1H), 11.93 (s, 1H).

methyl 6-methyl-2-({2,2,2-trifluoro-1-[3-(trifluoromethyl)phenyl]ethyl}carbamoyl)-1H-indole-5-carboxylate HPLC-MS: logP=3.85; mass (m/z): 459.10 (M+H)+; 1H NMR (D$_6$-DMSO): δ 1.99 (s, 3H), 3.83 (s, 3H), 6.30-6.35 (m, 1H), 7.31 (s, 1H), 7.55 (s, 1H), 7.61-7.63 (m, 1H), 7.70-7.74 (m, 1H), 8.06-8.08 (m, 1H), 8.21 (s, 1H), 8.30 (s, 1H), 9.60-9.63 (m, 1H), 11.91 (s, 1H).

methyl 6-methyl-2-({2,2,2-trifluoro-1-[3-chloro-4-fluorophenyl]ethyl}carbamoyl)-1H-indole-5-carboxylate HPLC-MS: logP=3.81; mass (m/z): 443.0 (M+H)+; 1H NMR (D$_6$-DMSO): δ 1.99 (s, 3H), 3.82 (s, 3H), 6.21-6.25 (m, 1H), 7.31 (s, 1H), 7.52-7.56 (m, 2H), 7.78-7.82 (m, 1H), 8.07-8.09 (m, 1H), 8.29 (s, 1H), 9.59-9.62 (m, 1H), 11.93 (s, 1H).

methyl 6-methyl-2-({2,2,2-trifluoro-1-[3-bromo-4-fluorophenyl]ethyl}carbamoyl)-1H-indole-5-carboxylate HPLC-MS: logP=3.86; mass (m/z): 487.0 (M+H)+.

methyl 6-methyl-2-({2,2,2-trifluoro-1-[3-chlorophenyl]ethyl}carbamoyl)-1H-indole-5-carboxylate HPLC-MS: logP=3.70; mass (m/z): 425.0 (M+H)+.

methyl 6-methyl-2-({2,2,2-trifluoro-1-[3,5-dichlorophenyl]ethyl}carbamoyl)-1H-indole-5-carboxylate HPLC-MS: logP=4.24; mass (m/z): 459.0 (M+H)+.

methyl 6-methyl-2-({2,2,2-trifluoro-1-[3-chloro-5-fluorophenyl]ethyl}carbamoyl)-1H-indole-5-carboxylate HPLC-MS: logP=3.83; mass (m/z): 443.0 (M+H)+.

methyl 6-methyl-2-({2,2,2-trifluoro-1-[3,4-dichlorophenyl]ethyl}carbamoyl)-1H-indole-5-carboxylate HPLC-MS: logP=4.14; mass (m/z): 459.0 (M+H)+.

methyl 6-methyl-2-({2,2,2-trifluoro-1-[3,5-dichloro-4-fluorophenyl]ethyl}carbamoyl)-1H-indole-5-carboxylate HPLC-MS: logP=4.31; mass (m/z): 477.0 (M+H)+; 1H NMR (D$_6$-DMSO): δ 1.99 (s, 3H), 3.83 (s, 3H), 6.28-6.32 (m, 1H), 7.31 (s, 1H), 7.53 (s, 2H), 8.11 (d, 1H), 8.29 (s, 1H), 9.47-9.49 (m, 1H), 11.92 (s, 1H).

methyl 6-methyl-2-({2,2,2-trifluoro-1-[3,4-difluorophenyl]ethyl}carbamoyl)-1H-indole-5-carboxylate HPLC-MS: logP=3.47; mass (m/z): 427.0 (M+H)+.

methyl 6-methyl-2-({2,2,2-trifluoro-1-[3,4,5-trichlorophenyl]ethyl}carbamoyl)-1H-indole-5-carboxylate HPLC-MS: logP=4.57; mass (m/z): 493.0 (M+H)+; 1H NMR (D$_6$-DMSO): δ 1.99 (s, 3H), 3.83 (s, 3H), 6.30-6.34 (m, 1H), 7.32 (s, 1H), 7.53 (s, 2H), 8.16 (s, 1H), 8.30 (s, 1H), 9.59-9.62 (m, 1H), 11.93 (s, 1H).

methyl 6-methyl-2-({2,2,2-trifluoro-1-[2,2-difluoro-1,3-benzodioxol-5-yl]ethyl}carbamoyl)-1H-indole-5-carboxylate HPLC-MS: logP=3.89; mass (m/z): 471.0 (M+H)+; 1H NMR (D$_6$-DMSO): δ 1.99 (s, 3H), 3.34 (s, 3H), 6.20-6.24 (m, 1H), 7.31 (s, 1H), 7.52-7.56 (m, 2H), 7.78-7.82 (m, 1H), 8.07-8.09 (m, 1H), 8.29 (s, 1H), 9.59-9.62 (m, 1H), 11.92 (s, 1H).

ethyl 6-ethyl-2-({2,2,2-trifluoro-1-[3-(trifluoromethyl)phenyl]ethyl}carbamoyl)-1H-indole-5-carboxylate HPLC-MS: logP=4.37; mass (m/z): 487.0 (M+H)+; 1H NMR (D$_6$-DMSO): δ 1.18 (t, 3H), 1.34 (t, 3H), 3.01 (q, 2H), 4.31 (q, 2H), 6.30-6.35 (m, 1H), 7.32 (s, 1H), 7.54 (s, 1H), 7.70-7.74 (m, 1H), 7.81-7.94 (m, 1H), 8.06-8.09 (m, 1H), 8.21 (s, 1H), 9.60-9.68 (m, 1H), 11.92 (s, 1H).

methyl 6-isopropyl-2-({2,2,2-trifluoro-1-[3-(trifluoromethyl)phenyl]ethyl}carbamoyl)-1H-indole-5-carboxylate HPLC-MS: logP=4.32; mass (m/z): 487.1 (M+H)+; 1H NMR (CD3CN): δ 1.26 (d, 6H), 3.78-3.83 (m, 1H), 3.86 (s, 3H), 6.13-6.18 (m, 1H), 7.32 (s, 1H), 7.50 (s, 1H), 7.64-7.68 (m, 1H), 7.76-7.78 (m, 1H), 7.88-7.90 (m, 1H), 7.98 (s, 1H), 8.08-8.11 (s, 1H), 8.16 (s, 1H), 10.081 (s, 1H).

Stage 4: ethyl 6-chloro-1-ethyl-2-({2,2,2-trifluoro-1-[4-fluoro-3-(trifluoromethyl)phenyl]ethyl}carbamoyl)-1H-indole-5-carboxylate

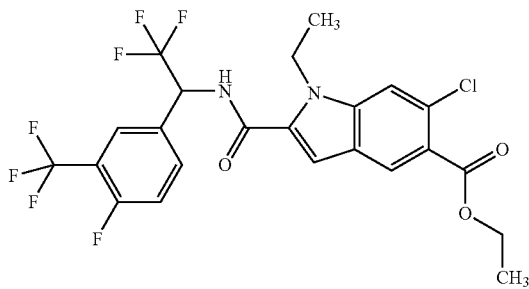 [SMILES: CCOC(=O)c1cc2cc(C(=O)NC(c3ccc(F)c(C(F)(F)F)c3)C(F)(F)F)n(CC)c2cc1Cl]

Ethyl 6-chloro-2-({2,2,2-trifluoro-1-[4-fluoro-3-(trifluoromethyl)phenyl]ethyl}carbamoyl)-1H-indole-5-carboxylate (0.42 g, 0.82 mmol) was dissolved under argon at 0° C. in N,N-dimethylformamide (6 ml). Sodium hydride (60%; 0.028 g, 0.72 mmol) was added and the mixture was stirred while cooling with ice for 2 h. Iodoethane (0.10 g, 0.65 mmol) was added. The reaction mixture was thawed while stirring within 36 h. Water and ethyl acetate were added and the phases were separated. The organic phase was washed with saturated sodium chloride solution and dried over magnesium sulphate, and the solvent was removed under reduced pressure. The residue was chromatographed with cyclohexane/ethyl acetate (4/1) and gave 0.23 g (53% of theory) of ethyl 6-chloro-1-ethyl-2-({2,2,2-trifluoro-1-[4-fluoro-3-(trifluoromethyl)phenyl]ethyl}carbamoyl)-1H-indole-5-carboxylate.

HPLC-MS: logP=5.16; mass (m/z): 539.0 (M+H)$^+$; $^1$H NMR (CD$_3$CN): δ 1.32 (t, 3H), 1.41 (t, 3H), 4.39 (q, 2H), 4.51 (q, 2H), 6.13-6.18 (m, 1H), 7.30 (s, 1H), 7.44-7.49 (m, 1H), 7.69 (s, 1H), 7.93-7.97 (m, 1H), 8.01-8.02 (m, 1H), 8.18-8.20 (m, 1H), 8.26 (s, 1H).

The following were obtained analogously:

ethyl 6-chloro-1-ethyl-2-({2,2,2-trifluoro-1-[3-chlorophenyl]ethyl}carbamoyl)-1H-indole-5-carboxylate HPLC-MS: logP=5.02; mass (m/z): 487.1 (M+H)$^+$; $^1$H NMR (D$_6$-DMSO): δ 1.23 (t, 3H), 1.35 (t, 3H), 4.34 (q, 2H), 4.52 (q, 2H), 6.12-6.21 (m, 1H), 7.43 (s, 1H), 7.50-7.54 (m, 2H), 7.70-7.71 (m, 1H), 7.88-7.90 (m, 2H), 8.25 (s, 1H), 9.79 (d, 1H).

ethyl 6-chloro-1-ethyl-2-({2,2,2-trifluoro-1-[3-bromophenyl]ethyl}carbamoyl)-1H-indole-5-carboxylate HPLC-MS: logP=5.15; mass (m/z): 531.1 (M+H)$^+$; $^1$H NMR (D$_6$-DMSO): δ 1.23 (t, 3H), 1.35 (t, 3H), 4.33 (q, 2H), 4.52 (q, 2H), 6.11-6.20 (m, 1H), 7.42-7.46 (m, 2H), 7.64-7.76 (m, 2H), 8.03 (s, 1H), 8.25 (s, 1H), 9.78 (d, 1H).

ethyl 6-chloro-1-ethyl-2-({2,2,2-trifluoro-1-[3,5-dichlorophenyl]ethyl}carbamoyl)-1H-indole-5-carboxylate HPLC-MS: logP=5.68; mass (m/z): 521.1 (M+H)$^+$; $^1$H NMR (D$_6$-DMSO): δ 1.24 (t, 3H), 1.35 (t, 3H), 4.34 (q, 2H), 4.52 (q, 2H), 6.22-6.31 (m, 1H), 7.44 (s, 1H), 7.73 (s, 1H), 7.88 (s, 1H), 7.92 (s, 2H), 8.26 (s, 1H), 9.75 (d, 1H).

ethyl 6-chloro-1-ethyl-2-({2,2,2-trifluoro-1-[3-chloro-4-fluorophenyl]ethyl}carbamoyl)-1H-indole-5-carboxylate HPLC-MS: logP=4.99; mass (m/z): 505.1 (M+H)$^+$; $^1$H NMR (CD$_3$CN): δ 1.33 (t, 3H), 1.41 (t, 3H), 4.39 (q, 2H), 4.51 (q, 2H), 6.01-6.10 (m, 1H), 7.29 (s, 1H), 7.35-7.39 (m, 1H), 7.59-7.63 (m, 1H), 7.69 (s, 1H), 7.79-7.81 (m, 1H), 8.07-8.10 (m, 1H), 8.26 (s, 1H).

ethyl 1-ethyl-6-chloro-2-({2,2,2-trifluoro-1-[3-bromo-4-fluorophenyl]ethyl}carbamoyl)-1H-indole-5-carboxylate HPLC-MS: logP=5.13; mass (m/z): 549.1 (M+H)$^+$; $^1$H NMR (D$_6$-DMSO): δ 1.23 (t, 3H), 1.34 (t, 3H), 4.33 (q, 2H), 4.51 (q, 2H), 6.16-6.25 (m, 1H), 7.42 (s, 1H), 7.48-7.52 (m, 1H), 7.80-7.84 (m, 1H), 7.88 (s, 1H), 8.18-8.20 (m, 1H), 8.25 (s, 1H), 9.76 (d, 1H).

ethyl 6-chloro-1-ethyl-2-({2,2,2-trifluoro-1-[3,4-dichlorophenyl]ethyl}carbamoyl)-1H-indole-5-carboxylate HPLC-MS: logP=5.49; mass (m/z): 520.9 (M+H)$^+$; $^1$H NMR (D$_6$-DMSO): δ 1.23 (t, 3H), 1.34 (t, 3H), 4.33 (q, 2H), 4.51 (q, 2H), 6.18-6.27 (m, 1H), 7.43 (s, 1H), 7.76 (s, 2H), 7.88 (s, 1H), 8.11 (s, 1H), 8.25 (s, 1H), 9.78 (d, 1H).

ethyl 6-chloro-1-ethyl-2-({2,2,2-trifluoro-1-[3,5-dichloro-4-fluorophenyl]ethyl}carbamoyl)-1H-indole-5-carboxylate HPLC-MS: logP=5.47; mass (m/z): 539.0 (M+H)$^+$; $^1$H NMR (D$_6$-DMSO): δ 1.24 (t, 3H), 1.34 (t, 3H), 4.34 (q, 2H), 4.52 (q, 2H), 6.23-6.32 (m, 1H), 7.43 (s, 1H), 7.89 (s, 1H), 8.10-8.12 (m, 2H), 8.26 (s, 1H), 9.72 (d, 1H).

ethyl 6-chloro-1-ethyl-2-({2,2,2-trifluoro-1-[3,5-dichloro-2,4-difluorophenyl]ethyl}carbamoyl)-1H-indole-5-carboxylate HPLC-MS: logP=4.93; mass (m/z): 557.0 (M+H)$^+$; $^1$H NMR (D$_6$-DMSO): δ 1.24 (t, 3H), 1.35 (t, 3H), 4.34 (q, 2H), 4.52 (q, 2H), 6.30-6.39 (m, 1H), 7.46 (s, 1H), 7.89 (s, 1H), 8.25-8.28 (m, 2H), 9.87 (d, 1H).

ethyl 6-chloro-1-ethyl-2-({2,2,2-trifluoro-1-[3,4-difluorophenyl]ethyl}carbamoyl)-1H-indole-5-carboxylate HPLC-MS: logP=4.79; mass (m/z): 489.1 (M+H)$^+$; $^1$H NMR (D$_6$-DMSO): δ 1.23 (t, 3H), 1.35 (t, 3H), 4.34 (q, 2H), 4.52 (q, 2H), 6.15-6.24 (m, 1H), 7.42 (s, 1H), 7.55-7.65 (m, 2H), 7.88-7.95 (m, 2H), 8.25 (s, 1H), 9.75 (d, 1H).

ethyl 6-chloro-1-ethyl-2-({2,2,2-trifluoro-1-[3,4,5-trichlorophenyl]ethyl}carbamoyl)-1H-indole-5-carboxylate HPLC-MS: logP=5.91; mass (m/z): 554.9 (M+H)$^+$; $^1$H NMR (D$_6$-DMSO): δ 1.24 (t, 3H), 1.34 (t, 3H), 4.33 (q, 2H), 4.51 (q, 2H), 6.25-6.34 (m, 1H), 7.43 (s, 1H), 7.89 (s, 1H), 8.15 (s, 2H), 8.26 (s, 1H), 9.74 (d, 1H).

ethyl 6-methyl-1-ethyl-2-({2,2,2-trifluoro-1-[3-(trifluoromethyl)phenyl]ethyl}-carbamoyl)-1H-indole-5-carboxylate HPLC-MS: logP=4.88; mass (m/z): 487.1 (M+H)$^+$.

ethyl 6-methyl-1-ethyl-2-({2,2,2-trifluoro-1-[3,4-dichlorophenyl]ethyl}carbamoyl)-1H-indole-5-carboxylate HPLC-MS: logP=4.13; mass (m/z): 487.0 (M+H)$^+$.

ethyl 6-methyl-1-ethyl-2-({2,2,2-trifluoro-1-[3,4-difluorophenyl]ethyl}carbamoyl)-1H-indole-5-carboxylate HPLC-MS: logP=4.44; mass (m/z): 455.1.0 (M+H)$^+$.

ethyl 6-methyl-1-ethyl-2-({2,2,2-trifluoro-1-[3,4,5-trichlorophenyl]ethyl}carbamoyl)-1H-indole-5-carboxylate HPLC-MS: logP=5.84; mass (m/z): 521.1 (M+H)$^+$.

methyl 1-ethyl-6-methyl-2-({2,2,2-trifluoro-1-[4-fluoro-3-(trifluoromethyl)phenyl]ethyl}carbamoyl)-1H-indole-5-carboxylate HPLC-MS: logP=4.89; mass (m/z): 505.0 (M+H)$^+$.

methyl 1-ethyl-6-methyl-2-({2,2,2-trifluoro-1-[3-chlorophenyl]ethyl}carbamoyl)-1H-indole-5-carboxylate HPLC-MS: logP=4.78; mass (m/z): 453.1.0 (M+H)$^+$.

methyl 1-ethyl-6-methyl-2-({2,2,2-trifluoro-1-[3,5-dichlorophenyl]ethyl}carbamoyl)-1H-indole-5-carboxylate HPLC-MS: logP=5.42; mass (m/z): 487.1.0 (M+H)$^+$.

methyl 1-ethyl-6-methyl-2-({2,2,2-trifluoro-1-[3-chloro-5-fluorophenyl]ethyl}carbamoyl)-1H-indole-5-carboxylate HPLC-MS: logP=4.89; mass (m/z): 471.1 (M+H)$^+$.

methyl 1-ethyl-6-methyl-2-({2,2,2-trifluoro-1-[3,5-dichloro-4-fluorophenyl]ethyl}carbamoyl)-1H-indole-5-carboxylate HPLC-MS: logP=4.89; mass (m/z): 505.0 (M+H)$^+$.

methyl 1-ethyl-6-methyl-2-({2,2,2-trifluoro-1-[3-chloro-4-fluorophenyl]ethyl}carbamoyl)-1H-indole-5-carboxylate HPLC-MS: logP=4.81; mass (m/z): 471.1 (M+H)$^+$.

methyl 1-ethyl-6-methyl-2-({2,2,2-trifluoro-1-[3-bromo-4-fluorophenyl]ethyl}carbamoyl)-1H-indole-5-carboxylate HPLC-MS: logP=4.87; mass (m/z): 515.1 (M+H)$^+$.

methyl 1-ethyl-6-methyl-2-({2,2,2-trifluoro-1-[2,2-difluoro-1,3-benzodioxol-5-yl]ethyl}carbamoyl)-1H-indole-5-carboxylate HPLC-MS: logP=4.90; mass (m/z): 499.0 (M+H)$^+$.

ethyl 1,6-diethyl-2-({2,2,2-trifluoro-1-[3-(trifluoromethyl)phenyl]ethyl}carbamoyl)-1H-indole-5-carboxylate HPLC-MS: logP=5.45; mass (m/z): 515.1.0 (M+H)$^+$.

methyl 1-ethyl-6-isopropyl-2-({2,2,2-trifluoro-1-[3-(trifluoromethyl)phenyl]ethyl}carbamoyl)-1H-indole-5-carboxylate HPLC-MS: logP=5.28; mass (m/z): 515.0 (M+H)$^+$.

Stage 5: 6-chloro-N$^5$-(2,2-difluoroethyl)-1-ethyl-N$^2$-{2,2,2-trifluoro-1-[4-fluoro-3-(trifluoromethyl)phenyl]ethyl}-1H-indole-2,5-dicarboxamide

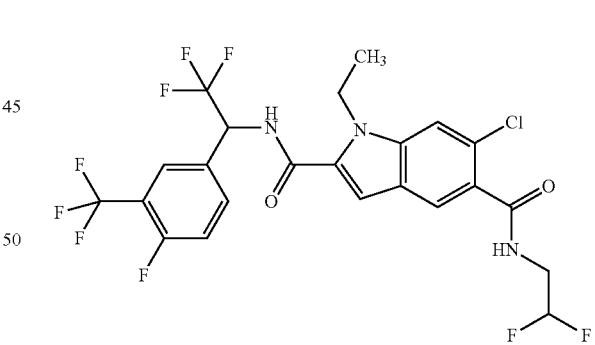

2,2-Difluoroethanamine (0.12 g, 1.42 mmol) was dissolved under argon in dichloromethane (2 ml). At room temperature, a solution of trimethylaluminium in dichloromethane (0.71 ml, 1.42 mmol) was added dropwise. The reaction mixture was stirred at room temperature for 30 min and then a solution of ethyl 6-chloro-1-ethyl-2-({2,2,2-trifluoro-1-[4-fluoro-3-(trifluoromethyl)phenyl]ethyl}carbamoyl)-1H-indole-5-carboxylate (0.078 g, 0.14 mmol) in dichloromethane (2 ml) was added dropwise. The reaction mixture was heated under reflux for 16 h and, after cooling, water was added. The aqueous phase was extracted three times with ethyl acetate. The combined organic phases were dried over sodium sulphate and the solvent was removed under reduced pressure. The residue was chromatographed with cyclohexane/ethyl acetate (4/1) and gave 0.065 g (81% of theory) of 6-chloro-$N^5$-(2,2-difluoroethyl)-1-ethyl-$N^2$-{2,2,2-trifluoro-1-[4-fluoro-3-(trifluoromethyl)phenyl]ethyl}-1H-indole-2,5-dicarboxamide.

HPLC-MS: logP=5.16; mass (m/z): 574.0 (M+H)$^+$; $^1$H NMR (CD$_3$CN): δ 1.32 (t, 3H), 3.74-3.84 (m, 2H), 4.51 (q, 2H), 5.93-6.23 (m, 2H), 7.15 (bs, 1H), 7.25 (s, 1H), 7.44-7.48 (m, 1H), 7.65 (s, 1H), 7.86 (s, 1H), 7.94-7.97 (m, 1H), 8.01-8.02 (m, 1H), 8.16-8.19 (m, 1H).

Synthesis Example 2

6-chloro-$N^5$-(1-cyanocyclopropyl)-1-ethyl-$N^2$-{2,2,2-trifluoro-1-[3-(trifluoromethyl)phenyl]ethyl}-1H-indole-2,5-dicarboxamide (Compound No. 7 in Table 1)

Stage 1: ethyl 6-chloro-2-({2,2,2-trifluoro-1-[3-(trifluoromethyl)phenyl]ethyl}carbamoyl)-1H-indole-5-carboxylate

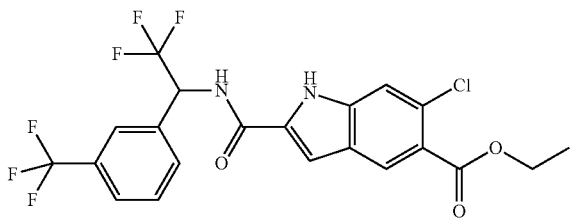 [SMILES: CCOC(=O)c1cc2cc(C(=O)NC(c3cccc(C(F)(F)F)c3)C(F)(F)F)[nH]c2cc1Cl]

A solution of the crude product of 6-chloro-5-(ethoxycarbonyl)-1H-indole-2-carboxylic acid (1.9 g) from Synthesis Example 1, Stage 2 and 2,2,2-trifluoro-1-[3-trifluoromethylphenyl]ethanamine (1.12 g, 4.60 mmol) (lit. DE 2723464) in N,N-dimethylformamide (15 ml) was admixed with 4-(4,6-dimethoxy[1.3.5]triazin-2-yl)-4-methylmorpholinium chloride hydrate (953 mg, 4.60 mmol), and the mixture was stirred at room temperature for 4 days. The reaction solution was admixed with hydrochloric acid (1 M) and extracted with ethyl acetate. The organic phase was washed with sat. sodium hydrogencarbonate solution and saturated sodium chloride solution, dried over sodium sulphate, filtered and concentrated to dryness under reduced pressure. Column chromatography purification on silica gel with cyclohexane/ethyl acetate as the eluent (gradient from 10% ethyl acetate to 25% ethyl acetate) gave 603 mg (26% of theory over 2 stages) of ethyl 6-chloro-2-({2,2,2-trifluoro-1-[3-(trifluoromethyl)phenyl]ethyl}carbamoyl)-1H-indole-5-carboxylate.

HPLC-MS: logP=4.12; mass (m/z): 493.1 (M+H)$^+$; $^1$H NMR (CD$_3$CN) 1.38 (t, 3H), 4.35 (q, 2H), 6.16 (quint, 1H), 7.36 (s, 1H), 7.58 (s, 1H), 7.65-7.69 (m, 1H), 7.76-7.79 (m, 1H), 7.87-7.89 (m, 1H), 7.98 (s, 1H), 8.07-8.09 (m, 1H), 8.25 (s, 1H), 10.22 (s, 1H).

Stage 2: ethyl 6-chloro-1-ethyl-2-({2,2,2-trifluoro-1-[3-(trifluoromethyl)phenyl]ethyl}carbamoyl)-1H-indole-5-carboxylate

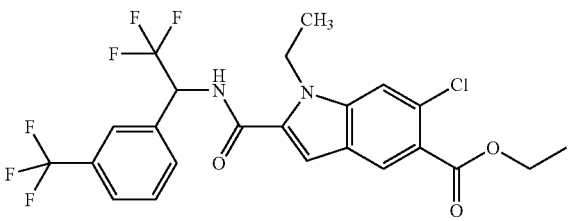 [SMILES: CCOC(=O)c1cc2cc(C(=O)NC(c3cccc(C(F)(F)F)c3)C(F)(F)F)n(CC)c2cc1Cl]

Ethyl 6-chloro-2-({2,2,2-trifluoro-1-[3-(trifluoromethyl)phenyl]ethyl}carbamoyl)-1H-indole-5-carboxylate (1.00 g, 2.03 mmol) was dissolved under argon at 0° C. in N,N-dimethylformamide (20 ml). Sodium hydride (60%; 0.079 g, 1.97 mmol) was added and the mixture was stirred while cooling with ice for 2 h. Subsequently, iodoethane (0.15 ml, 1.93 mmol) was added dropwise. The reaction mixture was thawed while stirring within 36 h. Water and ethyl acetate were added and the phases were separated. The organic phase was washed with saturated sodium chloride solution and dried over magnesium sulphate, and the solvent was removed under reduced pressure. The residue was chromatographed with cyclohexane/ethyl acetate (4/1) and gave 0.65 g (64% of theory) of ethyl 6-chloro-1-ethyl-2-({2,2,2-trifluoro-1-[3-(trifluoromethyl)phenyl]ethyl}carbamoyl)-1H-indole-5-carboxylate.

HPLC-MS: logP=5.00; mass (m/z): 521.1 (M+H)$^+$; $^1$H NMR (CD$_3$CN): δ 1.29 (t, 3H), 1.38 (t, 3H), 4.36 (q, 2H), 4.48 (q, 2H), 6.12-6.15 (m, 1H), 7.27 (s, 1H), 7.66-7.69 (m, 2H), 7.77-7.79 (m, 1H), 7.88-7.89 (m, 1H), 7.97 (s, 1H), 8.08-8.10 (m, 1H), 8.24 (s, 1H).

Stage 3: 6-chloro-1-ethyl-2-({2,2,2-trifluoro-1-[3-(trifluoromethyl)phenyl]ethyl}carbamoyl)-1H-indole-5-carboxylic acid

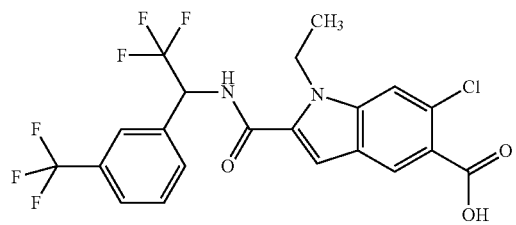 [SMILES: CCn1c(C(=O)NC(c2cccc(C(F)(F)F)c2)C(F)(F)F)cc2cc(C(=O)O)c(Cl)cc21]

Ethyl 6-chloro-1-ethyl-2-({2,2,2-trifluoro-1-[3-(trifluoromethyl)phenyl]ethyl}carbamoyl)-1H-indole-5-carboxylate (0.10 g, 0.19 mmol) was dissolved in 5 ml of dichloromethane and a solution of boron tribromide in dichloromethane (0.96 ml, 0.96 mmol) was added dropwise at −10° C. The reaction mixture was stirred at −10° C. for 1 h and then at room temperature for 2 h. Water was added and the precipitated solid was filtered off with suction and dried. 0.077 g (71% of theory) of 6-chloro-1-ethyl-2-({2,2,2-trifluoro-1-[3-(trifluoromethyl)phenyl]ethyl}carbamoyl)-1H-indole-5-carboxylic acid was obtained.

HPLC-MS: logP=3.71; mass (m/z): 493.3 (M+H)+; 1H NMR ($D_6$-DMSO): δ 1.22 (t, 3H), 4.50 (q, 2H), 6.24-6.31 (m, 1H), 7.42 (s, 1H), 7.70-7.74 (m, 1H), 7.81-7.83 (m, 2H), 8.05 (d, 1H), 8.19 (s, 1H), 8.26 (s, 1H), 9.85 (d, 1H).

The following were obtained analogously:

6-chloro-1-ethyl-2-({2,2,2-trifluoro-1-[3-chlorophenyl]ethyl}carbamoyl)-1H-indole-5-carboxylic acid HPLC-MS: logP=3.65; mass (m/z): 459.0 (M+H)$^+$; 1H NMR ($D_6$-DMSO): δ 1.23 (t, 3H), 4.51 (q, 2H), 6.12-6.21 (m, 1H), 7.43 (s, 1H), 7.50-7.53 (m, 2H), 7.68-7.71 (m, 1H), 7.84 (s, 1H), 7.90 (s, 1H), 8.26 (s, 1H), 9.76 (d, 1H), 13.00 (s, 1H).

6-chloro-1-ethyl-2-({2,2,2-trifluoro-1-[3-bromophenyl]ethyl}carbamoyl)-1H-indole-5-carboxylic acid HPLC-MS: logP=3.65; mass (m/z): 503.0 (M+H)$^+$; 1H NMR ($D_6$-DMSO): δ 1.23 (t, 3H), 4.51 (q, 2H), 6.11-6.20 (m, 1H), 7.41-7.45 (m, 2H), 7.64-7.66 (m, 1H), 7.73-7.75 (m, 1H), 7.84 (s, 1H), 8.03 (s, 1H), 8.26 (s, 1H), 9.73 (d, 1H), 13.01 (s, 1H).

6-chloro-1-ethyl-2-({2,2,2-trifluoro-1-[3,5-dichlorophenyl]ethyl}carbamoyl)-1H-indole-5-carboxylic acid HPLC-MS: logP=4.21; mass (m/z): 493.0 (M+H)$^+$; 1H NMR ($D_6$-DMSO): δ 1.23 (t, 3H), 4.51 (q, 2H), 6.21-6.30 (m, 1H), 7.43 (s, 1H), 7.73 (s, 1H), 7.84 (s, 1H), 7.92 (s, 1H), 8.27 (s, 1H), 9.73 (d, 1H), 13.01 (s, 1H).

6-chloro-1-ethyl-2-({2,2,2-trifluoro-1-[3-chloro-4-fluorophenyl]ethyl}carbamoyl)-1H-indole-5-carboxylic acid HPLC-MS: logP=3.68; mass (m/z): 477.0 (M+H)$^+$; 1H NMR ($D_6$-DMSO): δ 1.23 (t, 3H), 4.51 (q, 2H), 6.16-6.25 (m, 1H), 7.42 (s, 1H), 7.52-7.57 (m, 1H), 7.78-7.81 (m, 1H), 7.84 (s, 1H), 8.07-8.09 (m, 1H), 8.27 (s, 1H), 9.74 (d, 1H).

6-chloro-1-ethyl-2-({2,2,2-trifluoro-1-[3-bromo-4-fluorophenyl]ethyl}carbamoyl)-1H-indole-5-carboxylic acid HPLC-MS: logP=3.70; mass (m/z): 521.0 (M+H)$^+$; 1H NMR ($D_6$-DMSO): δ 1.23 (t, 3H), 4.51 (q, 2H), 6.16-6.24 (m, 1H), 7.42 (s, 1H), 7.48-7.52 (m, 1H), 7.80-7.84 (m, 2H), 8.18-8.20 (m, 1H), 8.27 (s, 1H), 9.73 (d, 1H), 13.00 (s, 1H).

6-chloro-1-ethyl-2-({2,2,2-trifluoro-1-[4-fluoro-3-(trifluoromethyl)phenyl]ethyl}carbamoyl)-1H-indole-5-carboxylic acid HPLC-MS: logP=3.81; mass (m/z): 510.9 (M+H)$^+$; 1H NMR ($D_6$-DMSO): δ 1.23 (t, 3H), 4.56 (q, 2H), 6.30-6.39 (m, 1H), 7.42 (s, 1H), 7.64-7.69 (m, 1H), 7.84 (s, 1H), 8.15-8.18 (m, 1H), 8.27-8.30 (m, 2H), 9.84 (d, 1H).

6-chloro-1-ethyl-2-({2,2,2-trifluoro-1-[3,4-dichlorophenyl]ethyl}carbamoyl)-1H-indole-5-carboxylic acid HPLC-MS: logP=3.90; mass (m/z): 493.0 (M+H)$^+$; 1H NMR ($D_6$-DMSO): δ 1.23 (t, 3H), 4.51 (q, 2H), 6.18-6.27 (m, 1H), 7.42 (s, 1H), 7.76 (s, 2H), 7.84 (s, 1H), 8.11 (s, 1H), 8.27 (s, 1H), 9.76 (d, 1H), 13.00 (s, 1H).

6-chloro-1-ethyl-2-({2,2,2-trifluoro-1-[3,5-dichloro-4-fluorophenyl]ethyl}carbamoyl)-1H-indole-5-carboxylic acid HPLC-MS: logP=4.23; mass (m/z): 510.9 (M+H)$^+$; 1H NMR ($D_6$-DMSO): δ 1.24 (t, 3H), 4.51 (q, 2H), 6.24-6.32 (m, 1H), 7.44 (s, 1H), 7.83 (s, 1H), 8.11 (s, 1H), 8.12 (s, 1H), 8.28 (s, 1H), 9.73 (d, 1H).

6-chloro-1-ethyl-2-({2,2,2-trifluoro-1-[3,5-dichloro-2,4-difluorophenyl]ethyl}carbamoyl)-1H-indole-5-carboxylic acid HPLC-MS: logP=4.44; mass (m/z): 529.0 (M+H)$^+$; 1H NMR ($D_6$-DMSO): δ 1.24 (t, 3H), 4.51 (q, 2H), 6.31-6.39 (m, 1H), 7.47 (s, 1H), 7.85 (s, 1H), 8.25-8.29 (m, 2H), 9.85 (d, 1H).

6-chloro-1-ethyl-2-({2,2,2-trifluoro-1-[3,4-difluorophenyl]ethyl}carbamoyl)-1H-indole-5-carboxylic acid HPLC-MS: logP=3.46; mass (m/z): 461.1 (M+H)$^+$; 1H NMR ($D_6$-DMSO): δ 1.23 (t, 3H), 4.51 (q, 2H), 6.14-6.23 (m, 1H), 7.42 (s, 1H), 7.53-7.66 (m, 2H), 7.84 (s, 1H), 7.90-7.95 (m, 1H), 8.26 (s, 1H), 9.73 (d, 1H).

6-chloro-1-ethyl-2-({2,2,2-trifluoro-1-[3,4,5-trichlorophenyl]ethyl}carbamoyl)-1H-indole-5-carboxylic acid HPLC-MS: logP=4.55; mass (m/z): 526.9 (M+H)$^+$; 1H NMR ($D_6$-DMSO): δ 1.23 (t, 3H), 4.51 (q, 2H), 6.25-6.34 (m, 1H), 7.43 (s, 1H), 7.84 (s, 1H), 8.15 (s, 2H), 8.28 (s, 1H), 9.72 (d, 1H), 13.0 (s, 1H).

1-ethyl-6-methyl-2-({2,2,2-trifluoro-[3-(trifluoromethyl)phenyl]ethyl}carbamoyl)-1H-indole-5-carboxylic acid HPLC-MS: logP=3.79; mass (m/z): 473.1 (M+H)$^+$.

1-ethyl-6-methyl-2-({2,2,2-trifluoro-1-[3,4-dichlorophenyl]ethyl}carbamoyl)-1H-indole-5-carboxylic acid HPLC-MS: logP=4.16; mass (m/z): 473.0 (M+H)$^+$.

1-ethyl-6-methyl-2-({2,2,2-trifluoro-1-[3,4-difluorophenyl]ethyl}carbamoyl)-1H-indole-5-carboxylic acid HPLC-MS: logP=3.45; mass (m/z): 441.1.0 (M+H)+.

1-ethyl-6-methyl-2-({2,2,2-trifluoro-[3,4,5-trichlorophenyl]ethyl}carbamoyl)-1H-indole-5-carboxylic acid HPLC-MS: logP=4.69; mass (m/z): 507.0 (M+H)+.

1-ethyl-6-methyl-2-({2,2,2-trifluoro-1-[4-fluoro-3-(trifluoromethyl)phenyl]ethyl}carbamoyl)-1H-indole-5-carboxylic acid HPLC-MS: logP=3.92; mass (m/z): 491.0 (M+H)+.

1-ethyl-6-methyl-2-({2,2,2-trifluoro-1-[3-chlorophenyl]ethyl}carbamoyl)-1H-indole-5-carboxylic acid HPLC-MS: logP=4.72; mass (m/z): 439.1 (M+H)+.

1-ethyl-6-methyl-2-({2,2,2-trifluoro-1-[3,5-dichlorophenyl]ethyl}carbamoyl)-1H-indole-5-carboxylic acid HPLC-MS: logP=4.19; mass (m/z): 473.0 (M+H)+.

1-ethyl-6-methyl-2-({2,2,2-trifluoro-1-[3-chloro-5-fluorophenyl]ethyl}carbamoyl)-1H-indole-5-carboxylic acid HPLC-MS: logP=4.83; mass (m/z): 457.1 (M+H)+.

1-ethyl-6-methyl-2-({2,2,2-trifluoro-1-[3,5-dichloro-4-fluorophenyl]ethyl}carbamoyl)-1H-indole-5-carboxylic acid HPLC-MS: logP=4.36; mass (m/z): 491.1 (M+H)+.

1-ethyl-6-methyl-2-({2,2,2-trifluoro-1-[3-chloro-4-fluorophenyl]ethyl}carbamoyl)-1H-indole-5-carboxylic acid HPLC-MS: logP=3.80; mass (m/z): 457.1 (M+H)+.

1-ethyl-6-methyl-2-({2,2,2-trifluoro-1-[3-bromo-4-fluorophenyl]ethyl}carbamoyl)-1H-indole-5-carboxylic acid HPLC-MS: logP=3.86; mass (m/z): 501.0 (M+H)+.

1-ethyl-6-methyl-2-({2,2,2-trifluoro-1-[2,2-difluoro-1,3-benzodioxol-5-yl]ethyl}carbamoyl)-1H-indole-5-carboxylic acid HPLC-MS: logP=3.85; mass (m/z): 485.0 (M+H)+.

1,6-diethyl-2-({2,2,2-trifluoro-1-[3-(trifluoromethyl)phenyl]ethyl}carbamoyl)-1H-indole-5-carboxylic acid HPLC-MS: logP=4.09; mass (m/z): 515.1.0 (M+H)+.

1-ethyl-6-isopropyl-2-({2,2,2-trifluoro-1-[3-(trifluoromethyl)phenyl]ethyl}carbamoyl)-1H-indole-5-carboxylic acid HPLC-MS: logP=4.23; mass (m/z): 487.0 (M+H)+.

Stage 4: 6-chloro-$N^5$-(1-cyanocyclopropyl)-1-ethyl-$N^2$-{2,2,2-trifluoro-1-[3-(trifluoromethyl)phenyl]ethyl}-1H-indole-2,5-dicarboxamide

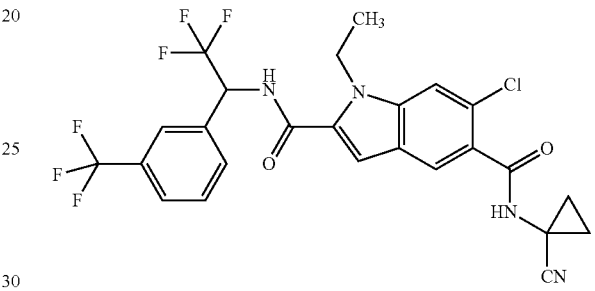

6-Chloro-1-ethyl-2-({2,2,2-trifluoro-1-[3-(trifluoromethyl)phenyl]ethyl}carbamoyl)-1H-indole-5-carboxylic acid (93% pure; 0.116 g, 0.22 mmol) was dissolved in dichloromethane (2.5 ml). N,N-Dimethylformamide (1 drop) and oxalyl chloride (0.058 ml, 0.66 mmol) were successively added dropwise. The reaction mixture was stirred at room temperature for 30 min and at 40° C. for 30 min, and then the solvent was removed under reduced pressure. The residue was dissolved in dichloromethane (2.5 ml) and added dropwise at room temperature to a solution of 1-aminocyclopropanecarbonitrile hydrochloride (0.052 g, 0.44 mmol) and diisopropylethylamine (0.085 g, 0.66 mmol) in dichloromethane (2.5 ml). The reaction mixture was stirred at room temperature for 16 h and then ethyl acetate was added. The organic phase was washed with saturated ammonium chloride solution and the aqueous phase was extracted twice with ethyl acetate. The combined organic phases were dried over sodium sulphate and the solvent was removed under reduced pressure. The residue was chromatographed with water and acetonitrile through RP silica gel and gave 0.033 g (24% of theory) of 6-chloro-$N^5$-(1-cyanocyclopropyl)-1-ethyl-$N^2$-{2,2,2-trifluoro-1-[3-(trifluoromethyl)phenyl]ethyl}-1H-indole-2,5-dicarboxamide.

HPLC-MS: logP=3.80; mass (m/z): 557.1 (M+H)+; $^1$H NMR (CD3CN): δ 1.31 (t, 3H), 1.33-1.39 (m, 2H), 1.58-1.62 (m, 2H), 4.50 (q, 2H), 6.11-6.20 (m, 1H), 7.26 (s, 1H), 7.58 (s, 1H), 7.66 (s, 1H), 7.69-7.72 (m, 1H), 7.80-7.82 (m, 1H), 7.85 (s, 1H), 7.90-7.92 (m, 1H), 7.99 (s, 1H), 8.15-8.19 (m, 1H).

Synthesis Example 3

5-(acetamidomethyl)-6-chloro-1-ethyl-N-{2,2,2-trifluoro-1-[3-(trifluoromethyl)phenyl]ethyl}-1H-indole-2-carboxamide (Compound No. 26 in Table 1)

Stage 1: 5-{[(tert-butoxycarbonyl)amino]methyl}-6-chloro-1H-indole-2-carboxylic acid

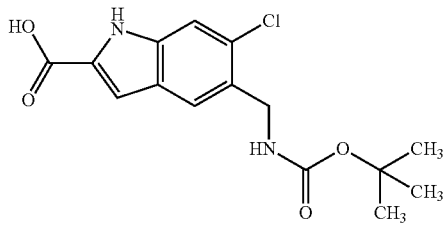 [SMILES: CC(C)(C)OC(=O)NCc1cc2cc(C(=O)O)[nH]c2cc1Cl]

tert-Butyl (4-amino-2-chloro-5-iodobenzyl)carbamate (1.18 g, 3.08 mmol) (known from WO-A-2006/101321) was initially charged under argon in N,N-dimethylformamide (12 ml). 2-Oxopropionic acid (0.88 g, 10.02 mmol), 1,4-diazabicyclo[2.2.2]octane (1.12 g, 10.02 mmol) and palladium acetate (0.034 g, 0.15 mmol) were added. The reaction mixture was stirred at 100° C. for 5 h. After cooling, the solution was filtered through Celite and the filtercake was washed with ethyl acetate. The filtrate was washed with hydrochloric acid (0.1 M) and saturated sodium chloride solution, the organic phase was dried over sodium sulphate and the solvent was removed under reduced pressure. 1.99 g of crude product were obtained, which were converted further without further purification.

$^1$H NMR (CD$_3$CN): δ 1.42 (s, 9H), 4.36 (d, 2H), 5.76 (bs, 1H), 7.16 (s, 1H), 7.54 (s, 1H), 7.64 (s, 1H), 9.95 (s, 1H).

Stage 2: tert-butyl {[6-chloro-2-({2,2,2-trifluoro-1-[3-(trifluoromethyl)phenyl]ethyl}carbamoyl)-1H-indol-5-yl]methyl}carbamate

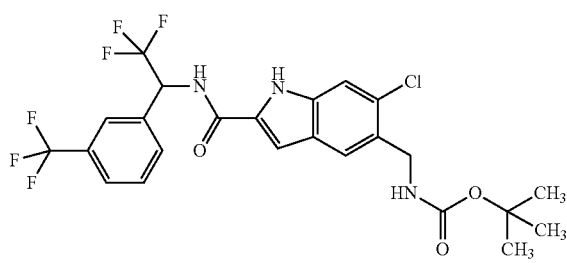 [SMILES: CC(C)(C)OC(=O)NCc1cc2cc(C(=O)NC(c3cccc(C(F)(F)F)c3)C(F)(F)F)[nH]c2cc1Cl]

2,2,2-Trifluoro-1-[3-fluoro-3-(trifluoromethyl)phenyl]ethanamine (0.75 g, 3.08 mmol) was dissolved in N,N-dimethylformamide (52 ml), and 5-{[(tert-butoxycarbonyl)amino]methyl}-6-chloro-1H-indole-2-carboxylic acid (1.00 g, 3.08 mmol), N-[(1H-benzotriazol-1-yloxy)(dimethylamino)methylene]-N-methylmethanaminium hexafluorophosphate (1.17 g, 3.08 mmol) and 4-methylmorpholine (0.93 g, 9.24 mmol) were added. The reaction mixture was stirred at room temperature for 16 h and then water and ethyl acetate were added. After phase separation, the organic phase was washed with dilute sodium hydrogencarbonate solution and saturated sodium chloride solution and dried over sodium sulphate, and the solvent was removed under reduced pressure. The residue was chromatographed with cyclohexane/ethyl acetate (5/1). 0.75 g (40% of theory) of tert-butyl {[6-chloro-2-({2,2,2-trifluoro-1-[3-(trifluoromethyl)phenyl]ethyl}carbamoyl)-1H-indol-5-yl]methyl}carbamate was obtained.

HPLC-MS: logP=4.37; mass (m/z): 548.1 (M−H)$^-$; $^1$H NMR (CD$_3$CN): δ 1.43 (s, 9H), 4.36 (d, 2H), 5.76 (bs, 1H), 6.14-6.17 (m, 1H), 7.25 (s, 1H), 7.51 (s, 1H), 7.65-7.68 (m, 2H), 7.76-7.78 (m, 1H), 7.87-7.89 (m, 1H), 7.97 (s, 1H), 8.02 (d, 1H), 10.01 (s, 1H).

Stage 3: tert-butyl {[6-chloro-1-ethyl-2-({2,2,2-trifluoro-1-[3-(trifluoromethyl)phenyl]ethyl}carbamoyl)-1H-indol-5-yl]methyl}carbamate

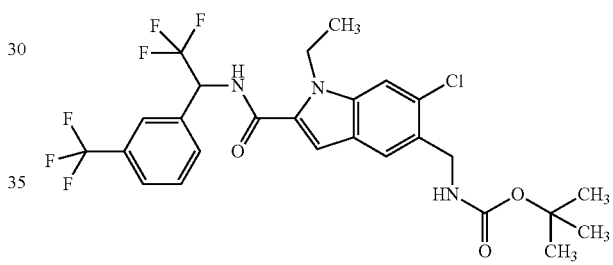

tert-Butyl {[6-chloro-2-({2,2,2-trifluoro-1-[3-(trifluoromethyl)phenyl]ethyl}carbamoyl)-1H-indol-5-yl]methyl}carbamate (90% pure; 0.74 g, 1.21 mmol) was dissolved under argon at 0° C. in N,N-dimethylformamide (12.5 ml). Sodium hydride (60%; 0.053 g, 1.33 mmol) was added and the mixture was stirred while cooling with ice for 2 h. Subsequently, iodoethane (0.19 g, 1.21 mmol) was added dropwise. The reaction mixture was thawed while stirring within 16 h. Water and ethyl acetate were added and the phases were separated. The organic phase was washed with saturated sodium chloride solution and dried over magnesium sulphate, and the solvent was removed under reduced pressure. The residue was chromatographed with cyclohexane/ethyl acetate (4/1) and gave 0.42 g (60% of theory) of tert-butyl {[6-chloro-1-ethyl-2-({2,2,2-trifluoro-1-[3-(trifluoromethyl)phenyl]ethyl}carbamoyl)-1H-indol-5-yl]methyl}carbamate.

HPLC-MS: logP=5.14; mass (m/z): 576.1 (M−H)$^-$; $^1$H NMR (CD$_3$CN): δ 1.30 (t, 3H), 1.45 (s, 9H), 4.39 (d, 2H), 4.49 (q, 2H), 5.78 (bs, 1H), 6.14-6.18 (m, 1H), 7.20 (s, 1H), 7.61 (s, 1H), 7.68-7.72 (m, 2H), 7.79-7.81 (m, 1H), 7.90-7.92 (m, 1H), 7.99-8.04 (m, 2H).

Stage 4: [6-chloro-1-ethyl-2-({2,2,2-trifluoro-1-[3-(trifluoromethyl)phenyl]ethyl}carbamoyl)-1H-indol-5-yl]methanaminium trifluoroacetate

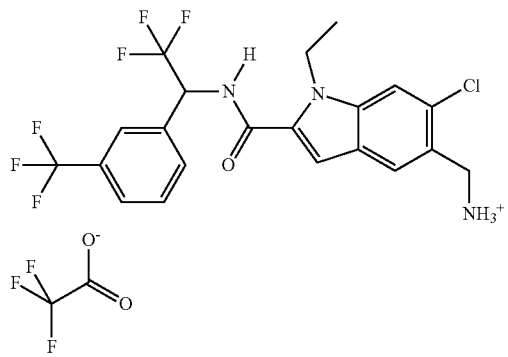

tert-Butyl {[6-chloro-1-ethyl-2-({2,2,2-trifluoro-1-[3-(trifluoromethyl)phenyl]ethyl}carbamoyl)-1H-indol-5-yl]methyl}carbamate (0.42 g, 0.72 mmol) was dissolved in dichloromethane (5 ml), and trifluoroacetic acid (0.82 g, 7.18 mmol) was added. The reaction mixture was stirred at room temperature for 2 h and then the solvent was removed under reduced pressure. 0.42 g (97% of theory) of [6-chloro-1-ethyl-2-({2,2,2-trifluoro-1-[3-(trifluoromethyl)phenyl]ethyl}carbamoyl)-1H-indol-5-yl]methanaminium trifluoroacetate was obtained.

HPLC-MS: logP=2.15; mass (m/z): 476.0 (M−H−TFA)$^-$; $^1$H NMR (CD$_3$CN): δ 1.31 (t, 3H), 4.37 (s, 2H), 4.50 (q, 2H), 6.12-6.20 (m, 1H), 7.25 (s, 1H), 7.58 (bs, 3H), 7.68-7.72 (m, 2H), 7.80-7.82 (m, 1H), 7.88 (s, 1H), 7.90-7.92 (m, 1H), 8.00 (s, 1H), 8.19 (d, 1H).

Stage 5: 5-(acetamidomethyl)-6-chloro-1-ethyl-N-{2,2,2-trifluoro-1-[3-(trifluoromethyl)phenyl]ethyl}-1H-indole-2-carboxamide

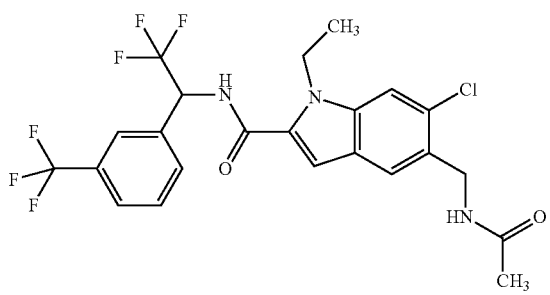 [SMILES: CCn1c(C(=O)NC(c2cccc(C(F)(F)F)c2)C(F)(F)F)cc2cc(CNC(C)=O)c(Cl)cc21]

At 0° C., [6-chloro-1-ethyl-2-({2,2,2-trifluoro-1-[3-(trifluoromethyl)phenyl]ethyl}carbamoyl)-1H-indol-5-yl]methanaminium trifluoroacetate (0.07 g, 0.15 mmol), triethylamine (0.036 g, 0.36 mmol) and N,N-dimethylpyridin-4-amine (0.002 g, 0.12 mmol) were initially charged in dichloromethane (1 ml). Acetic anhydride (0.021 g, 0.21 mmol) was added dropwise and the reaction mixture was stirred at room temperature for 16 h. Ethyl acetate was added and the organic phase was washed successively with water, saturated ammonium chloride solution and saturated sodium hydrogencarbonate solution. The organic phase was dried over sodium sulphate and the solvent was removed under reduced pressure. 0.06 g (98% of theory) of 5-(acetamidomethyl)-6-chloro-1-ethyl-N-{2,2,2-trifluoro-1-[3-(trifluoromethyl)phenyl]ethyl}-1H-indole-2-carboxamide was obtained.

HPLC-MS: logP=3.77; mass (m/z): 518.1 (M−H)$^-$; $^1$H NMR (D$_6$-DMSO): δ 1.20 (t, 3H), 3.33 (s, 3H), 4.37 (d, 2H), 4.49 (q, 2H), 6.27-6.31 (m, 1H), 7.33 (s, 1H), 7.67 (s, 1H), 7.72-7.74 (m, 1H), 7.77 (s, 1H), 7.81-7.83 (m, 1H), 8.06 (d, 1H), 8.20 (s, 1H), 8.29 (t, 1H), 9.70 (d, 1H).

Synthesis Example 4

6-chloro-N$^5$-cyclopropyl-1-ethyl-N$^2$-{2,2,2-trifluoro-1-[3-(trifluoromethyl)phenyl]ethyl}-1H-benzimidazole-2,5-dicarboxamide (Compound No. 4 in Table 1)

Stage 1: 2-chloro-N-cyclopropyl-4,5-dinitrobenzamide

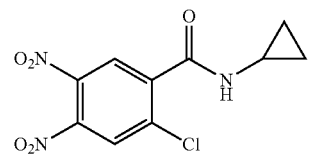 [SMILES: O=C(NC1CC1)c1cc([N+](=O)[O-])c([N+](=O)[O-])cc1Cl]

2-Chloro-4,5-dinitrobenzoic acid (known from WO-A-2009/47558) (8.0 g, 32.5 mmol) was dissolved in 1,2-dichloroethane (80 ml), and thionyl chloride (20 ml) was added under nitrogen. The reaction mixture was heated under reflux for 4 h and then the solvent was removed under reduced pressure. The residue was dissolved in dichloromethane (80 ml) and, at 0° C., cyclopropylamine (2.4 ml, 39 mmol) was added. The reaction mixture was stirred at room temperature for 2 h and then the solvent was removed under reduced pressure. The residue was stirred with diethyl ether (50 ml) for 30 min and then filtered off with suction. The residue was washed with water (100 ml) and dried. 7.5 g (81% of theory) of 2-chloro-N-cyclopropyl-4,5-dinitrobenzamide were thus obtained.

HPLC-MS: mass (m/z): 286.0 (M+H)$^+$; $^1$H NMR (D$_6$-DMSO) δ 0.53-0.57 (m, 2H), 0.71-0.76 (m, 2H), 2.80-2.84 (m, 1H), 8.41 (s, 1H), 8.55 (s, 1H), 8.84-8.85 (m, 1H).

The following were obtained analogously:

2-bromo-N-cyclopropyl-4,5-dinitrobenzamide

HPLC-MS: logP=1.92; mass (m/z): 329.9 (M+H)$^+$; $^1$H NMR (D$_6$-DMSO): δ 0.52-0.62 (m, 2H), 0.72-0.77 (m, 2H), 2.68-2.85 (m, 1H), 8.35 (s, 1H), 8.64 (s, 1H), 8.81-8.83 (d, 1H).

2-chloro-N-ethyl-4,5-dinitrobenzamide

HPLC-MS: logP=1.84; mass (m/z): 274.0 (M+H)$^+$; $^1$H NMR (D$_6$-DMSO): δ 1.11-1-19 (t, 3H), 3.25-3.35 (m, 2H), 8.40 (s, 1H), 8.55 (s, 1H), 8.78-8.80 (t broad, 1H).

2-chloro-4,5-dinitro-N-(2,2,2-trifluoroethyl)benzamide

HPLC-MS: logP=2.35; mass (m/z): 328.0 (M+H)$^+$; $^1$H NMR (D$_6$-DMSO): δ 4.14-4.20 (m, 2H), 8.44 (s, 1H), 8.60 (s, 1H), 9.51-9.54 (t, 1H).

2-chloro-N-cyclobutyl-4,5-dinitrobenzamide

HPLC-MS: logP=2.36; mass (m/z): 300.0 (M+H)+; 1H NMR (D6-DMSO): δ 1.68-1.75 (m, 2H), 1.95-2.05 (m, 2H), 2.22-2.30 (m, 2H), 4.32-4.40 (m, 1H), 8.41 (s, 1H), 8.57 (s, 1H), 9.03-9.07 (d, 1H).

Stage 2:
4,5-diamino-2-chloro-N-cyclopropylbenzamide

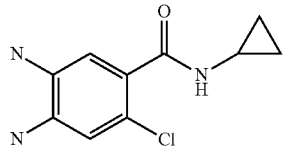 [SMILES: Nc1cc(Cl)c(C(=O)NC2CC2)cc1N]

2-Chloro-N-cyclopropyl-4,5-dinitrobenzamide (7.5 g, 26.3 mmol) was initially charged in ethanol (200 ml) and water (40 ml). At room temperature, ammonium chloride (2.53 g, 47.4 mmol) was added and the reaction mixture was heated to 60° C. At this temperature, iron powder (14.7 g, 263 mmol) was added in portions and the reaction mixture was then heated under reflux for 4 h. The ethanol was removed under reduced pressure and the remaining aqueous suspension was filtered through Celite. The filtrate was extracted three times with ethyl acetate, and the combined organic phases were washed with saturated sodium chloride solution and dried over sodium sulphate. After removing the solvent under reduced pressure, 4 g (68% of theory) of 4,5-diamino-2-chloro-N-cyclopropylbenzamide were obtained. 1H NMR (D6-DMSO): δ 0.44-0.48 (m, 2H), 0.61-0.64 (m, 2H), 2.71-2.75 (m, 1H), 4.68 (bs, 2H), 4.98 (bs, 2H), 6.47 (s, 1H), 6.55 (s, 1H), 7.95-7.97 (d, 1H).

The following were obtained analogously:

4,5-diamino-2-chloro-N-ethylbenzamide

HPLC-MS: logP=0.27; mass (m/z): 214.2 (M+H)+; 1H NMR (D6-DMSO): δ 1.03-1.14 (t, 3H), 3.14-3.20 (m, 2H), 4.60-4.75 (broad, 2H), 4.9-5.1 (broad, 2H), 6.49 (s, 1H), 6.61 (s, 1H), 7.86-7.90 (t broad, 1H).

4,5-diamino-2-chloro-N-(2,2,2-trifluoroethyl)benzamide

HPLC-MS: logP=0.93; mass (m/z): 268.1 (M+H)+; 1H NMR (D6-DMSO): δ 3.95-4.07 (m, 2H), 4.72-4.78 (broad, 2H), 5.08-5.12 (broad, 2H), 6.52 (s, 1H), 6.64 (s, 1H), 8.52-8.58 (broad, 1H).

4,5-diamino-2-chloro-N-cyclobutylbenzamide

HPLC-MS: logP=0.98; mass (m/z): 240.0 (M+H)+; 1H NMR (D6-DMSO): δ 1.57-1.66 (m, 2H), 1.92-2.02 (m, 2H), 2.12-2.20 (m, 2H), 4.24-4.35 (m, 1H), 4.6-4.75 (broad, 2H), 4.95-5.5 (broad, 2H), 6.49 (s, 1H), 6.58 (s, 1H), 8.13-8.15 (d broad, 1H).

Stage 3: 6-chloro-N-cyclopropyl-2-(trichloromethyl)-1H-benzimidazole-5-carboxamide

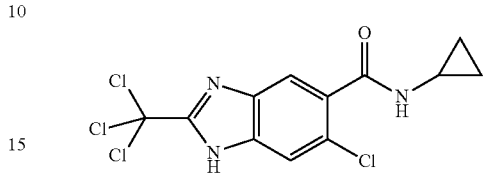

To a solution of 4,5-diamino-2-chloro-N-cyclopropylbenzamide (4.1 g, 18.2 mmol) in glacial acetic acid (50 ml) was added, at 0° C., methyl 2,2,2-trichloroacetimidate (2.21 ml, 18.2 mmol). The reaction mixture was stirred at room temperature for 16 h and then the solvent was removed under reduced pressure. The 6-chloro-N-cyclopropyl-2-(trichloromethyl)-1H-benzimidazole-5-carboxamide was used for Stage 4 directly without purification.

Stage 4: methyl 6-chloro-5-(cyclopropylcarbamoyl)-1H-benzimidazole-2-carboxylate

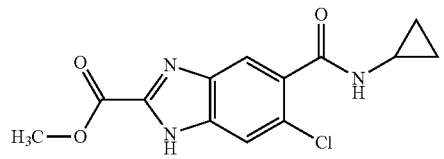 [SMILES: COC(=O)c1nc2cc(C(=O)NC3CC3)c(Cl)cc2[nH]1]

The 6-chloro-N-cyclopropyl-2-(trichloromethyl)-1H-benzimidazole-5-carboxamide from Stage 3 was dissolved in methanol (200 ml) and heated under reflux for 4 h. After removing the solvent under reduced pressure, the residue was taken up in ethyl acetate and washed with saturated sodium hydrogencarbonate solution. The organic phase was dried over sodium sulphate and the solvent was removed under reduced pressure. The residue was chromatographed with dichloromethane/methanol (95/5). 2.1 g (53% of theory) of methyl 6-chloro-5-(cyclopropylcarbamoyl)-1H-benzimidazole-2-carboxylate were obtained.

HPLC-MS: mass (m/z): 293.9 (M+H)+; 1H NMR (D6-DMSO): δ 0.54 (m, 2H), 0.67-0.72 (m, 2H), 2.80-2.85 (m 1H), 3.95 (s, 3H), 7.51-7.59 (m, 1H), 7.78-7.90 (m, 1H), 8.49-8.51 (d, 1H), 13.76-13.85 (m, 1H).

The following were obtained analogously:

methyl 6-chloro-5-(ethylcarbamoyl)-1H-benzimidazole-2-carboxylate

HPLC-MS: logP=0.87; mass (m/z): 282.0 (M+H)$^+$;

methyl 6-chloro-5-(cyclobutylcarbamoyl)-1H-benzimidazole-2-carboxylate

HPLC-MS: logP=1.34; mass (m/z): 308.1 (M+H)$^+$;

methyl 6-chloro-5-[(2,2,2-trifluoroethyl)carbamoyl]-1H-benzimidazole-2-carboxylate HPLC-MS: logP=1.37; mass (m/z): 336.0 (M+H)$^+$;

Stage 5: 6-chloro-5-(cyclopropylcarbamoyl)-1H-benzimidazole-2-carboxylic acid

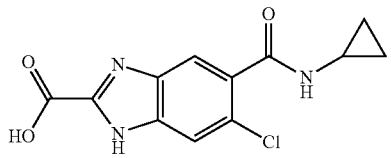 [SMILES: O=C(O)c1nc2cc(C(=O)NC3CC3)c(Cl)cc2[nH]1]

To a solution of methyl 6-chloro-5-(cyclopropylcarbamoyl)-1H-benzimidazole-2-carboxylate (2.1 g, 7.2 mmol) in tetrahydrofuran (50 ml) was added dropwise, at 0° C., a solution of lithium hydroxide monohydrate (0.6 g, 14.3 mmol) in water (25 ml). The reaction mixture was stirred at this temperature for 14 h. After removing the tetrahydrofuran under reduced pressure, the aqueous solution was acidified with hydrochloric acid (2 M). The precipitated solid was filtered off with suction. 1.7 g (81% of theory) of 6-chloro-5-(cyclopropylcarbamoyl)-1H-benzimidazole-2-carboxylic acid were obtained.

HPLC-MS: mass (m/z): 290.9 (M+H)$^+$; $^1$H NMR (D$_6$-DMSO): δ 0.48-0.52 (m, 2H), 0.64-0.67 (m, 2H), 2.77-2.80 (m, 1H), 7.59 (s, 1H), 7.69 (s, 1H), 8.47-8.48 (d, 1H).

The following were obtained analogously:

6-chloro-5-(ethylcarbamoyl)-1H-benzimidazole-2-carboxylic acid

HPLC-MS: logP=0.07; mass (m/z): 268.1 (M+H)$^+$;

6-chloro-5-(cyclobutylcarbamoyl)-1H-benzimidazole-2-carboxylic acid

HPLC-MS: logP=0.80; mass (m/z): 294.1 (M+H)$^+$;

Stage 6: 6-chloro-N$^5$-cyclopropyl-N$^2$-{2,2,2-trifluoro-1-[3-(trifluoromethyl)phenyl]ethyl}-1H-benzimidazole-2,5-dicarboxamide

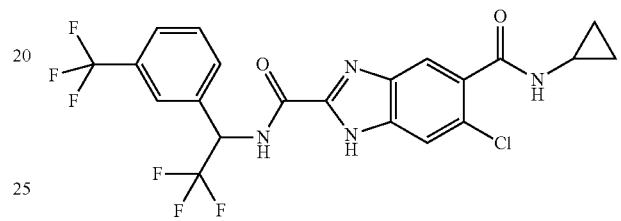

2,2,2-Trifluoro-1-[3-(trifluoromethyl)phenyl]ethanamine (0.23 g, 0.82 mmol) was dissolved in N,N-dimethylformamide (4 ml), and 6-chloro-5-(cyclopropylcarbamoyl)-1H-benzimidazole-2-carboxylic acid (0.23 g, 0.82 mmol), N-[(1H-benzotriazol-1-yloxy)(dimethylamino)methylene]-N-methylmethanaminium hexafluorophosphate (0.31 g, 0.82 mmol) and 4-methylmorpholine (0.25 g, 2.47 mmol) were added. The reaction mixture was stirred at room temperature for 16 h and then ethyl acetate was added. The organic phase was washed with saturated sodium hydrogencarbonate solution and saturated sodium chloride solution and dried over sodium sulphate, and the solvent was removed under reduced pressure. The residue was chromatographed with cyclohexane/ethyl acetate (1/1) and gave 0.24 g (57% of theory) of 6-chloro-N$^5$-cyclopropyl-N$^2$-{2,2,2-trifluoro-1-[3-(trifluoromethyl)phenyl]ethyl}-1H-benzimidazole-2,5-dicarboxamide.

HPLC-MS: logP=2.97; mass (m/z): 505.1 (M+H)$^+$; $^1$H NMR (CD$_3$CN): δ 0.58-0.65 (m, 2H), 0.72-0.79 (m, 2H), 2.82-2.89 (m, 1H), 6.06-6.15 (m, 1H), 6.92 (bs, 1H), 7.63-7.69 (m, 2H), 7.77-7.85 (m, 2H), 7.89 (d, 1H), 7.98 (s, 1H), 8.65 (d, 1H), 11.44-11.53 (m, 1H).

The following were obtained analogously:

6-chloro-N$^5$-cyclobutyl-N$^2$-{2,2,2-trifluoro-1-[4-fluoro-3-(trifluoromethyl)phenyl]ethyl}-1H-benzimidazole-2,5-dicarboxamide HPLC-MS: logP=3.38; mass (m/z): 537.1 (M+H)$^+$; $^1$H NMR (D$_6$-DMSO): δ 1.64-1.72 (m, 2H), 1.97-2.06 (m, 2H), 2.12-2.28 (m, 2H), 4.35-4.41 (m, 1H), 6.32-6.39 (m, 1H), 7.52-7.89 (m, 3H), 8.20-8.26 (broad, 1H), 8.49-8.51 (broad, 1H), 8.56-8.75 (dd, 1H), 10.6 (s, 1H), 13.67-13.78 (d, 1H).

6-chloro-N$^5$-cyclobutyl-N$^2$-{2,2,2-trifluoro-1-[3-(trifluoromethyl)phenyl]ethyl}-1H-benzimidazole-2,5-dicarboxamide HPLC-MS: logP=3.33; mass (m/z): 519.1 (M+H)$^+$; $^1$H NMR (D$_6$-DMSO): δ 1.62-1.73 (m, 2H), 1.95-2.08 (m, 2H), 2.20-2.29 (m, 2H), 4.32-4.44 (m, 1H), 6.28-6.38 (m, 1H), 7.50-7.95 (m, 4H), 8.12-8.17 (d, 1H), 8.41 (s, 1H), 8.66-8.77 (d broad, 1H), 10.5 (s, 1H), 13.5-13.9 (d broad, 1H).

$N^2$-[1-(3-bromo-4-fluorophenyl)-2,2,2-trifluoroethyl]-6-chloro-$N^5$-cyclopropyl-1H-benzimidazole-2,5-dicarboxamide HPLC-MS: logP=2.93; mass (m/z): 533.0 (M+H)$^+$; $^1$H NMR (D$_6$-DMSO): δ 0.50-058 (m, 2H), 0.68-0.75 (m, 2H), 2.80-2.88 (m, 1H), 6.15-6.27 (q, 1H), 7.38-7.95 (m, 4H), 8.35-8.40 (d, 1H), 8.48-8.55 (dd, 1H), 10.4 (s broad, 1H), 13.6-13.8 (d, 1H).

6-chloro-$N^5$-(2,2,2-trifluoroethyl)-$N^2$-{2,2,2-trifluoro-1-[3-(trifluoromethyl)phenyl]ethyl}-1H-benzimidazole-2,5-dicarboxamide HPLC-MS: logP=3.30; mass (m/z): 547.0 (M+H)$^+$; $^1$H NMR (D$_6$-DMSO): δ 4.05-4.15 (m, 2H), 6.28-6.38 (m, 1H), 7.55-7.86 (m, 4H), 8.12-8.17 (d, 1H), 8.39-8.43 (s broad, 1H), 9.13-9.25 (m, 1H), 10.5 (s, 1H), 13.7-13.9 (d, 1H).

Stage 7: 5-chloro-$N^6$-cyclopropyl-1-ethyl-$N^2$-{2,2,2-trifluoro-1-[3-(trifluoromethyl)phenyl]ethyl}-1H-benzimidazole-2,6-dicarboxamide and 6-chloro-$N^5$-cyclopropyl-1-ethyl-$N^2$-{2,2,2-trifluoro-1-[3-(trifluoromethyl)phenyl]ethyl}-1H-benzimidazole-2,5-dicarboxamide

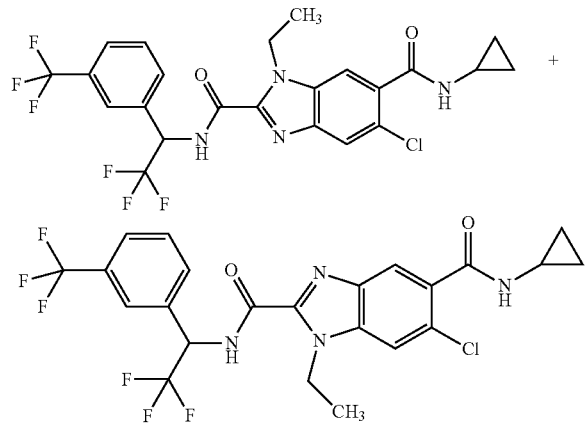

6-Chloro-$N^5$-cyclopropyl-$N^2$-{2,2,2-trifluoro-1-[3-(trifluoromethyl)phenyl]ethyl}-1H-benzimidazole-2,5-dicarboxamide (0.1 g, 0.22 mmol) was dissolved under argon at 0° C. in N,N-dimethylformamide (2 ml). Sodium hydride (60%; 0.0082 g, 0.22 mmol) was added and the mixture was stirred while cooling with ice for 1 h. Subsequently, iodoethane (0.034 g, 0.22 mmol) was added dropwise. The reaction mixture was thawed while stirring within 16 h. Water and ethyl acetate were added and the phases were separated. The organic phase was washed with saturated sodium chloride solution and dried over magnesium sulphate, and the solvent was removed under reduced pressure. The residue was chromatographed with cyclohexane/ethyl acetate (4/1) and gave 0.012 g (12% of theory) of 5-chloro-$N^6$-cyclopropyl-1-ethyl-$N^2$-{2,2,2-trifluoro-1-[3-(trifluoromethyl)phenyl]ethyl}-1H-benzimidazole-2,6-dicarboxamide and 0.018 g (18% of theory) of 6-chloro-$N^5$-cyclopropyl-1-ethyl-$N^2$-{2,2,2-trifluoro-1-[3-(trifluoromethyl)phenyl]ethyl}-1H-benzimidazole-2,5-dicarboxamide.

HPLC-MS: logP=3.67; mass (m/z): 533.2 (M+H)$^+$; $^1$H NMR (CD$_3$CN): δ 0.59-0.62 (m, 2H), 0.76-0.79 (m, 2H), 1.38 (t, 3H), 2.83-2.89 (m, 1H), 4.61-4.64 (m, 2H), 6.08-6.13 (m, 1H), 6.92-6.93 (m, 1H), 7.68 (t, 1H), 7.71 (s, 1H), 7.77-7.79 (m, 2H), 7.90 (d, 1H), 7.98 (s, 1H), 8.76 (d, 1H).

HPLC-MS: logP=3.71; mass (m/z): 533.1 (M+H)$^+$; $^1$H NMR (CD$_3$CN): δ 0.60-0.63 (m, 2H), 0.76-0.79 (m, 2H), 1.39 (t, 3H), 2.84-2.88 (m, 1H), 4.62-4.66 (m, 2H), 6.08-6.14 (m, 1H), 6.97-6.98 (m, 1H), 7.66-7.69 (m, 2H), 7.78-7.79 (m, 2H), 7.90 (d, 1H), 7.98 (s, 1H), 8.81 (d, 1H).

Synthesis Example 5

6-chloro-$N^5$,1-dicyclopropyl-$N^2$-{2,2,2-trifluoro-1-[3-(trifluoromethyl)phenyl]ethyl}-1H-benzimidazole-2,5-dicarboxamide (Compound No. 312 in Table 1)

Stage 1: 2-chloro-N-cyclopropyl-4-(cyclopropylamino)-5-nitrobenzamide

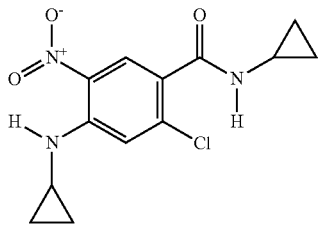 [SMILES: O=C(NC1CC1)c1cc([N+](=O)[O-])c(NC2CC2)cc1Cl]

2.00 g (5.95 mmol) of 2-chloro-N-cyclopropyl-4,5-dinitrobenzamide (see Synthesis Example 4, Stage 1) were initially charged in 150 ml of 1,2-dichloroethane, 0.85 g (14.88 mmol) of cyclopropylamine was added and the mixture was heated under reflux for three hours. After cooling, water was added and the 2-chloro-N-cyclopropyl-4-(cyclopropylamino)-5-nitrobenzamide was filtered off with suction and dried. Yield 1.16 g (66% of theory)

HPLC/MS: logP=2.33; mass (m/z): 296.1 (M+1); $^1$H NMR (D$_6$-DMSO): δ 0.50-0.58 (m, 2H), 0.61-0.71 (m, 4H), 0.88-0.94 (m, 2H), 2.64-2.72 (m, 1H), 2.75-2.83 (m, 1H), 7.39 (s, 1H), 8.11 (s broad, 1H), 8.45-8.50 (d broad, 1H).

The following were prepared in an analogous manner:

2-bromo-N-cyclopropyl-4-(ethylamino)-5-nitrobenzamide

HPLC/MS: logP=2.06; mass (m/z): 328 (M+1); $^1$H NMR (D$_6$-DMSO): δ 0.50-0.60 (m, 2H), 0.62-0.74 (m, 2H), 1.18-1.24 (t, 3H), 2.72-2.82 (m, 1H), 3.36-3.46 (m, 2H), 7.28 (s, 1H), 8.03 (s, 1H), 8.21-8.27 (t broad, 1H), 8.42-8.47 (d broad, 1H).

2-chloro-N-cyclopropyl-4-(isopropylamino)-5-nitrobenzamide

HPLC/MS: logP=2.39; mass (m/z): 298.1 (M+1); $^1$H NMR (D$_6$-DMSO): δ 0.48-0.55 (m, 2H), 0.66-0.72 (m, 2H), 1.24-1.28 (d, 2H), 2.75-2.82 (m, 1H), 3.98-4.08 (m, 1H), 7.18 (s, 1H), 7.95-7.99 (d, 1H), 8.11 (s, 1H), 8.45-8.48 (d, 1H).

Using the example of the preparation of 2-chloro-N-cyclopropyl-4-(ethylamino)-5-nitrobenzamide, the preparability of corresponding intermediates proceeding from 3-nitro-4-F-benzoic acids was demonstrated:

A) 2-chloro-N-cyclopropyl-4-fluoro-5-nitrobenzamide

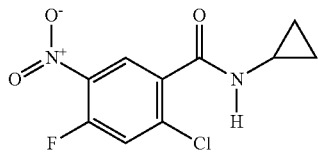 [SMILES: O=C(NC1CC1)c1cc([N+](=O)[O-])c(F)cc1Cl]

2 g (9.11 mmol) of 2-chloro-4-fluoro-5-nitrobenzoic acid were dissolved in 91 g of dichloroethane, 22.66 g of thionyl chloride were added and the mixture was boiled until the evolution of gas had ended. The volatile constituents were distilled off and the acid chloride thus obtained was used directly in the next step. 2.166 g (9.1 mmol) of 2-chloro-4-fluoro-5-nitrobenzoyl chloride were dissolved in 100 ml of dichloromethane, this solution was cooled to 0° C., and 0.52 g (9.1 mmol) of cyclopropylamine and 1.38 g (13.65 mmol) of triethylamine were added together, predissolved in 5 ml of dichloromethane. After stirring at room temperature for two hours, the volatile constituents were distilled off, the resulting residue was slurried with a little diethyl ether, the diethyl ether phase was decanted off and the residue was stirred with water.

Filtration with suction and drying gave the 2-chloro-N-cyclopropyl-4-fluoro-5-nitrobenzamide Yield: 2.0 g (93% of theory)

HPLC/MS: logP=1.59; mass (m/z): 259.0 (M+1); $^1$H NMR (D$_6$-DMSO): δ 0.50-0.59 (m, 2H), 0.68-0.77 (m, 2H), 2.75-2.86 (m, 1H), 7.96-8.01 (d, 1H), 8.20-8.27 (d, 1H), 8.68-8.79 (d broad, 1H).

B) 2-chloro-N-cyclopropyl-4-(ethylamino)-5-nitrobenzamide

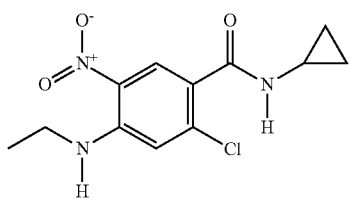 [SMILES: CCNc1cc(Cl)c(C(=O)NC2CC2)cc1[N+](=O)[O-]]

2.17 g (8.40 mmol) of 2-chloro-N-cyclopropyl-4-fluoro-5-nitrobenzamide were initially charged in 100 ml of THF, 12 ml of a 2 molar solution of ethylamine in THF (16.79 mmol) were added and the mixture was stirred in a closed ampoule at room temperature for 18 hours. The reaction mixture was poured onto water, the organic solvents were distilled off and the residue obtained was filtered off with suction. Yield: 2.10 g (81% of theory)

HPLC/MS: logP=2.03; mass (m/z): 284.0 (M+1); $^1$H NMR (D$_6$-DMSO): δ 0.48-0.58 (m, 2H), 0.64-0.72 (m, 2H), 1.17-1.23 (t, 3H), 2.74-2.83 (m, 1H), 3.4 (m, 2H), 7.13 (s, 1H), 8.11 (s, 1H), 8.26-8.31 (t broad, 1H), 8.44-8.50 (d broad, 1H).

Stage 2: 5-amino-2-chloro-N-cyclopropyl-4-(cyclopropylamino)benzamide

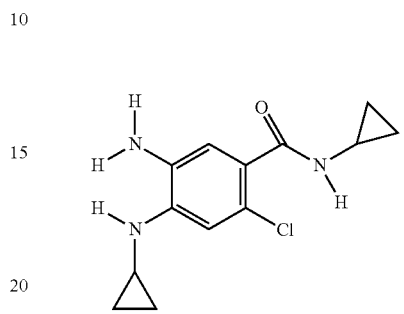

5.50 g (18.6 mmol) of 2-chloro-N-cyclopropyl-4-(cyclopropylamino)-5-nitrobenzamide were initially charged in a mixture of 550 g of ethanol and 110 g of water, and 1.79 g (33.48 mmol) of ammonium chloride were added. This mixture was heated to 60° C., 10.39 g (185.98 mmol) of iron powder (325 mesh) were added and then the mixture was stirred under reflux for five hours.

For workup, the volatile constituents were distilled off, diluted with 250 ml of water and filtered through kieselguhr. The aqueous phase was extracted with plenty of ethyl acetate (3×100 ml), and the organic phase was washed with saturated sodium chloride solution and dried over sodium sulphate to obtain 5-amino-2-chloro-N-cyclopropyl-4-(cyclopropylamino)benzamide.

Yield: 4.40 g (89% of theory)

HPLC/MS: logP=1.61; mass (m/z): 266.1 (M+1); $^1$H NMR (D$_6$-DMSO): δ 0.38-0.54 (m, 4H), 0.58-0.75 (m, 4H), 2.30-2.39 (m, 1H), 2.70-2.79 (m, 1H), 4.70-4.79 (broad, 2H), 6.55 (s, 1H), 6.65 (s, 1H), 7.98-8.02 (d, 1H).

The following were prepared in an analogous manner:

5-amino-2-chloro-N-cyclopropyl-4-(ethylamino)benzamide

HPLC/MS: logP=1.42; mass (m/z): 254.2 (M+1); $^1$H NMR (D$_6$-DMSO): δ 0.42-0.50 (m, 2H), 0.60-0.67 (m, 2H), 1.16-1.22 (t, 3H), 2.70-2.78 (m, 1H), 3.00-3.09 (m, 1H), 4.75-4.82 (s broad, 2H), 4.86-4.92 (t broad, 1H), 6.29 (s, 1H), 6.58 (s, 1H), 7.96-8.62 (d broad, 1H).

5-amino-2-bromo-N-cyclopropyl-4-(cyclopropylamino)benzamide

HPLC/MS: logP=1.61; mass (m/z): 310 (M+1); $^1$H NMR (D$_6$-DMSO): δ 0.38-0.42 (m, 2H), 0.45-0.52 (m, 2H), 0.60-0.65 (m, 2H), 0.69-0.78 (m, 2H), 2.30-2.39 (m, 1H), 2.70-

2.78 (m, 1H), 4.72-4.81 (broad, 2H), 5.47-5.49 (s, 1H), 6.53 (s, 1H), 6.80 (s, 1H), 7.98-8.04 (d, 1H).

Stage 3: methyl 6-chloro-1-cyclopropyl-5-(cyclopropylcarbamoyl)-1H-benzimidazole-2-carboxylate

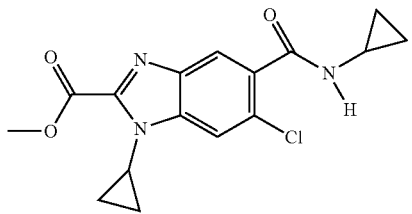 [SMILES: COC(=O)c1nc2cc(C(=O)NC3CC3)c(Cl)cc2n1C1CC1]

0.30 g (1.13 mmol) of 5-amino-2-chloro-N-cyclopropyl-4-(cyclopropylamino)benzamide was dissolved in 30 ml of acetic acid, the mixture was cooled to 0° C. and 0.20 g (1.13 mmol) of methyl 2,2,2-trichloroacetamidate was added. This solution was stirred at room temperature for 18 hours in order to obtain, after the distillative removal of the volatile constituents, the 6-chloro-N,1-dicyclopropyl-2-(trichloromethyl)-1H-benzimidazole-5-carboxamide intermediate.

The latter was dissolved in 20 ml of methanol and stirred under reflux for four hours (TLC monitoring). The residue obtained after distillative removal of the volatile constituents was purified by means of silica gel chromatography, cyclohexane/ethyl acetate (0% ethyl acetate to 60%).

Yield: 0.10 g (24% of theory)

HPLC/MS: logP=1.63; mass (m/z): 334.1 (M+1); $^1$H NMR (D$_6$-DMSO): δ 0.52-0.58 (m, 2H), 0.66-0.74 (m, 2H), 0.92-0.98 (m, 2H), 1.18-1.26 (m, 2H), 2.79-2.88 (m, 1H), 3.57-3.64 (m, 1H), 3.93 (s, 3H), 7.78 (s, 1H), 7.79 (s, 1H), 8.46-8.51 (d broad, 1H).

The following was prepared in an analogous manner:

methyl 6-bromo-1-cyclopropyl-5-(cyclopropylcarbamoyl)-1H-benzimidazole-2-carboxylate HPLC/MS: logP=1.68; mass (m/z): 378 (M+1); $^1$H NMR (D$_6$-DMSO): δ 0.50-0.59 (m, 2H), 0.66-0.73 (m, 2H), 0.92-0.98 (m, 2H), 1.20-1.28 (m, 2H), 2.79-2.87 (m, 1H), 3.54-3.64 (m, 1H), 3.96 (s, 3H), 7.75 (s, 1H), 7.94 (s, 1H), 8.47-8.50 (d broad, 1H).

Stage 4: 6-chloro-1-cyclopropyl-5-(cyclopropylcarbamoyl)-1H-benzimidazole-2-carboxylic acid

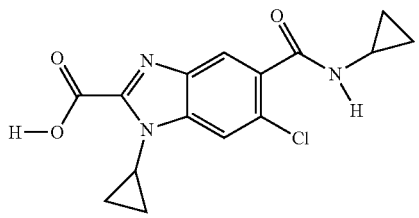 [SMILES: O=C(NC1CC1)c1cc2nc(C(=O)O)n(C3CC3)c2cc1Cl]

1.65 g (4.9 mmol) of methyl 6-chloro-1-cyclopropyl-5-(cyclopropylcarbamoyl)-1H-benzimidazole-2-carboxylate were dissolved in 82 ml of THF and admixed at 0° C. with 0.24 g (9.89 mmol) of lithium hydroxide predissolved in 18 ml of water, and the reaction mixture was stirred at room temperature for 18 hours. The THF was distilled off and the aqueous phase was extracted three times with ethyl acetate; the aqueous phase was adjusted to pH=3 with HCl. The solid which precipitates out was filtered off with suction. Due to its relative instability, the acid was used for subsequent reactions without further purification.

Yield: 600 mg (38% of theory).

The following was prepared in an analogous manner:

6-bromo-1-cyclopropyl-5-(cyclopropylcarbamoyl)-1H-benzimidazole-2-carboxylic acid Stage 5: 6-chloro-N$^5$,1-dicyclopropyl-N$^2$-{2,2,2-trifluoro-1-[3-(trifluoromethyl)phenyl]ethyl}-1H-benzimidazole-2,5-dicarboxamide

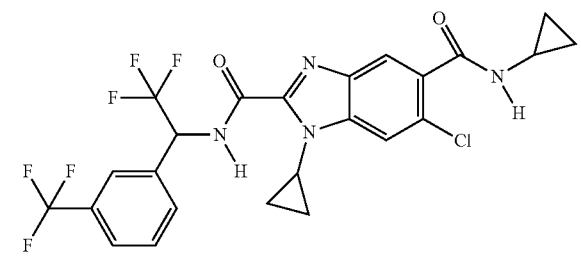 [SMILES: O=C(NC1CC1)c1cc2nc(C(=O)NC(c3cccc(C(F)(F)F)c3)C(F)(F)F)n(C3CC3)c2cc1Cl]

0.063 g (0.20 mmol) of 6-chloro-1-cyclopropyl-5-(cyclopropylcarbamoyl)-1H-benzimidazole-2-carboxylic acid was dissolved under argon in 2 ml of DMF, 0.048 g (0.20 mmol) of 2,2,2-trifluoro-3-trifluoromethylphenethylamine, 0.075 g (0.20 mmol) of HBTU and 0.060 g (0.59 mmol) of 4-methylmorpholine were added, and the reaction mixture was stirred at room temperature over 18 hours. Subsequently, the reaction mixture was added to water and extracted with plenty of methyl acetate, the organic phase was washed with saturated sodium chloride solution and dried over sodium sulphate, and the target product was isolated by means of silica gel chromatography, cyclohexane/ethyl acetate (0% ethyl acetate to 60%).

Yield: 13 mg (12% of theory)

HPLC/MS: logP=3.48; mass (m/z): 545.0 (M+1); $^1$H NMR (D$_6$-DMSO): δ 0.52-0.60 (m, 2H), 0.69-0.74 (m, 2H), 0.74-0.88 (m, 2H), 1.00-1.14 (m, 2H), 2.80-2.89 (m, 1H), 3.50-3.59 (m, 1H), 6.28-6.38 (m, 1H), 7.70-7.88 (m, 4H), 8.06-8.10 (d, 1H), 8.25 (s, 1H), 8.44-8.49 (d, 1H), 10.44 (s, 1H).

Synthesis Example 6

6-chloro-$N^5$-(1-cyanocyclopropyl)-1-(prop-2-yn-1-yl)-$N^2$-{2,2,2-trifluoro-1-[3-(trifluoromethyl)phenyl]ethyl}-1H-indole-2,5-dicarboxamide (Compound No. 57 in Table 1) and 6-chloro-$N^5$-(1-cyanocyclopropyl)-1-cyclopropyl-$N^2$-{2,2,2-trifluoro-1-[3-(trifluoromethyl)phenyl]ethyl}-1H-indole-2,5-dicarboxamide (Compound No. 302 in Table 1)

Stage 1: 6-chloro-2-({2,2,2-trifluoro-1-[3-(trifluoromethyl)phenyl]carbamoyl)-1H-indole-5-carboxylic acid

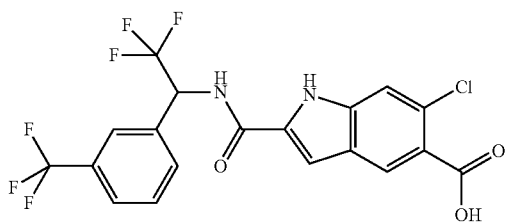 [SMILES: O=C(NC(c1cccc(C(F)(F)F)c1)C(F)(F)F)c1cc2cc(C(=O)O)c(Cl)cc2[nH]1]

Ethyl 6-chloro-2-({2,2,2-trifluoro-1-[3-(trifluoromethyl)phenyl]ethyl}carbamoyl)-1H-indole-5-carboxylate (2.90 g, 5.0 mmol, 85% pure) was dissolved in 5 ml of dichloromethane and a solution of boron tribromide in dichloromethane (27.5 ml, 27.5 mmol) was added dropwise at −10° C. The reaction mixture was stirred at −10° C. for 1 h and then at room temperature for 2 h. Water was added and the precipitated solid was filtered off with suction and dried. 1.85 g (79% of theory) of 6-chloro-2-({2,2,2-trifluoro-1-[3-(trifluoromethyl)phenyl]carbamoyl)-1H-indole-5-carboxylic acid were obtained.

HPLC-MS: logP=3.02; mass (m/z): 465.0 (M+H)$^+$; $^1$H NMR (CD$_3$CN): δ 6.11-6.19 (m, 1H), 7.38 (s, 1H), 7.59 (s, 1H), 7.64-7.69 (m, 1H), 7.76-7.78 (m, 1H), 7.88-7.90 (m, 1H), 7.98 (s, 1H), 8.24 (d, 1H), 8.33 (s, 1H), 10.39 (s, 1H).

The following were obtained analogously:

6-chloro-2-{[1-(3-chloro-4-fluorophenyl)-2,2,2-trifluoroethyl]carbamoyl}-1H-indole-5-carboxylic acid HPLC-MS: logP=2.93; mass (m/z): 448.9 (M+H)$^+$; $^1$H NMR (D$_6$-DMSO): δ 6.20-6.28 (m, 1H), 7.52-7.57 (m, 2H), 7.60 (s, 1H), 7.78-7.82 (m, 1H), 8.07-8.09 (m, 1H), 8.28 (s, 1H), 9.59 (d, 1H), 12.08 (s, 1H), 12.97 (s, 1H).

6-chloro-2-({2,2,2-trifluoro-1-[4-fluoro-3-(trifluoromethyl)phenyl]ethyl}carbamoyl)-1H-indole-5-carboxylic acid HPLC-MS: logP=3.08; mass (m/z): 483.0 (M+H)$^+$; $^1$H NMR (D$_6$-DMSO): δ 6.33-6.42 (m, 1H), 7.52 (s, 1H), 7.59-7.60 (m, 1H), 7.64-7.69 (m, 1H), 8.16-8.19 (m, 1H), 8.26-8.30 (m, 2H), 9.70 (d, 1H), 12.09 (s, 1H).

6-chloro-2-{[1-(3-chlorophenyl)-2,2,2-trifluoroethyl]carbamoyl}-1H-indole-5-carboxylic acid HPLC-MS: logP=2.90; mass (m/z): 431.0 (M+H)$^+$; $^1$H NMR (D$_6$-DMSO): δ 6.15-6.24 (m, 1H), 7.48-7.54 (m, 3H), 7.62 (s, 1H), 7.70-7.72 (m, 1H), 7.90 (s, 1H), 8.28 (s, 1H), 9.63 (d, 1H), 12.08 (s, 1H).

Stage 2: 6-chloro-$N^5$-(1-cyanocyclopropyl)-$N^2$-{2,2,2-trifluoro-1-[3-(trifluoromethyl)phenyl]ethyl}-1H-indole-2,5-dicarboxamide

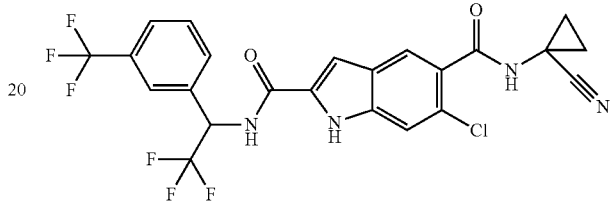

6-Chloro-2-({2,2,2-trifluoro-1-[3-(trifluoromethyl)phenyl]ethyl}carbamoyl)-1H-indole-5-carboxylic acid (2.74 g, 5.07 mmol, 86% pure) was dissolved in N,N-dimethylformamide (14 ml), and 1-aminocyclopropanecarbonitrile hydrochloride (0.78 g, 6.59 mmol), N-[(1H-benzotriazol-1-yloxy)(dimethylamino)methylene]-N-methylmethanaminium hexafluorophosphate (2.12 g, 5.07 mmol) and 4-methylmorpholine (1.54 g, 15.2 mmol) were added. The reaction mixture was stirred at room temperature for 16 h and then ethyl acetate was added. The organic phase was washed with hydrochloric acid (1 mol/l) and the aqueous phase was once again extracted with ethyl acetate. The combined organic phases were washed with saturated sodium chloride solution and the portion which was insoluble in both phases was filtered off. The filtercake is triturated with boiling ethyl acetate (15 ml) and the precipitate is washed with warm ethyl acetate. This leaves 2.01 g (74% of theory) of 6-chloro-$N^5$-(1-cyanocyclopropyl)-$N^2$-{2,2,2-trifluoro-1-[3-(trifluoromethyl)phenyl]ethyl}-1H-indole-2,5-dicarboxamide.

HPLC-MS: logP=3.12; mass (m/z): 529.0 (M+H)$^+$; $^1$H NMR (D$_6$-DMSO): δ 1.25-1.29 (m, 2H), 1.56-1.60 (m, 2H), 6.30-6.38 (m, 1H), 7.50 (s, 1H), 7.57 (s, 1H), 7.70-7.74 (m, 1H), 7.82-7.86 (m, 2H), 8.07-8.09 (m, 1H), 8.21 (s, 1H), 9.30 (s, 1H), 9.73 (d, 1H), 12.07 (s, 1H).

The following were obtained analogously:

6-chloro-$N^2$-[1-(3-chloro-4-fluorophenyl)-2,2,2-trifluoroethyl]-$N^5$-(1-cyanocyclopropyl)-1H-indole-2,5-dicarboxamide HPLC-MS: logP=2.98; mass (m/z): 513.0 (M+H)$^+$; $^1$H NMR (D$_6$-DMSO): δ 1.26-1.28 (m, 2H), 1.56-1.58 (m, 2H), 6.19-6.28 (m, 1H), 7.50-7.56 (m, 3H), 7.77-7.82 (m, 1H), 7.85 (s, 1H), 8.07-8.09 (m, 1H), 9.29 (s, 1H), 9.58 (d, 1H), 12.00 (s, 1H).

6-chloro-$N^2$-[1-(3-chlorophenyl)-2,2,2-trifluoroethyl]-$N^5$-(1-cyanocyclopropyl)-1H-indole-2,5-dicarboxamide HPLC-MS: logP=2.88; mass (m/z): 495.1 (M+H)$^+$; $^1$H NMR (D$_6$-DMSO): δ 1.26-1.28 (m, 2H), 1.56-1.58 (m, 2H), 6.15-6.24 (m, 1H), 7.50-7.57 (m, 3H), 7.69-7.73 (m, 1H), 7.85 (s, 1H), 7.89 (s, 2H), 9.29 (s, 1H), 9.60 (d, 1H), 11.98 (s, 1H).

6-chloro-$N^5$-(1-cyanocyclopropyl)-$N^2$-{2,2,2-trifluoro-1-[4-fluoro-3-(trifluoromethyl)phenyl]ethyl}-1H-indole-2,5-dicarboxamide HPLC-MS: logP=3.10; mass (m/z): 547.1 (M+H)$^+$; $^1$H NMR (D$_6$-DMSO): δ 1.25-1.29 (m, 2H), 1.56-1.60 (m, 2H), 6.33-6.42 (m, 1H), 7.50 (s, 1H), 7.55 (s, 1H), 7.64-7.69 (m, 1H), 7.86 (s, 1H), 8.17 (bs, 1H), 8.28-8.30 (m, 1H), 9.28 (s, 1H), 9.67 (d, 1H), 12.03 (s, 1H).

6-chloro-$N^5$-(1-cyanocyclopropyl)-$N^2$-[2,2,2-trifluoro-1-(3,4,5-trichlorophenyl)ethyl]-1H-indole-2,5-dicarboxamide HPLC-MS: logP=3.71; mass (m/z): 562.9 (M+H)$^+$; $^1$H NMR (D$_6$-DMSO): δ 1.26-1.28 (m, 2H), 1.57-1.59 (m, 2H), 6.30-6.34 (m, 1H), 7.50 (s, 1H), 7.54 (s, 1H), 7.86 (s, 1H), 8.15 (s, 2H), 9.28 (s, 1H), 9.58 (d, 1H), 12.05 (s, 1H).

6-chloro-$N^5$-(1-cyanocyclopropyl)-$N^2$-[1-(3,5-dichlorophenyl)-2,2,2-trifluoroethyl]-1H-indole-2,5-dicarboxamide HPLC-MS: logP=3.38; mass (m/z): 529.0 (M+H)$^+$; $^1$H NMR (D$_6$-DMSO): δ 1.23-1.27 (m, 2H), 1.56-1.59 (m, 2H), 6.25-6.34 (m, 1H), 7.50 (s, 1H), 7.55 (s, 1H), 7.86 (s, 1H), 7.92 (s, 1H), 9.28 (s, 1H), 9.57 (d, 1H), 12.03 (s, 1H).

$N^2$-[1-(3-bromo-4-fluorophenyl)-2,2,2-trifluoroethyl]-6-chloro-$N^5$-(1-cyanocyclopropyl)-1H-indole-2,5-dicarboxamide HPLC-MS: logP=2.98; mass (m/z): 556.9 (M+H)$^+$.

$N^2$-[1-(3-bromophenyl)-2,2,2-trifluoroethyl]-6-chloro-$N^5$-(1-cyanocyclopropyl)-1H-indole-2,5-dicarboxamide HPLC-MS: logP=2.96; mass (m/z): 539.0 (M+H)$^+$; $^1$H NMR (D$_6$-DMSO): δ 1.24-1.27 (m, 2H), 1.56-1.61 (m, 2H), 6.12-6.23 (m, 1H), 7.42-7.46 (m, 1H), 7.50 (s, 1H), 7.56 (s, 1H), 7.64-7.66 (m, 1H), 7.69-7.73 (m, 1H), 7.85 (s, 1H), 8.03 (s, 1H), 9.28 (s, 1H), 9.59 (d, 1H), 12.02 (s, 1H).

Stage 3 (Variant A): 6-chloro-$N^5$-(1-cyanocyclopropyl)-1-(prop-2-yn-1-yl)-$N^2$-{2,2,2-trifluoro-1-[3-(trifluoromethyl)phenyl]ethyl}-1H-indole-2,5-dicarboxamide (Compound No. 57 in Table 1)

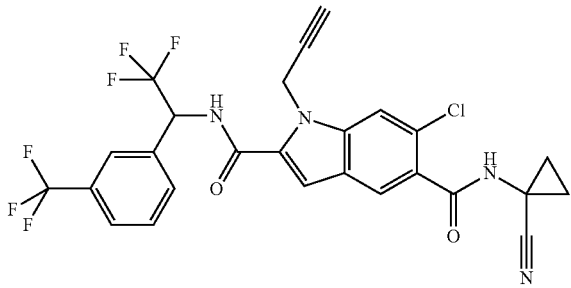 [SMILES: C#CCn1c(C(=O)NC(c2cccc(C(F)(F)F)c2)C(F)(F)F)cc2cc(C(=O)NC3(C#N)CC3)c(Cl)cc21]

6-Chloro-$N^5$-(1-cyanocyclopropyl)-$N^2$-{2,2,2-trifluoro-1-[3-(trifluoromethyl)phenyl]ethyl}-1H-indole-2,5-dicarboxamide (0.14 g, 0.26 mmol) was dissolved under argon at 0° C. in N,N-dimethylformamide (1 ml). Sodium hydride (60%; 0.079 g, 1.97 mmol) was added and the mixture was stirred while cooling with ice for 1.5 h. Subsequently, propargyl bromide (0.04 mg, 0.26 mmol) was added dropwise. The reaction mixture was thawed while stirring within 16 h. Water and ethyl acetate were added and the phases were separated. The organic phase was washed with saturated sodium chloride solution and dried over magnesium sulphate, and the solvent was removed under reduced pressure. The residue is purified by means of preparative HPLC (Kromasil100, C18 250×20; eluent: acetonitrile in water, gradient: 10-100%) to obtain 0.075 g (50% of theory) of 6-chloro-$N^5$-(1-cyanocyclopropyl)-1-(prop-2-yn-1-yl)-$N^2$-{2,2,2-trifluoro-1-[3-(trifluoromethyl)phenyl]ethyl}-1H-indole-2,5-dicarboxamide.

HPLC-MS: logP=3.49; mass (m/z): 567.1 (M+H)$^+$; $^1$H NMR (D$_6$-DMSO): δ 1.26-1.33 (m, 2H), 1.57-1.61 (m, 2H), 3.21 (t, 1H), 5.45 (s, 2H), 6.27-6.35 (m, 1H), 7.50 (s, 1H), 7.70-7.74 (m, 1H), 7.82-7.84 (m, 1H), 7.88-7.89 (m, 2H), 8.05-8.07 (m, 1H), 8.21 (s, 1H), 9.33 (s, 1H), 9.88 (d, 1H).

Stage 3 (Variant B): 6-chloro-$N^5$-(1-cyanocyclopropyl)-1-cyclopropyl-$N^2$-{2,2,2-trifluoro-1-[3-(trifluoromethyl)phenyl]ethyl}-1H-indole-2,5-dicarboxamide (Compound No. 302 in Table 1)

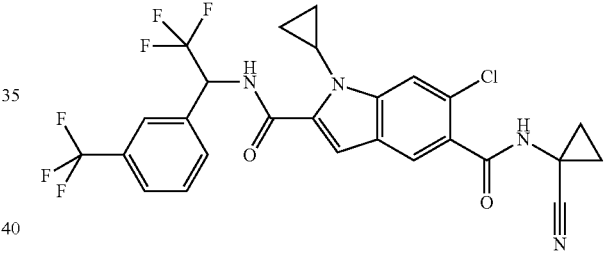

6-Chloro-$N^5$-(1-cyanocyclopropyl)-$N^2$-{2,2,2-trifluoro-1-[3-(trifluoromethyl)phenyl]ethyl}-1H-indole-2,5-dicarboxamide (0.20 g, 0.34 mmol), cyclopropylboronic acid (0.063 g, 0.69 mmol) and sodium carbonate (0.074 g, 0.69 mmol) were initially charged as a suspension in N,N-dimethylformamide (1 ml), and a hot solution of copper(II) acetate (0.064 g, 0.34 mmol) and 2,2'-bipyridyl (0.054 g, 0.34 mmol) was added. The reaction mixture was stirred at 70° C. over 16 h. After cooling, hydrochloric acid (10 ml, 1 mol/l) was added and the organic phase was removed. The aqueous phase was extracted with ethyl acetate (3×) and the combined organic phases were washed with saturated sodium chloride solution and dried over magnesium sulphate, and the solvent was removed under reduced pressure. The residue is purified by means of preparative HPLC (Kromasil100, C18 250×20; eluent: acetonitrile in water, gradient: 10-100%) to obtain 0.013 g (6% of theory) of 6-chloro-$N^5$-(1-cyanocyclopropyl)-1-cyclopropyl-$N^2$-{2,2,2-trifluoro-1-[3-(trifluoromethyl)phenyl]ethyl}-1H-indole-2,5-dicarboxamide.

HPLC-MS: logP=3.59; mass (m/z): 569.1 (M+H)$^+$; $^1$H NMR (D$_6$-DMSO): δ 0.58-0.72 (m, 2H), 0.99-1.04 (m, 2H), 1.25-1.29 (m, 2H), 1.56-1.60 (m, 2H), 3.47-0.53 (m, 1H), 6.24-6.32 (m, 1H), 7.02 (s, 1H), 7.68 (s, 1H), 7.71-7.75 (m, 1H), 7.80-7.84 (m, 2H), 8.04-8.06 (m, 1H), 8.18 (s, 1H), 9.29 (s, 1H), 9.91 (d, 1H).

Synthesis Example 7

3,6-dichloro-$N^5$-(1-cyanocyclopropyl)-1-ethyl-$N^2$-{2,2,2-trifluoro-1-[3-(trifluoromethyl)phenyl]ethyl}-1H-indole-2,5-dicarboxamide (Compound No. 271 in Table 1)

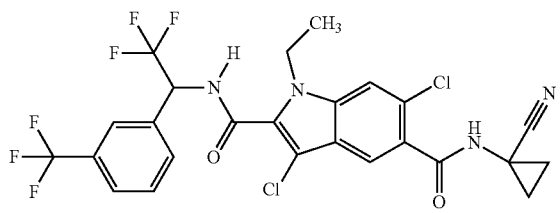 [SMILES: CCn1c(C(=O)NC(c2cccc(C(F)(F)F)c2)C(F)(F)F)c(Cl)c2cc(C(=O)NC3(C#N)CC3)c(Cl)cc21]

6-Chloro-$N^5$-(1-cyanocyclopropyl)-1-ethyl-$N^2$-{2,2,2-trifluoro-1-[3-(trifluoromethyl)phenyl]ethyl}-1H-indole-2,5-dicarboxamide (0.100 g, 0.18 mmol) is partly dissolved in tetrahydrofuran (2 ml), N-chlorosuccinimide (0.024 g, 0.18 mmol) is added and the mixture is stirred at room temperature for 48 h. The reaction mixture is then concentrated under reduced pressure and the residue is chromatographed with cyclohexane/ethyl acetate (1/1) to give 0.104 g (98% of theory) of 3,6-dichloro-N-5-(1-cyanocyclopropyl)-1-ethyl-$N^2$-{2,2,2-trifluoro-1-[3-(trifluoromethyl)phenyl]ethyl}-1H-indole-2,5-dicarboxamide.

HPLC-MS: logP=3.95; mass (m/z): 591.0 (M+H)$^+$; $^1$H NMR (D$_6$-DMSO): δ 1.16 (t, 3H), 1.30-1.34 (m, 2H), 1.56-1.59 (m, 2H), 4.29 (q, 2H), 6.28-6.36 (m, 1H), 7.72-7.75 (m, 2H), 7.83-7.85 (m, 1H), 7.97 (s, 1H), 8.03-8.05 (m, 1H), 8.18 (s, 1H), 9.36 (s, 1H), 10.30 (d, 1H).

Synthesis Example 8

6-chloro-3-cyano-N5-(1-cyanocyclopropyl)-1-ethyl-N2-{2,2,2-trifluoro-1-[3-(trifluoromethyl)phenyl]ethyl}-1H-indole-2,5-dicarboxamide (Compound No. 279 in Table 1)

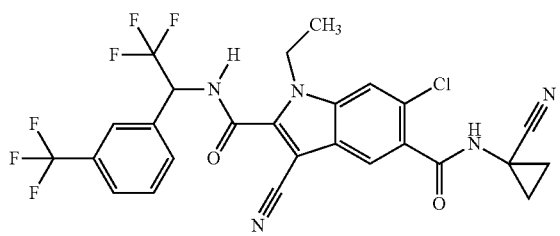 [SMILES: CCn1c(C(=O)NC(c2cccc(C(F)(F)F)c2)C(F)(F)F)c(C#N)c2cc(C(=O)NC3(C#N)CC3)c(Cl)cc21]

6-Chloro-$N^5$-(1-cyanocyclopropyl)-1-ethyl-$N^2$-{2,2,2-trifluoro-1-[3-(trifluoromethyl)phenyl]ethyl}-1H-indole-2,5-dicarboxamide (0.100 g, 0.18 mmol) is initially charged in dry acetonitrile (2 ml) under argon and cooled to 0° C., and chlorosulphonyl isocyanate (0.028 g, 0.19 mmol) is added dropwise. After 30 min, N,N-dimethylformamide (0.015 g, 0.19 mmol) is added and the mixture is stirred at 0° C. for a further 30 min and at room temperature overnight. Then the mixture is cooled again to 0° C. and chlorosulphonyl isocyanate (0.028 g, 0.19 mmol) is added dropwise, N,N-dimethylformamide (0.015 g, 0.19 mmol) is added after 30 min, and the mixture is stirred at room temperature for a further 48 h. The reaction mixture is then concentrated under reduced pressure, and the residue is admixed with sodium hydrogencarbonate and extracted with dichloromethane. The organic phase is dried with sodium sulphate, filtered and concentrated under reduced pressure. The residue is purified by means of preparative HPLC (Kromasil100, C18 250×20; eluent: acetonitrile in water, gradient: 10-100%) to obtain 0.006 g (5% of theory) of 6-chloro-3-cyano-N5-(1-cyanocyclopropyl)-1-ethyl-N2-{2,2,2-trifluoro-1-[3-(trifluoromethyl)phenyl]ethyl}-1H-indole-2,5-dicarboxamide.

HPLC-MS: logP=3.45; mass (m/z): 582.1 (M+H)$^+$; $^1$H NMR (D$_6$-DMSO): δ 1.22 (t, 3H), 1.33-1.36 (m, 2H), 1.56-1.60 (m, 2H), 4.38 (q, 2H), 6.31-6.40 (m, 1H), 7.71-7.75 (m, 1H), 7.83-7.85 (m, 1H), 7.92 (s, 1H), 8.03-8.05 (m, 1H), 8.13 (s, 1H), 8.20 (s, 1H), 9.40 (s, 1H), 10.64 (d, 1H).

Synthesis Example 9

$N^5$-(1-carbamothioylcyclopropyl)-6-chloro-1-ethyl-$N^2$-{2,2,2-trifluoro-1-[3-(trifluoromethyl)phenyl]ethyl}-1H-indole-2,5-dicarboxamide (Compound No. 273 in Table 1)

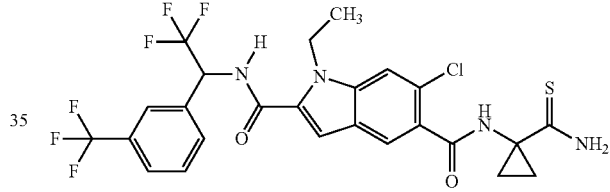

6-Chloro-$N^5$-(1-cyanocyclopropyl)-1-ethyl-$N^2$-{2,2,2-trifluoro-1-[3-(trifluoromethyl)phenyl]ethyl}-1H-indole-2,5-dicarboxamide (0.200 g, 0.35 mmol) is initially charged in tetrahydrofuran (5.5 ml) under argon, 2,4-bis(4-methoxyphenyl)-1,3,2,4-dithiadiphosphetane 2,4-disulphide (0.305 g, 0.75 mmol) is added and the mixture is stirred at room temperature for 48 h. Then 2,4-bis(4-methoxyphenyl)-1,3,2,4-dithiadiphosphetane 2,4-disulphide (0.150 g, 0.38 mmol) is added again and the mixture is stirred at room temperature for a further 12 h. The reaction mixture is then diluted with ethyl acetate and washed with a sodium hydrogencarbonate solution. The organic phase is dried with magnesium sulphate, filtered and concentrated under reduced pressure. The residue is purified by means of preparative HPLC (Kromasil100, C18 250×20; eluent: acetonitrile in water, gradient: 10-100%) to obtain 0.025 g (11% of theory) of $N^5$-(1-carbamothioylcyclopropyl)-6-chloro-1-ethyl-$N^2$-{2,2,2-trifluoro-1-[3-(trifluoromethyl)phenyl]ethyl}-1H-indole-2,5-dicarboxamide.

HPLC-MS: logP=3.56; mass (m/z): 591.1 (M+H)$^+$; $^1$H NMR (D$_6$-DMSO): δ 1.20 (t, 3H), 1.24-1.27 (m, 2H), 1.83-1.86 (m, 2H), 4.52 (q, 2H), 6.26-6.35 (m, 1H), 7.39 (s, 1H), 7.70-7.74 (m, 1H), 7.80-7.84 (m, 2H), 8.05-8.07 (m, 1H), 8.12 (s, 1H), 8.21 (s, 1H), 8.78 (s, 1H), 8.87 (s, 1H), 9.77-9.80 (m, 2H).

Synthesis of Amines of the Formula (III)

2,2,2-trifluoro-1-[4-fluoro-3-(trifluoromethyl)phenyl]ethanamine

Stage 1: 2,2,2-trifluoro-1-[4-fluoro-3-(trifluoromethyl)phenyl]ethanone

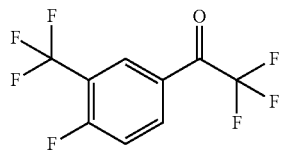 [SMILES: O=C(c1ccc(F)c(C(F)(F)F)c1)C(F)(F)F]

n-Butyllithium (2.5 M in hexane, 46 ml) was initially charged at −90° C. in tetrahydrofuran (250 ml). At −95° C., 4-bromo-1-fluoro-2-(trifluoromethyl)benzene (25 g, 103 mmol) was added dropwise. The reaction mixture was stirred at −78° C. for 40 min, then cooled to −100° C., and ethyl trifluoroacetate (16.1 g, 113 mmol) was added dropwise, in the course of which the temperature was kept between −90° C. and −80° C. The reaction mixture was gradually warmed up to −20° C. and then cooled to −80° C. 10% hydrochloric acid and saturated sodium chloride solution were added dropwise. The reaction mixture was thawed within 16 h and then extracted with diethyl ether. The organic phase was washed with water and saturated sodium chloride solution and dried over sodium sulphate, and the solvent was removed under reduced pressure. The residue was taken up in toluene and distilled first at standard pressure, then under reduced pressure. 22.5 g (86% of theory) of 2,2,2-trifluoro-1-[4-fluoro-3-(trifluoromethyl)phenyl]ethanone were obtained.

b.p.: 99-101° C. (100 Torr)

$^1$H (CDCl$_3$): δ 7.42 (m, 1H); 8.20-8.37 (m, 2H).

Stage 2: 2,2,2-trifluoro-1-[4-fluoro-3-(trifluoromethyl)phenyl]ethanamine

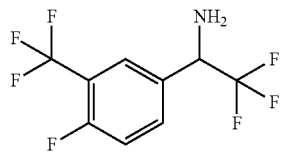

2,2,2-Trifluoro-1-[4-fluoro-3-(trifluoromethyl)phenyl]ethanone (21.0 g, 81 mmol) was initially charged in diethyl ether (200 ml), and benzylamine (9.1 g, 85 mmol) and triethylamine (16.4 g, 162 mmol) were added at 0° C. Subsequently, a solution of titanium tetrachloride (7.8 g, 41 mmol) in hexane (100 ml) was added dropwise. The reaction mixture was stirred at room temperature for 3 h. The resulting suspension was filtered, and the solids were washed with diethyl ether and discarded. The solvent of the filtrate was removed under reduced pressure and the residue was taken up in triethylamine (100 ml). The solution was left to stand at room temperature for 16 h. The triethylamine was removed under reduced pressure, and the residue was taken up in dichloromethane and acidified with 10% hydrochloric acid. The mixture was stirred at room temperature for 16 h and then the phases were separated. The organic phase was washed with water and the combined aqueous phases were adjusted to pH 12 with 33% sodium hydroxide solution while cooling with ice. The aqueous phase was extracted three times with dichloromethane and the combined organic phases were dried over magnesium sulphate. The solvent was removed under reduced pressure. 6.5 g (31% of theory) of 2,2,2-trifluoro-1-[4-fluoro-3-(trifluoromethyl)phenyl]ethanamine were obtained.

$^1$H (CDCl$_3$): δ 1.8 (br.s, 2H); 4.46 (q, J=7.0 Hz, 1H); 7.22 (m, 1H); 7.64-7.72 (m, 2H).

The following were obtained analogously:

1-(3-bromo-4-fluorophenyl)-2,2,2-trifluoroethanamine $^1$H (CDCl$_3$): δ 1.76 (br.s, 2H); 4.38 (q, 1H); 7.14-7.26 (m, 1H); 7.38 (m, 1H); 7.68 (m, 1H);

1-(3-chlorophenyl)-2,2,2-trifluoroethanamine (CDCl$_3$): δ 1.75 (br.s, 2H); 4.40 (q, 1H); 7.31-7.38 (m, 3H); 7.45 (s, 1H).

1-(3,5-dichlorophenyl)-2,2,2-trifluoroethanamine (CDCl$_3$): δ 1.77 (br.s, 2H); 4.36 (q, 1H); 7.35-7.39 (m, 3H).

1-(3-chloro-5-fluorophenyl)-2,2,2-trifluoroethanamine $^1$H (CDCl$_3$): δ 1.77 (br.s, 2H); 4.38 (q, 1H); 7.10 (m, 2H); 7.26 (s, 1H).

1-(3,4-dichlorophenyl)-2,2,2-trifluoroethanamine $^1$H (CDCl$_3$): δ 1.76 (br.s, 2H); 4.38 (q, 1H); 7.14-7.26 (m, 1H); 7.38 (m, 1H); 7.68 (m, 1H);

1-(3,5-dichloro-4-fluorophenyl)-2,2,2-trifluoroethanamine $^1$H (CDCl$_3$): δ 1.75 (br.s, 2H); 4.36 (q, 1H); 7.50 (s, 2H).

1-(3,5-dichloro-2,4-difluorophenyl)-2,2,2-trifluoroethanamine $^1$H (CDCl$_3$): δ 1.84 (br.s, 2H); 4.76 (q, 1H); 7.53 (m, 1H).

1-(3,4-difluorophenyl)-2,2,2-trifluoroethanamine $^1$H (CDCl$_3$): δ 1.61 (br.s, 2H); 4.40 (q, 1H); 7.18-7.34 (m, 3H).

1-(3,4,5-trichlorophenyl)-2,2,2-trifluoroethanamine $^1$H (CDCl$_3$): δ 1.76 (br.s, 2H); 4.36 (q, 1H); 7.50 (s, 2H).

1-(2,2-difluoro-1,3-benzodioxol-5-yl)-2,2,2-trifluoroethanamine $^1$H (CDCl$_3$): δ 1.75 (br.s, 2H); 4.43 (q, 1H); 7.07-7.26 (m, 3H).

Synthesis of Amines of the Formula (A-9)

methyl 4-amino-2-ethylbenzoate and methyl 4-amino-2-isopropylbenzoate

Stage 1: methyl 4-nitro-2-vinylbenzoate

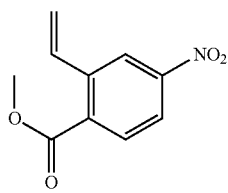

12.0 g (46.1 mmol) of methyl 2-bromo-4-nitrobenzoate were initially charged in 240 ml of 1,2-dimethoxyethane, 2.66 g (2.30 mmol) of tetrakis(triphenylphosphine)palladium were added, and the mixture was stirred for 20 min. Subsequently, a solution of 6.38 g (46.1 mmol) of potassium carbonate in 80 ml of water and 11.11 g (46.1 mmol) of 2,4,6-trivinylcyclotriboroxane were added. The reaction mixture was stirred at reflux temperature for 20 hours. After cooling, the mixture was added to water and extracted with ethyl acetate, the organic phases were dried with magnesium sulphate, and the solvent was distilled off under reduced pressure. The residue was chromatographed using silica gel with cyclohexane/ethyl acetate (ratio 6:1) as the eluent. 4.5 g (46% of theory) of methyl 4-nitro-2-vinylbenzoate were obtained.

HPLC/MS: logP=2.74; mass (m/z): 208.0 (M+1); $^1$H NMR (d$_6$-DMSO): δ 5.75 (d, 1H), 6.01 (d, 1H), 7.2-7.3 (m, 1H), 8.00 (d, 1H), 8.20 (d, 1H), 8.42 (s, 1H).

The following was obtained in an analogous manner:

methyl 4-nitro-2-(prop-1-en-2-yl)benzoate from methyl 2-bromo-4-nitrobenzoate and 4,4,5,5-tetramethyl-2-(prop-1-en-2-yl)-1,3,2-dioxaborolane HPLC/MS: logP=2.99; mass (m/z): 222.1 (M+1); $^1$H NMR (d$_6$-DMSO): δ 2.07 (s, 3H), 3.83 (s, 3H), 4.92 (s, 1H), 5.23 (m, 2H), 7.91 (d, 1H), 8.10 (s, 1H), 8.23 (d, 1H).

Stage 2: methyl 4-amino-2-ethylbenzoate

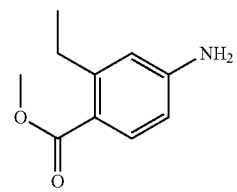

15.0 g (72.3 mmol) of methyl 4-nitro-2-vinylbenzoate in 150 ml of methanol were hydrogenated in an autoclave at 5 bar for 15 hours. The solution was filtered through kieselguhr, the solvent was distilled off under reduced pressure, and the residue was chromatographed using silica gel with cyclohexane/ethyl acetate (ratio 3:1) as the eluent. 2.4 g (24% of theory) of methyl 4-amino-2-ethylbenzoate were obtained.

HPLC/MS: logP=1.84; mass (m/z): 180.2 (M+1); $^1$H NMR (CD$_3$CN): δ 1.14 (t, 3H), 2.88 (q, 2H), 3.75 (s, 3H), 4.60 (br.s, 2H), 6.45-6.50 (m, 2H), 7.68 (d, 1H).

The following was obtained in an analogous manner:

methyl 4-amino-2-isopropylbenzoate by hydrogenation of methyl 4-nitro-2-(prop-1-en-2-yl)benzoate HPLC/MS: logP=2.14; mass (m/z): 194.2 (M+1); $^1$H NMR (CD$_3$CN): δ 1.18 (d, 6H), 3.76 (s, 3H), 3.85-3.91 (m, 1H), 4.59 (br.s, 2H), 6.44 (d, 1H), 6.67 (s, 1H), 7.61 (d, 1H).

The inventive compounds of the formula (I) described in Table 1 below are likewise preferred inventive compounds which are obtained according to or analogously to the Synthesis Examples described above.

TABLE 1

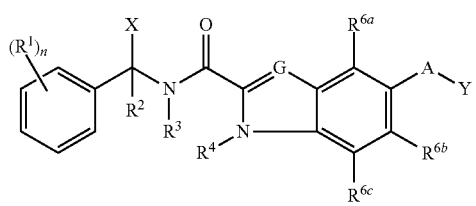

| No. | (R$^1$)$_n$ | X | R$^2$ | R$^3$ | R$^4$ | G | R$^{6a}$ | R$^{6b}$ | R$^{6c}$ | A | Y | (M+H)$^{+\ a)}$ | log p $^{a)}$ |
|---|---|---|---|---|---|---|---|---|---|---|---|---|---|
| 1 | 3-CF$_3$ | CF$_3$ | H | H | CH$_3$ | N | H | Cl | H | CONH | cyclopropyl | 519.1 | 3.4 |
| 2 | 3-Cl | CF$_3$ | H | H | Et | CH | H | Cl | H | CONH | cyclopropyl | 498.1 | 3.65 |
| 3 | 3-CF$_3$; 4-F | CF$_3$ | H | H | Et | CH | H | Cl | H | CONH | cyclopropyl | 550.1 | 3.93 |
| 4 (Synthesis Ex. 4) | 3-CF$_3$ | CF$_3$ | H | H | Et | N | H | Cl | H | CONH | cyclopropyl | 533.2 | 3.67 |
| 5 | 3-Cl | CF$_3$ | H | H | prop-2-yn-1-yl | CH | H | Cl | H | CONH | cyclopropyl | 508.0 | 3.45 |
| 6 | 3-CF$_3$; 4-F | CF$_3$ | H | H | prop-2-yn-1-yl | CH | H | Cl | H | CONH | cyclopropyl | 560.1 | 3.59 |
| 7 (Synthesis Ex. 2) | 3-CF$_3$ | CF$_3$ | H | H | Et | CH | H | Cl | H | CONH | 1-cyanocyclopropyl | 557.2 | 3.78 |

TABLE 1-continued

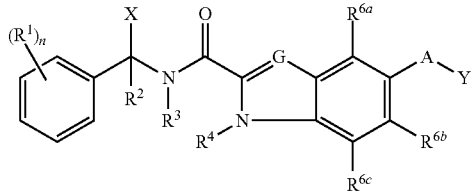

(I)

| No. | $(R^1)_n$ | X | $R^2$ | $R^3$ | $R^4$ | G | $R^{6a}$ | $R^{6b}$ | $R^{6c}$ | A | Y | $(M+H)^{+a)}$ | log $p^{a)}$ |
|---|---|---|---|---|---|---|---|---|---|---|---|---|---|
| 8 | 3-CF$_3$ | CF$_3$ | H | H | Et | CH | H | Cl | H | CONH | 1-fluoropropan-2-yl | 552.1 | 3.88 |
| 9 | 3-CF$_3$ | CF$_3$ | H | H | Et | CH | H | Cl | H | CONH | 1-cyanoethyl | 545.1 | 3.72 |
| 10 | 3-CF$_3$ | CF$_3$ | H | H | Et | CH | H | Cl | H | CONH | 2,2-difluoropropan-1-yl | 570.1 | 4.06 |
| 11 | 3-CF$_3$ | CF$_3$ | H | H | Et | CH | H | Cl | H | CONH | 1,3-difluoropropan-2-yl | 570.1 | 3.86 |
| 12 | 3-Br; 4-F | CF$_3$ | H | H | Et | CH | H | Cl | H | CONH | cyclopropyl | 560.1 | 3.82 |
| 13 | 3-Cl; 5-Cl | CF$_3$ | H | H | Et | CH | H | Cl | H | CONH | cyclopropyl | 532.0 | 4.27 |
| 14 | 3-Br; 4-F | CF$_3$ | H | H | prop-2-yn-1-yl | CH | H | Cl | H | CONH | cyclopropyl | 570.0 | 3.52 |
| 15 | 3-CF$_3$ | CF$_3$ | H | H | Et | CH | H | Cl | H | CONH | 2-cyanopropan-2-yl | 559.1 | 3.89 |
| 16 | 3-CF$_3$; 4-F | CF$_3$ | H | H | Et | CH | H | Cl | H | CONH | 1-cyanocyclopropyl | 575.1 | 3.88 |
| 17 | 3-CF$_3$; 4-F | CF$_3$ | H | H | Et | CH | H | Cl | H | CONH | Et | 538.1 | 3.91 |
| 18 | 3-Cl; 4-F | CF$_3$ | H | H | Et | CH | H | Cl | H | CONH | cyclopropyl | 516.1 | 3.82 |
| 19 (Synthesis Ex. 1) | 3-CF$_3$; 4-F | CF$_3$ | H | H | Et | CH | H | Cl | H | CONH | 2,2-difluoroethyl | 574.0 | 4.03 |
| 20 | 3-Cl; 4-F | CF$_3$ | H | H | Et | CH | H | Cl | H | CONH | 1-cyanocyclopropyl | 541.1 | 3.79 |
| 21 | 3-CF$_3$ | CF$_3$ | H | H | Et | CH | H | Cl | H | CONH | cyanomethyl | 531.0 | 3.64 |
| 22 | 3-CF$_3$ | CF$_3$ | H | H | Et | CH | H | Cl | H | CONH | 1-methylcyclopropyl | 546.2 | 4.16 |
| 23 | 3-CF$_3$ | CF$_3$ | H | H | Et | CH | H | CF$_3$ | H | CH$_2$NHCO | cyclopropyl | 580.3 | 4.37 |
| 24 | 3-CF$_3$ | CF$_3$ | H | H | Et | CH | H | Cl | H | CH$_2$NHCO | cyclopropyl | 546.2 | 4.19 |
| 25 | 3-CF$_3$ | CF$_3$ | H | H | Et | CH | H | Cl | H | CH$_2$NHCO | Et | 534.1 | 4.06 |
| 26 (Synthesis Ex. 3) | 3-CF$_3$ | CF$_3$ | H | H | Et | CH | H | Cl | H | CH$_2$NHCO | CH$_3$ | 520.2 | 3.77 |
| 27 | 3-CF$_3$; 4-F | CF$_3$ | H | H | Et | CH | H | H | H | CONH | cyclopropyl | 550.2 | 3.74 |
| 28 | 3-CF$_3$ | CF$_3$ | H | H | Et | CH | H | Cl | H | CONH | 1-(methoxycarbonyl)cyclopropyl | 590.2 | 3.86 |
| 29 | 3-CF$_3$ | CF$_3$ | H | H | Et | CH | H | Cl | H | CONH | 1,1'-bi(cyclopropyl)-1-yl | 572.2 | 4.45 |
| 30 | 3-CF$_3$ | CF$_3$ | H | H | Et | CH | H | Cl | H | CONH | 1-ethylcyclopropyl | 560.1 | 4.45 |
| 31 | 3-CF$_3$ | CF$_3$ | H | H | Et | CH | H | Cl | H | CONH | 1-ethoxycyclopropyl | 576.2 | 4.19 |
| 32 | 3-CF$_3$ | CF$_3$ | H | H | Et | CH | H | Cl | H | CONH | 1-ethynylcyclopropyl | 556.4 | 3.86 |
| 33 | 3-CF$_3$ | CF$_3$ | H | H | Et | CH | H | Cl | H | CONH | 1-ethynylcyclobutyl | 570.4 | 4.20 |
| 34 | 3-CF$_3$ | CF$_3$ | H | H | Et | CH | H | Cl | H | CONH | 1-(ethoxycarbonyl)cyclopropyl | 604.4 | 3.99 |
| 35 | 3-CF$_3$ | CF$_3$ | H | H | Et | CH | H | Cl | H | CONH | 3-cyanopropan-1-yl | | |
| 36 | 3-CF$_3$ | CF$_3$ | H | H | Et | CH | H | Cl | H | CONH | 1-cyanocyclobutyl | 571.2 | 4.09 |
| 37 | 3-Cl; 4-F | CF$_3$ | H | H | Et | N | H | Cl | H | CONH | cyclopropyl | 517.1 | 3.59 |
| 38 | 3-CF$_3$; 4-F | CF$_3$ | H | H | Et | N | H | Cl | H | CONH | cyclopropyl | 551.1 | 3.71 |
| 39 | 3-Cl | CF$_3$ | H | H | Et | CH | H | Cl | H | CONH | 1-cyanocyclopropyl | 523.1 | 3.67 |
| 40 | 3-Br | CF$_3$ | H | H | Et | CH | H | Cl | H | CONH | cyclopropyl | 542.0 | 3.71 |
| 41 | 3-Br | CF$_3$ | H | H | Et | CH | H | Cl | H | CONH | 1-cyanocyclopropyl | 567.0 | 3.75 |
| 42 | 3-Br; 4-F | CF$_3$ | H | H | Et | CH | H | Cl | H | CONH | 1-cyanocyclopropyl | 585.0 | 3.76 |
| 43 | 3-Cl; 5-Cl | CF$_3$ | H | H | Et | CH | H | Cl | H | CONH | 1-cyanocyclopropyl | 557.0 | 4.14 |
| 44 | 3-CF$_3$ | CF$_3$ | H | H | Me | CH | H | Cl | H | CONH | 1-cyanocyclopropyl | 543.1 | 3.55 |
| 45 | 3-Cl | CF$_3$ | H | H | Me | CH | H | Cl | H | CONH | cyclopropyl | 484.1 | 3.33 |
| 46 | 3-Cl | CF$_3$ | H | H | Me | CH | H | Cl | H | CONH | 1-cyanocyclopropyl | 509.0 | 3.31 |
| 47 | 3-Br | CF$_3$ | H | H | Me | CH | H | Cl | H | CONH | cyclopropyl | 528.0 | 3.42 |
| 48 | 3-Br | CF$_3$ | H | H | Me | CH | H | Cl | H | CONH | 1-cyanocyclopropyl | 553.0 | 3.39 |
| 49 | 3-CF$_3$; 4-F | CF$_3$ | H | H | Me | CH | H | Cl | H | CONH | cyclopropyl | 536.1 | 3.70 |
| 50 | 3-CF$_3$; 4-F | CF$_3$ | H | H | Me | CH | H | Cl | H | CONH | 1-cyanocyclopropyl | 561.1 | 3.52 |
| 51 | 3-Br; 4-F | CF$_3$ | H | H | Me | CH | H | Cl | H | CONH | cyclopropyl | 546.0 | 3.61 |
| 52 | 3-Br; 4-F | CF$_3$ | H | H | Me | CH | H | Cl | H | CONH | 1-cyanocyclopropyl | 570.9 | 3.44 |
| 53 | 3-Cl; 4-F | CF$_3$ | H | H | Me | CH | H | Cl | H | CONH | cyclopropyl | 502.1 | 3.42 |
| 54 | 3-Cl; 4-F | CF$_3$ | H | H | Me | CH | H | Cl | H | CONH | 1-cyanocyclopropyl | 527.0 | 3.52 |
| 55 | 3-Cl; 5-Cl | CF$_3$ | H | H | Me | CH | H | Cl | H | CONH | cyclopropyl | | |
| 56 | 3-Cl; 5-Cl | CF$_3$ | H | H | Me | CH | H | Cl | H | CONH | 1-cyanocyclopropyl | | |
| 57 | 3-CF$_3$ | CF$_3$ | H | H | prop-2- | CH | H | Cl | H | CONH | 1-cyanocyclopropyl | 567.1 | 3.49 |

TABLE 1-continued

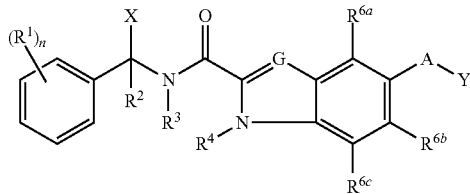

| No. | $(R^1)_n$ | X | $R^2$ | $R^3$ | $R^4$ | G | $R^{6a}$ | $R^{6b}$ | $R^{6c}$ | A | Y | $(M+H)^{+a)}$ | log $p^{a)}$ |
|---|---|---|---|---|---|---|---|---|---|---|---|---|---|
| (Synthesis Ex. 6) | | | | | yn-1-yl | | | | | | | | |
| 58 | 3-Cl | $CF_3$ | H | H | prop-2-yn-1-yl | CH | H | Cl | H | CONH | 1-cyanocyclopropyl | 533.0 | 3.42 |
| 59 | 3-Br | $CF_3$ | H | H | prop-2-yn-1-yl | CH | H | Cl | H | CONH | cyclopropyl | 552.0 | 3.44 |
| 60 | 3-Br | $CF_3$ | H | H | prop-2-yn-1-yl | CH | H | Cl | H | CONH | 1-cyanocyclopropyl | 577.0 | 3.48 |
| 61 | 3-$CF_3$; 4-F | $CF_3$ | H | H | prop-2-yn-1-yl | CH | H | Cl | H | CONH | 1-cyanocyclopropyl | 585.1 | 3.65 |
| 62 | 3-Br; 4-F | $CF_3$ | H | H | prop-2-yn-1-yl | CH | H | Cl | H | CONH | 1-cyanocyclopropyl | 595.0 | 3.57 |
| 63 | 3-Cl; 4-F | $CF_3$ | H | H | prop-2-yn-1-yl | CH | H | Cl | H | CONH | cyclopropyl | 526.1 | 3.57 |
| 64 | 3-Cl; 4-F | $CF_3$ | H | H | prop-2-yn-1-yl | CH | H | Cl | H | CONH | 1-cyanocyclopropyl | 551.1 | 3.41 |
| 65 | 3-Cl; 5-Cl | $CF_3$ | H | H | prop-2-yn-1-yl | CH | H | Cl | H | CONH | cyclopropyl | 542.0 | 3.90 |
| 66 | 3-Cl; 5-Cl | $CF_3$ | H | H | prop-2-yn-1-yl | CH | H | Cl | H | CONH | 1-cyanocyclopropyl | 567.0 | 3.87 |
| 67 | 3-$CF_3$ | $CF_3$ | H | H | Et | N | H | Cl | H | CONH | 1-cyanocyclopropyl | | |
| 68 | 3-Cl | $CF_3$ | H | H | Et | N | H | Cl | H | CONH | cyclopropyl | | |
| 69 | 3-Cl | $CF_3$ | H | H | Et | N | H | Cl | H | CONH | 1-cyanocyclopropyl | | |
| 70 | 3-Br | $CF_3$ | H | H | Et | N | H | Cl | H | CONH | cyclopropyl | | |
| 71 | 3-Br | $CF_3$ | H | H | Et | N | H | Cl | H | CONH | 1-cyanocyclopropyl | | |
| 72 | 3-$CF_3$; 4-F | $CF_3$ | H | H | Et | N | H | Cl | H | CONH | 1-cyanocyclopropyl | | |
| 73 | 3-Br; 4-F | $CF_3$ | H | H | Et | N | H | Cl | H | CONH | cyclopropyl | | |
| 74 | 3-Br; 4-F | $CF_3$ | H | H | Et | N | H | Cl | H | CONH | 1-cyanocyclopropyl | | |
| 75 | 3-Cl; 4-F | $CF_3$ | H | H | Et | N | H | Cl | H | CONH | 1-cyanocyclopropyl | | |
| 76 | 3-Cl; 5-Cl | $CF_3$ | H | H | Et | N | H | Cl | H | CONH | cyclopropyl | | |
| 77 | 3-Cl; 5-Cl | $CF_3$ | H | H | Et | N | H | Cl | H | CONH | 1-cyanocyclopropyl | | |
| 78 | 3-$CF_3$ | $CF_3$ | H | H | Me | N | H | Cl | H | CONH | 1-cyanocyclopropyl | | |
| 79 | 3-Cl | $CF_3$ | H | H | Me | N | H | Cl | H | CONH | cyclopropyl | | |
| 80 | 3-Cl | $CF_3$ | H | H | Me | N | H | Cl | H | CONH | 1-cyanocyclopropyl | | |
| 81 | 3-Br | $CF_3$ | H | H | Me | N | H | Cl | H | CONH | cyclopropyl | | |
| 82 | 3-Br | $CF_3$ | H | H | Me | N | H | Cl | H | CONH | 1-cyanocyclopropyl | | |
| 83 | 3-$CF_3$; 4-F | $CF_3$ | H | H | Me | N | H | Cl | H | CONH | cyclopropyl | | |
| 84 | 3-$CF_3$; 4-F | $CF_3$ | H | H | Me | N | H | Cl | H | CONH | 1-cyanocyclopropyl | | |
| 85 | 3-Br; 4-F | $CF_3$ | H | H | Me | N | H | Cl | H | CONH | cyclopropyl | | |
| 86 | 3-Br; 4-F | $CF_3$ | H | H | Me | N | H | Cl | H | CONH | 1-cyanocyclopropyl | | |
| 87 | 3-Cl; 4-F | $CF_3$ | H | H | Me | N | H | Cl | H | CONH | cyclopropyl | | |
| 88 | 3-Cl; 4-F | $CF_3$ | H | H | Me | N | H | Cl | H | CONH | 1-cyanocyclopropyl | | |
| 89 | 3-Cl; 5-Cl | $CF_3$ | H | H | Me | N | H | Cl | H | CONH | cyclopropyl | | |
| 90 | 3-Cl; 5-Cl | $CF_3$ | H | H | Me | N | H | Cl | H | CONH | 1-cyanocyclopropyl | | |
| 91 | 3-$CF_3$ | $CF_3$ | H | H | prop-2-yn-1-yl | N | H | Cl | H | CONH | cyclopropyl | 543.1 | 3.55 |
| 92 | 3-$CF_3$ | $CF_3$ | H | H | prop-2-yn-1-yl | N | H | Cl | H | CONH | 1-cyanocyclopropyl | | |
| 93 | 3-Cl | $CF_3$ | H | H | prop-2-yn-1-yl | N | H | Cl | H | CONH | cyclopropyl | | |
| 94 | 3-Cl | $CF_3$ | H | H | prop-2-yn-1-yl | N | H | Cl | H | CONH | 1-cyanocyclopropyl | | |
| 95 | 3-Br | $CF_3$ | H | H | prop-2-yn-1-yl | N | H | Cl | H | CONH | cyclopropyl | | |
| 96 | 3-Br | $CF_3$ | H | H | prop-2-yn-1-yl | N | H | Cl | H | CONH | 1-cyanocyclopropyl | | |
| 97 | 3-$CF_3$; 4-F | $CF_3$ | H | H | prop-2-yn-1-yl | N | H | Cl | H | CONH | cyclopropyl | 561.0 | 3.62 |
| 98 | 3-$CF_3$; 4-F | $CF_3$ | H | H | prop-2-yn-1-yl | N | H | Cl | H | CONH | 1-cyanocyclopropyl | | |
| 99 | 3-Br; 4-F | $CF_3$ | H | H | prop-2-yn-1-yl | N | H | Cl | H | CONH | cyclopropyl | | |
| 100 | 3-Br; 4-F | $CF_3$ | H | H | prop-2-yn-1-yl | N | H | Cl | H | CONH | 1-cyanocyclopropyl | | |

TABLE 1-continued

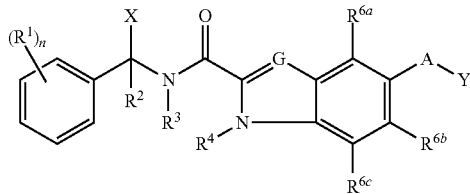

(I)

| No. | $(R^1)_n$ | X | $R^2$ | $R^3$ | $R^4$ | G | $R^{6a}$ | $R^{6b}$ | $R^{6c}$ | A | Y | $(M+H)^{+a)}$ | log $p^{a)}$ |
|---|---|---|---|---|---|---|---|---|---|---|---|---|---|
| 101 | 3-Cl; 4-F | CF₃ | H | H | prop-2-yn-1-yl | N | H | Cl | H | CONH | cyclopropyl | 527.0 | 3.50 |
| 102 | 3-Cl; 4-F | CF₃ | H | H | prop-2-yn-1-yl | N | H | Cl | H | CONH | 1-cyanocyclopropyl | | |
| 103 | 3-Cl; 5-Cl | CF₃ | H | H | prop-2-yn-1-yl | N | H | Cl | H | CONH | cyclopropyl | | |
| 104 | 3-Cl; 5-Cl | CF₃ | H | H | prop-2-yn-1-yl | N | H | Cl | H | CONH | 1-cyanocyclopropyl | | |
| 105 | 3-CF₃ | CF₃ | H | H | Et | CH | H | F | H | CONH | 1-cyanocyclopropyl | | |
| 106 | 3-Cl | CF₃ | H | H | Et | CH | H | F | H | CONH | cyclopropyl | | |
| 107 | 3-Cl | CF₃ | H | H | Et | CH | H | F | H | CONH | 1-cyanocyclopropyl | | |
| 108 | 3-Br | CF₃ | H | H | Et | CH | H | F | H | CONH | cyclopropyl | | |
| 109 | 3-Br | CF₃ | H | H | Et | CH | H | F | H | CONH | 1-cyanocyclopropyl | | |
| 110 | 3-CF₃; 4-F | CF₃ | H | H | Et | CH | H | F | H | CONH | cyclopropyl | | |
| 111 | 3-CF₃; 4-F | CF₃ | H | H | Et | CH | H | F | H | CONH | 1-cyanocyclopropyl | | |
| 112 | 3-Br; 4-F | CF₃ | H | H | Et | CH | H | F | H | CONH | cyclopropyl | | |
| 113 | 3-Br; 4-F | CF₃ | H | H | Et | CH | H | F | H | CONH | 1-cyanocyclopropyl | | |
| 114 | 3-Cl; 4-F | CF₃ | H | H | Et | CH | H | F | H | CONH | cyclopropyl | | |
| 115 | 3-Cl; 4-F | CF₃ | H | H | Et | CH | H | F | H | CONH | 1-cyanocyclopropyl | | |
| 116 | 3-Cl; 5-Cl | CF₃ | H | H | Et | CH | H | F | H | CONH | cyclopropyl | | |
| 117 | 3-Cl; 5-Cl | CF₃ | H | H | Et | CH | H | F | H | CONH | 1-cyanocyclopropyl | | |
| 118 | 3-CF₃ | CF₃ | H | H | Me | CH | H | F | H | CONH | 1-cyanocyclopropyl | | |
| 119 | 3-Cl | CF₃ | H | H | Me | CH | H | F | H | CONH | cyclopropyl | | |
| 120 | 3-Cl | CF₃ | H | H | Me | CH | H | F | H | CONH | 1-cyanocyclopropyl | | |
| 121 | 3-Br | CF₃ | H | H | Me | CH | H | F | H | CONH | cyclopropyl | | |
| 122 | 3-Br | CF₃ | H | H | Me | CH | H | F | H | CONH | 1-cyanocyclopropyl | | |
| 123 | 3-CF₃; 4-F | CF₃ | H | H | Me | CH | H | F | H | CONH | cyclopropyl | | |
| 124 | 3-CF₃; 4-F | CF₃ | H | H | Me | CH | H | F | H | CONH | 1-cyanocyclopropyl | | |
| 125 | 3-Br; 4-F | CF₃ | H | H | Me | CH | H | F | H | CONH | cyclopropyl | | |
| 126 | 3-Br; 4-F | CF₃ | H | H | Me | CH | H | F | H | CONH | 1-cyanocyclopropyl | | |
| 127 | 3-Cl; 4-F | CF₃ | H | H | Me | CH | H | F | H | CONH | cyclopropyl | | |
| 128 | 3-Cl; 4-F | CF₃ | H | H | Me | CH | H | F | H | CONH | 1-cyanocyclopropyl | | |
| 129 | 3-Cl; 5-Cl | CF₃ | H | H | Me | CH | H | F | H | CONH | cyclopropyl | | |
| 130 | 3-Cl; 5-Cl | CF₃ | H | H | Me | CH | H | F | H | CONH | 1-cyanocyclopropyl | | |
| 131 | 3-CF₃ | CF₃ | H | H | prop-2-yn-1-yl | CH | H | F | H | CONH | 1-cyanocyclopropyl | | |
| 132 | 3-Cl | CF₃ | H | H | prop-2-yn-1-yl | CH | H | F | H | CONH | cyclopropyl | | |
| 133 | 3-Cl | CF₃ | H | H | prop-2-yn-1-yl | CH | H | F | H | CONH | 1-cyanocyclopropyl | | |
| 134 | 3-Br | CF₃ | H | H | prop-2-yn-1-yl | CH | H | F | H | CONH | cyclopropyl | | |
| 135 | 3-Br | CF₃ | H | H | prop-2-yn-1-yl | CH | H | F | H | CONH | 1-cyanocyclopropyl | | |
| 136 | 3-CF₃; 4-F | CF₃ | H | H | prop-2-yn-1-yl | CH | H | F | H | CONH | cyclopropyl | | |
| 137 | 3-CF₃; 4-F | CF₃ | H | H | prop-2-yn-1-yl | CH | H | F | H | CONH | 1-cyanocyclopropyl | | |
| 138 | 3-Br; 4-F | CF₃ | H | H | prop-2-yn-1-yl | CH | H | F | H | CONH | cyclopropyl | | |
| 139 | 3-Br; 4-F | CF₃ | H | H | prop-2-yn-1-yl | CH | H | F | H | CONH | 1-cyanocyclopropyl | | |
| 140 | 3-Cl; 4-F | CF₃ | H | H | prop-2-yn-1-yl | CH | H | F | H | CONH | cyclopropyl | | |
| 141 | 3-Cl; 4-F | CF₃ | H | H | prop-2-yn-1-yl | CH | H | F | H | CONH | 1-cyanocyclopropyl | | |
| 142 | 3-Cl; 5-Cl | CF₃ | H | H | prop-2-yn-1-yl | CH | H | F | H | CONH | cyclopropyl | | |
| 143 | 3-Cl; 5-Cl | CF₃ | H | H | prop-2-yn-1-yl | CH | H | F | H | CONH | 1-cyanocyclopropyl | | |
| 144 | 3-CF₃ | CF₃ | H | H | Et | CH | H | Br | H | CONH | 1-cyanocyclopropyl | | |
| 145 | 3-Cl | CF₃ | H | H | Et | CH | H | Br | H | CONH | cyclopropyl | | |
| 146 | 3-Cl | CF₃ | H | H | Et | CH | H | Br | H | CONH | 1-cyanocyclopropyl | | |
| 147 | 3-Br | CF₃ | H | H | Et | CH | H | Br | H | CONH | cyclopropyl | | |
| 148 | 3-Br | CF₃ | H | H | Et | CH | H | Br | H | CONH | 1-cyanocyclopropyl | | |
| 149 | 3-CF₃; 4-F | CF₃ | H | H | Et | CH | H | Br | H | CONH | cyclopropyl | | |

TABLE 1-continued

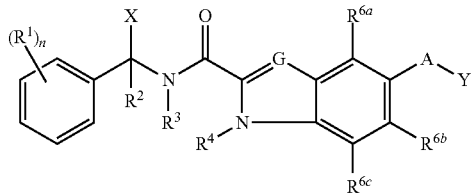

(I)

| No. | $(R^1)_n$ | X | $R^2$ | $R^3$ | $R^4$ | G | $R^{6a}$ | $R^{6b}$ | $R^{6c}$ | A | Y | $(M+H)^{+a)}$ | log p $^{a)}$ |
|---|---|---|---|---|---|---|---|---|---|---|---|---|---|
| 150 | 3-CF₃; 4-F | CF₃ | H | H | Et | CH | H | Br | H | CONH | 1-cyanocyclopropyl | | |
| 151 | 3-Br; 4-F | CF₃ | H | H | Et | CH | H | Br | H | CONH | cyclopropyl | | |
| 152 | 3-Br; 4-F | CF₃ | H | H | Et | CH | H | Br | H | CONH | 1-cyanocyclopropyl | | |
| 153 | 3-Cl; 4-F | CF₃ | H | H | Et | CH | H | Br | H | CONH | cyclopropyl | | |
| 154 | 3-Cl; 4-F | CF₃ | H | H | Et | CH | H | Br | H | CONH | 1-cyanocyclopropyl | | |
| 155 | 3-Cl; 5-Cl | CF₃ | H | H | Et | CH | H | Br | H | CONH | cyclopropyl | | |
| 156 | 3-Cl; 5-Cl | CF₃ | H | H | Et | CH | H | Br | H | CONH | 1-cyanocyclopropyl | | |
| 157 | 3-CF₃ | CF₃ | H | H | Me | CH | H | Br | H | CONH | 1-cyanocyclopropyl | | |
| 158 | 3-Cl | CF₃ | H | H | Me | CH | H | Br | H | CONH | cyclopropyl | | |
| 159 | 3-Cl | CF₃ | H | H | Me | CH | H | Br | H | CONH | 1-cyanocyclopropyl | | |
| 160 | 3-Br | CF₃ | H | H | Me | CH | H | Br | H | CONH | cyclopropyl | | |
| 161 | 3-Br | CF₃ | H | H | Me | CH | H | Br | H | CONH | 1-cyanocyclopropyl | | |
| 162 | 3-CF₃; 4-F | CF₃ | H | H | Me | CH | H | Br | H | CONH | cyclopropyl | | |
| 163 | 3-CF₃; 4-F | CF₃ | H | H | Me | CH | H | Br | H | CONH | 1-cyanocyclopropyl | | |
| 164 | 3-Br; 4-F | CF₃ | H | H | Me | CH | H | Br | H | CONH | cyclopropyl | | |
| 165 | 3-Br; 4-F | CF₃ | H | H | Me | CH | H | Br | H | CONH | 1-cyanocyclopropyl | | |
| 166 | 3-Cl; 4-F | CF₃ | H | H | Me | CH | H | Br | H | CONH | cyclopropyl | | |
| 167 | 3-Cl; 4-F | CF₃ | H | H | Me | CH | H | Br | H | CONH | 1-cyanocyclopropyl | | |
| 168 | 3-Cl; 5-Cl | CF₃ | H | H | Me | CH | H | Br | H | CONH | cyclopropyl | | |
| 169 | 3-Cl; 5-Cl | CF₃ | H | H | Me | CH | H | Br | H | CONH | 1-cyanocyclopropyl | | |
| 170 | 3-CF₃ | CF₃ | H | H | prop-2-yn-1-yl | CH | H | Br | H | CONH | 1-cyanocyclopropyl | | |
| 171 | 3-Cl | CF₃ | H | H | prop-2-yn-1-yl | CH | H | Br | H | CONH | cyclopropyl | | |
| 172 | 3-Cl | CF₃ | H | H | prop-2-yn-1-yl | CH | H | Br | H | CONH | 1-cyanocyclopropyl | | |
| 173 | 3-Br | CF₃ | H | H | prop-2-yn-1-yl | CH | H | Br | H | CONH | cyclopropyl | | |
| 174 | 3-Br | CF₃ | H | H | prop-2-yn-1-yl | CH | H | Br | H | CONH | 1-cyanocyclopropyl | | |
| 175 | 3-CF₃; 4-F | CF₃ | H | H | prop-2-yn-1-yl | CH | H | Br | H | CONH | cyclopropyl | | |
| 176 | 3-CF₃; 4-F | CF₃ | H | H | prop-2-yn-1-yl | CH | H | Br | H | CONH | 1-cyanocyclopropyl | | |
| 177 | 3-Br; 4-F | CF₃ | H | H | prop-2-yn-1-yl | CH | H | Br | H | CONH | cyclopropyl | | |
| 178 | 3-Br; 4-F | CF₃ | H | H | prop-2-yn-1-yl | CH | H | Br | H | CONH | 1-cyanocyclopropyl | | |
| 179 | 3-Cl; 4-F | CF₃ | H | H | prop-2-yn-1-yl | CH | H | Br | H | CONH | cyclopropyl | | |
| 180 | 3-Cl; 4-F | CF₃ | H | H | prop-2-yn-1-yl | CH | H | Br | H | CONH | 1-cyanocyclopropyl | | |
| 181 | 3-Cl; 5-Cl | CF₃ | H | H | prop-2-yn-1-yl | CH | H | Br | H | CONH | cyclopropyl | | |
| 182 | 3-Cl; 5-Cl | CF₃ | H | H | prop-2-yn-1-yl | CH | H | Br | H | CONH | 1-cyanocyclopropyl | | |
| 183 | 3-CF₃ | CF₃ | H | H | Et | CH | H | Me | H | CONH | 1-cyanocyclopropyl | 537.1 | 3.75 |
| 184 | 3-Cl | CF₃ | H | H | Et | CH | H | Me | H | CONH | cyclopropyl | 478.1 | 3.57 |
| 185 | 3-Cl | CF₃ | H | H | Et | CH | H | Me | H | CONH | 1-cyanocyclopropyl | 503.1 | 3.58 |
| 186 | 3-Br | CF₃ | H | H | Et | CH | H | Me | H | CONH | cyclopropyl | | |
| 187 | 3-Br | CF₃ | H | H | Et | CH | H | Me | H | CONH | 1-cyanocyclopropyl | | |
| 188 | 3-CF₃; 4-F | CF₃ | H | H | Et | CH | H | Me | H | CONH | cyclopropyl | 530.1 | 3.76 |
| 189 | 3-CF₃; 4-F | CF₃ | H | H | Et | CH | H | Me | H | CONH | 1-cyanocyclopropyl | 555.1 | 3.77 |
| 190 | 3-Br; 4-F | CF₃ | H | H | Et | CH | H | Me | H | CONH | cyclopropyl | 540.1 | 3.70 |
| 191 | 3-Br; 4-F | CF₃ | H | H | Et | CH | H | Me | H | CONH | 1-cyanocyclopropyl | 565.1 | 3.71 |
| 192 | 3-Cl; 4-F | CF₃ | H | H | Et | CH | H | Me | H | CONH | cyclopropyl | 496.1 | 3.65 |
| 193 | 3-Cl; 4-F | CF₃ | H | H | Et | CH | H | Me | H | CONH | 1-cyanocyclopropyl | 521.1 | 3.66 |
| 194 | 3-Cl; 5-Cl | CF₃ | H | H | Et | CH | H | Me | H | CONH | cyclopropyl | | |
| 195 | 3-Cl; 5-Cl | CF₃ | H | H | Et | CH | H | Me | H | CONH | 1-cyanocyclopropyl | 537.1 | 4.09 |
| 196 | 3-CF₃ | CF₃ | H | H | Me | CH | H | Me | H | CONH | 1-cyanocyclopropyl | 523.1 | 3.49 |
| 197 | 3-Cl | CF₃ | H | H | Me | CH | H | Me | H | CONH | cyclopropyl | | |
| 198 | 3-Cl | CF₃ | H | H | Me | CH | H | Me | H | CONH | 1-cyanocyclopropyl | | |
| 199 | 3-Br | CF₃ | H | H | Me | CH | H | Me | H | CONH | cyclopropyl | | |
| 200 | 3-Br | CF₃ | H | H | Me | CH | H | Me | H | CONH | 1-cyanocyclopropyl | | |
| 201 | 3-CF₃; 4-F | CF₃ | H | H | Me | CH | H | Me | H | CONH | cyclopropyl | | |
| 202 | 3-CF₃; 4-F | CF₃ | H | H | Me | CH | H | Me | H | CONH | 1-cyanocyclopropyl | | |

TABLE 1-continued

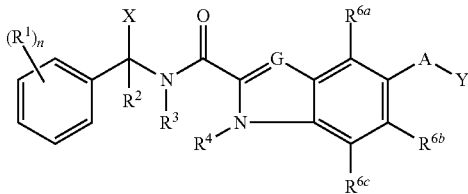

| No. | $(R^1)_n$ | X | $R^2$ | $R^3$ | $R^4$ | G | $R^{6a}$ | $R^{6b}$ | $R^{6c}$ | A | Y | $(M+H)^{+ a)}$ | log p $^{a)}$ |
|---|---|---|---|---|---|---|---|---|---|---|---|---|---|
| 203 | 3-Br; 4-F | $CF_3$ | H | H | Me | CH | H | Me | H | CONH | cyclopropyl | | |
| 204 | 3-Br; 4-F | $CF_3$ | H | H | Me | CH | H | Me | H | CONH | 1-cyanocyclopropyl | | |
| 205 | 3-Cl; 4-F | $CF_3$ | H | H | Me | CH | H | Me | H | CONH | cyclopropyl | | |
| 206 | 3-Cl; 4-F | $CF_3$ | H | H | Me | CH | H | Me | H | CONH | 1-cyanocyclopropyl | | |
| 207 | 3-Cl; 5-Cl | $CF_3$ | H | H | Me | CH | H | Me | H | CONH | cyclopropyl | | |
| 208 | 3-Cl; 5-Cl | $CF_3$ | H | H | Me | CH | H | Me | H | CONH | 1-cyanocyclopropyl | | |
| 209 | 3-$CF_3$ | $CF_3$ | H | H | prop-2-yn-1-yl | CH | H | Me | H | CONH | 1-cyanocyclopropyl | 547.1 | 3.48 |
| 210 | 3-Cl | $CF_3$ | H | H | prop-2-yn-1-yl | CH | H | Me | H | CONH | cyclopropyl | | |
| 211 | 3-Cl | $CF_3$ | H | H | prop-2-yn-1-yl | CH | H | Me | H | CONH | 1-cyanocyclopropyl | | |
| 212 | 3-Br | $CF_3$ | H | H | prop-2-yn-1-yl | CH | H | Me | H | CONH | cyclopropyl | | |
| 213 | 3-Br | $CF_3$ | H | H | prop-2-yn-1-yl | CH | H | Me | H | CONH | 1-cyanocyclopropyl | | |
| 214 | 3-$CF_3$; 4-F | $CF_3$ | H | H | prop-2-yn-1-yl | CH | H | Me | H | CONH | cyclopropyl | | |
| 215 | 3-$CF_3$; 4-F | $CF_3$ | H | H | prop-2-yn-1-yl | CH | H | Me | H | CONH | 1-cyanocyclopropyl | | |
| 216 | 3-Br; 4-F | $CF_3$ | H | H | prop-2-yn-1-yl | CH | H | Me | H | CONH | cyclopropyl | | |
| 217 | 3-Br; 4-F | $CF_3$ | H | H | prop-2-yn-1-yl | CH | H | Me | H | CONH | 1-cyanocyclopropyl | | |
| 218 | 3-Cl; 4-F | $CF_3$ | H | H | prop-2-yn-1-yl | CH | H | Me | H | CONH | cyclopropyl | | |
| 219 | 3-Cl; 4-F | $CF_3$ | H | H | prop-2-yn-1-yl | CH | H | Me | H | CONH | 1-cyanocyclopropyl | | |
| 220 | 3-Cl; 5-Cl | $CF_3$ | H | H | prop-2-yn-1-yl | CH | H | Me | H | CONH | cyclopropyl | | |
| 221 | 3-Cl; 5-Cl | $CF_3$ | H | H | prop-2-yn-1-yl | CH | H | Me | H | CONH | 1-cyanocyclopropyl | | |
| 222 | 3-$CF_3$ | $CF_3$ | H | H | Et | CH | H | $CF_3$ | H | CONH | 1-cyanocyclopropyl | | |
| 223 | 3-Cl | $CF_3$ | H | H | Et | CH | H | $CF_3$ | H | CONH | cyclopropyl | | |
| 224 | 3-Cl | $CF_3$ | H | H | Et | CH | H | $CF_3$ | H | CONH | 1-cyanocyclopropyl | | |
| 225 | 3-Br | $CF_3$ | H | H | Et | CH | H | $CF_3$ | H | CONH | cyclopropyl | | |
| 226 | 3-Br | $CF_3$ | H | H | Et | CH | H | $CF_3$ | H | CONH | 1-cyanocyclopropyl | | |
| 227 | 3-$CF_3$; 4-F | $CF_3$ | H | H | Et | CH | H | $CF_3$ | H | CONH | cyclopropyl | | |
| 228 | 3-$CF_3$; 4-F | $CF_3$ | H | H | Et | CH | H | $CF_3$ | H | CONH | 1-cyanocyclopropyl | | |
| 229 | 3-Br; 4-F | $CF_3$ | H | H | Et | CH | H | $CF_3$ | H | CONH | cyclopropyl | | |
| 230 | 3-Br; 4-F | $CF_3$ | H | H | Et | CH | H | $CF_3$ | H | CONH | 1-cyanocyclopropyl | | |
| 231 | 3-Cl; 4-F | $CF_3$ | H | H | Et | CH | H | $CF_3$ | H | CONH | cyclopropyl | | |
| 232 | 3-Cl; 4-F | $CF_3$ | H | H | Et | CH | H | $CF_3$ | H | CONH | 1-cyanocyclopropyl | | |
| 233 | 3-Cl; 5-Cl | $CF_3$ | H | H | Et | CH | H | $CF_3$ | H | CONH | cyclopropyl | | |
| 234 | 3-Cl; 5-Cl | $CF_3$ | H | H | Et | CH | H | $CF_3$ | H | CONH | 1-cyanocyclopropyl | | |
| 235 | 3-$CF_3$ | $CF_3$ | H | H | Me | CH | H | $CF_3$ | H | CONH | 1-cyanocyclopropyl | | |
| 236 | 3-Cl | $CF_3$ | H | H | Me | CH | H | $CF_3$ | H | CONH | cyclopropyl | | |
| 237 | 3-Cl | $CF_3$ | H | H | Me | CH | H | $CF_3$ | H | CONH | 1-cyanocyclopropyl | | |
| 238 | 3-Br | $CF_3$ | H | H | Me | CH | H | $CF_3$ | H | CONH | cyclopropyl | | |
| 239 | 3-Br | $CF_3$ | H | H | Me | CH | H | $CF_3$ | H | CONH | 1-cyanocyclopropyl | | |
| 240 | 3-$CF_3$; 4-F | $CF_3$ | H | H | Me | CH | H | $CF_3$ | H | CONH | cyclopropyl | | |
| 241 | 3-$CF_3$; 4-F | $CF_3$ | H | H | Me | CH | H | $CF_3$ | H | CONH | 1-cyanocyclopropyl | | |
| 242 | 3-Br; 4-F | $CF_3$ | H | H | Me | CH | H | $CF_3$ | H | CONH | cyclopropyl | | |
| 243 | 3-Br; 4-F | $CF_3$ | H | H | Me | CH | H | $CF_3$ | H | CONH | 1-cyanocyclopropyl | | |
| 244 | 3-Cl; 4-F | $CF_3$ | H | H | Me | CH | H | $CF_3$ | H | CONH | cyclopropyl | | |
| 245 | 3-Cl; 4-F | $CF_3$ | H | H | Me | CH | H | $CF_3$ | H | CONH | 1-cyanocyclopropyl | | |
| 246 | 3-Cl; 5-Cl | $CF_3$ | H | H | Me | CH | H | $CF_3$ | H | CONH | cyclopropyl | | |
| 247 | 3-Cl; 5-Cl | $CF_3$ | H | H | Me | CH | H | $CF_3$ | H | CONH | 1-cyanocyclopropyl | | |
| 248 | 3-$CF_3$ | $CF_3$ | H | H | prop-2-yn-1-yl | CH | H | $CF_3$ | H | CONH | 1-cyanocyclopropyl | | |
| 249 | 3-Cl | $CF_3$ | H | H | prop-2-yn-1-yl | CH | H | $CF_3$ | H | CONH | cyclopropyl | | |
| 250 | 3-Cl | $CF_3$ | H | H | prop-2-yn-1-yl | CH | H | $CF_3$ | H | CONH | 1-cyanocyclopropyl | | |
| 251 | 3-Br | $CF_3$ | H | H | prop-2-yn-1-yl | CH | H | $CF_3$ | H | CONH | cyclopropyl | | |

TABLE 1-continued

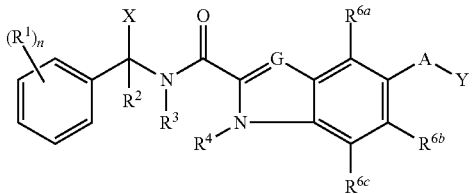

(I)

| No. | $(R^1)_n$ | X | $R^2$ | $R^3$ | $R^4$ | G | $R^{6a}$ | $R^{6b}$ | $R^{6c}$ | A | Y | $(M+H)^{+a)}$ | log $p^{a)}$ |
|---|---|---|---|---|---|---|---|---|---|---|---|---|---|
| 252 | 3-Br | $CF_3$ | H | H | prop-2-yn-1-yl | CH | H | $CF_3$ | H | CONH | 1-cyanocyclopropyl | | |
| 253 | 3-$CF_3$; 4-F | $CF_3$ | H | H | prop-2-yn-1-yl | CH | H | $CF_3$ | H | CONH | cyclopropyl | | |
| 254 | 3-$CF_3$; 4-F | $CF_3$ | H | H | prop-2-yn-1-yl | CH | H | $CF_3$ | H | CONH | 1-cyanocyclopropyl | | |
| 255 | 3-Br; 4-F | $CF_3$ | H | H | prop-2-yn-1-yl | CH | H | $CF_3$ | H | CONH | cyclopropyl | | |
| 256 | 3-Br; 4-F | $CF_3$ | H | H | prop-2-yn-1-yl | CH | H | $CF_3$ | H | CONH | 1-cyanocyclopropyl | | |
| 257 | 3-Cl; 4-F | $CF_3$ | H | H | prop-2-yn-1-yl | CH | H | $CF_3$ | H | CONH | cyclopropyl | | |
| 258 | 3-Cl; 4-F | $CF_3$ | H | H | prop-2-yn-1-yl | CH | H | $CF_3$ | H | CONH | 1-cyanocyclopropyl | | |
| 259 | 3-Cl; 5-Cl | $CF_3$ | H | H | prop-2-yn-1-yl | CH | H | $CF_3$ | H | CONH | cyclopropyl | | |
| 260 | 3-Cl; 5-Cl | $CF_3$ | H | H | prop-2-yn-1-yl | CH | H | $CF_3$ | H | CONH | 1-cyanocyclopropyl | | |
| 262 | 3-$CF_3$ | 3-$CF_3$ | H | H | Et | CH | H | Cl | H | CONH | 1-cyano-1-methyl-cyclopropylmethyl | 585.2 | 4.28 |
| 263 | 3-$CF_3$ | 3-$CF_3$ | H | H | Et | CH | H | Cl | H | CONH | 2-cyanoethyl | 545.2 | 3.53 |
| 264 | 3-$CF_3$ | 3-$CF_3$ | H | H | Et | CH | H | Cl | H | CONH | 1-cyano-1-ethylpropan-1-yl | 587.2 | 4.41 |
| 266 | 3-$CF_3$ | 3-$CF_3$ | H | H | Et | CH | H | Cl | H | CONH | 1,2-dimethylcyclopropyl | 560.1 | 4.41 |
| 267 | 3-$CF_3$ | 3-$CF_3$ | H | H | Et | CH | H | Cl | H | CONH | 1-trifluoromethyl-cyclopropyl | 600.0 | 4.30 |
| 268 | 3-$CF_3$ | 3-$CF_3$ | H | H | Et | CH | H | Cl | H | CONH | 1-cyanobut-3-yn-1-yl | 569.1 | 3.91 |
| 269 | 3-$CF_3$ | 3-$CF_3$ | H | H | Et | CH | H | Cl | H | CONH | 3-cyanopropan-2-yl | 559.2 | 3.78 |
| 270 | 3-$CF_3$ | 3-$CF_3$ | H | H | Et | CH | H | Cl | H | CONH | 1-cyano-2-methylpropan-1-yl | 573.2 | 4.37 |
| 271 (Synthesis Ex. 7) | 3-$CF_3$ | 3-$CF_3$ | H | H | Et | CCl | H | Cl | H | CONH | 1-cyanocyclopropyl | 591.0 | 3.95 |
| 272 | 3-$CF_3$ | 3-$CF_3$ | H | H | cyclo-propyl-methyl | CH | H | Cl | H | CONH | 1-cyanocyclopropyl | 583.2 | 4.03 |
| 273 (Synthesis Ex. 9) | 3-$CF_3$ | 3-$CF_3$ | H | H | Et | CH | H | Cl | H | CONH | 1-aminothiocarbonyl-cyclopropyl | 591.0 | 3.56 |
| 274 | 3-$CF_3$ | $CF_3$ | H | H | cyclo-butyl | CH | H | Cl | H | CONH | 1-cyanocyclopropyl | 583.2 | 4.03 |
| 275 | 3-Cl; 4-Cl; 5-Cl | $CF_3$ | H | H | Et | CH | H | Cl | H | CONH | 1-cyanocyclopropyl | 590.9 | 4.43 |
| 276 | 3-$OCHF_2$ | $CF_3$ | H | H | Et | CH | H | Cl | H | CONH | cyclopropyl | 530.1 | 3.48 |
| 277 | 3-Cl; 4-Cl; 5-Cl | $CF_3$ | H | H | prop-2-yn-1-yl | CH | H | Cl | H | CONH | 1-cyanocyclopropyl | 601.0 | 4.24 |
| 278 | 3-$OCHF_2$ | $CF_3$ | H | H | prop-2-yn-1-yl | CH | H | Cl | H | CONH | cyclopropyl | 540.0 | 3.32 |
| 279 (Synthesis Ex. 8) | 3-$CF_3$ | $CF_3$ | H | H | Et | C—CN | H | Cl | H | CONH | 1-cyanocyclopropyl | 582.1 | 3.45 |
| 281 | 3-$CF_3$; 4-F | $CF_3$ | H | H | prop-2-en-1-yl | N | H | Cl | H | CONH | cyclopropyl | 563.1 | 3.79 |
| 282 | 3-$CF_3$ | $CF_3$ | H | H | Et | CH | H | Et | H | CONH | 1-cyanocyclopropyl | 551.1 | 3.98 |
| 283 | 3-$CF_3$ | $CF_3$ | H | H | prop-2-en-1-yl | CH | H | Cl | H | CONH | 1-cyanocyclopropyl | 569.1 | 3.74 |
| 284 | 3-$CF_3$ | $CF_3$ | H | H | phenyl-methyl | CH | H | Cl | H | CONH | 1-cyanocyclopropyl | 619.1 | 4.07 |
| 285 | 3-$CF_3$ | $CF_3$ | H | H | but-2-yn-1-yl | CH | H | Cl | H | CONH | 1-cyanocyclopropyl | 581.1 | 3.87 |

TABLE 1-continued

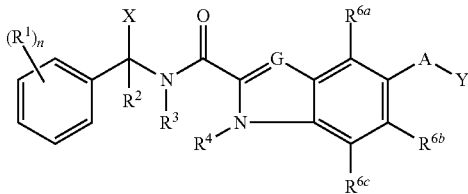

| No. | (R¹)ₙ | X | R² | R³ | R⁴ | G | R⁶ᵃ | R⁶ᵇ | R⁶ᶜ | A | Y | (M + H)⁺ ᵃ⁾ | log p ᵃ⁾ |
|---|---|---|---|---|---|---|---|---|---|---|---|---|---|
| 286 | 3-CF₃ | CF₃ | H | H | benzyloxy-methyl | CH | H | Cl | H | CONH | 1-cyanocyclopropyl | 649.1 | 4.17 |
| 287 | 3-CF₃ | CF₃ | H | H | ethoxy-methyl | CH | H | Cl | H | CONH | 1-cyanocyclopropyl | 587.1 | 3.70 |
| 288 | 3-CF₃ | CF₃ | H | H | prop-1-yl | CH | H | Cl | H | CONH | 1-cyanocyclopropyl | 571.1 | 4.03 |
| 289 | 3-Cl; 4-Cl; 5-Cl | CF₃ | H | H | Et | CH | H | Me | H | CONH | 1-cyanocyclopropyl | 571.1 | 4.43 |
| 290 | 3-Cl; 5-Cl; 4-F | CF₃ | H | H | Et | CH | H | Me | H | CONH | 1-cyanocyclopropyl | 555.0 | 4.13 |
| 291 | 3-Cl; 5-Cl | CF₃ | H | H | Et | CH | H | Me | H | CONH | 1-cyanocyclopropyl | 537.1 | 4.07 |
| 292 | 3-F; 4-F | CF₃ | H | H | Et | CH | H | Me | H | CONH | 1-cyanocyclopropyl | 505.1 | 3.48 |
| 293 | 3-Cl; 5-F | CF₃ | H | H | Et | CH | H | Me | H | CONH | 1-cyanocyclopropyl | 521.1 | 3.85 |
| 294 | 3-CF₃ | CF₃ | H | H | cyano-methyl | CH | H | Cl | H | CONH | 1-cyanocyclopropyl | 568.1 | 3.30 |
| 295 | 3-F; 4-F | CF₃ | H | H | Et | CH | H | Me | H | CONH | cyclopropyl | 480.1 | 3.40 |
| 296 | 3-Cl; 5-Cl; 4-F | CF₃ | H | H | Et | CH | H | Me | H | CONH | cyclopropyl | 530.1 | 4.16 |
| 297 | 3-Cl; 4-Cl | CF₃ | H | H | Et | CH | H | Me | H | CONH | cyclopropyl | 512.1 | 3.99 |
| 298 | 3-Cl; 5-F | CF₃ | H | H | Et | CH | H | Me | H | CONH | cyclopropyl | 496.1 | 3.77 |
| 299 | 3-CF₃ | CF₃ | H | H | 2-methyl-propan-1-yl | CH | H | Cl | H | CONH | 1-cyanocyclopropyl | 585.1 | 4.13 |
| 300 | 3-CF₃; 4-F | CF₃ | H | H | cyclopropyl | N | H | Br | H | CONH | cyclopropyl | 607.0 | 3.59 |
| 301 | 3-CF₃; 4-F | CF₃ | H | H | cyano-methyl | N | H | Cl | H | CONH | cyclopropyl | 562.0 | 3.28/3.43 |
| 302 (Synthesis Ex. 6) | 3-CF₃ | CF₃ | H | H | cyclopropyl | CH | H | Cl | H | CONH | 1-cyanocyclopropyl | 569.1 | 3.60 |
| 303 | 3-Cl; 4-F | CF₃ | H | H | prop-2-en-1-yl | N | H | Cl | H | CON(CH₂CH=CH₂) | cyclopropyl | 569.1 | 4.75 |
| 304 | 3-CF₃; 4-F | CF₃ | H | H | Et | CH | H | Me | H | CONH | cyclobutyl | 544.1 | 4.24 |
| 305 | 3-CF₃; 4-F | CF₃ | H | H | Et | CH | H | Me | H | CONH | propan-2-yl | 532.2 | 4.16 |
| 306 | 3-CF₃; 4-F | CF₃ | H | H | Et | CH | H | Me | H | CONH | 1,3-difluoropropan-2-yl | 568.1 | 4.03 |
| 307 | 3,4-(—OCF₂O—) | CF₃ | H | H | Et | CH | H | Me | H | CONH | cyclopropyl | 524.1 | 3.81 |
| 308 | 3,4-(—OCF₂O—) | CF₃ | H | H | Et | CH | H | Me | H | CONH | 1-cyanocyclopropyl | 549.1 | 3.80 |
| 309 | 3-CF₃ | CF₃ | H | H | prop-2-en-1-yl | N | H | Cl | H | CON(CH₂CH=CH₂) | cyclopropyl | 585.1 | 4.74 |
| 310 | 3-Cl; 5-Cl; 2-F; 5-F | CF₃ | H | H | Et | CH | H | Cl | H | CONH | 1-cyanocyclopropyl | 593.0 | 4.25 |
| 311 | 3-Cl; 5-Cl; 4-F | CF₃ | H | H | Et | CH | H | Cl | H | CONH | 1-cyanocyclopropyl | 575.0 | 4.19 |
| 312 (Synthesis Ex. 5) | 3-CF₃ | CF₃ | H | H | cyclopropyl | N | H | Cl | H | CONH | cyclopropyl | 545.0 | 3.48 |
| 313 | 3-CF₃; 4-F | CF₃ | H | H | cyclopropyl | N | H | Cl | H | CONH | cyclopropyl | 563.1 | 3.38 |
| 314 | 3-Br | CF₃ | H | H | cyclopropyl | N | H | Cl | H | CONH | cyclopropyl | 555.0 | 3.43 |
| 315 | 3-F; 4-F | CF₃ | H | H | Et | CH | H | Cl | H | CONH | 1-cyanocyclopropyl | 525.1 | 3.47 |
| 316 | 3-Cl; 4-Cl | CF₃ | H | H | Et | CH | H | Cl | H | CONH | 1-cyanocyclopropyl | 557.0 | 4.06 |
| 317 | 3-Cl; 5-Cl | CF₃ | H | H | Et | N | H | Cl | H | CONH | cyclopropyl | 533.0 | 4.07/4.15 |
| 318 | 3-CF₃ | CF₃ | H | H | Et | CH | H | Cl | H | CONH | 1-cyano-1-phenylmethyl | 607.1 | 4.37 |
| 319 | 3-CF₃ | CF₃ | H | H | Et | CH | H | iPr | H | CONH | 1-cyanocyclopropyl | 565.1 | 4.08 |
| 320 | 3-Cl; 4-F | CF₃ | H | H | Et | CH | H | Me | H | CON(Et) | Et | 512.1 | 4.35 |
| 321 | 3-F; 4-F | CF₃ | H | H | Et | CH | H | Me | H | CONH | 1-(methylsulphinyl)propan-2-yl | 544.1 | 2.76 |
| 322 | 3-CF₃ | CF₃ | H | H | cyclopropyl-methyl | N | H | Cl | H | CONH | cyclopropyl | 559.1 | 4.04/4.04 |
| 323 | 3-F | CF₃ | H | H | Et | N | H | Cl | H | CON(Et) | Et | 499.1 | 3.95/4.00 |
| 324 | 3-CF₃ | CF₃ | H | H | ethenyl | CH | H | H | H | CONH | 1-cyanocyclopropyl | 521.1 | 3.48 |

TABLE 1-continued

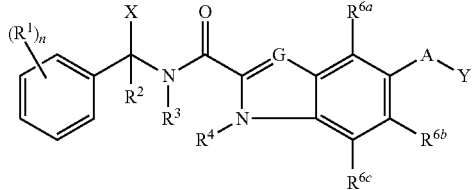

(I)

| No. | $(R^1)_n$ | X | $R^2$ | $R^3$ | $R^4$ | G | $R^{6a}$ | $R^{6b}$ | $R^{6c}$ | A | Y | $(M+H)^{+\,a)}$ | log p $^{a)}$ |
|---|---|---|---|---|---|---|---|---|---|---|---|---|---|
| 325 | 3-CF₃ | CF₃ | H | H | Et | CH | H | Cl | H | CONH | 2-cyano-1,3-dimethoxypropan-2-yl | 619.1 | 4.16 |
| 326 | 3-CF₃ | CF₃ | H | H | methoxy-carbonyl-methyl | CH | H | Cl | H | CONH | 1-cyanocyclopropyl | 601.1 | 3.36 |
| 327 | 3-Cl; 5-Cl; 4-F | CF₃ | H | H | Et | CH | H | Cl | H | CONH | cyclopropyl | 550.0 | 4.29 |
| 328 | 3-Cl; 5-Cl; 2-F; 4-F; | CF₃ | H | H | Et | CH | H | Cl | H | CONH | cyclopropyl | 568.0 | 4.46 |
| 329 | 3-F; 4-F; | CF₃ | H | H | Et | CH | H | Cl | H | CONH | cyclopropyl | 500.1 | 3.52 |
| 330 | 3-Cl; 5-Cl; 2-F; 4-F; | CF₃ | H | H | Et | CH | H | Me | H | CONH | 1-cyanocyclopropyl | 573.1 | 4.34 |
| 331 | 3-CF₃; 5-F | CF₃ | H | H | Et | CH | H | Me | H | CONH | 1-cyanocyclopropyl | 555.1 | 4.02 |
| 332 | 3-CF₃; 4-F | CF₃ | H | H | Et | N | H | Br | H | CONH | cyclopropyl | 597.0 | 3.76 |

Abbreviations: Et = ethyl, Me = methyl;
Some of the benzimidazole derivatives (G = N) listed in the table are present in the form of regioisomer mixtures of the —$R^{6b}$ and —A—Y substituents.
In this case, the log p values and NMR data are reported for both isomers.
1H NMR data $^{b)}$ Compound No. 1 [CD₃CN] 8.74 0.59; 8.73 0.59; 7.98 1.91; 7.90 1.03; 7.89 1.17; 7.81 2.24; 7.80 2.16; 7.79 1.02; 7.78 1.32; 7.77 4.03; 7.69 1.00; 7.68 1.74; 7.67 4.03; 7.66 0.88; 7.66 2.56; 6.91 0.50; 6.11 0.64; 6.10 0.81; 6.08 0.65; 5.45 7.05; 4.11 0.38; 4.10 9.61; 4.09 0.34; 4.08 16.00; 4.06 0.41; 4.05 0.39; 2.88 0.67; 2.88 0.39; 2.87 0.71; 2.87 0.76; 2.86 1.07; 2.86 1.38; 2.85 1.25; 2.85 0.79; 2.84 0.52; 2.17 6.43; 1.97 1.74; 1.97 0.87; 1.96 1.15; 1.95 0.06; 1.95 9.78; 1.95 18.25; 1.94 17.31; 1.93 8.94; 1.27 0.37; 1.27 0.46; 1.22 0.52; 1.20 1.03; 1.19 0.48; 0.79 0.34; 0.79 0.64; 0.78 0.86; 0.78 1.25; 0.78 1.52; 0.77 2.06; 0.77 1.47; 0.77 1.05; 0.77 2.04; 0.76 1.53; 0.76 1.05; 0.75 0.70; 0.62 0.42; 0.62 0.72; 0.61 0.92; 0.61 1.06; 0.61 2.19; 0.61 2.23; 0.60 2.10; 0.60 1.53; 0.59 0.42; 0.59 0.53; 0.01 0.64; 0.00 21.51; −0.01 0.58

Compound No. 2 [CD₃CN] 8.20 1.56; 8.19 1.60; 7.72 10.66; 7.70 4.31; 7.58 1.96; 7.56 2.30; 7.55 8.41; 7.51 0.32; 7.51 0.38; 7.49 0.55; 7.48 1.02; 7.48 0.78; 7.47 4.48; 7.47 9.40; 7.47 3.10; 7.46 3.95; 7.45 0.97; 7.16 7.89; 6.89 1.56; 6.05 0.40; 6.04 1.42; 6.02 2.03; 6.01 1.49; 5.99 0.44; 4.47 1.97; 4.46 6.18; 4.45 6.23; 4.43 1.99; 4.06 0.50; 4.05 0.50; 2.88 0.39; 2.88 1.13; 2.87 1.55; 2.86 2.49; 2.86 2.46; 2.85 1.66; 2.85 1.22; 2.84 0.44; 2.28 0.35; 2.27 0.46; 2.25 0.65; 2.21 502.49; 2.05 0.45; 2.05 0.48; 1.97 2.50; 1.97 23.78; 1.96 2.48; 1.96 3.35; 1.95 30.00; 1.95 56.18; 1.94 79.93; 1.94 52.48; 1.93 26.64; 1.83 0.43; 1.32 0.47; 1.31 0.51; 1.30 0.51; 1.29 7.47; 1.28 16.00; 1.27 8.13; 1.22 0.70; 1.20 1.27; 1.19 0.66; 0.91 0.48; 0.79 1.46; 0.78 4.14; 0.77 5.29; 0.77 5.30; 0.76 4.01; 0.75 1.68; 0.60 1.73; 0.60 4.22; 0.60 4.23; 0.59 4.33; 0.59 3.97; 0.59 4.05; 0.58 1.26; 0.00 0.59

Compound No. 3 [CD₃CN] 8.17 1.45; 8.16 1.52; 8.00 2.07; 7.99 2.00; 7.95 1.08; 7.94 1.28; 7.93 1.47; 7.93 1.32; 7.92 1.35; 7.74 10.98; 7.57 8.39; 7.45 1.88; 7.43 2.50; 7.42 1.77; 7.19 8.10; 7.19 7.92; 6.86 1.70; 6.16 0.36; 6.14 1.31; 6.13 1.87; 6.11 1.34; 6.10 0.38; 4.48 2.08; 4.47 6.40; 4.45 6.43; 4.44 2.02; 2.89 0.89; 2.88 0.38; 2.87 1.14; 2.86 1.60; 2.86 2.84; 2.85 2.52; 2.84 1.60; 2.84 1.16; 2.83 0.40; 2.77 0.75; 2.18 491.55; 2.16 0.71; 2.16 0.69; 2.06 0.34; 2.06 0.61; 2.05 0.87; 2.05 0.60; 1.97 5.10; 1.96 4.52; 1.96 7.56; 1.95 58.87; 1.95 107.34; 1.94 152.89; 1.94 107.55; 1.94 55.32; 1.84 0.35; 1.83 0.63; 1.83 0.90; 1.82 0.62; 1.82 0.33; 1.44 0.41; 1.30 0.43; 1.29 7.24; 1.28 16.00; 1.27 7.58; 0.78 1.43; 0.77 4.21; 0.77 5.36; 0.76 5.34; 0.76 4.17; 0.75 1.71; 0.60 1.71; 0.59 4.31; 0.59 4.52; 0.59 4.59; 0.58 4.35; 0.57 1.35; 0.01 0.57; 0.00 12.97; −0.01 0.50

Compound No. 4 [CD₃CN] cf. Synthesis Example 4

Compound No. 5 [CD₃CN] 9.20 0.40; 8.15 2.63; 8.14 1.17; 8.13 2.75; 7.84 0.55; 7.76 16.00; 7.72 0.35; 7.69 7.16; 7.67 0.44; 7.62 12.62; 7.58 0.36; 7.58 0.35; 7.57 3.16; 7.56 3.89; 7.55 0.59; 7.54 0.73; 7.48 1.91; 7.48 1.63; 7.47 8.50; 7.47 14.44; 7.47 14.33; 7.47 5.60; 7.46 6.33; 7.45 1.52; 7.42 0.35; 7.26 12.22; 7.26 11.69; 6.86 2.74; 6.86 2.74; 6.05 0.60; 6.04 2.20; 6.02 3.14; 6.01 2.29; 6.00 0.69; 5.34 0.35; 5.34 0.39; 5.32 15.34; 5.32 15.59; 5.00 0.44; 4.99 0.45; 4.98 0.35; 4.97 0.36; 3.80 0.34; 3.79 0.39; 3.79 0.39; 3.78 0.33; 2.88 0.67; 2.87 1.78; 2.87 2.48; 2.86 3.89; 2.85 3.93; 2.85 2.62; 2.84 1.96; 2.84 0.80; 2.53 4.69; 2.52 10.42; 2.52 4.69; 2.51 0.40; 2.26 0.60; 2.25 1.62; 2.24 0.64; 2.15 77.87; 2.06 0.39; 2.06 0.73; 2.05 1.11; 2.05 0.80; 2.04 0.37; 1.97 5.16; 1.96 5.34; 1.95 8.34; 1.95 69.92; 1.95 132.87; 1.94 192.91; 1.94 134.93; 1.93 68.76; 1.84 0.43; 1.83 0.78; 1.83 1.12; 1.82 0.79; 1.82 0.43; 1.54 0.37; 1.47 0.69; 1.42 0.33; 1.32 0.45; 1.31 0.51; 1.31 0.80; 1.31 0.67; 1.30 0.74; 1.28 1.76; 1.27 11.23; 0.91 0.36; 0.90 0.38; 0.89 0.87; 0.88 2.07; 0.87 1.09; 0.79 2.41; 0.78 6.66; 0.77 8.61; 0.76 8.44; 0.76 7.02; 0.75 3.09; 0.74 0.43; 0.73 0.36; 0.63 0.38; 0.62 0.43; 0.61 0.43; 0.60 2.71; 0.59 6.68; 0.59 7.06; 0.59 7.53; 0.59 7.22; 0.58 7.26; 0.57 2.45; 0.10 0.43; 0.01 3.93; 0.00 115.18; −0.01 5.12; −0.10 0.44

Compound No. 6 [CD₃CN] 8.28 2.57; 8.26 2.64; 8.01 2.97; 8.00 2.82; 8.00 2.91; 7.96 1.55; 7.95 1.65; 7.95 1.80; 7.94 2.04; 7.94 1.78; 7.93 1.81; 7.93 1.49; 7.81 0.52; 7.75 16.00; 7.72 0.39; 7.61 12.15; 7.49 0.49; 7.45 2.91; 7.43 3.70; 7.26 11.64; 7.26 11.39; 7.25 0.41; 6.87 2.47; 6.87 2.48; 6.16 0.58; 6.14 2.02; 6.13 2.80; 6.11 2.04; 6.10 0.61; 5.33 0.34; 5.33 0.36; 5.31 12.81; 5.31 12.94; 4.97 0.42; 4.96 0.42; 3.78 0.38; 3.78 0.39; 2.88 0.62; 2.88 0.33; 2.87 1.75; 2.87 2.41; 2.86 3.84; 2.86 3.80; 2.85 2.41; 2.84 1.80; 2.84 0.66; 2.52 4.57; 2.52 10.28; 2.52 4.46; 2.50 0.32; 2.15 45.05; 2.06 0.46; 2.05 0.68; 2.05 0.46; 1.97 3.45; 1.96 3.58; 1.95 4.97; 1.95 43.63; 1.95 82.51; 1.94 120.35; 1.94 82.65; 1.93 41.76; 1.93 0.87; 1.83 0.46; 1.83 0.66; 1.82 0.46; 1.29 0.59; 1.28 0.42; 1.27 1.01; 1.01 0.48; 0.79 2.29; 0.78 6.09; 0.77 8.00; 0.76 7.69; 0.76 6.29; 0.75 2.62; 0.74 0.40; 0.73 0.33; 0.63 0.33; 0.62 0.38; 0.61 0.53; 0.61 0.56; 0.60 2.64; 0.59 5.96; 0.59 6.30; 0.59 6.54; 0.59 6.13; 0.58 6.26; 0.57 2.06; 0.01 2.51; 0.00 73.98; −0.01 2.61

Compound No. 7 cf. Synthesis Example 2

Compound No. 8 [DMSO-D₆] 11.19 0.47; 9.80 3.66; 9.78 3.87; 8.41 3.59; 8.39 3.58; 8.19 5.48; 8.06 3.01; 8.04 3.36; 7.83 2.88; 7.81 4.14; 7.80 10.53; 7.77 13.82; 7.74 2.89; 7.72 4.42; 7.70 1.89; 7.38 9.74; 6.33 0.40; 6.31 1.52; 6.29 2.28; 6.27 1.67; 6.24 0.43; 4.54 1.79; 4.52 5.20; 4.50 5.36; 4.49 2.38; 4.48 2.96; 4.47 3.10; 4.46 3.28; 4.45 2.81; 4.44 0.73; 4.43 0.62; 4.38 0.56; 4.37 0.80; 4.36 2.48; 4.35 3.55; 4.34 2.91; 4.33 0.65; 4.31 0.66; 4.29 0.45; 4.28 0.83; 4.26 1.10; 4.25 1.07; 4.23 1.08; 4.22 0.98; 4.20 0.72; 4.18 0.33; 3.96 0.74; 3.79 0.37; 3.50 0.37; 3.48 0.34; 3.45 0.45; 3.43 0.70; 3.41 0.80; 3.40 0.85; 3.31 1512.34; 3.28 18.26; 3.22 0.34; 2.67 1.02; 2.67 1.37; 2.66 1.02; 2.59 0.40; 2.57 0.51; 2.54 1.82; 2.51 79.38; 2.50 147.87; 2.50 192.53; 2.50 132.91; 2.49 63.33; 2.33 0.95; 2.33 1.25; 2.32 0.88; 1.99 0.57; 1.40 1.04; 1.38 0.33; 1.36 0.34;

TABLE 1-continued
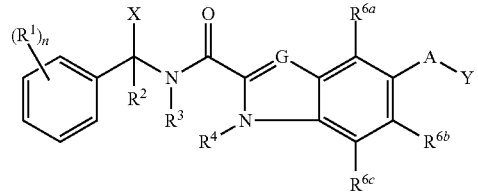
| No. | (R¹)ₙ | X | R² | R³ | R⁴ | G | R⁶ᵃ | R⁶ᵇ | R⁶ᶜ | A | Y | (M + H)⁺ ᵃ⁾ | log p ᵃ⁾ |
|---|---|---|---|---|---|---|---|---|---|---|---|---|---|
1.32 0.33; 1.30 0.36; 1.28 0.54; 1.24 2.53; 1.22 7.34; 1.21 15.56; 1.19 16.00; 1.18 12.44; 1.17 11.62; 1.13 0.38; 1.03 0.80; 1.01 0.79; 0.87 0.35; 0.85 0.40; 0.01 1.08; 0.00 25.51; −0.01 1.06
Compound No. 9 [CD₃CN] 8.18 1.42; 8.16 1.45; 7.98 3.46; 7.91 1.85; 7.89 2.06; 7.83 10.49; 7.79 1.79; 7.77 2.28; 7.69 1.89; 7.68 3.09; 7.67 1.32; 7.61 7.34; 7.59 0.36; 7.56 0.52; 7.36 1.32; 7.35 1.30; 7.22 6.92; 7.21 6.90; 6.17 0.35; 6.15 1.26; 6.14 1.75; 6.13 1.31; 6.11 0.40; 4.97 0.63; 4.96 2.72; 4.95 4.18; 4.93 2.75; 4.92 0.64; 4.48 1.79; 4.47 5.75; 4.46 5.80; 4.45 1.83; 3.28 5.15; 3.27 5.27; 3.06 2.00; 2.79 0.69; 2.19 0.33; 2.18 0.91; 2.17 1.08; 2.16 29.01; 2.08 0.34; 1.97 0.45; 1.97 59.93; 1.96 1.43; 1.95 1.57; 1.95 17.56; 1.95 32.81; 1.94 48.55; 1.94 33.14; 1.93 16.55; 1.93 0.49; 1.85 0.34; 1.61 15.77; 1.60 15.78; 1.30 6.92; 1.29 16.00; 1.27 6.99; 1.10 0.48; 0.01 0.66; 0.00 24.15; −0.01 0.73
Compound No. 10 [CD₃CN] 8.15 1.40; 8.14 1.44; 7.98 4.36; 7.90 2.31; 7.88 2.59; 7.81 11.55; 7.79 2.21; 7.77 2.80; 7.69 2.26; 7.68 3.73; 7.66 1.60; 7.62 9.13; 7.22 9.07; 7.14 0.86; 7.13 1.53; 7.12 0.88; 6.17 0.37; 6.15 1.37; 6.14 1.99; 6.12 1.41; 6.11 0.40; 4.49 2.03; 4.48 6.49; 4.47 6.55; 4.46 2.12; 3.82 1.98; 3.81 2.02; 3.80 4.21; 3.79 4.14; 3.77 2.13; 3.76 2.07; 2.18 202.01; 2.06 0.40; 2.05 0.57; 2.05 0.39; 1.97 12.34; 1.96 2.76; 1.95 3.48; 1.95 33.73; 1.95 62.60; 1.94 92.49; 1.94 63.69; 1.93 32.30; 1.83 0.39; 1.83 0.55; 1.82 0.38; 1.73 6.45; 1.70 13.71; 1.67 6.87; 1.30 7.30; 1.29 16.00; 1.28 7.47; 0.00 7.31
Compound No. 11 [CD₃CN] 8.13 1.63; 8.10 1.66; 7.97 3.77; 7.90 1.99; 7.88 2.35; 7.82 10.28; 7.79 1.81; 7.77 2.57; 7.69 2.19; 7.67 3.20; 7.65 1.28; 7.61 7.88; 7.22 7.76; 7.22 7.61; 7.09 1.17; 7.07 1.15; 6.18 0.45; 6.16 1.55; 6.13 2.08; 6.11 1.53; 6.09 0.46; 4.73 0.40; 4.72 0.41; 4.71 0.86; 4.70 2.27; 4.69 5.08; 4.68 3.86; 4.67 0.48; 4.67 0.50; 4.66 0.97; 4.65 0.46; 4.64 0.36; 4.64 0.44; 4.63 0.43; 4.63 0.39; 4.62 0.53; 4.60 0.72; 4.60 1.32; 4.59 1.21; 4.58 3.19; 4.57 7.14; 4.56 3.10; 4.55 1.09; 4.54 0.84; 4.54 0.79; 4.53 0.44; 4.52 0.47; 4.50 2.11; 4.49 6.29; 4.47 6.32; 4.45 2.01; 2.15 292.31; 2.12 0.82; 2.11 0.81; 2.11 0.82; 2.10 0.59; 2.09 0.40; 1.97 0.91; 1.96 4.51; 1.96 4.96; 1.95 31.38; 1.95 58.32; 1.94 81.47; 1.93 55.88; 1.93 28.58; 1.77 0.37; 1.77 0.49; 1.76 0.33; 1.44 11.91; 1.31 7.09; 1.29 16.00; 1.27 7.18; 0.01 0.36; 0.00 7.84
Compound No. 13 [DMSO-D₆] 9.69 3.84; 9.67 4.02; 8.41 4.28; 8.41 4.40; 7.92 12.71; 7.92 12.80; 7.80 10.36; 7.77 15.06; 7.74 4.91; 7.73 9.01; 7.73 4.52; 7.66 0.33; 7.38 9.85; 6.28 0.33; 6.27 1.19; 6.26 1.80; 6.24 1.31; 6.23 0.38; 5.76 0.33; 4.53 1.65; 4.51 5.04; 4.50 5.03; 4.49 1.65; 3.52 0.35; 3.38 0.62; 3.35 1337.04; 3.33 9.64; 2.85 0.48; 2.85 1.18; 2.84 1.48; 2.84 2.51; 2.83 2.56; 2.82 1.49; 2.82 1.27; 2.81 0.55; 2.62 0.97; 2.62 1.36; 2.61 0.95; 2.61 0.44; 2.54 0.61; 2.52 1.74; 2.52 2.28; 2.52 2.46; 2.51 72.44; 2.51 157.19; 2.50 215.78; 2.50 156.91; 2.50 71.56; 2.39 0.97; 2.39 1.36; 2.38 0.95; 2.08 1.34; 1.38 0.51; 1.26 0.42; 1.24 0.87; 1.23 2.94; 1.22 7.55; 1.21 16.00; 1.19 7.49; 1.18 0.78; 1.17 1.27; 1.15 0.59; 1.13 0.34; 1.12 0.41; 0.85 0.48; 0.71 1.81; 0.70 4.65; 0.70 6.42; 0.69 5.91; 0.69 5.21; 0.68 2.04; 0.55 2.06; 0.54 5.83; 0.54 5.43; 0.54 5.15; 0.53 5.35; 0.52 1.67; 0.01 1.33; 0.00 42.82; −0.01 1.25
Compound No. 14 [CD₃CN] 8.09 1.05; 8.07 1.07; 7.93 1.48; 7.92 1.52; 7.92 1.52; 7.91 1.47; 7.77 6.96; 7.64 6.28; 7.62 0.93; 7.62 0.93; 7.62 0.82; 7.52 0.39; 7.42 0.50; 7.33 1.93; 7.31 3.67; 7.30 1.86; 7.27 5.84; 6.85 1.08; 6.04 0.92; 6.03 1.30; 6.01 0.92; 5.33 6.44; 5.32 6.47; 4.06 0.38; 4.05 0.38; 2.87 2.06; 2.87 1.00; 2.86 1.47; 2.85 1.49; 2.85 1.02; 2.84 0.71; 2.53 1.63; 2.52 3.46; 2.52 1.64; 2.15 128.09; 2.06 0.45; 2.05 0.67; 2.05 0.46; 1.97 1.73; 1.97 4.22; 1.96 3.29; 1.95 4.63; 1.95 42.72; 1.95 78.84; 1.94 115.42; 1.94 79.69; 1.93 40.87; 1.92 1.06; 1.83 0.46; 1.83 0.65; 1.82 0.44; 1.47 1.52; 1.44 16.00; 1.27 0.56; 1.22 0.45; 1.20 0.85; 1.19 0.45; 1.11 0.50; 0.79 0.87; 0.78 2.61; 0.77 3.25; 0.77 3.62; 0.76 2.53; 0.75 1.27; 0.60 1.06; 0.59 2.84; 0.59 3.03; 0.59 2.77; 0.58 2.90; 0.57 0.90; 0.01 1.11; 0.00 36.58; −0.01 1.28
Compound No. 15 [CD₃CN] 8.12 0.47; 8.11 0.48; 7.97 1.13; 7.90 0.58; 7.89 0.67; 7.83 2.73; 7.79 0.60; 7.77 0.77; 7.69 0.61; 7.68 1.00; 7.67 0.43; 7.62 2.24; 7.23 2.18; 7.16 0.78; 6.15 0.38; 6.14 0.55; 6.13 0.40; 4.50 0.51; 4.48 1.60; 4.47 1.62; 4.46 0.53; 2.16 4.22; 1.97 0.88; 1.97 0.77; 1.96 0.69; 1.95 0.84; 1.95 8.36; 1.95 15.52; 1.94 22.59; 1.94 15.46; 1.93 7.98; 1.74 16.00; 1.44 0.57; 1.30 1.84; 1.29 4.00; 1.28 1.89; 1.20 0.46; 0.01 0.34; 0.00 11.62; −0.01 0.40
Compound No. 16 [CD₃CN] 8.31 0.58; 8.11 1.76; 8.10 1.80; 7.99 2.10; 7.98 1.94; 7.98 2.00; 7.95 1.07; 7.94 1.24; 7.93 1.42; 7.93 1.27; 7.92 1.35; 7.81 10.66; 7.66 0.46; 7.61 7.99; 7.50 2.97; 7.45 2.02; 7.44 2.58; 7.42 1.94; 7.27 0.45; 7.21 7.59; 6.16 0.40; 6.14 1.44; 6.13 2.01; 6.12 1.45; 6.10 0.44; 5.45 1.09; 4.49 1.90; 4.47 5.91; 4.46 5.93; 4.45 1.89; 3.82 0.36; 3.81 0.40; 2.89 0.89; 2.77 0.79; 2.77 0.75; 2.15 3.45; 2.06 0.36; 2.05 0.53; 2.05 0.38; 1.97 0.50; 1.97 0.70; 1.97 47.78; 1.96 2.45; 1.95 3.14; 1.95 33.04; 1.95 62.70; 1.94 91.90; 1.94 62.55; 1.93 31.53; 1.93 0.55; 1.83 0.38; 1.83 0.54; 1.82 0.38; 1.59 2.55; 1.58 6.23; 1.57 6.32; 1.56 3.04; 1.54 0.41; 1.42 0.34; 1.38 0.41; 1.37 0.37; 1.36 3.36; 1.35 6.35; 1.34 6.80; 1.33 2.88; 1.32 0.62; 1.31 1.04; 1.30 1.30; 1.30 7.34; 1.29 2.62; 1.29 16.00; 1.27 8.13; 1.22 0.33; 1.21 0.41; 1.20 0.46; 1.19 0.53; 1.19 0.34; 1.09 0.67; 1.08 0.76; 1.08 0.82; 1.07 0.73; 0.91 1.36; 0.90 1.33; 0.89 0.51; 0.88 0.91; 0.87 0.53; 0.01 1.50; 0.00 48.78; −0.01 1.52
Compound No. 17 [CD₃CN] 8.14 0.49; 8.12 0.49; 8.00 0.62; 7.99 0.58; 7.93 0.33; 7.93 0.36; 7.92 0.41; 7.92 0.34; 7.92 0.35; 7.77 3.80; 7.59 2.73; 7.45 0.60; 7.43 0.74; 7.42 0.56; 7.21 2.58; 7.21 2.55; 6.79 0.36; 6.15 0.44; 6.13 0.60; 6.12 0.44; 4.49 0.67; 4.48 2.15; 4.47 2.15; 4.45 0.66; 4.06 0.47; 4.05 0.47; 3.40 0.50; 3.39 0.62; 3.39 1.66; 3.38 1.71; 3.38 1.77; 3.37 1.68; 3.36 0.66; 3.35 0.53; 3.28 1.85; 3.27 1.89; 2.20 0.46; 2.19 0.66; 2.17 389.10; 2.06 0.48; 2.05 0.72; 2.05 0.48; 1.97 2.18; 1.97 5.41; 1.96 2.44; 1.95 3.22; 1.95 45.19; 1.95 87.72; 1.94 128.83; 1.94 88.19; 1.93 44.11; 1.93 1.32; 1.93 0.59; 1.83 0.49; 1.83 0.73; 1.82 0.50; 1.44 16.00; 1.30 2.42; 1.29 5.59; 1.28 2.47; 1.22 0.61; 1.21 3.51; 1.20 1.94; 1.19 7.21; 1.18 3.37; 1.13 0.40; 1.11 0.79; 1.10 0.40; 0.00 11.09; −0.01 0.33
Compound No. 18 [CD₃CN] 8.28 0.50; 8.15 1.11; 8.13 1.07; 7.83 1.69; 7.82 1.88; 7.81 1.87; 7.81 1.88; 7.76 10.36; 7.64 0.92; 7.63 0.96; 7.63 0.95; 7.62 1.23; 7.61 1.58; 7.61 1.22; 7.60 1.18; 7.59 7.27; 7.39 3.80; 7.38 0.55; 7.37 4.93; 7.35 3.02; 7.21 6.94; 7.20 7.32; 6.89 1.23; 6.09 0.39; 6.07 1.35; 6.05 1.80; 6.03 1.38; 6.01 0.47; 4.52 1.76; 4.51 0.38; 4.50 5.87; 4.48 5.91; 4.46 1.79; 4.39 0.74; 4.38 0.76; 4.36 0.35; 4.10 0.89; 4.08 0.93; 2.92 0.36; 2.91 1.11; 2.90 1.55; 2.89 2.47; 2.88 2.56; 2.87 1.48; 2.86 1.19; 2.85 0.41; 2.26 0.41; 2.25 0.60; 2.25 0.65; 2.25 0.67; 2.24 0.67; 2.24 0.80; 2.24 0.81; 2.24 0.77; 2.24 0.78; 2.24 0.85; 2.24 0.81; 2.24 0.90; 2.24 0.91; 2.23 1.03; 2.23 1.26; 2.23 1.29; 2.23 1.43; 2.23 1.55; 2.23 1.73; 2.23 2.08; 2.23 2.23; 2.23 2.45; 2.23 2.55; 2.23 2.59; 2.23 2.83; 2.22 2.99; 2.22 3.21; 2.22 3.50; 2.22 3.90; 2.21 667.68; 2.21 569.48; 2.20 4.79; 2.20 3.26; 2.19 2.52; 2.19 1.75; 2.19 1.56; 2.19 1.24; 2.19 0.89; 2.19 0.94; 2.19 0.95; 2.18 0.99; 2.18 0.93; 2.18 0.79; 2.18 0.61; 2.15 0.54; 2.14 0.94; 2.14 1.22; 2.13 0.81; 2.12 0.44; 2.00 4.26; 1.99 14.57; 1.99 7.14; 1.98 73.25; 1.98 138.96; 1.97 199.67; 1.96 135.48; 1.96 68.26; 1.95 1.31; 1.94 0.50; 1.81 0.34; 1.80 0.72; 1.80 1.09; 1.79 0.74; 1.79 0.38; 1.47 5.71; 1.42 0.80; 1.41 1.61; 1.39 0.79; 1.36 0.38; 1.33 6.86; 1.31 16.00; 1.29 6.79; 1.25 1.18; 1.23 2.27; 1.22 2.16; 1.22 1.16; 1.17 0.46; 1.16 0.45; 1.13 0.44; 0.82 1.22; 0.81 3.58; 0.80 4.61; 0.79 4.98; 0.79 3.22; 0.77 1.66; 0.64 1.74; 0.63 3.70; 0.63 3.58; 0.62 3.70; 0.62 3.28; 0.61 3.40; 0.60 1.12
Compound No. 19 cf. Synthesis Example 1
Compound No. 20 [CD₃CN] 10.05 0.35; 8.08 1.73; 8.07 1.78; 7.92 1.11; 7.80 11.27; 7.79 2.42; 7.79 2.41; 7.78 2.38; 7.77 2.33; 7.77 0.32; 7.65 0.34; 7.61 1.14; 7.61 1.23; 7.61 1.36; 7.60 9.54; 7.59 1.73; 7.59 1.48; 7.56 0.40; 7.51 3.11; 7.36 3.51; 7.35 5.57; 7.33 3.16; 7.19 7.87; 6.06 0.40; 6.04 1.48; 6.03 2.08; 6.01 1.52; 6.00 0.45; 5.45 8.25; 4.48 2.15; 4.47 6.36; 4.46 6.25; 4.45 1.94; 3.28 0.84; 3.27 0.85; 3.07 1.33; 2.89 12.88; 2.79 0.45; 2.77 11.04; 2.77 10.95; 2.18 0.66; 2.16 15.18; 2.06 0.37; 2.05 0.59; 2.05 0.59; 2.05 0.40; 1.97 0.47; 1.97 1.48; 1.96 2.62; 1.95 2.54; 1.95 33.61; 1.95 64.49; 1.94 95.43; 1.94 64.69; 1.93 32.56; 1.93 0.45; 1.83 0.37; 1.83 0.55; 1.82 0.38; 1.59 2.67; 1.58 6.55; 1.58 6.50; 1.57 3.11; 1.54 0.39; 1.39 0.35; 1.36 3.36; 1.35 6.55; 1.35 6.90; 1.34 2.99; 1.32 0.56; 1.32 0.49; 1.31 0.60; 1.31 0.89; 1.30 7.09; 1.29 2.16; 1.29

TABLE 1-continued
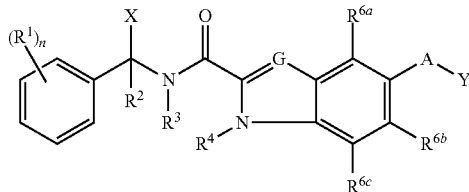
| No. | $(R^1)_n$ | X | $R^2$ | $R^3$ | $R^4$ | G | $R^{6a}$ | $R^{6b}$ | $R^{6c}$ | A | Y | $(M+H)^{+ a)}$ | log p $^{a)}$ |
|---|---|---|---|---|---|---|---|---|---|---|---|---|---|
16.00; 1.28 7.40; 1.20 0.41; 0.01 1.36; 0.00 47.99; −0.01 1.45
Compound No. 21 [CD₃CN] 12.98 0.36; 10.12 0.47; 8.42 0.42; 8.32 0.55; 8.18 1.61; 8.15 1.59; 8.13 0.41; 8.00 5.20; 7.97 0.37; 7.97 0.40; 7.92 2.76; 7.90 13.49; 7.86 0.34; 7.83 0.47; 7.82 2.46; 7.80 3.74; 7.75 0.35; 7.72 2.77; 7.70 3.99; 7.68 8.79; 7.38 1.74; 7.37 1.74; 7.36 0.96; 7.29 0.69; 7.27 8.33; 6.20 0.58; 6.19 1.84; 6.16 2.63; 6.14 1.80; 6.12 0.62; 4.54 2.18; 4.52 6.42; 4.50 6.42; 4.49 2.04; 4.30 12.44; 4.29 1 11.85; 3.9 0.32; 2.83 0.41; 2.37 0.40; 2.36 0.51; 2.23 737.55; 2.16 2.08; 2.15 1.39; 2.14 1.64; 2.14 1.89; 2.13 1.46; 2.13 1.06; 2.06 0.39; 2.05 0.39; 2.05 0.35; 2.04 0.39; 1.99 144.56; 1.99 18.81; 1.98 80.99; 1.98 153.45; 1.97 214.98; 1.96 148.87; 1.96 75.24; 1.94 1.18; 1.89 0.32; 1.82 0.76; 1.81 0.54; 1.80 0.90; 1.80 1.13; 1.79 1.03; 1.79 0.56; 1.39 0.34; 1.37 0.46; 1.35 0.55; 1.34 7.34; 1.32 16.00; 1.30 7.59; 1.29 0.33; 1.16 0.44; 1.14 0.97; 1.13 0.36; 0.94 0.44
Compound No. 22 [CD₃CN] 10.04 0.44; 8.25 0.85; 8.22 0.88; 8.15 0.35; 7.98 2.26; 7.92 1.16; 7.90 1.35; 7.79 1.08; 7.77 1.60; 7.69 7.18; 7.67 2.02; 7.65 0.78; 7.54 4.90; 7.17 4.85; 7.17 4.70; 7.02 1.22; 6.15 0.93; 6.13 1.22; 6.11 0.93; 4.48 1.16; 4.46 3.81; 4.44 3.82; 4.43 1.18; 3.60 0.50; 2.18 0.34; 2.16 224.20; 2.14 0.43; 2.11 0.34; 1.96 3.08; 1.96 2.40; 1.95 21.84; 1.95 41.43; 1.94 58.70; 1.93 39.49; 1.93 19.74; 1.77 0.32; 1.49 0.80; 1.46 16.00; 1.32 0.50; 1.29 4.32; 1.27 10.04; 1.26 4.19; 1.11 0.35; 0.84 1.05; 0.83 3.37; 0.82 3.41; 0.81 1.38; 0.67 1.85; 0.66 4.08; 0.66 4.19; 0.65 1.32; 0.00 1.40
Compound No. 23 [DMSO-D₆] 16.04 0.54; 12.04 0.82; 9.82 4.25; 9.79 4.29; 8.60 2.17; 8.58 4.26; 8.57 2.41; 8.24 0.63; 8.20 6.47; 8.08 3.64; 8.06 3.77; 8.00 8.99; 7.84 3.46; 7.82 4.79; 7.79 9.51; 7.74 3.42; 7.72 5.22; 7.70 2.17; 7.39 11.10; 6.36 0.77; 6.34 1.92; 6.32 2.68; 6.29 2.05; 6.27 0.56; 4.61 2.01; 4.60 5.79; 4.58 5.74; 4.56 2.00; 4.53 0.96; 4.51 6.97; 4.50 6.99; 3.47 0.57; 3.32 906.68; 3.30 14.04; 3.29 1.07; 3.27 0.75; 2.67 3.22; 2.50 481.75; 2.46 0.65; 2.33 2.75; 2.22 0.60; 2.07 1.88; 1.81 0.78; 1.80 1.72; 1.79 1.97; 1.78 2.79; 1.77 1.90; 1.76 1.97; 1.75 1.02; 1.73 1.01; 1.72 1.79; 1.71 2.01; 1.70 3.41; 1.69 1.98; 1.68 1.81; 1.67 0.95; 1.52 0.57; 1.50 0.69; 1.49 0.93; 1.47 0.63; 1.30 0.57; 1.28 0.72; 1.24 8.40; 1.22 16.00; 1.21 7.30; 1.17 0.55; 1.14 0.59; 1.12 0.72; 1.10 1.63; 1.09 1.71; 1.09 3.82; 1.08 6.74; 1.07 3.80; 1.06 6.19; 1.05 2.84; 1.04 1.82; 1.04 1.40; 1.02 3.19; 1.02 6.25; 1.00 6.06; 1.00 3.95; 0.98 1.55; 0.87 0.61; 0.81 1.49; 0.79 1.64; 0.78 1.47; 0.77 1.82; 0.76 1.25; 0.74 1.42; 0.72 8.94; 0.71 12.85; 0.69 7.49; 0.63 0.75; 0.15 0.95; 0.00 178.64; −0.15 0.82
Compound No. 24 [DMSO-D₆] 9.70 3.97; 9.67 4.09; 8.52 1.93; 8.51 3.95; 8.50 1.89; 8.20 5.68; 8.07 3.10; 8.05 3.38; 7.83 2.97; 7.81 4.14; 7.78 10.87; 7.74 3.12; 7.72 4.83; 7.70 2.03; 7.66 11.30; 7.34 10.44; 6.34 0.44; 6.31 1.61; 6.29 2.34; 6.27 1.64; 6.25 0.52; 4.52 1.87; 4.50 5.32; 4.49 5.36; 4.47 1.78; 4.41 8.23; 4.40 8.08; 4.02 0.38; 3.33 277.41; 3.30 3.78; 2.68 0.77; 2.67 0.96; 2.67 0.73; 2.51 114.66; 2.50 149.84; 2.50 104.34; 2.33 0.69; 2.33 0.96; 2.32 0.65; 2.08 0.56; 1.99 1.72; 1.78 0.37; 1.71 0.79; 1.70 1.72; 1.69 1.73; 1.69 1.49; 1.68 3.20; 1.67 1.82; 1.66 1.76; 1.65 0.86; 1.23 1.39; 1.22 7.31; 1.20 16.00; 1.18 7.00; 1.17 1.59; 1.16 0.61; 1.09 0.63; 1.08 0.84; 1.07 0.51; 1.06 0.84; 1.05 0.38; 1.02 0.50; 1.02 0.83; 1.01 0.63; 1.00 0.71; 1.00 0.50; 0.77 0.38; 0.75 0.33; 0.73 1.06; 0.71 3.87; 0.71 8.37; 0.70 7.10; 0.69 9.87; 0.69 10.14; 0.68 3.51; 0.67 4.08; 0.67 7.14; 0.66 2.85; 0.65 0.83; 0.01 3.05; 0.00 70.59; −0.01 2.33; −0.15 0.36
Compound No. 25 [DMSO-D₆] 11.97 0.37; 9.70 2.29; 9.68 2.38; 8.25 1.21; 8.23 2.24; 8.22 1.12; 8.20 3.32; 8.07 1.80; 8.05 1.98; 7.83 1.82; 7.81 2.45; 7.77 6.29; 7.74 1.88; 7.72 2.72; 7.70 1.17; 7.64 6.33; 7.33 6.14; 6.31 0.96; 6.29 1.38; 6.27 1.01; 4.52 1.15; 4.50 3.19; 4.48 3.03; 4.46 1.01; 4.39 4.80; 4.37 4.71; 3.40 0.69; 3.33 198.12; 3.30 3.13; 2.68 0.68; 2.67 0.87; 2.67 0.62; 2.54 3.26; 2.51 105.26; 2.50 137.72; 2.50 95.59; 2.33 0.66; 2.33 0.91; 2.32 0.65; 2.22 2.19; 2.20 6.35; 2.18 6.43; 2.16 2.13; 2.08 0.48; 2.04 0.35; 2.03 0.44; 1.99 1.14; 1.24 0.98; 1.22 4.30; 1.20 9.25; 1.18 4.05; 1.18 1.05; 1.09 0.32; 1.07 7.67; 1.05 16.00; 1.03 7.23; 1.02 0.47; 1.01 0.91; 0.99 1.88; 0.97 1.21; 0.95 0.51; 0.01 2.66; 0.00 63.20; −0.01 2.15
Compound No. 26 cf. Synthesis Example 3
Compound No. 27 [CD3CN] 8.22 1.05; 8.17 0.39; 8.14 4.49; 8.14 4.53; 8.05 0.39; 8.02 1.35; 8.00 3.01; 7.98 2.01; 7.94 1.16; 7.93 1.22; 7.92 1.46; 7.91 1.13; 7.75 2.74; 7.74 2.60; 7.73 3.39; 7.72 3.16; 7.60 1.16; 7.53 3.98; 7.51 3.12; 7.47 0.44; 7.46 1.87; 7.45 0.51; 7.43 2.29; 7.41 1.74; 7.27 7.45; 7.25 0.59; 7.05 0.42; 7.02 1.42; 6.18 0.42; 6.16 1.52; 6.14 1.99; 6.12 1.45; 6.09 0.53; 6.05 0.36; 4.55 1.84; 4.53 5.87; 4.52 5.78; 4.50 1.87; 4.38 0.49; 4.36 1.39; 4.34 1.26; 4.32 0.39; 4.07 0.57; 4.05 0.50; 2.88 1.24; 2.88 1.55; 2.87 2.19; 2.86 2.08; 2.85 1.53; 2.84 1.05; 2.83 0.49; 2.77 0.49; 2.55 0.39; 2.45 0.44; 2.39 0.36; 2.33 0.48; 2.28 0.86; 2.27 0.96; 2.25 1.58; 2.15 225.44; 2.11 5.65; 2.11 5.08; 2.10 3.74; 2.05 0.99; 1.97 9.62; 1.96 27.51; 1.96 28.81; 1.95 161.86; 1.95 296.23; 1.94 411.76; 1.93 278.85; 1.93 141.11; 1.78 0.92; 1.77 1.80; 1.77 2.35; 1.76 1.53; 1.76 0.72; 1.54 0.39; 1.42 0.37; 1.39 1.46; 1.37 2.90; 1.35 1.49; 1.34 1.19; 1.32 7.27; 1.30 16.00; 1.28 9.53; 1.27 8.80; 1.22 0.97; 1.20 1.61; 1.19 0.85; 1.16 0.45; 1.09 0.56; 0.93 0.41; 0.92 1.06; 0.90 1.20; 0.88 1.70; 0.86 0.86; 0.84 0.53; 0.83 0.51; 0.82 0.36; 0.78 1.28; 0.77 3.56; 0.76 4.51; 0.75 4.64; 0.74 3.49; 0.73 1.66; 0.71 0.37; 0.69 0.43; 0.66 0.43; 0.63 1.80; 0.62 4.18; 0.61 3.92; 0.61 3.55; 0.60 3.30; 0.59 1.12; 0.15 0.69; 0.08 0.70; 0.05 0.64; 0.01 6.88; 0.00 170.47; −0.01 6.32; −0.15 0.66
Compound No. 28 [CD₃CN] 8.18 0.39; 8.16 0.37; 7.98 1.20; 7.91 0.62; 7.89 0.74; 7.82 3.51; 7.79 0.59; 7.77 0.86; 7.70 0.70; 7.68 1.03; 7.66 0.41; 7.60 2.59; 7.37 0.77; 7.22 2.44; 7.22 2.59; 6.16 0.48; 6.14 0.65; 6.12 0.49; 4.50 0.58; 4.48 1.92; 4.46 1.96; 4.45 0.61; 3.70 16.00; 3.69 0.71; 2.19 28.42; 2.19 49.69; 2.18 49.25; 2.18 64.19; 2.18 80.87; 2.11 0.38; 1.97 3.24; 1.96 2.10; 1.96 22.00; 1.95 43.08; 1.94 60.93; 1.94 41.83; 1.93 21.51; 1.77 0.35; 1.55 0.97; 1.54 2.62; 1.53 2.76; 1.52 1.17; 1.30 2.30; 1.28 5.38; 1.27 2.31; 1.25 1.23; 1.24 2.72; 1.24 2.67; 1.22 0.97; 0.00 3.98
Compound No. 29 [CD₃CN] 8.24 1.00; 8.22 1.00; 7.98 3.32; 7.92 1.72; 7.90 2.07; 7.79 1.60; 7.77 2.37; 7.70 10.21; 7.70 2.27; 7.68 2.96; 7.66 1.19; 7.55 7.36; 7.18 7.14; 7.18 7.22; 7.07 1.89; 6.18 0.38; 6.16 1.36; 6.14 1.83; 6.11 1.39; 6.09 0.43; 4.48 1.68; 4.46 5.59; 4.45 5.69; 4.43 1.77; 2.19 95.85; 2.19 90.53; 2.18 90.68; 2.12 0.45; 2.11 0.60; 2.10 0.46; 1.97 0.49; 1.97 3.31; 1.96 3.09; 1.96 33.15; 1.95 62.98; 1.94 87.69; 1.94 60.24; 1.93 31.13; 1.92 0.68; 1.78 0.37; 1.77 0.53; 1.77 0.37; 1.46 0.59; 1.45 1.24; 1.44 1.39; 1.43 1.04; 1.43 2.50; 1.42 0.82; 1.41 1.36; 1.40 1.32; 1.39 0.68; 1.31 0.32; 1.29 6.89; 1.28 16.00; 1.27 2.61; 1.26 6.71; 0.88 0.33; 0.80 2.01; 0.79 5.40; 0.78 5.95; 0.77 3.09; 0.73 0.42; 0.71 0.43; 0.67 3.18; 0.66 5.99; 0.65 5.60; 0.64 2.14; 0.46 1.38; 0.45 3.99; 0.44 4.30; 0.44 1.85; 0.43 2.09; 0.43 4.24; 0.42 3.95; 0.41 1.87; 0.28 1.96; 0.27 4.50; 0.26 4.72; 0.26 4.31; 0.25 4.62; 0.24 1.39; 0.00 5.98
Compound No. 30 [CD₃CN] 8.15 1.21; 8.13 1.16; 7.97 3.52; 7.91 1.83; 7.89 2.20; 7.79 1.66; 7.77 2.49; 7.71 9.31; 7.69 2.11; 7.67 2.98; 7.66 1.20; 7.57 7.16; 7.19 7.26; 7.02 1.93; 6.18 0.38; 6.16 1.41; 6.14 1.91; 6.11 1.44; 6.09 0.44; 4.49 1.71; 4.47 5.49; 4.46 5.61; 4.44 1.83; 2.18 175.31; 2.18 238.15; 2.17 224.02; 2.12 0.68; 2.12 0.92; 2.11 1.17; 2.10 0.89; 2.10 0.50; 1.97 6.51; 1.96 7.95; 1.96 63.19; 1.95 119.53; 1.94 166.08; 1.94 115.93; 1.93 62.19; 1.78 0.40; 1.78 0.72; 1.77 1.00; 1.76 0.72; 1.76 0.40; 1.71 1.75; 1.69 5.75; 1.67 6.14; 1.66 2.20; 1.30 6.80; 1.28 14.82; 1.26 6.61; 1.05 7.68; 1.03 16.00; 1.01 7.14; 0.98 0.33; 0.82 1.86; 0.80 5.68; 0.80 6.10; 0.79 2.93; 0.75 0.38; 0.72 0.40; 0.68 3.15; 0.67 6.41; 0.67 6.28; 0.65 2.31; 0.00 7.26; −0.01 0.41
Compound No. 31 [CD₃CN] 8.10 1.23; 8.07 1.27; 7.97 3.27; 7.90 1.70; 7.88 2.06; 7.79 1.74; 7.78 8.88; 7.77 2.61; 7.70 1.88; 7.68 2.84; 7.66 1.38; 7.64 2.13; 7.61 6.78; 7.22 6.69; 6.18 0.36; 6.16 1.31; 6.14 1.80; 6.12 1.35; 6.09 0.40; 4.51 1.53; 4.49 4.96; 4.47 5.06; 4.45 1.68; 3.73 2.19; 3.71 7.11; 3.70 7.26; 3.68 2.40; 2.23 0.51; 2.23 0.52; 2.22 0.56; 2.18 648.78; 2.17 518.21; 2.12 1.13; 2.12 1.53; 2.11 1.99; 2.10 1.57;

TABLE 1-continued
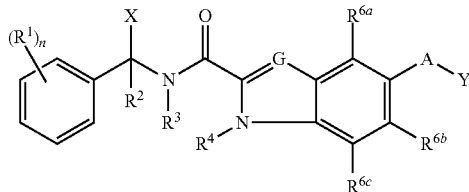
(I)
| No. | $(R^1)_n$ | X | $R^2$ | $R^3$ | $R^4$ | G | $R^{6a}$ | $R^{6b}$ | $R^{6c}$ | A | Y | $(M+H)^{+ a)}$ | log p $^{a)}$ |
|---|---|---|---|---|---|---|---|---|---|---|---|---|---|
2.10 0.88; 1.97 11.38; 1.96 13.56; 1.95 111.69; 1.95 210.38; 1.94 293.25; 1.94 204.62; 1.93 109.92; 1.78 0.70; 1.78 1.23; 1.77 1.72; 1.76 1.25; 1.76 0.68; 1.44 6.16; 1.30 6.30; 1.29 13.52; 1.27 6.58; 1.17 7.81; 1.15 16.00; 1.13 7.65; 1.11 1.82; 1.09 4.12; 1.09 5.24; 1.07 3.28; 1.04 0.73; 1.03 0.74; 1.00 3.10; 0.99 5.17; 0.99 4.28; 0.97 1.92; 0.88 0.32; 0.01 0.46; 0.00 13.02; −0.01 0.67
Compound No. 32 [CD3CN] 8.1153 1.33; 8.0916 1.34; 7.9638 3.77; 7.8920 1.97; 7.8727 2.40; 7.7862 1.77; 7.7666 2.75; 7.7574 10.19; 7.6920 2.20; 7.6724 3.28; 7.6528 1.31; 7.6028 8.02; 7.3257 2.33; 7.2191 8.01; 6.1732 0.43; 6.1521 1.53; 6.1302 2.11; 6.1082 1.59; 6.0866 0.48; 4.5010 1.89; 4.4832 6.03; 4.4654 6.13; 4.4477 1.99; 2.4235 10.57; 2.1921 679.25; 2.1866 1166.03; 2.1206 1.65; 2.1144 2.02; 2.1081 2.56; 2.1020 1.83; 2.0959 1.16; 2.0874 0.63; 2.0266 0.32; 1.9723 1.39; 1.9651 12.24; 1.9590 13.12; 1.9532 108.76; 1.9470 204.00; 1.9408 285.97; 1.9346 201.93; 1.9284 107.88; 1.7816 0.73; 1.7754 1.29; 1.7692 1.77; 1.7631 1.25; 1.7569 0.71; 1.3401 0.78; 1.2988 7.42; 1.2811 16.00; 1.2712 2.44; 1.2631 7.98; 1.2456 4.52; 1.2385 6.39; 1.2298 4.80; 1.2039 0.81; 1.1957 4.78; 1.1866 6.22; 1.1799 4.51; 1.1639 1.94; 0.8823 0.43; −0.0002 1.43
Compound No. 33 [CD3CN] 8.2991 1.30; 8.2763 1.22; 8.0004 4.10; 7.9518 2.13; 7.9322 2.52; 7.8159 2.03; 7.8045 10.53; 7.7967 3.25; 7.7241 2.34; 7.7045 3.45; 7.6850 1.38; 7.6041 8.01; 7.3015 2.45; 7.2284 8.32; 6.2051 0.46; 6.1838 1.62; 6.1621 2.24; 6.1398 1.68; 6.1185 0.51; 4.5195 1.89; 4.5018 6.08; 4.4840 6.22; 4.4663 2.06; 2.7331 9.82; 2.5678 0.64; 2.5540 5.18; 2.5406 3.87; 2.5343 10.14; 2.5158 4.82; 2.4853 0.49; 2.2520 143.31; 2.2459 247.47; 2.1724 0.52; 2.1526 0.84; 2.1440 0.85; 2.1371 0.50; 2.1314 1.21; 2.1244 2.02; 2.1126 1.27; 2.1036 2.67; 2.0978 1.36; 2.0924 1.62; 2.0837 2.15; 2.0773 2.39; 2.0711 1.19; 2.0606 1.32; 2.0564 1.38; 2.0492 0.89; 2.0400 0.68; 2.0322 0.40; 2.0282 0.46; 2.0008 0.63; 1.9941 0.85; 1.9877 1.06; 1.9822 13.07; 1.9760 25.24; 1.9698 36.59; 1.9637 25.98; 1.9575 14.01; 1.4639 1.63; 1.3282 7.27; 1.3105 16.00; 1.2927 7.23
Compound No. 34 [CD3CN] 8.2615 1.06; 8.2383 1.07; 7.9739 3.19; 7.9178 1.67; 7.8984 2.02; 7.8036 8.10; 7.7891 1.63; 7.7691 2.24; 7.6951 1.82; 7.6755 2.70; 7.6559 1.09; 7.5778 6.44; 7.3743 2.32; 7.2042 6.38; 6.1764 0.34; 6.1550 1.26; 6.1330 1.74; 6.1110 1.30; 6.0897 0.38; 4.4911 1.46; 4.4734 4.72; 4.4556 4.82; 4.4379 1.56; 4.1794 2.38; 4.1616 7.49; 4.1438 7.62; 4.1261 2.52; 2.7272 1.66; 2.2079 105.08; 2.2051 173.86; 2.1998 226.53; 2.1211 0.34; 2.1148 0.38; 2.1087 0.43; 2.1025 0.34; 1.9656 2.26; 1.9595 2.36; 1.9537 20.05; 1.9475 37.63; 1.9413 52.81; 1.9351 37.22; 1.9289 19.88; 1.7697 0.33; 1.5411 2.16; 1.5290 6.01; 1.5208 6.43; 1.5098 2.69; 1.3399 0.43; 1.3001 5.46; 1.2824 12.39; 1.2730 8.84; 1.2646 5.87; 1.2552 16.00; 1.2444 3.31; 1.2374 8.66; 1.2335 7.07; 1.2252 6.35; 1.2131 2.32; −0.0002 0.47
Compound No. 36 [CD3CN] 8.1771 1.48; 8.1536 1.50; 7.9698 3.98; 7.8988 2.47; 7.8799 2.51; 7.8698 10.29; 7.7895 1.90; 7.7700 2.83; 7.6960 2.32; 7.6846 0.73; 7.6764 3.47; 7.6567 1.42; 7.6415 7.92; 7.5847 2.31; 7.5540 0.56; 7.2632 0.42; 7.2436 7.70; 6.1794 0.44; 6.1583 1.61; 6.1363 2.23; 6.1141 1.67; 6.0929 0.50; 4.5137 1.96; 4.4959 6.14; 4.4781 6.22; 4.4603 2.00; 2.7968 1.43; 2.7905 0.77; 2.7821 1.77; 2.7752 2.20; 2.7711 1.45; 2.7686 1.58; 2.7637 2.24; 2.7609 2.26; 2.7535 1.53; 2.7494 2.69; 2.7430 2.31; 2.7359 0.95; 2.7285 2.02; 2.5332 1.65; 2.5261 0.76; 2.5139 2.44; 2.5103 3.11; 2.5013 1.78; 2.4907 2.48; 2.4817 2.58; 2.4776 2.09; 2.4647 0.90; 2.4583 1.74; 2.3550 0.54; 2.3029 1.34; 2.2273 1287.97; 2.1851 6.41; 2.1694 3.77; 2.1652 4.69; 2.1550 2.51; 2.1460 4.42; 2.1377 1.76; 2.1320 2.07; 2.1233 2.08; 2.1158 1.62; 2.1092 2.07; 2.1032 1.43; 2.0971 0.86; 2.0796 0.52; 1.9778 0.37; 1.9663 19.95; 1.9602 6.07; 1.9543 62.78; 1.9482 120.34; 1.9420 170.65; 1.9358 119.46; 1.9296 62.77; 1.7827 0.48; 1.7766 0.80; 1.7704 1.12; 1.7642 0.79; 1.7581 0.48; 1.3290 0.38; 1.3228 0.57; 1.3105 7.44; 1.2927 16.00; 1.2749 7.57; −0.0002 0.50
Compound No. 37 [CD3CN] 8.6889 1.03; 8.6646 1.06; 7.8020 9.28; 7.7956 2.00; 7.7903 2.05; 7.7781 1.70; 7.7726 1.75; 7.7326 9.09; 7.6121 0.85; 7.6064 0.88; 7.6009 0.95; 7.5908 1.16; 7.5849 1.09; 7.5796 1.11; 7.5738 0.96; 7.3655 2.95; 7.3431 4.41; 7.3211 2.48; 6.9170 1.22; 6.0344 0.35; 6.0137 1.19; 5.9931 1.43; 5.9902 1.38; 5.9696 1.20; 5.9491 0.37; 4.6651 1.48; 4.6474 4.19; 4.6460 4.15; 4.6280 4.35; 4.6103 1.53; 3.8138 0.76; 2.8902 0.33; 2.8804 0.99; 2.8709 1.35; 2.8624 2.14; 2.8528 2.20; 2.8443 1.33; 2.8348 1.05; 2.8251 0.35; 2.1831 633.66; 2.1361 1.24; 2.1206 0.80; 2.1144 1.00; 2.1082 1.22; 2.1021 0.91; 2.0959 0.56; 1.9723 0.40; 1.9651 3.88; 1.9591 4.61; 1.9532 54.93; 1.9470 105.13; 1.9409 148.37; 1.9347 102.58; 1.9285 53.01; 1.9156 1.08; 1.7816 0.36; 1.7754 0.64; 1.7693 0.92; 1.7631 0.65; 1.7569 0.35; 1.4369 16.00; 1.4054 6.74; 1.3875 15.23; 1.3695 6.56; 1.2699 1.44; 0.7976 1.17; 0.7852 3.35; 0.7798 4.56; 0.7673 4.79; 0.7619 3.29; 0.7497 1.64; 0.6233 1.57; 0.6133 3.57; 0.6116 3.68; 0.6060 3.86; 0.6017 3.43; 0.5964 3.51; 0.5842 1.11; −0.0002 1.95
Compound No. 38 [CD3CN] 8.9188 1.19; 8.8949 1.19; 8.0219 1.76; 8.0051 1.74; 7.9656 0.90; 7.9551 1.08; 7.9460 1.25; 7.9328 1.12; 7.8106 9.49; 7.7983 0.44; 7.7393 9.63; 7.7388 9.63; 7.4584 1.98; 7.4340 2.24; 7.4112 1.65; 7.3980 0.52; 7.3761 0.33; 7.0326 1.41; 6.1454 0.38; 6.1251 1.31; 6.1044 1.62; 6.0811 1.32; 6.0604 0.42; 5.4517 5.94; 4.6619 1.63; 4.6442 4.51; 4.6248 4.65; 4.6072 1.67; 4.0691 0.69; 4.0513 0.70; 3.7405 0.88; 2.8914 0.43; 2.8814 1.04; 2.8719 1.45; 2.8634 2.28; 2.8538 2.35; 2.8453 1.43; 2.8358 1.13; 2.8260 0.39; 2.4848 1.89; 2.4800 3.77; 2.4752 5.38; 2.4705 3.92; 2.4658 2.08; 2.2778 2202.44; 2.1965 3.08; 2.1225 1.17; 2.1164 1.75; 2.1102 2.26; 2.1040 1.68; 2.0978 1.09; 1.9735 3.75; 1.9671 8.20; 1.9610 9.45; 1.9552 111.09; 1.9490 213.30; 1.9428 303.85; 1.9366 212.15; 1.9304 110.51; 1.9176 2.53; 1.7836 0.78; 1.7774 1.37; 1.7712 1.95; 1.7651 1.36; 1.7589 0.78; 1.5433 0.33; 1.4367 0.85; 1.4029 7.09; 1.3850 16.00; 1.3671 7.10; 1.3516 0.68; 1.3399 0.56; 1.3341 0.40; 1.2850 1.06; 1.2763 2.37; 1.2702 4.09; 1.2536 0.41; 1.2221 1.08; 1.2042 1.91; 1.1864 0.98; 0.8813 0.57; 0.8633 0.32; 0.7968 1.27; 0.7845 3.59; 0.7791 4.90; 0.7666 5.12; 0.7612 3.59; 0.7491 1.76; 0.6237 1.70; 0.6120 4.02; 0.6063 4.22; 0.6021 3.77; 0.5967 3.80; 0.5845 1.19; −0.0002 1.57
Compound No. 39 [DMSO] 9.7457 1.86; 9.7216 1.91; 9.2863 4.17; 7.8934 3.63; 7.8414 13.84; 7.7099 1.59; 7.6938 1.81; 7.5332 0.68; 7.5284 0.64; 7.5140 7.38; 7.5084 2.45; 7.4981 3.17; 7.4780 0.76; 7.3880 5.50; 6.1853 0.81; 6.1730 0.58; 6.1632 1.20; 6.1525 0.56; 6.1409 0.86; 4.5444 1.01; 4.5271 3.02; 4.5093 3.01; 4.4916 0.99; 3.3212 35.22; 3.2954 4.16; 2.6708 0.42; 2.5238 1.18; 2.5105 24.10; 2.5061 48.56; 2.5017 64.11; 2.4972 46.11; 2.4929 22.30; 2.3327 0.32; 2.2385 0.42; 2.3236 0.33; 1.5997 1.71; 1.5856 4.32; 1.5786 4.64; 1.5656 1.96; 1.3972 16.00; 1.2880 1.97; 1.2747 4.22; 1.2681 4.40; 1.2535 1.61; 1.2280 4.23; 1.2107 9.21; 1.1930 4.13; 0.0079 1.64; −0.0002 44.65; −0.0084 1.64
Compound No. 40 [DMSO] 9.7064 3.95; 9.6822 4.05; 8.3926 4.38; 8.3815 4.43; 8.0263 6.39; 7.7860 11.15; 7.7567 15.77; 7.7306 3.83; 7.6602 3.18; 7.6577 3.05; 7.6401 3.70; 7.6376 3.77; 7.4515 4.55; 7.4318 7.49; 7.4120 3.51; 7.3754 10.81; 7.3631 0.69; 6.1910 0.41; 6.1699 1.60; 6.1477 2.41; 6.1252 1.74; 6.1027 0.48; 4.5370 1.77; 4.5196 5.40; 4.5019 5.40; 4.4845 1.76; 4.0556 0.40; 4.0379 1.23; 4.0201 1.23; 4.0023 0.43; 3.3202 93.01; 3.2965 0.67; 2.8659 0.42; 2.8560 1.19; 2.8464 1.63; 2.8378 2.60; 2.8276 2.63; 2.8194 1.65; 2.8094 1.25; 2.7993 0.47; 2.6748 0.73; 2.6705 1.00; 2.6658 0.72; 2.5405 0.53; 2.5237 2.39; 2.5102 54.27; 2.5058 109.67; 2.5013 144.43; 2.4968 103.66; 2.4925 49.60; 2.3326 0.80; 2.3281 1.03; 2.3236 0.77; 1.9888 5.45; 1.4003 0.98; 1.3357 1.00; 1.2985 0.50; 1.2583 0.93; 1.2493 1.42; 1.2341 0.83; 1.2199 7.32; 1.2025 16.00; 1.1922 3.38; 1.1849 7.16; 1.1745 3.45; 1.1567 1.57; 0.7181 1.73; 0.7052 4.85; 0.7000 6.78; 0.6880 6.25; 0.6820 5.30; 0.6708 2.20; 0.5562 2.30; 0.5456 6.83; 0.5393 6.13; 0.5300 5.47; 0.5178 1.68; −0.0002 1.81
Compound No. 41 [DMSO] 9.7421 2.31; 9.7180 2.36; 9.2859 5.24; 8.0247 3.68; 7.8417 16.00; 7.7495 1.92; 7.7303 2.17; 7.6619 1.82; 7.6594 1.70; 7.6438 2.03; 7.6418 2.11; 7.6392 2.15; 7.4534 2.60; 7.4337 4.31; 7.4139 2.02; 7.3858 6.36; 6.1751 0.92; 6.1528 1.39;

TABLE 1-continued

Structure (I): Formula with substituents $(R^1)_n$, X, $R^2$, $R^3$, $R^4$, G, $R^{6a}$, $R^{6b}$, $R^{6c}$, A, Y

| No. | $(R^1)_n$ | X | $R^2$ | $R^3$ | $R^4$ | G | $R^{6a}$ | $R^{6b}$ | $R^{6c}$ | A | Y | $(M+H)^{+\,a)}$ | log p $^{a)}$ |
|---|---|---|---|---|---|---|---|---|---|---|---|---|---|

6.1301 0.99; 4.5426 1.03; 4.5254 3.02; 4.5078 2.99; 4.4903 1.00; 3.3206 67.32; 2.8904 2.49; 2.7313 2.01; 2.6750 0.49; 2.6706 0.63; 2.6661 0.46; 2.5407 0.43; 2.5103 35.69; 2.5059 70.33; 2.5015 91.34; 2.4969 64.57; 2.4925 30.39; 2.3326 0.48; 2.3282 0.63; 2.3238 0.45; 1.5992 1.77; 1.5850 4.33; 1.5782 4.63; 1.5652 1.98; 1.2981 0.48; 1.2876 2.14; 1.2742 4.39; 1.2675 4.64; 1.2585 1.05; 1.2529 1.76; 1.2274 4.20; 1.2100 9.01; 1.1923 4.01; −0.0002 0.78

Compound No. 42 [DMSO] 9.7154 2.28; 9.6912 2.36; 9.2860 5.27; 8.1984 1.75; 8.1936 1.85; 8.1818 1.81; 8.1771 1.79; 7.8428 16.00; 7.8271 1.11; 7.8174 1.21; 7.8117 1.13; 7.8053 1.08; 7.8003 0.95; 7.5212 2.33; 7.4995 4.33; 7.4778 2.10; 7.3757 6.40; 6.2220 0.91; 6.1995 1.38; 6.1772 0.97; 4.5414 1.00; 4.5241 3.01; 4.5064 3.01; 4.4887 0.98; 4.0380 0.86; 4.0202 0.87; 3.3202 49.11; 3.2967 0.34; 2.6751 0.46; 2.6707 0.61; 2.6663 0.45; 2.5239 1.46; 2.5105 32.58; 2.5061 66.20; 2.5016 87.59; 2.4971 62.89; 2.4927 30.01; 2.3329 0.44; 2.3284 0.61; 2.3241 0.43; 1.9890 3.79; 1.6000 1.77; 1.5858 4.34; 1.5790 4.67; 1.5660 1.95; 1.3973 6.45; 1.2982 0.63; 1.2870 2.17; 1.2736 4.45; 1.2669 4.71; 1.2587 1.25; 1.2525 1.82; 1.2282 4.30; 1.2108 9.23; 1.1928 5.00; 1.1747 2.20; 1.1569 1.07; −0.0002 0.64

Compound No. 43 601.6 MHz 9.7088 3.55; 9.6926 3.72; 9.2857 8.18; 7.9153 12.63; 7.9125 12.15; 7.8497 14.94; 7.8459 10.09; 7.7894 0.48; 7.7656 0.69; 7.7511 0.50; 7.7324 4.65; 7.7293 8.71; 7.7262 4.47; 7.3893 8.90; 7.3787 0.52; 6.2682 1.14; 6.2539 1.72; 6.2390 1.24; 6.2245 0.35; 4.5318 1.64; 4.5202 4.94; 4.5083 4.93; 4.4965 1.61; 3.3176 270.67; 3.3038 0.66; 3.2938 10.10; 2.6188 0.87; 2.6158 1.91; 2.6127 2.65; 2.6097 1.91; 2.6067 0.88; 2.5404 0.76; 2.5221 3.50; 2.5190 4.48; 2.5159 4.78; 2.5071 140.39; 2.5040 305.21; 2.5010 425.77; 2.4979 304.51; 2.4949 139.92; 2.3912 0.80; 2.3882 1.82; 2.3852 2.56; 2.3821 1.81; 2.3791 0.79; 1.5934 2.88; 1.5841 6.60; 1.5796 7.45; 1.5708 2.91; 1.2812 3.23; 1.2721 6.65; 1.2678 7.24; 1.2582 2.67; 1.2333 1.07; 1.2249 7.45; 1.2132 16.00; 1.2015 7.58; 1.1941 0.74; 0.6979 0.42; 0.6896 0.38; 0.6859 0.32; 0.5429 0.40; 0.5390 0.37; 0.5360 0.34; 0.5328 0.37; 0.0965 0.36; 0.0052 2.82; −0.0002 98.55; −0.0058 2.84; −0.1001 0.37

Compound No. 44 [DMSO] 9.8069 1.75; 9.7827 1.77; 9.2977 3.88; 8.2115 2.69; 8.0711 1.46; 8.0516 1.59; 7.8521 6.19; 7.8339 1.37; 7.8069 5.19; 7.7378 1.38; 7.7183 2.12; 7.6987 0.88; 7.4165 4.75; 7.3976 6.73; 6.2956 1.10; 6.2733 0.77; 3.9506 16.00; 3.3229 57.78; 3.2999 0.87; 2.6710 0.46; 2.6666 0.33; 2.5063 53.36; 2.5020 67.56; 2.4976 49.02; 2.3287 0.46; 2.0749 0.36; 1.6006 1.31; 1.5865 3.43; 1.5797 3.66; 1.5666 1.50; 1.2929 1.62; 1.2795 3.44; 1.2727 3.62; 1.2583 1.27; 0.0077 0.86; −0.0002 20.79; −0.0083 0.89

Compound No. 45 [CD3CN] 601.6 MHz 7.9352 0.45; 7.9190 0.46; 7.7552 3.80; 7.6635 1.36; 7.5683 2.77; 7.5542 0.61; 7.5435 0.70; 7.4802 0.36; 7.4705 1.77; 7.4671 3.39; 7.4637 1.27; 7.4573 1.42; 7.4440 0.32; 7.2106 2.58; 7.2095 2.58; 6.8092 0.42; 6.0289 0.52; 6.0145 0.66; 5.9996 0.50; 3.9539 0.88; 3.9331 16.00; 3.2798 1.74; 3.2707 1.66; 2.8640 0.43; 2.8576 0.55; 2.8520 0.94; 2.8456 0.97; 2.8399 0.56; 2.8336 0.45; 2.1445 0.57; 2.1403 0.52; 2.1284 469.72; 2.1154 0.61; 2.0970 1.26; 2.0952 1.43; 2.0935 1.21; 2.0578 1.12; 2.0536 2.17; 2.0495 3.37; 2.0455 2.29; 2.0414 1.11; 1.9673 0.35; 1.9632 18.26; 1.9551 13.85; 1.9510 16.92; 1.9472 206.75; 1.9431 406.53; 1.9390 590.12; 1.9349 383.37; 1.9307 193.46; 1.9261 5.03; 1.9219 2.17; 1.9170 0.58; 1.9128 0.49; 1.9087 0.36; 1.8325 1.11; 1.8283 2.13; 1.8242 3.32; 1.8201 2.27; 1.8160 1.10; 1.5417 1.26; 1.2705 0.49; 0.7789 0.52; 0.7702 1.37; 0.7673 1.90; 0.7588 1.77; 0.7555 1.43; 0.7472 0.61; 0.5986 0.60; 0.5919 1.32; 0.5905 1.39; 0.5875 1.41; 0.5840 1.37; 0.5811 1.38; 0.5726 0.47; 0.0053 0.56; −0.0002 20.93; −0.0058 0.54

Compound No. 46 [DMSO] 9.7177 1.65; 9.6936 1.70; 9.3061 3.76; 7.9008 2.66; 7.8451 6.36; 7.8077 4.50; 7.7126 1.22; 7.7075 1.01; 7.6962 1.37; 7.5323 0.59; 7.5170 2.36; 7.5127 5.56; 7.5073 2.04; 7.4957 2.30; 7.4757 0.61; 7.4146 4.28; 6.1804 0.65; 6.1578 0.98; 6.1357 0.71; 3.9517 16.00; 3.3290 77.33; 3.0294 0.55; 2.7612 0.45; 2.6757 0.39; 2.6711 0.54; 2.6666 0.40; 2.5411 0.34; 2.5244 2.18; 2.5197 3.53; 2.5111 29.97; 2.5066 59.78; 2.5020 78.80; 2.4975 57.13; 2.4930 27.54; 2.3334 0.41; 2.3287 0.56; 2.3242 0.41; 2.0758 1.77; 1.6010 1.29; 1.5869 3.02; 1.5799 3.23; 1.5670 1.40; 1.2916 1.50; 1.2781 3.02; 1.2715 3.24; 1.2570 1.18; −0.0002 4.80

Compound No. 47 [DMSO] 9.6807 1.52; 9.6565 1.59; 8.4128 1.74; 8.4017 1.77; 8.0338 2.48; 7.7598 6.87; 7.7535 5.80; 7.7333 1.48; 7.6594 1.24; 7.6568 1.16; 7.6412 1.35; 7.6394 1.42; 7.6367 1.47; 7.4490 1.92; 7.4293 3.17; 7.4095 1.77; 7.4010 4.22; 6.1651 0.61; 6.1427 0.92; 6.1200 0.67; 5.7594 0.46; 3.9558 0.73; 3.9433 16.00; 3.3282 84.57; 2.8574 0.49; 2.8475 0.63; 2.8392 1.04; 2.8289 1.04; 2.8207 0.63; 2.8107 0.51; 2.6752 0.37; 2.6708 0.51; 2.6663 0.38; 2.5409 0.36; 2.5241 1.87; 2.5193 2.86; 2.5107 27.89; 2.5063 55.35; 2.5017 72.54; 2.4972 51.80; 2.4927 24.17; 2.3331 0.36; 2.3285 0.50; 2.3238 0.35; 2.0756 7.64; 0.7193 0.75; 0.7067 1.95; 0.7013 2.70; 0.6894 2.48; 0.6832 2.08; 0.6721 0.90; 0.5614 0.97; 0.5509 2.72; 0.5448 2.32; 0.5408 2.17; 0.5352 2.06; 0.5230 0.65; 0.0078 0.42; −0.0002 11.44; −0.0085 0.34

Compound No. 48 [DMSO] 9.7155 1.75; 9.6913 1.83; 9.3066 4.00; 8.0333 2.73; 7.8470 6.64; 7.8081 4.79; 7.7530 1.43; 7.7335 1.61; 7.6612 1.31; 7.6586 1.27; 7.6431 1.47; 7.6411 1.53; 7.6385 1.60; 7.4514 2.04; 7.4316 3.39; 7.4124 5.72; 6.1709 0.68; 6.1488 1.03; 6.1259 0.74; 3.9517 16.00; 3.3294 43.11; 2.6714 0.35; 2.5246 1.40; 2.5198 2.20; 2.5113 18.47; 2.5068 36.37; 2.5023 47.55; 2.4978 34.41; 2.4934 16.82; 2.3291 0.35; 2.0760 6.18; 1.6014 1.35; 1.5874 3.20; 1.5804 3.45; 1.5675 1.48; 1.2924 1.57; 1.2790 3.18; 1.2722 3.42; 1.2579 1.23; −0.0002 2.97

Compound No. 49 [DMSO] 9.7478 1.71; 9.7236 1.77; 8.4075 1.90; 8.3966 1.90; 8.3062 1.33; 8.2918 1.30; 8.1819 0.75; 8.1755 0.82; 8.1680 0.94; 8.1609 0.85; 8.1554 0.82; 7.7986 0.34; 7.7682 6.24; 7.7555 4.83; 7.6808 1.15; 7.6556 1.51; 7.6326 1.03; 7.3905 4.74; 6.3533 0.74; 6.3314 1.11; 6.3089 0.78; 4.0573 0.36; 4.0396 1.07; 4.0218 1.08; 4.0040 0.39; 3.9571 1.23; 3.9451 16.00; 3.3256 19.43; 2.8610 0.55; 2.8515 0.78; 2.8428 1.19; 2.8327 1.18; 2.8244 0.79; 2.8146 0.56; 2.5081 17.65; 2.5037 22.63; 2.4993 16.52; 1.9903 4.64; 1.3969 7.24; 1.1937 1.24; 1.1759 2.45; 1.1581 1.20; 0.7221 0.76; 0.7093 2.22; 0.7042 2.99; 0.6922 2.79; 0.6862 2.40; 0.6751 0.99; 0.5651 1.03; 0.5546 3.10; 0.5482 2.87; 0.5390 2.54; 0.5268 0.81; 0.0078 0.41; −0.0002 8.76; −0.0082 0.42

Compound No. 50 9.7819 1.66; 9.7577 1.72; 9.3013 3.79; 8.3043 1.17; 8.2884 1.13; 8.1818 0.62; 8.1754 0.69; 8.1679 0.80; 8.1603 0.72; 8.1543 0.70; 7.8549 6.24; 7.8097 4.65; 7.6832 1.05; 7.6577 1.34; 7.6349 0.98; 7.4016 4.48; 6.3584 0.65; 6.3362 0.98; 6.3138 0.71; 4.0574 0.65; 4.0395 1.99; 4.0217 2.02; 4.0039 0.69; 3.9526 16.00; 3.3247 8.89; 2.5259 0.34; 2.5127 7.59; 2.5083 15.50; 2.5038 20.53; 2.4993 14.66; 2.4949 6.96; 1.9904 8.57; 1.6037 1.30; 1.5896 3.15; 1.5826 3.38; 1.5697 1.43; 1.3968 1.47; 1.2946 1.57; 1.2812 3.22; 1.2745 3.42; 1.2599 1.41; 1.1938 2.39; 1.1760 4.76; 1.1581 2.33; −0.0002 3.14

Compound No. 51 [DMSO] 9.6543 1.61; 9.6300 1.66; 8.4134 1.78; 8.4024 1.78; 8.2082 1.25; 8.2032 1.29; 8.1918 1.27; 8.1868 1.23; 7.8429 0.63; 7.8377 0.66; 7.8312 0.72; 7.8223 0.84; 7.8160 0.79; 7.8098 0.76; 7.8050 0.68; 7.7615 6.44; 7.7549 4.66; 7.5173 1.68; 7.4956 3.10; 7.4739 1.51; 7.3895 4.35; 6.2129 0.64; 6.1909 0.96; 6.1681 0.69; 3.9558 0.72; 3.9429 16.00; 3.3285 48.82; 2.8579 0.49; 2.8483 0.66; 2.8398 1.05; 2.8295 1.06; 2.8213 0.65; 2.8113 0.50; 2.6714 0.35; 2.5246 1.01; 2.5112 19.18; 2.5068 38.58; 2.5022 51.16; 2.4977 37.41; 2.4933 18.10; 2.3289 0.37; 2.0761 6.37; 1.4756 0.43; 0.7201 0.71; 0.7074 1.90; 0.7021 2.72; 0.6901 2.47; 0.6840 2.13; 0.6728 0.88; 0.5617 0.94; 0.5512 2.75; 0.5450 2.42; 0.5412 2.28; 0.5356 2.16; 0.5234 0.67; 0.0080 0.36; −0.0002 10.08; −0.0085 0.36

Compound No. 52 [DMSO] 9.6888 1.62; 9.6645 1.66; 9.3070 3.80; 8.2063 1.21; 8.2013 1.29; 8.1899 1.25; 8.1848 1.23; 7.8470 6.42; 7.8369 0.82; 7.8307 0.80; 7.8206 0.92; 7.8086 5.19; 7.5193 1.74; 7.4976 3.19; 7.4759 1.56; 7.4009 4.13; 7.3998 4.15; 6.2175 0.62; 6.1953 0.93; 6.1729 0.67; 3.9500 16.00; 3.3322 147.58; 2.6760 0.39; 2.6715 0.52; 2.6670 0.40; 2.5417 0.51; 2.5249 2.41; 2.5202 3.47;

TABLE 1-continued
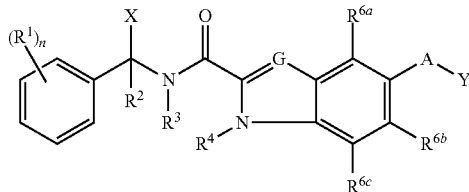
| No. | (R¹)ₙ | X | R² | R³ | R⁴ | G | R⁶ᵃ | R⁶ᵇ | R⁶ᶜ | A | Y | (M+H)⁺ ᵃ⁾ | log p ᵃ⁾ |
|---|---|---|---|---|---|---|---|---|---|---|---|---|---|
2.5115 27.71; 2.5070 55.43; 2.5024 73.26; 2.4978 53.27; 2.4933 26.16; 2.3338 0.37; 2.3291 0.51; 2.3246 0.39; 2.0760 1.51; 1.6017 1.30; 1.5876 3.04; 1.5807 3.26; 1.5678 1.42; 1.2914 1.52; 1.2779 3.07; 1.2712 3.28; 1.2568 1.21; −0.0002 4.96
Compound No. 53 [DMSO] 9.6580 1.62; 9.6337 1.66; 8.4145 1.84; 8.4035 1.87; 8.0974 1.29; 8.0927 1.33; 8.0798 1.33; 8.0750 1.29; 7.8131 0.66; 7.8079 0.71; 7.8014 0.85; 7.7926 1.06; 7.7863 0.89; 7.7805 0.87; 7.7751 0.82; 7.7616 6.63; 7.7554 4.91; 7.5605 1.64; 7.5379 2.63; 7.5156 1.41; 7.3914 4.60; 6.2176 0.66; 6.1958 1.00; 6.1735 0.72; 3.9572 0.76; 3.9442 16.00; 3.3294 27.25; 2.8585 0.52; 2.8492 0.71; 2.8402 1.12; 2.8301 1.12; 2.8217 0.71; 2.8120 0.54; 2.5248 0.92; 2.5111 15.08; 2.5070 29.42; 2.5026 38.48; 2.4981 28.16; 2.4938 13.84; 2.0766 11.26; 0.7205 0.81; 0.7077 2.14; 0.7026 2.90; 0.6905 2.68; 0.6845 2.28; 0.6734 0.95; 0.5622 0.99; 0.5517 2.92; 0.5455 2.60; 0.5360 2.32; 0.5239 0.70; −0.0002 5.57
Compound No. 54 [DMSO] 9.6934 1.71; 9.6691 1.77; 9.3093 3.86; 8.0972 1.30; 8.0925 1.37; 8.0796 1.34; 8.0747 1.32; 7.8493 6.31; 7.8105 5.31; 7.7971 0.86; 7.7933 0.91; 7.7872 0.88; 7.7814 0.84; 7.7764 0.72; 7.5635 1.70; 7.5410 2.60; 7.5187 1.46; 7.4049 4.53; 6.2242 0.68; 6.2023 1.02; 6.1799 0.73; 3.9531 16.00; 3.3315 12.11; 2.5258 0.85; 2.5211 1.27; 2.5123 12.27; 2.5080 23.95; 2.5035 30.69; 2.4990 22.10; 2.4947 10.69; 2.0776 1.14; 1.6039 1.32; 1.5898 3.23; 1.5829 3.46; 1.5700 1.45; 1.2935 1.56; 1.2801 3.26; 1.2735 3.44; 1.2589 1.22; 0.0080 0.64; −0.0002 16.93; −0.0085 0.60
Compound No. 57 cf. Synthesis Example 6
Compound No. 58 [DMSO] 9.7970 2.74; 9.7729 2.83; 9.3210 6.19; 7.8916 5.10; 7.8818 16.00; 7.7126 2.00; 7.6964 2.23; 7.5342 0.82; 7.5291 0.78; 7.5154 8.89; 7.5096 3.06; 7.4954 8.57; 7.4799 1.02; 6.1908 1.15; 6.1689 1.75; 6.1462 1.26; 6.1244 0.36; 5.7571 1.24; 5.4521 6.47; 3.3200 67.51; 3.2964 0.58; 3.2185 2.35; 3.2127 4.86; 3.2071 2.20; 2.6746 0.62; 2.6704 0.82; 2.6663 0.60; 2.5405 0.58; 2.5099 46.23; 2.5057 91.90; 2.5013 120.36; 2.4969 86.86; 2.3324 0.61; 2.3280 0.81; 2.3238 0.60; 1.6055 2.13; 1.5912 5.38; 1.5844 5.75; 1.5715 2.39; 1.2917 2.60; 1.2784 5.49; 1.2717 5.79; 1.2572 2.07; −0.0002 7.42
Compound No. 59 [DMSO] 9.7587 1.84; 9.7345 1.89; 8.4255 2.13; 8.4145 2.11; 8.0259 3.08; 7.8262 5.35; 7.7973 6.91; 7.7533 1.65; 7.7337 1.83; 7.6614 1.55; 7.6591 1.50; 7.6414 1.80; 7.6390 1.83; 7.4845 5.09; 7.4536 2.14; 7.4339 3.53; 7.4141 1.63; 7.3630 0.61; 6.1763 0.77; 6.1544 1.16; 6.1319 0.84; 5.4453 4.32; 3.3199 32.28; 3.2047 1.58; 3.1988 3.42; 3.1930 1.50; 2.8601 0.58; 2.8509 0.81; 2.8421 1.25; 2.8318 1.27; 2.8230 0.81; 2.8138 0.61; 2.6744 0.34; 2.6703 0.44; 2.6658 0.35; 2.5234 1.11; 2.5098 24.06; 2.5056 48.23; 2.5012 63.50; 2.4967 46.01; 2.4926 22.53; 2.3325 0.36; 2.3280 0.47; 2.3238 0.35; 1.9887 0.61; 1.3973 16.00; 1.3358 0.66; 1.2985 0.37; 1.2584 0.53; 1.2494 0.79; 1.2350 0.42; 1.1744 0.38; 0.7234 0.86; 0.7102 2.38; 0.7053 3.28; 0.6932 3.03; 0.6873 2.61; 0.6761 1.06; 0.5582 1.12; 0.5476 3.30; 0.5414 3.01; 0.5321 2.72; 0.5197 0.82; −0.0002 0.77
Compound No. 60 [DMSO] 9.7921 2.95; 9.7679 3.08; 9.3201 6.98; 8.0233 5.42; 7.8827 16.00; 7.7524 2.91; 7.7330 3.34; 7.6626 2.82; 7.6602 2.70; 7.6425 3.28; 7.6400 3.37; 7.4941 8.74; 7.4551 4.26; 7.4354 7.02; 7.4156 3.27; 6.2012 0.36; 6.1800 1.23; 6.1586 1.91; 6.1362 1.35; 6.1144 0.41; 5.4506 7.81; 3.3190 330.09; 3.2954 33.08; 3.2169 3.23; 3.2109 7.17; 3.2050 3.00; 2.6747 3.23; 2.6701 4.45; 2.6655 3.26; 2.6611 1.51; 2.5403 2.58; 2.5234 11.20; 2.5100 237.85; 2.5056 489.39; 2.5010 649.51; 2.4965 460.97; 2.4920 215.78; 2.3323 3.21; 2.3278 4.43; 2.3232 3.20; 2.0742 0.47; 1.6050 2.72; 1.5910 6.60; 1.5840 7.11; 1.5709 3.02; 1.2911 3.06; 1.2778 6.43; 1.2712 6.74; 1.2567 2.42; 0.1461 1.63; 0.0080 14.72; −0.0002 439.89; −0.0085 14.03; −0.1496 1.72
Compound No. 61 [DMSO] 9.8666 1.29; 9.8425 1.32; 9.3231 2.97; 8.2961 0.94; 8.2818 0.92; 8.1794 0.51; 8.1729 0.56; 8.1650 0.65; 8.1577 0.58; 8.1521 0.57; 7.8935 5.03; 7.8863 3.74; 7.6886 0.83; 7.6631 1.09; 7.6402 0.76; 7.4810 3.57; 6.3693 0.51; 6.3475 0.78; 6.3253 0.56; 5.4475 3.01; 3.3248 9.07; 3.2176 1.16; 3.2117 2.40; 3.2060 1.08; 2.5120 5.62; 2.5079 11.09; 2.5034 14.46; 2.4990 10.43; 1.6091 1.00; 1.5949 2.47; 1.5881 2.66; 1.5751 1.10; 1.3968 16.00; 1.2943 1.20; 1.2809 2.51; 1.2742 2.65; 1.2597 0.95; −0.0002 2.04
Compound No. 62 [DMSO] 9.7682 2.39; 9.7440 2.46; 9.3209 5.48; 8.1959 2.03; 8.1914 2.24; 8.1795 2.08; 8.1749 1.97; 7.8836 13.57; 7.8401 1.02; 7.8347 1.05; 7.8284 1.14; 7.8196 1.34; 7.8133 1.25; 7.8071 1.21; 7.5230 2.57; 7.5012 4.87; 7.4805 8.91; 6.2276 1.00; 6.2051 1.49; 6.1830 1.07; 5.4481 5.84; 3.3204 92.12; 3.2968 4.01; 3.2214 2.16; 3.2156 4.49; 3.2098 1.98; 2.6891 6.05; 2.6750 0.61; 2.6705 0.80; 2.6662 0.59; 2.5405 0.44; 2.5236 1.97; 2.5100 43.69; 2.5059 86.70; 2.5015 113.27; 2.4970 80.43; 2.3327 0.59; 2.3282 0.80; 2.3238 0.58; 1.6062 1.96; 1.5921 4.94; 1.5852 5.29; 1.5722 2.25; 1.3975 16.00; 1.2913 2.34; 1.2779 4.94; 1.2713 5.22; 1.2570 1.98; 0.0077 0.35; −0.0002 9.89; −0.0084 0.35
Compound No. 63 [CD3CN] 601.6 MHz 8.0370 1.89; 8.0214 1.92; 7.7787 16.00; 7.7718 3.16; 7.7638 2.91; 7.7603 2.94; 7.7470 0.41; 7.6428 11.45; 7.5938 1.57; 7.5899 1.63; 7.5864 1.69; 7.5826 1.70; 7.5797 1.81; 7.5756 1.74; 7.5721 1.76; 7.5684 1.60; 7.3544 4.83; 7.3396 7.48; 7.3248 4.30; 7.2831 11.01; 7.2822 10.83; 7.1990 0.32; 6.8340 2.03; 6.6523 0.52; 6.0383 1.85; 6.0240 2.58; 6.0094 1.88; 5.9953 0.56; 5.3438 0.35; 5.3301 15.28; 5.3260 15.29; 3.9267 1.21; 2.8758 0.56; 2.8693 1.65; 2.8631 2.28; 2.8573 3.61; 2.8509 3.70; 2.8451 2.32; 2.8389 1.78; 2.8325 0.63; 2.5204 4.23; 2.5163 9.64; 2.5122 4.16; 2.1549 0.47; 2.1303 172.30; 2.0974 0.95; 2.0578 0.93; 2.0537 1.70; 2.0496 2.51; 2.0455 1.72; 2.0414 0.88; 1.9633 9.94; 1.9552 10.32; 1.9511 13.24; 1.9473 155.24; 1.9431 294.24; 1.9390 434.91; 1.9349 295.37; 1.9308 148.09; 1.9263 4.86; 1.9220 2.19; 1.9168 0.79; 1.9128 0.51; 1.8325 0.84; 1.8284 1.62; 1.8243 2.40; 1.8202 1.65; 1.8161 0.82; 1.2702 1.00; 0.7838 2.12; 0.7751 5.63; 0.7721 7.57; 0.7635 7.41; 0.7603 5.95; 0.7520 2.67; 0.7377 0.32; 0.6258 0.35; 0.6193 0.34; 0.5994 2.56; 0.5925 5.65; 0.5913 6.11; 0.5882 6.31; 0.5848 5.96; 0.5818 6.01; 0.5733 1.98; −0.0002 3.80
Compound No. 64 [DMSO] 601.6 MHz 9.7659 2.32; 9.7499 2.42; 9.3182 5.41; 8.0786 1.98; 8.0753 1.79; 8.0669 2.01; 8.0636 1.67; 7.8815 16.00; 7.8014 0.95; 7.7979 1.04; 7.7940 1.10; 7.7901 1.19; 7.7873 1.07; 7.7835 1.19; 7.7797 1.14; 7.5574 2.62; 7.5425 4.18; 7.5277 2.42; 7.4826 2.26; 7.4799 5.99; 6.2220 0.80; 6.2073 1.21; 6.1925 0.84; 5.4799 0.33; 5.4760 0.33; 5.4499 3.80; 5.4463 6.46; 5.4427 3.86; 4.0348 0.88; 4.0229 0.86; 3.3171 236.70; 3.2932 23.65; 3.2201 2.86; 3.2161 6.05; 3.2121 2.71; 2.6187 0.88; 2.6157 1.98; 2.6126 2.81; 2.6095 1.99; 2.6065 0.87; 2.5402 0.86; 2.5219 3.87; 2.5188 4.93; 2.5157 4.89; 2.5070 143.70; 2.5039 317.56; 2.5009 443.31; 2.4978 317.16; 2.4947 143.64; 2.3911 0.86; 2.3881 1.94; 2.3850 2.75; 2.3820 1.94; 2.3789 0.86; 1.9884 4.02; 1.5989 2.16; 1.5896 5.05; 1.5851 5.69; 1.5762 2.28; 1.3977 2.75; 1.3875 0.36; 1.3344 0.64; 1.2980 4.65; 1.2852 2.48; 1.2759 5.21; 1.2717 5.52; 1.2621 2.34; 1.2584 7.00; 1.2358 1.37; 1.1863 1.25; 1.1744 2.40; 1.1626 1.16; 0.0965 0.56; 0.0053 4.52; −0.0002 169.32; −0.0057 4.88; −0.1000 0.57
Compound No. 66 [DMSO] 9.7689 3.60; 9.7446 3.74; 9.3232 8.54; 9.2848 0.39; 7.9157 14.13; 7.9119 13.66; 7.8924 16.00; 7.8849 11.58; 7.8587 0.51; 7.7347 4.60; 7.7301 8.13; 7.7255 4.11; 7.4929 10.32; 6.3044 0.44; 6.2837 1.50; 6.2620 2.18; 6.2397 1.58; 6.2179 0.47; 5.4952 0.35; 5.4892 0.36; 5.4456 9.05; 5.4023 0.33; 5.3959 0.33; 3.3204 162.89; 3.2968 9.09; 3.2183 3.49; 3.2124 7.51; 3.2065 3.24; 2.6750 0.89; 2.6705 1.23; 2.6659 0.89; 2.5407 0.66; 2.5237 2.91; 2.5103 63.65; 2.5059 130.33; 2.5014 173.33; 2.4968 123.03; 2.4924 57.79; 2.3327 0.89; 2.3282 1.21; 2.3236 0.88; 2.0745 7.43; 1.6069 3.07; 1.5927 7.55; 1.5858 8.12; 1.5729 3.77; 1.3312 0.33; 1.2914 3.54; 1.2779 7.45; 1.2713 8.01; 1.2568 2.79; 0.0080 1.36; −0.0002 39.71; −0.0085 1.29
Compound No. 91 [CD3CN] 8.7486 2.37; 8.7240 2.39; 7.9765 6.87; 7.9050 3.61; 7.8853 4.58; 7.8792 5.02; 7.8560 0.65; 7.8365

TABLE 1-continued (I)

| No. | $(R^1)_n$ | X | $R^2$ | $R^3$ | $R^4$ | G | $R^{6a}$ | $R^{6b}$ | $R^{6c}$ | A | Y | $(M+H)^+$ [a] | log p [a] |
|---|---|---|---|---|---|---|---|---|---|---|---|---|---|

13.00; 7.7970 16.00; 7.7786 4.95; 7.7657 4.34; 7.7009 3.71; 7.6812 5.48; 7.6620 2.19; 6.9523 0.78; 6.8957 2.35; 6.1485 0.72; 6.1281 2.46; 6.1070 3.16; 6.0842 2.44; 6.0634 0.76; 5.5563 0.37; 5.5164 14.05; 5.5116 14.36; 5.4476 0.88; 2.8899 0.68; 2.8801 1.76; 2.8706 2.65; 2.8622 3.53; 2.8526 3.49; 2.8442 2.24; 2.8347 1.47; 2.8250 0.49; 2.6591 4.32; 2.6528 8.90; 2.1421 256.79; 2.1202 1.75; 2.1139 1.84; 2.1078 2.36; 2.1016 1.42; 2.0955 0.75; 1.9646 11.57; 1.9585 16.50; 1.9527 107.06; 1.9466 198.34; 1.9404 270.76; 1.9342 185.68; 1.9280 94.72; 1.7812 0.75; 1.7750 1.27; 1.7688 1.70; 1.7627 1.17; 1.7565 0.63; 1.4368 0.39; 1.3721 5.45; 1.3405 1.37; 1.2852 2.06; 1.2766 6.85; 1.2214 0.35; 1.2037 0.49; 0.8815 0.54; 0.8571 0.63; 0.8360 0.54; 0.8170 0.34; 0.8064 0.75; 0.7981 2.06; 0.7937 2.20; 0.7858 6.62; 0.7804 7.35; 0.7679 8.40; 0.7627 5.55; 0.7507 2.55; 0.7289 0.43; 0.7109 0.38; 0.6601 0.32; 0.6503 0.33; 0.6269 0.94; 0.6200 2.90; 0.6096 8.04; 0.6028 8.03; 0.5937 5.98; 0.5812 1.81; 0.5118 0.33; 0.1461 0.66; −0.0002 157.86; −0.0086 6.00; −0.1494 0.68

Compound No. 97 [CD3CN] 8.8074 1.10; 8.7869 1.11; 8.0314 2.91; 8.0149 2.81; 7.9835 1.51; 7.9729 1.73; 7.9635 2.03; 7.9555 1.77; 7.9510 1.84; 7.9086 0.68; 7.8864 0.45; 7.8666 15.78; 7.8661 16.00; 7.8276 15.88; 7.7962 0.73; 7.4899 2.84; 7.4648 3.51; 7.4420 2.57; 6.9337 2.17; 6.1687 0.37; 6.1484 1.36; 6.1280 1.99; 6.1075 3.34; 6.0881 0.34; 5.5934 0.94; 5.5871 0.95; 5.5485 8.87; 5.5419 10.86; 5.5401 11.03; 5.5335 8.71; 5.4949 0.88; 5.4885 0.88; 4.1157 0.48; 4.0980 1.45; 4.0802 1.45; 4.0624 0.51; 2.9195 2.26; 2.9109 1.77; 2.9015 2.42; 2.8930 3.77; 2.8834 3.81; 2.8748 2.33; 2.8654 1.74; 2.8558 0.62; 2.8013 1.57; 2.7010 0.32; 2.6920 4.27; 2.6857 9.83; 2.6794 4.24; 2.2823 0.48; 2.1905 1004.56; 2.1892 1061.22; 2.1495 1.97; 2.1433 2.38; 2.1371 2.87; 2.1310 2.02; 2.1248 1.17; 2.0016 7.46; 1.9940 7.47; 1.9879 10.13; 1.9821 140.92; 1.9759 271.11; 1.9697 384.92; 1.9636 264.86; 1.9574 135.48; 1.9445 1.98; 1.8105 0.80; 1.8044 1.54; 1.7982 2.23; 1.7920 1.55; 1.7858 0.79; 1.4667 8.22; 1.3063 0.37; 1.2513 1.90; 1.2335 3.79; 1.2157 1.88; 0.8289 1.99; 0.8165 5.84; 0.8112 7.79; 0.7986 8.29; 0.7933 5.65; 0.7811 2.75; 0.7595 0.39; 0.7417 0.38; 0.6808 0.33; 0.6508 2.72; 0.6407 6.37; 0.6391 6.57; 0.6334 6.78; 0.6292 6.09; 0.6239 6.02; 0.6116 1.89; 0.0294 0.58

Compound No. 101 [CD3CN] 8.7086 1.49; 8.6854 1.47; 7.8774 0.42; 7.8570 0.39; 7.8336 11.35; 7.7974 13.62; 7.7858 2.67; 7.7805 4.42; 7.7660 0.46; 7.6161 1.34; 7.6104 1.42; 7.6050 1.51; 7.5950 1.79; 7.5889 1.84; 7.5839 1.74; 7.5782 1.37; 7.3680 3.48; 7.3457 5.57; 7.3235 2.89; 6.9284 1.96; 6.0399 0.52; 6.0195 1.75; 5.9986 2.19; 5.9754 1.70; 5.9551 0.53; 5.5636 0.39; 5.5572 0.40; 5.5185 7.36; 5.5131 10.44; 5.5079 7.02; 5.4691 0.38; 5.4629 0.38; 2.8902 0.41; 2.8807 1.20; 2.8713 1.79; 2.8627 2.63; 2.8531 2.67; 2.84451.72; 2.8351 1.19; 2.8255 0.40; 2.6693 3.14; 2.6631 6.40; 2.6569 2.91; 2.6017 0.59; 2.4732 0.34; 2.4692 0.67; 2.4646 0.94; 2.4600 0.67; 2.4551 0.36; 2.1690 418.23; 2.1206 1.13; 2.1144 1.40; 2.1083 1.65; 2.1022 1.22; 2.0960 1.73; 1.9652 9.20; 1.9587 14.22; 1.9532 85.29; 1.9471 156.52; 1.9410 213.28; 1.9348 146.60; 1.9286 75.33; 1.7816 0.57; 1.7755 0.99; 1.7693 1.34; 1.7632 0.95; 1.7570 0.52; 1.4366 16.00; 1.3717 0.84; 1.2765 1.13; 0.9982 1.52; 0.7856 4.60; 0.7805 5.92; 0.7679 6.20; 0.7627 4.55; 0.7505 2.06; 0.7289 0.35; 0.6205 2.05; 0.6089 5.58; 0.6032 5.70; 0.5992 5.22; 0.5939 4.82; 0.5814 1.45; 0.1460 0.52; −0.0002 122.15; −0.0084 5.33; −0.1497 0.58

Compound No. 183 [DMSO] 9.7242 2.09; 9.6999 2.16; 9.1083 4.26; 8.2077 3.27; 8.0689 1.15; 8.0493 1.96; 7.83211.61; 7.8123 2.34; 7.7385 1.96; 7.7275 7.41; 7.7193 2.99; 7.6997 1.17; 7.4652 4.63; 7.3422 5.76; 6.3167 0.86; 6.2944 1.29; 6.2718 0.92; 4.5201 0.99; 4.5027 3.05; 4.4850 3.05; 4.4676 0.99; 4.0565 0.38; 4.0387 1.16; 4.0209 1.19; 4.0031 0.39; 3.3229 24.97; 3.2992 1.30; 2.6896 0.63; 2.5245 0.68; 2.5113 14.16; 2.5070 28.91; 2.5024 38.42; 2.4979 27.55; 2.4935 13.30; 2.4695 16.00; 1.9894 5.08; 1.5764 1.59; 1.5623 4.07; 1.5555 4.36; 1.5426 1.87; 1.2949 2.13; 1.2815 4.40; 1.2749 4.62; 1.2604 1.77; 1.2348 4.45; 1.2174 9.24; 1.1998 4.14; 1.1929 1.98; 1.1751 2.90; 1.1573 1.44; 0.0080 1.01; −0.0002 28.99; −0.0085 1.02

Compound No. 184 [DMSO] 9.5877 2.32; 9.5633 2.38; 8.2463 2.47; 8.2354 2.47; 7.8998 3.74; 7.7110 1.65; 7.69511.86; 7.6282 7.08; 7.5924 0.38; 7.5293 0.74; 7.5244 0.73; 7.5102 7.29; 7.5045 2.67; 7.4947 3.12; 7.4747 0.72; 7.4143 4.60; 7.3337 6.39; 6.1758 0.96; 6.1537 1.41; 6.1308 1.00; 4.5181 1.03; 4.5008 3.06; 4.4830 3.05; 4.4657 1.02; 3.9041 10.55; 3.5076 0.32; 3.3383 1.71; 3.1744 1.28; 3.1614 1.22; 2.8593 0.70; 2.8496 1.03; 2.8411 1.57; 2.8310 1.62; 2.8230 1.09; 2.8129 0.89; 2.8028 0.34; 2.6759 0.82; 2.6715 1.09; 2.6671 0.83; 2.5414 0.96; 2.5244 4.39; 2.5112 67.80; 2.5069 131.36; 2.5024 169.10; 2.4979 124.48; 2.4936 63.19; 2.4449 16.00; 2.3337 0.75; 2.3292 1.01; 2.3248 0.75; 2.2886 0.33; 1.2579 0.45; 1.2302 4.88; 1.2127 8.90; 1.1951 3.99; 1.1252 0.47; 1.1038 0.36; 1.0847 0.57; 0.8536 0.47; 0.8347 0.34; 0.7075 1.00; 0.6946 2.83; 0.6896 3.97; 0.6776 3.57; 0.6716 3.16; 0.6606 1.30; 0.5540 1.46; 0.5435 4.01; 0.5374 3.49; 0.5337 3.41; 0.5278 3.10; 0.5157 0.94; 0.0078 0.84; −0.0002 20.49; −0.0084 0.93

Compound No. 185 [DMSO] 9.6302 2.19; 9.6059 2.24; 9.1185 4.39; 7.8969 3.68; 7.7179 7.56; 7.7110 2.07; 7.6949 2.21; 7.5370 0.33; 7.5314 0.81; 7.5266 0.86; 7.5124 7.29; 7.5067 2.61; 7.4970 3.21; 7.4768 1.08; 7.4646 4.47; 7.3412 5.93; 6.1814 0.94; 6.1589 1.40; 6.1364 0.98; 4.5217 1.00; 4.5046 2.93; 4.4869 2.92; 4.4694 1.02; 3.9042 8.49; 3.5086 0.34; 3.4184 0.35; 3.3433 493.98; 3.2899 0.52; 3.1746 1.50; 3.1616 1.43; 2.6763 0.84; 2.6719 1.15; 2.6674 0.88; 2.6624 0.54; 2.6583 0.63; 2.5421 0.94; 2.5247 4.82; 2.5116 74.43; 2.5073 143.87; 2.5028 184.99; 2.4983 134.34; 2.4939 66.92; 2.4664 16.00; 2.2385 0.44; 2.3340 0.86; 2.3296 1.17; 2.3250 0.85; 1.5759 1.61; 1.5617 4.09; 1.5549 4.41; 1.5420 1.88; 1.2932 2.43; 1.2799 4.56; 1.2732 4.86; 1.2587 2.11; 1.2382 5.94; 1.2211 9.23; 1.2035 4.04; 1.1531 0.34; 1.1399 0.47; 1.1352 0.57; 1.1166 0.34; 1.1122 0.38; 1.0935 0.66; 1.0744 0.35; 0.8536 0.58; 0.8351 0.40; 0.0079 0.92; −0.0002 23.77; −0.0085 0.99

Compound No. 188 [DMSO] 9.6601 2.22; 9.6358 2.27; 8.3016 1.62; 8.2873 1.58; 8.2437 2.40; 8.2329 2.41; 8.1790 0.88; 8.1726 0.97; 8.1633 1.11; 8.1577 1.00; 8.1519 0.96; 7.6821 1.45; 7.6568 1.87; 7.6344 8.33; 7.4171 4.58; 7.3168 6.31; 6.3494 0.89; 6.3271 1.34; 6.3052 0.96; 4.5131 1.00; 4.4957 3.01; 4.4780 3.02; 4.4605 1.03; 3.9044 6.77; 3.3818 0.82; 3.3377 384.21; 3.1744 1.57; 3.1617 1.51; 2.8588 0.67; 2.8491 0.96; 2.8406 1.50; 2.8305 1.54; 2.8222 0.96; 2.8125 0.77; 2.6761 0.87; 2.6718 1.18; 2.6674 0.88; 2.5421 0.89; 2.5248 3.97; 2.5114 75.20; 2.5072 146.53; 2.5027 189.17; 2.4982 138.90; 2.4940 70.08; 2.4454 16.00; 2.3339 0.88; 2.3294 1.19; 2.3251 0.89; 1.2491 0.37; 1.2280 4.18; 1.2105 8.78; 1.1929 3.94; 0.7081 0.95; 0.6952 2.71; 0.6901 3.83; 0.6781 3.45; 0.6722 3.07; 0.6611 1.26; 0.5537 1.32; 0.5431 3.89; 0.5370 3.46; 0.5332 3.34; 0.5274 3.10; 0.5153 0.95; 0.0080 0.70; −0.0002 19.39; −0.0085 0.85

Compound No. 189 [DMSO] 9.7021 2.25; 9.6777 2.28; 9.1149 4.59; 8.2999 1.67; 8.2856 1.55; 8.1781 0.88; 8.1718 0.97; 8.1627 1.11; 8.1558 0.99; 8.1507 0.95; 7.7249 7.04; 7.6847 1.45; 7.6590 1.84; 7.6363 1.31; 7.4673 4.59; 7.3246 6.12; 6.3553 0.89; 6.3333 1.34; 6.3105 0.93; 4.5168 1.00; 4.4995 2.94; 4.4818 2.92; 4.4646 1.00; 3.9045 8.93; 3.3950 0.43; 3.3873 0.46; 3.3815 0.50; 3.3346 305.34; 3.1746 0.65; 3.1616 0.61; 2.6761 0.90; 2.6716 1.20; 2.6673 0.90; 2.5419 0.99; 2.5111 76.43; 2.5071 147.69; 2.5027 190.11; 2.4982 138.56; 2.4664 16.00; 2.3339 0.88; 2.3294 1.18; 2.3248 0.86; 1.5771 1.56; 1.5629 4.06; 1.5562 4.38; 1.5433 1.81; 1.2919 2.21; 1.2786 4.55; 1.2719 4.82; 1.2575 2.06; 1.2358 7.26; 1.2189 9.00; 1.2013 4.03; 1.1400 0.53; 0.8535 0.59; 0.8353 0.38; 0.0079 1.06; −0.0002 27.66; −0.0083 1.09

Compound No. 190 [DMSO] 9.5580 2.34; 9.5337 2.38; 8.2449 2.54; 8.2339 2.56; 8.2055 1.89; 8.2007 1.90; 8.1890 1.81; 8.1840 1.81; 7.8406 0.90; 7.8355 0.97; 7.8294 1.06; 7.8198 1.21; 7.8141 1.14; 7.8078 1.09; 7.8026 0.99; 7.6298 7.11; 7.5180 2.31; 7.4962 4.26; 7.4745 2.06; 7.4152 4.62; 7.3212 6.28; 6.2119 0.92; 6.1897 1.37; 6.1672 0.98; 4.5156 1.02; 4.4982 3.06; 4.4806 3.07; 4.4633 1.00; 3.9043 11.54; 3.3801 0.46; 3.3338 318.57; 3.1742 0.50; 3.1613 0.48; 2.8590 0.69; 2.8491 0.99; 2.8408 1.50; 2.8307 1.53; 2.8221 0.98; 2.8125 0.75; 2.6757 0.89; 2.6713 1.19; 2.6669 0.91; 2.5415 0.85; 2.5110 74.65; 2.5068 146.15; 2.5023 189.80; 2.4978 140.81; 2.4935 72.44; 2.4445

TABLE 1-continued (I)

| No. | $(R^1)_n$ | X | $R^2$ | $R^3$ | $R^4$ | G | $R^{6a}$ | $R^{6b}$ | $R^{6c}$ | A | Y | $(M+H)^{+a)}$ | log p $^{a)}$ |
|---|---|---|---|---|---|---|---|---|---|---|---|---|---|

16.00; 2.3336 0.87; 2.3290 1.19; 2.3245 0.88; 1.2581 0.39; 1.2304 4.64; 1.2129 8.81; 1.1952 3.99; 0.8529 0.42; 0.8345 0.34; 0.7075 0.94; 0.6946 2.72; 0.6895 3.84; 0.6775 3.44; 0.6716 3.09; 0.6606 1.27; 0.5536 1.31; 0.5431 3.90; 0.5370 3.47; 0.5335 3.42; 0.5275 3.14; 0.5153 0.94; 0.0079 0.99; −0.0002 25.82; −0.0084 1.28

Compound No. 191 [DMSO] 9.5999 2.22; 9.5756 2.29; 9.1163 4.59; 8.2030 1.69; 8.1983 1.79; 8.1866 1.73; 8.1818 1.72; 7.8401 0.85; 7.8349 0.91; 7.8286 0.97; 7.8191 1.13; 7.8135 1.09; 7.8070 1.04; 7.8022 0.94; 7.7197 7.01; 7.5206 2.24; 7.4988 4.13; 7.4771 2.22; 7.4657 4.54; 7.3290 6.00; 6.2178 0.88; 6.1953 1.31; 6.1727 0.93; 4.5193 0.95; 4.5022 2.86; 4.4844 2.88; 4.4668 0.96; 3.9043 8.00; 3.3330 294.83; 3.1740 0.86; 3.1615 0.80; 2.6758 0.86; 2.6714 1.19; 2.6668 0.89; 2.5416 0.74; 2.5244 3.81; 2.5110 74.69; 2.5068 146.49; 2.5023 189.94; 2.4978 138.63; 2.4935 68.83; 2.4657 16.00; 2.3335 0.94; 2.3290 1.25; 2.3247 0.94; 2.1798 0.42; 1.5766 1.55; 1.5624 3.98; 1.5556 4.31; 1.5427 1.81; 1.2923 2.21; 1.2790 4.45; 1.2723 4.77; 1.2578 2.13; 1.2354 7.77; 1.2214 9.03; 1.2037 3.99; 0.8535 0.77; 0.8354 0.41; 0.0078 1.06; −0.0002 27.74; −0.0081 1.11

Compound No. 192 [DMSO] 9.5619 2.27; 9.5376 2.33; 8.2464 2.40; 8.2355 2.40; 8.0944 1.73; 8.0892 1.83; 8.0767 1.78; 8.0715 1.74; 7.8103 0.88; 7.8050 0.94; 7.7990 1.02; 7.7895 1.17; 7.7834 1.14; 7.7776 1.10; 7.7722 0.96; 7.6288 7.18; 7.5605 2.33; 7.5380 3.52; 7.5158 2.01; 7.4154 4.52; 7.3220 6.24; 6.2157 0.90; 6.1937 1.35; 6.1710 0.95; 4.5161 1.02; 4.4991 3.02; 4.4813 3.03; 4.4636 1.03; 3.9041 11.27; 3.4103 0.48; 3.3409 535.29; 3.2843 0.35; 3.1743 0.64; 3.1617 0.55; 2.8591 0.69; 2.8493 0.98; 2.8409 1.50; 2.8307 1.54; 2.8227 0.98; 2.8126 0.76; 2.6807 0.44; 2.6764 0.86; 2.6718 1.16; 2.6673 0.86; 2.6627 0.42; 2.5420 1.19; 2.5248 5.09; 2.5116 75.01; 2.5073 145.71; 2.5027 188.12; 2.4982 136.59; 2.4937 67.93; 2.4445 16.00; 2.3340 0.89; 2.3295 1.19; 2.3249 0.88; 2.3205 0.44; 1.2580 0.40; 1.2308 4.62; 1.2133 9.00; 1.1957 3.99; 0.8537 0.40; 0.7080 1.01; 0.6952 2.74; 0.6901 3.89; 0.6781 3.48; 0.6721 3.05; 0.6610 1.30; 0.5537 1.39; 0.5431 3.94; 0.5371 3.42; 0.5333 3.30; 0.5275 3.08; 0.5154 0.97; 0.0080 1.04; −0.0002 27.14; −0.0085 1.14

Compound No. 193 [DMSO] 9.6033 2.25; 9.5790 2.29; 9.1176 4.57; 8.0921 1.76; 8.0873 1.82; 8.0746 1.76; 8.0696 1.73; 7.8099 0.90; 7.8046 0.97; 7.7987 1.06; 7.7890 1.20; 7.7830 1.16; 7.7774 1.12; 7.7722 0.99; 7.7185 7.11; 7.5635 2.30; 7.5408 3.54; 7.5187 1.97; 7.4658 4.55; 7.3299 6.05; 6.2216 0.91; 6.1999 1.36; 6.1773 0.97; 4.5205 1.01; 4.5030 2.94; 4.4852 2.95; 4.4674 1.01; 3.9043 10.45; 3.3818 0.77; 3.3370 369.94; 3.1742 0.70; 3.1616 0.66; 2.6761 0.86; 2.6716 1.18; 2.6671 0.90; 2.6626 0.51; 2.5419 1.02; 2.5248 4.54; 2.5114 75.06; 2.5071 146.50; 2.5026 189.12; 2.4981 138.44; 2.4937 69.51; 2.4656 16.00; 2.3337 0.85; 2.3293 1.16; 2.3247 0.88; 1.5768 1.60; 1.5626 4.07; 1.5558 4.39; 1.5429 1.85; 1.2924 2.32; 1.2790 4.56; 1.2723 4.89; 1.2579 2.06; 1.2391 4.76; 1.2218 9.13; 1.2041 4.05; 1.1398 0.39; 0.8533 0.39; 0.8349 0.33; 0.0080 0.96; −0.0002 25.38; −0.0085 1.11

Compound No. 195 [DMSO] 9.6007 2.28; 9.5762 2.36; 9.1189 4.76; 7.9208 7.64; 7.9168 8.09; 7.7330 3.35; 7.7284 11.36; 7.4684 4.60; 7.3430 6.15; 6.2729 0.88; 6.2506 1.30; 6.2282 0.95; 4.5188 0.98; 4.5017 2.93; 4.4841 2.93; 4.4667 0.96; 3.9044 6.44; 3.3344 307.19; 3.1744 0.96; 3.1614 0.94; 2.6757 0.82; 2.6714 1.12; 2.6669 0.86; 2.5412 0.73; 2.5068 139.98; 2.5024 182.48; 2.4980 135.92; 2.4667 16.00; 2.3335 0.84; 2.3291 1.13; 2.3247 0.86; 1.5774 1.54; 1.5630 4.03; 1.5563 4.39; 1.5434 1.83; 1.2925 2.12; 1.2791 4.49; 1.2725 4.80; 1.2580 1.97; 1.2411 4.44; 1.2239 8.86; 1.2062 4.02; 0.8527 0.38; 0.8344 0.32; 0.0075 0.92; −0.0002 24.40; −0.0081 1.28

Compound No. 196 [DMSO] 9.6977 1.66; 9.6734 1.73; 9.1262 3.41; 8.2154 2.29; 8.0709 1.22; 8.0515 1.37; 7.8306 1.09; 7.8107 1.58; 7.7340 6.12; 7.7162 1.92; 7.6966 0.79; 7.4395 3.29; 7.3741 4.28; 6.3131 0.63; 6.2909 0.95; 6.2682 0.69; 3.9365 16.00; 3.3291 48.92; 2.5252 0.86; 2.5204 1.29; 2.5117 16.09; 2.5073 32.47; 2.5027 43.26; 2.4981 31.94; 2.4936 15.63; 2.4749 10.86; 1.5762 1.10; 1.5621 2.77; 1.5552 2.98; 1.5424 1.26; 1.2994 1.47; 1.2861 2.99; 1.2793 3.19; 1.2649 1.16; 0.0079 1.10; −0.0002 32.32; −0.0085 1.09

Compound No. 209 [DMSO] 10.0423 0.40; 10.0183 0.41; 9.7798 2.09; 9.7557 2.20; 9.1526 4.85; 8.3182 0.51; 8.2081 3.05; 8.1472 0.58; 8.0721 1.61; 8.0526 1.81; 8.0334 0.40; 8.0142 0.44; 7.8599 1.33; 7.8330 1.74; 7.8134 2.54; 7.7555 6.59; 7.7404 2.01; 7.7208 2.99; 7.7014 1.30; 7.5136 4.58; 7.4533 5.47; 6.3267 0.89; 6.3042 1.32; 6.2817 0.95; 5.4091 4.45; 5.1217 0.47; 5.1153 0.51; 5.1087 0.51; 5.1032 0.45; 4.0556 0.39; 4.0377 1.12; 4.0199 1.15; 4.0022 0.53; 3.8259 0.85; 3.8204 0.85; 3.3313 66.80; 3.1717 1.85; 3.1657 4.27; 3.1597 1.77; 3.1287 0.36; 3.1228 0.82; 3.1168 0.33; 2.7225 0.36; 2.7158 0.82; 2.7090 0.34; 2.6762 0.52; 2.6716 0.72; 2.6671 0.52; 2.5250 1.84; 2.5203 2.88; 2.5116 39.16; 2.5071 80.18; 2.5025 106.71; 2.4979 78.78; 2.4935 38.88; 2.4735 16.00; 2.3472 0.65; 2.3385 0.36; 2.3339 0.60; 2.3293 0.80; 2.3247 0.64; 2.3205 0.35; 2.3009 0.58; 1.9895 4.95; 1.5827 1.64; 1.5682 4.29; 1.5617 4.29; 1.5488 1.89; 1.3364 1.77; 1.2996 2.13; 1.2862 4.60; 1.2796 4.41; 1.2651 1.66; 1.2591 0.58; 1.2496 2.24; 1.2350 0.56; 1.1929 1.39; 1.1751 2.73; 1.1573 1.34; 0.0080 1.26; −0.0002 41.83; −0.0085 1.51

Compound No. 262 [CD3CN] 8.1075 0.75; 8.0917 0.73; 7.9737 1.70; 7.9030 0.91; 7.8900 1.00; 7.8416 5.10; 7.7880 0.88; 7.7749 1.13; 7.6927 0.93; 7.6797 1.53; 7.6667 0.65; 7.6277 3.70; 7.2536 1.28; 7.2390 3.43; 7.2383 3.44; 6.1575 0.60; 6.1431 0.84; 6.1283 0.62; 4.5007 0.85; 4.4888 2.76; 4.4769 2.79; 4.4651 0.87; 2.1530 27.63; 1.9583 0.58; 1.9542 0.94; 1.9504 16.58; 1.9463 33.29; 1.9422 49.12; 1.9381 32.72; 1.9340 15.98; 1.9295 0.49; 1.7820 0.56; 1.7752 16.00; 1.4320 0.38; 1.4293 0.70; 1.4272 0.44; 1.4230 0.43; 1.4184 0.96; 1.4159 0.73; 1.4081 0.64; 1.4049 0.44; 1.3960 0.40; 1.3032 3.34; 1.2914 7.71; 1.2796 3.40; 1.2714 0.32; 1.2684 0.33; 0.6950 0.81; 0.6904 1.05; 0.6878 1.62; 0.6868 1.48; 0.6845 1.49; 0.6838 1.48; 0.6808 1.94; 0.6786 1.44; 0.6758 1.75; 0.6730 1.26; 0.6709 1.71; 0.6671 0.67; 0.6648 1.32; 0.6622 0.68; 0.6575 0.81; 0.6561 0.77; 0.6543 0.76; 0.6494 1.13; 0.6412 0.64; 0.6384 0.36; 0.0053 2.18; −0.0002 74.22; −0.00582.44

Compound No. 263 [CD3CN] 8.1743 1.18; 8.1515 1.19; 7.9742 3.61; 7.8978 1.87; 7.8782 2.28; 7.8229 10.03; 7.7874 1.68; 7.7677 2.48; 7.6933 2.11; 7.6736 3.16; 7.6541 1.26; 7.6195 7.90; 7.2359 7.97; 7.1875 1.18; 6.1779 0.43; 6.1571 1.51; 6.1351 2.04; 6.1129 1.55; 6.0918 0.47; 4.5064 1.89; 4.4887 6.16; 4.4709 6.28; 4.4531 2.02; 3.6271 2.65; 3.6110 7.66; 3.5953 7.87; 3.5793 2.96; 2.7517 5.98; 2.7355 12.14; 2.7193 5.66; 2.4718 0.37; 2.4670 0.52; 2.4623 0.38; 2.1864 317.72; 2.1818 416.45; 2.1203 0.77; 2.1142 1.00; 2.1080 1.20; 2.1018 0.86; 2.0956 0.56; 1.9649 14.55; 1.9588 6.12; 1.9529 56.15; 1.9468 107.20; 1.9406 151.90; 1.9344 107.30; 1.9282 57.22; 1.7814 0.38; 1.7752 0.65; 1.7690 0.94; 1.7628 0.67; 1.7567 0.38; 1.3066 7.00; 1.2889 16.00; 1.2710 8.08; 0.0081 1.30; −0.0002 47.92; −0.0085 2.38

Compound No. 264 [CD3CN] 8.2107 0.52; 8.1875 0.52; 7.9701 1.75; 7.9082 0.92; 7.8887 1.09; 7.8175 4.48; 7.7886 0.85; 7.7690 1.24; 7.6957 1.05; 7.6762 1.53; 7.6566 0.61; 7.6146 3.52; 7.2248 3.69; 7.0082 1.06; 6.1576 0.72; 6.1355 0.97; 6.1135 0.74; 4.5025 0.85; 4.4847 2.71; 4.4669 2.75; 4.4492 0.88; 2.2209 97.12; 2.1448 0.47; 2.1260 1.29; 2.1074 1.71; 2.0907 2.72; 2.0719 2.59; 2.0532 0.92; 2.0497 0.88; 2.0310 2.43; 2.0127 2.79; 1.9954 1.72; 1.9774 1.28; 1.9663 2.77; 1.9600 1.12; 1.9543 9.87; 1.9481 18.68; 1.9420 26.78; 1.9358 18.71; 1.9296 9.80; 1.3037 3.42; 1.2861 7.49; 1.2683 3.46; 1.0957 7.61; 1.0771 16.00; 1.0585 7.05; −0.0002 0.57

Compound No. 266 [CD3CN] 8.1744 0.69; 8.1510 0.69; 7.9715 2.11; 7.9060 1.02; 7.8862 1.29; 7.7868 5.10; 7.7669 1.49; 7.7509 5.68; 7.6926 1.22; 7.6731 1.81; 7.6535 0.70; 7.5809 4.44; 7.2009 4.29; 6.8697 1.09; 6.1555 0.86; 6.1339 1.17; 6.1115 0.87; 4.4967 1.08; 4.4789 3.43; 4.4612 3.47; 4.4433 1.09; 2.1748 229.04; 2.1417 1.79; 2.1203 0.36; 2.1140 0.45; 2.1078 0.53; 2.1016 0.42; 1.9647 1.01; 1.9585 1.55; 1.9528 24.12; 1.9466 46.56; 1.9404 66.70; 1.9343 46.07; 1.9281 23.85; 1.7689 0.40; 1.4332 16.00; 1.2988 3.91; 1.2811 8.69; 1.2633 3.82; 1.1694 7.24; 1.1540 8.39; 0.9599 0.60; 0.9446 0.84; 0.9381 0.82; 0.9288 0.57; 0.9226 1.09; 0.9072 0.68; 0.7795 1.51; 0.7669 1.62;

TABLE 1-continued
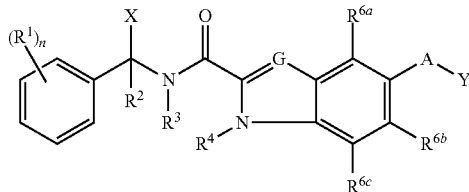
| No. | (R¹)ₙ | X | R² | R³ | R⁴ | G | R⁶ᵃ | R⁶ᵇ | R⁶ᶜ | A | Y | (M + H)⁺ᵃ⁾ | log pᵃ⁾ |
|---|---|---|---|---|---|---|---|---|---|---|---|---|---|
0.7576 1.22; 0.7450 1.26; 0.4141 1.11; 0.4003 1.71; 0.3862 1.01; −0.0002 3.31
Compound No. 267 [CD3CN] 10.0848 1.09; 8.2814 0.93; 8.1224 1.53; 8.0987 1.58; 7.9663 3.82; 7.9386 0.40; 7.8959 2.17; 7.8766 2.41; 7.7877 1.85; 7.7687 12.47; 7.7062 0.96; 7.6932 2.28; 7.6736 3.29; 7.6538 1.32; 7.6128 8.06; 7.4079 2.56; 7.2197 7.98; 6.1755 0.47; 6.1547 1.56; 6.1330 2.15; 6.1106 1.60; 6.0893 0.48; 4.5026 1.92; 4.4849 6.17; 4.4671 6.28; 4.4493 2.01; 4.3786 0.35; 4.3576 0.35; 2.1718 684.33; 2.1203 1.15; 2.1141 1.16; 2.1079 1.22; 2.1017 0.95; 2.0955 0.62; 2.0871 0.35; 1.9766 0.49; 1.9648 41.98; 1.9587 4.23; 1.9529 46.51; 1.9467 89.72; 1.9405 128.18; 1.9343 88.79; 1.9281 45.95; 1.7812 0.33; 1.7751 0.58; 1.7689 0.79; 1.7628 0.55; 1.3926 2.21; 1.3783 5.53; 1.3719 5.92; 1.3582 3.53; 1.3363 1.47; 1.3182 1.29; 1.3023 7.24; 1.2845 16.00; 1.2668 7.49; 1.2583 1.99; 1.2543 2.06; 1.2406 4.81; 1.2237 1.09; 1.2201 1.02; −0.0002 2.17
Compound No. 268 [CD3CN] 10.0914 0.78; 8.3863 0.67; 8.1436 1.42; 8.1205 1.49; 7.9700 3.99; 7.8977 2.20; 7.8780 2.74; 7.8645 9.54; 7.7892 1.94; 7.7694 2.78; 7.7402 0.67; 7.6952 2.28; 7.6756 3.34; 7.6560 1.42; 7.6388 7.45; 7.6172 0.90; 7.5828 1.10; 7.5433 1.38; 7.5232 1.41; 7.2386 7.51; 7.1952 0.77; 6.1787 0.48; 6.1575 1.61; 6.1356 2.19; 6.1135 1.64; 6.0922 0.49; 5.1375 1.28; 5.1207 2.95; 5.1181 1.86; 5.1037 1.65; 5.1009 2.99; 5.0841 1.26; 4.5068 1.92; 4.4891 6.09; 4.4713 6.21; 4.4535 2.00; 3.6587 0.33; 3.0637 3.88; 2.9240 0.43; 2.9174 0.47; 2.9038 4.67; 2.8973 4.80; 2.8871 4.76; 2.8805 4.73; 2.7998 2.50; 2.5061 0.42; 2.5000 2.77; 2.4934 5.63; 2.4868 2.61; 2.1766 287.45; 2.1208 0.58; 2.1144 0.56; 2.1082 0.62; 2.1021 0.56; 2.0959 0.35; 1.9651 11.86; 1.9591 1.89; 1.9532 24.21; 1.9470 47.23; 1.9409 67.90; 1.9347 47.47; 1.9285 24.85; 1.7694 0.42; 1.3572 0.46; 1.3393 1.00; 1.3214 0.67; 1.3086 7.13; 1.2910 16.00; 1.2731 7.31; −0.0002 1.49
Compound No. 269 [CD3CN] 10.0865 0.59; 10.0836 0.59; 8.3186 0.81; 8.1251 1.25; 8.1016 1.27; 7.9714 3.40; 7.9536 0.33; 7.8975 1.80; 7.8778 2.15; 7.7940 9.95; 7.7684 2.36; 7.6942 2.05; 7.6746 2.96; 7.6551 1.14; 7.6079 7.28; 7.2258 7.04; 7.2245 7.21; 6.9842 1.10; 6.9654 1.09; 6.1780 0.41; 6.1567 1.40; 6.1346 1.89; 6.1126 1.42; 6.0911 0.42; 4.5037 1.77; 4.4859 5.66; 4.4681 5.72; 4.4504 1.79; 4.3726 0.85; 4.3578 1.35; 4.3556 1.35; 4.3407 1.59; 4.3390 1.60; 4.3220 1.23; 4.3073 0.59; 3.2822 0.40; 3.2686 0.39; 2.8687 1.94; 2.8545 1.91; 2.8265 3.52; 2.8122 3.32; 2.7297 0.44; 2.7244 3.72; 2.7099 3.69; 2.6822 2.15; 2.6677 2.09; 2.1585 403.11; 2.1253 1.36; 2.1136 0.91; 2.1074 1.08; 2.1012 0.82; 2.0951 0.49; 1.9643 2.30; 1.9581 3.00; 1.9524 46.88; 1.9462 90.98; 1.9400 130.48; 1.9338 90.21; 1.9277 46.59; 1.7747 0.57; 1.7684 0.79; 1.7623 0.54; 1.3676 1.27; 1.3537 15.72; 1.3367 16.00; 1.3184 0.69; 1.3059 6.52; 1.2882 14.61; 1.2704 6.60; −0.0002 2.78
Compound No. 270 [CD3CN] 8.1925 0.96; 8.1732 0.97; 7.9763 3.71; 7.9008 1.94; 7.8813 2.32; 7.8389 10.04; 7.7888 1.76; 7.7690 2.57; 7.6946 2.18; 7.6750 3.19; 7.6553 1.26; 7.6321 7.89; 7.4234 1.05; 7.4085 1.00; 7.2373 7.69; 6.1806 0.44; 6.1593 1.50; 6.1376 2.07; 6.1153 1.54; 6.0940 0.46; 4.8560 2.70; 4.8386 3.05; 4.8354 3.17; 4.8179 2.72; 4.5075 1.80; 4.4897 5.83; 4.4719 5.91; 4.4541 1.88; 2.2284 0.87; 2.2110 3.10; 2.1912 139.92; 2.1604 2.87; 2.1435 0.87; 2.1145 0.32; 2.1082 0.41; 2.1021 0.34; 1.9652 4.58; 1.9590 1.25; 1.9532 18.39; 1.9471 35.49; 1.9409 50.97; 1.9347 35.38; 1.9285 18.38; 1.3071 6.84; 1.2894 15.23; 1.2716 6.82; 1.1469 15.99; 1.1301 15.54; 1.1124 16.00; 1.0955 15.48; −0.0002 1.02
Compound No. 271 cf. Synthesis Example 7
Compound No. 272 [DMSO] 9.9368 2.72; 9.9127 2.80; 9.3005 6.36; 8.2007 4.24; 8.0693 2.30; 8.0496 2.58; 7.8966 7.87; 7.8633 0.45; 7.8452 11.17; 7.8358 2.69; 7.8165 3.05; 7.7411 2.36; 7.7216 3.59; 7.7021 1.50; 7.3469 8.07; 6.3325 0.32; 6.3110 1.14; 6.2892 1.72; 6.2667 1.23; 6.2443 0.35; 4.4962 0.79; 4.4788 0.90; 4.4598 2.21; 4.4423 2.26; 4.4315 2.24; 4.4137 2.21; 4.3950 0.86; 4.3776 0.79; 3.3425 94.06; 3.3372 93.06; 3.3357 91.86; 2.6725 0.36; 2.5256 1.07; 2.5120 20.13; 2.5078 40.51; 2.5034 53.71; 2.4990 39.45; 2.3341 0.38; 2.3303 0.45; 2.0764 16.00; 1.6020 2.25; 1.5878 5.45; 1.5809 6.01; 1.5681 2.55; 1.2891 2.64; 1.2757 5.50; 1.2690 5.85; 1.2546 2.13; 1.1130 0.47; 1.0985 0.94; 1.0943 0.93; 1.0810 1.44; 1.0677 0.92; 1.0631 1.02; 1.0493 0.55; 0.3510 0.46; 0.3448 0.83; 0.3384 1.03; 0.3313 0.72; 0.3231 1.87; 0.3186 2.12; 0.3024 2.09; 0.2887 2.11; 0.2826 2.39; 0.2767 2.29; 0.2700 2.86; 0.2577 1.95; 0.2529 2.01; 0.2402 0.71; 0.2361 0.67; 0.1993 0.95; 0.1943 1.08; 0.1807 1.83; 0.1674 1.65; 0.1535 0.71; 0.0080 0.95; −0.0002 27.45; −0.0085 1.05
Compound No. 273 cf. Synthesis Example 9
Compound No. 274 [DMSO] 9.9336 3.68; 9.9095 3.77; 9.2953 8.64; 8.1942 5.55; 8.0637 3.06; 8.0445 3.44; 7.8888 10.25; 7.8556 1.00; 7.8400 16.00; 7.8154 4.12; 7.7854 0.37; 7.7406 3.18; 7.7210 4.77; 7.7013 1.99; 7.3433 10.64; 6.3036 1.51; 6.2815 2.25; 6.2587 1.60; 6.2369 0.44; 5.7528 0.57; 4.5866 0.36; 4.4927 1.14; 4.4753 1.26; 4.4562 3.00; 4.4388 3.11; 4.4285 3.02; 4.4107 2.99; 4.3921 1.21; 4.3746 1.13; 3.3628 2627.74; 2.6777 1.84; 2.6733 2.54; 2.6688 1.85; 2.5430 1.59; 2.5265 9.31; 2.5217 13.51; 2.5130 143.04; 2.5087 285.87; 2.5042 374.45; 2.4997 271.01; 2.4954 133.10; 2.3352 1.93; 2.3309 2.67; 2.3265 1.87; 2.0731 7.39; 1.5991 3.09; 1.5850 7.36; 1.5781 8.02; 1.5652 3.48; 1.5253 0.40; 1.3293 0.40; 1.2899 3.67; 1.2764 7.51; 1.2698 8.00; 1.2553 3.03; 1.2369 0.93; 1.0918 1.23; 1.0790 1.85; 1.0604 1.34; 1.0476 0.82; 0.3453 1.14; 0.3385 1.30; 0.3190 2.75; 0.3031 2.63; 0.2888 2.66; 0.2775 3.42; 0.2694 2.96; 0.2565 2.63; 0.2447 1.89; 0.1916 1.40; 0.1786 2.50; 0.1655 2.17; −0.0002 2.56
Compound No. 275 [DMSO] 9.7120 2.64; 9.6876 2.69; 9.2902 5.91; 8.1512 16.00; 7.8551 12.37; 7.8510 9.01; 7.3884 7.52; 6.3348 0.33; 6.3140 1.15; 6.2922 1.70; 6.2700 1.20; 6.2473 0.36; 4.5420 1.46; 4.5247 4.11; 4.5070 4.10; 4.4898 1.40; 4.0565 0.35; 4.0387 1.04; 4.0209 1.07; 4.0030 0.35; 3.3215 41.62; 3.2979 3.30; 2.6717 0.56; 2.6670 0.41; 2.5069 63.97; 2.5025 79.84; 2.4981 57.24; 2.3335 0.43; 2.3293 0.57; 1.9896 4.47; 1.6024 2.34; 1.5882 5.99; 1.5816 6.26; 1.5686 2.58; 1.3970 1.10; 1.2988 0.89; 1.2882 2.85; 1.2748 6.08; 1.2684 6.18; 1.2538 2.52; 1.2349 5.94; 1.2175 11.86; 1.1999 5.54; 1.1933 2.31; 1.1753 2.65; 1.1574 1.30; −0.0083 2.39
Compound No. 276 [DMSO] 9.7201 3.68; 9.6959 3.80; 8.3922 4.13; 8.3812 4.17; 7.7866 11.03; 7.7533 14.99; 7.7054 0.33; 7.6806 0.34; 7.6168 7.38; 7.6000 4.80; 7.5452 4.09; 7.5247 7.01; 7.5164 0.62; 7.5127 0.63; 7.5043 3.26; 7.4514 4.08; 7.3740 10.69; 7.2668 11.16; 7.2524 2.73; 7.2476 2.80; 7.0822 4.24; 6.1876 0.41; 6.1666 1.55; 6.1444 2.32; 6.1220 1.65; 6.0997 0.47; 4.5407 1.74; 4.5233 5.13; 4.5055 5.11; 4.4878 1.72; 3.3216 34.66; 3.2980 1.01; 2.8662 0.42; 2.8562 1.20; 2.8466 1.65; 2.8381 2.64; 2.8278 2.70; 2.8193 1.35; 2.8097 1.35; 2.7994 0.57; 2.6704 0.44; 2.5104 25.15; 2.5060 50.96; 2.5015 67.18; 2.4970 47.95; 2.4927 22.78; 2.3328 0.39; 2.3282 0.49; 2.3238 0.41; 2.0748 0.88; 1.2427 0.52; 1.2220 7.34; 1.2046 16.00; 1.1870 7.11; 1.1207 0.36; 1.0636 0.44; 0.7183 1.79; 0.7056 4.90; 0.7003 6.91; 0.6883 6.34; 0.6823 5.37; 0.6711 2.22; 0.5572 2.40; 0.5468 6.90; 0.5405 6.05; 0.5311 5.42; 0.5189 1.64; 0.0080 1.48; −0.0002 41.80; −0.0085 1.34
Compound No. 277 [DMSO] 9.7692 2.45; 9.7450 2.53; 9.3249 5.95; 8.1478 16.00; 7.8960 10.70; 7.8876 7.85; 7.4875 7.24; 6.3199 1.02; 6.2979 1.54; 6.2756 1.10; 5.4448 6.19; 5.4419 6.13; 3.3217 53.71; 3.2981 2.39; 3.2273 2.37; 3.2215 5.01; 3.2156 2.24; 3.0365 0.35; 2.6755 0.41; 2.6712 0.57; 2.6665 0.40; 2.5413 0.33; 2.5244 1.34; 2.5109 29.72; 2.5065 60.24; 2.5020 79.50; 2.4975 56.85; 2.4931 27.09; 2.3334 0.41; 2.3288 0.55; 2.3243 0.40; 1.6082 2.12; 1.5940 5.21; 1.5872 5.64; 1.5742 2.38; 1.2919 2.53; 1.2785 5.28; 1.2719 5.61; 1.2574 2.07; 1.2338 0.41; −0.0002 8.23
Compound No. 278 [DMSO] 9.7680 4.02; 9.7438 4.12; 8.4241 4.69; 8.4130 4.67; 7.8696 0.37; 7.8249 12.00; 7.7932 16.00; 7.6197

TABLE 1-continued (I)

| No. | (R¹)ₙ | X | R² | R³ | R⁴ | G | R⁶ᵃ | R⁶ᵇ | R⁶ᶜ | A | Y | (M + H)⁺ ᵃ⁾ | log p ᵃ⁾ |
|---|---|---|---|---|---|---|---|---|---|---|---|---|---|

6.77; 7.6148 6.39; 7.6057 5.47; 7.5469 4.53; 7.5401 0.65; 7.5264 7.68; 7.5162 0.86; 7.5060 3.67; 7.4869 11.33; 7.4512 4.45; 7.2666 11.88; 7.2532 2.83; 7.2485 2.72; 7.0820 4.67; 6.1927 0.43; 6.1713 1.63; 6.1494 2.47; 6.1269 1.75; 6.1047 0.49; 5.4506 9.39; 5.4466 9.33; 3.3199 95.53; 3.2964 1.70; 3.2062 3.57; 3.2002 7.80; 3.1944 3.33; 2.8695 0.45; 2.8594 1.28; 2.8499 1.73; 2.8412 2.78; 2.8310 2.80; 2.8227 1.75; 2.8128 1.33; 2.8026 0.49; 2.6746 0.75; 2.6701 1.03; 2.6655 0.74; 2.6608 0.35; 2.5404 0.51; 2.5234 2.41; 2.5099 52.90; 2.5055 108.20; 2.5010 143.74; 2.4965 102.43; 2.4921 48.28; 2.3324 0.81; 2.3277 1.09; 2.3233 0.78; 1.2339 0.38; 0.7230 1.87; 0.7101 5.06; 0.7050 7.22; 0.6929 6.63; 0.6869 5.69; 0.6757 2.34; 0.5580 2.42; 0.5475 7.19; 0.5413 6.39; 0.5318 5.83; 0.5196 1.80; −0.0002 4.95
Compound No. 279 cf. Synthesis Example 8
Compound No. 281 [CD3CN] 8.8068 2.52; 8.7832 2.51; 7.9986 3.57; 7.9818 3.44; 7.9493 1.87; 7.9386 2.12; 7.9295 2.47; 7.9168 2.25; 7.8583 3.08; 7.8333 0.60; 7.8209 15.55; 7.8111 0.58; 7.8017 0.34; 7.7913 2.92; 7.7838 1.37; 7.7726 1.23; 7.7669 1.22; 7.7204 0.44; 7.6584 16.00; 7.6310 3.38; 7.6200 0.39; 7.5930 0.43; 7.5745 3.01; 7.4575 3.71; 7.4326 4.43; 7.4198 0.61; 7.4096 3.11; 7.3422 0.44; 7.3167 0.73; 7.2926 0.44; 7.2414 0.37; 7.2359 0.41; 7.1721 0.33; 7.1656 0.42; 6.9632 0.83; 6.9332 2.88; 6.1649 0.40; 6.1384 0.52; 6.1237 1.12; 6.1040 2.76; 6.0957 1.03; 6.0830 3.39; 6.0681 1.44; 6.0597 2.98; 6.0554 2.63; 6.0421 2.29; 6.0293 2.42; 6.0254 1.47; 6.0205 0.93; 6.0161 1.40; 6.0123 2.47; 5.9993 2.09; 5.9948 0.85; 5.9863 2.36; 5.9733 1.10; 5.8775 0.34; 5.8591 0.96; 5.8403 1.01; 5.8219 0.69; 5.8092 0.35; 5.7961 0.49; 5.7792 0.48; 5.7662 0.36; 5.7534 0.46; 5.4843 0.88; 5.4807 0.88; 5.4490 14.25; 5.4414 0.93; 5.4376 0.89; 5.3522 0.93; 5.3490 0.91; 5.3258 0.87; 5.3228 0.85; 5.2664 9.20; 5.2627 7.16; 5.2573 5.89; 5.2534 7.87; 5.2211 0.62; 5.1889 0.32; 5.1580 5.01; 5.1552 4.99; 5.1320 4.71; 5.1292 4.66; 5.1088 0.32; 5.0697 0.96; 5.0669 0.86; 5.0437 0.84; 5.0413 0.82; 5.0021 4.43; 4.9994 4.63; 4.9829 1.07; 4.9632 2.84; 4.9593 4.46; 4.9563 4.39; 4.9524 2.80; 4.9301 1.33; 4.9274 1.29; 4.9166 0.54; 4.8997 0.34; 4.8872 0.68; 4.8848 0.69; 4.8440 1.67; 4.8404 1.07; 4.8305 1.73; 4.8267 1.12; 2.8871 0.55; 2.8775 1.74; 2.8683 2.65; 2.8594 4.19; 2.8500 4.24; 2.8414 3.18; 2.8320 2.17; 2.8225 0.76; 2.4667 0.36; 2.1871 524.56; 2.1212 0.70; 2.1153 0.91; 2.1091 0.99; 2.1030 0.76; 2.0969 0.49; 1.9660 5.24; 1.9597 6.14; 1.9540 50.24; 1.9479 93.65; 1.9417 130.32; 1.9356 90.46; 1.9294 47.10; 1.7825 0.40; 1.7763 0.65; 1.7702 0.87; 1.7640 0.61; 1.7577 0.38; 1.4360 0.53; 1.3859 0.48; 1.3720 8.60; 1.3403 4.32; 1.2849 5.63; 1.2764 10.49; 1.2699 3.57; 1.2166 0.43; 0.8812 0.85; 0.8759 0.68; 0.8581 0.88; 0.8389 0.64; 0.8143 0.36; 0.7957 2.72; 0.7830 7.96; 0.7779 10.62; 0.7654 10.91; 0.7601 8.24; 0.7480 3.78; 0.7263 0.59; 0.7085 0.56; 0.6597 0.38; 0.6499 0.40; 0.6198 3.08; 0.6080 8.57; 0.6026 9.63; 0.5985 9.28; 0.5932 8.66; 0.5807 2.40; 0.0081 1.05; −0.0002 32.31; −0.00851.14
Compound No. 282 [DMSO] 9.7255 1.68; 9.7012 1.73; 9.1573 3.54; 8.2097 2.53; 8.0695 1.34; 8.0500 1.50; 7.8333 1.23; 7.8137 1.78; 7.7387 1.33; 7.7193 2.05; 7.6997 0.92; 7.6854 5.33; 7.4638 3.87; 7.3404 4.50; 6.3203 0.69; 6.2980 1.06; 6.2749 0.75; 4.5364 0.73; 4.5192 2.21; 4.5015 2.24; 4.4842 0.74; 4.0554 1.21; 4.0376 3.74; 4.0198 3.79; 4.0020 1.27; 3.3267 27.82; 2.8915 0.93; 2.8729 2.78; 2.8542 2.83; 2.8357 1.00; 2.6752 0.35; 2.6710 0.50; 2.6665 0.40; 2.5104 27.73; 2.5063 55.55; 2.5019 75.05; 2.4975 58.23; 2.3332 0.37; 2.3287 0.51; 2.3243 0.41; 1.9893 16.00; 1.5789 1.19; 1.5646 3.06; 1.5580 3.43; 1.5452 1.41; 1.2831 1.64; 1.2697 3.28; 1.2630 3.50; 1.2487 1.39; 1.2350 3.15; 1.2177 6.58; 1.2052 4.94; 1.2004 4.06; 1.1923 5.92; 1.1867 8.90; 1.1745 9.49; 1.1681 4.46; 1.1567 4.55; 1.1211 0.36; 1.1027 0.33; 1.0839 0.38; 0.0080 0.58; −0.0002 14.36; −0.0083 0.77
Compound No. 283 [DMSO] 9.8678 4.27; 9.8437 4.39; 9.3073 9.71; 8.1818 6.31; 8.0520 3.36; 8.0325 3.78; 7.869016.00; 7.8293 3.13; 7.8096 4.46; 7.7835 11.92; 7.7331 3.31; 7.7136 5.12; 7.6940 2.13; 7.4200 11.88; 6.3148 0.46; 6.2934 1.72; 6.2714 2.60; 6.2488 1.86; 6.2266 0.53; 5.9349 0.74; 5.9225 1.71; 5.9095 1.49; 5.8967 1.99; 5.8928 1.14; 5.8836 1.25; 5.8798 2.03; 5.8667 1.61; 5.8539 1.91; 5.8414 0.90; 5.1771 5.92; 5.1676 5.66; 4.9893 3.83; 4.9861 3.80; 4.9635 3.59; 4.9603 3.55; 4.7348 3.61; 4.7314 3.57; 4.6919 3.36; 4.6885 3.34; 3.3300 55.87; 2.6762 0.58; 2.6718 0.80; 2.6674 0.59; 2.5247 2.89; 2.5114 46.37; 2.5072 89.90; 2.5028 116.81; 2.4983 86.43; 2.4941 44.35; 2.3340 0.59; 2.3295 0.80; 2.3251 0.59; 2.0762 3.80; 1.6003 3.27; 1.5862 8.10; 1.5793 8.90; 1.5664 3.69; 1.3255 0.38; 1.2854 3.88; 1.2720 8.18; 1.2653 8.78; 1.2509 3.10; 0.0076 1.23; −0.0002 29.41; −0.0083 1.62
Compound No. 284 [DMSO] 9.9380 1.18; 9.9137 1.22; 9.3023 2.75; 8.1638 1.86; 8.0237 1.01; 8.0049 1.12; 7.95392.38; 7.8736 7.51; 7.8287 0.95; 7.8096 1.27; 7.7228 0.92; 7.7031 1.41; 7.6834 0.60; 7.4147 3.23; 7.1682 2.68; 7.1584 3.75; 7.1520 3.90; 6.9908 1.71; 6.9819 1.98; 6.9729 1.64; 6.2880 0.51; 6.2657 0.75; 6.2432 0.54; 5.7843 2.86; 3.3309 43.45; 2.8909 16.00; 2.7318 13.98; 2.6716 0.39; 2.5066 46.43; 2.5024 55.22; 2.4983 40.55; 2.3291 0.37; 1.9896 0.80; 1.5928 0.89; 1.5786 2.34; 1.5721 2.51; 1.5590 1.06; 1.3974 0.83; 1.2715 1.10; 1.2583 2.63; 1.2517 2.59; 1.2372 0.92; 1.1747 0.46; −0.0002 12.25
Compound No. 285 [DMSO] 9.8909 0.70; 9.8668 0.72; 9.3242 1.67; 8.2072 1.01; 8.0741 0.54; 8.0549 0.61; 7.95362.01; 7.8771 2.86; 7.8566 2.00; 7.8394 0.51; 7.8197 0.71; 7.7465 0.54; 7.7270 0.83; 7.7076 0.35; 7.4390 1.90; 6.3073 0.41; 5.3754 1.30; 5.3698 1.29; 3.3330 26.73; 2.8909 16.00; 2.7312 12.93; 2.5252 0.46; 2.5204 0.73; 2.5118 7.74; 2.5074 15.58; 2.5028 20.47; 2.4982 14.94; 2.4937 7.41; 1.6180 1.92; 1.6125 3.86; 1.6071 2.35; 1.5936 1.39; 1.5868 1.48; 1.5739 0.65; 1.2933 0.67; 1.2797 1.34; 1.2731 1.44; 1.2586 0.71; −0.0002 3.10
Compound No. 286 [DMSO] 9.9937 2.01; 9.9695 2.11; 9.9154 0.63; 9.8911 0.61; 9.3368 6.19; 8.2236 3.00; 8.19820.83; 8.0784 1.62; 8.0583 2.03; 8.0345 0.43; 7.8931 16.00; 7.8869 3.08; 7.8707 1.78; 7.8186 2.15; 7.7906 0.53; 7.7286 1.55; 7.7091 2.56; 7.6889 1.24; 7.4640 1.28; 7.4428 0.43; 7.4243 6.17; 7.3227 0.38; 7.3199 0.42; 7.3049 0.46; 7.2980 1.07; 7.2802 1.34; 7.2765 0.97; 7.2717 0.65; 7.2609 0.40; 7.2454 0.39; 7.2337 0.43; 7.2291 0.50; 7.2169 1.14; 7.2143 1.30; 7.2044 2.28; 7.1999 7.39; 7.1952 3.89; 7.1899 1.21; 7.1853 2.09; 7.1815 4.37; 7.1744 0.90; 7.1713 0.87; 7.1670 1.42; 7.1596 1.86; 7.1407 0.71; 7.0751 3.50; 7.0716 3.83; 7.0566 2.83; 7.0518 2.65; 6.3374 0.84; 6.3159 1.32; 6.2935 0.98; 6.2715 0.33; 6.0699 1.70; 6.0604 0.67; 6.0426 0.90; 6.0157 4.31; 6.0083 4.32; 5.9815 0.80; 4.6898 0.44; 4.6844 0.54; 4.6730 0.33; 4.6659 0.36; 4.6485 1.21; 4.6410 1.19; 4.5421 0.88; 4.4114 0.39; 4.4067 0.39; 4.3513 1.81; 4.3298 2.77; 4.3222 4.32; 4.2829 4.12; 4.2537 1.80; 3.3301 51.21; 2.6756 0.38; 2.6714 0.56; 2.6668 0.42; 2.5244 1.88; 2.5112 31.82; 2.5068 63.42; 2.5023 83.54; 2.4977 61.33; 2.4932 30.60; 2.3335 0.41; 2.3289 0.57; 2.3246 0.41; 2.0759 1.12; 1.6078 2.10; 1.5936 5.01; 1.5868 5.49; 1.5739 2.36; 1.2917 2.27; 1.2783 4.82; 1.2717 5.12; 1.2571 1.86; 0.0080 0.92; −0.0002 23.96; −0.0085 1.09
Compound No. 287 [DMSO] 9.9661 1.39; 9.9419 1.44; 9.3341 3.33; 8.1896 2.05; 8.0603 1.09; 8.0409 1.22; 7.9532 1.92; 7.8925 4.08; 7.8760 5.64; 7.8341 1.00; 7.8143 1.42; 7.7375 1.09; 7.7179 1.66; 7.6984 0.68; 7.3768 3.92; 6.3133 0.55; 6.2912 0.83; 6.2684 0.59; 5.9262 0.68; 5.8992 2.76; 5.8880 2.77; 5.8610 0.70; 3.3309 76.09; 3.2815 0.64; 3.2756 0.55; 3.2638 0.72; 3.2578 1.65; 3.2506 0.61; 3.2463 0.44; 3.2402 1.66; 2.3332 1.63; 3.2271 0.42; 3.2226 0.62; 3.2156 1.64; 3.2096 0.73; 3.1981 0.53; 3.1920 0.42; 2.8908 16.00; 2.7316 12.37; 2.7309 12.27; 2.6715 0.43; 2.5249 1.57; 2.5200 2.45; 2.5115 24.25; 2.5070 48.66; 2.5025 63.89; 2.4979 46.66; 2.4934 23.07; 2.3338 0.32; 2.3292 0.44; 2.3245 0.35; 1.6062 1.13; 1.5921 2.64; 1.5853 2.89; 1.5723 1.25; 1.3972 1.05; 1.2986 0.46; 1.2894 1.31; 1.2759 2.66; 1.2693 2.86; 1.2582 0.94; 1.2549 1.14; 1.2495 0.53; 0.9118 4.24; 0.8943 8.73; 0.8767 4.10; 0.0079 0.71; −0.0002 19.85; −0.0085 0.82
Compound No. 288 [DMSO] 9.8833 3.58; 9.8591 3.71; 9.2967 8.30; 8.1963 5.23; 8.0650 2.78; 8.0457 3.15; 7.8642 9.90; 7.8432 13.73; 7.8321 2.88; 7.8122 3.64; 7.7363 2.74; 7.7167 4.24; 7.6972 1.77; 7.3547 9.86; 6.3407 0.38; 6.3194 1.40; 6.2972 2.14; 6.2747 1.54;

TABLE 1-continued
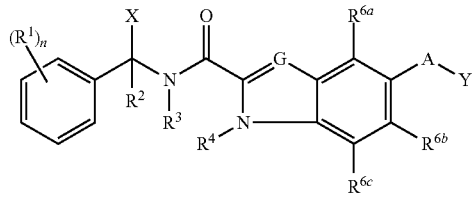
| No. | $(R^1)_n$ | X | $R^2$ | $R^3$ | $R^4$ | G | $R^{6a}$ | $R^{6b}$ | $R^{6c}$ | A | Y | $(M+H)^{+\ a)}$ | log p $^{a)}$ |
|---|---|---|---|---|---|---|---|---|---|---|---|---|---|
6.2522 0.44; 4.5062 0.63; 4.4883 1.92; 4.4713 3.50; 4.4605 3.57; 4.4433 1.93; 4.4259 0.63; 3.3293 92.63; 2.6759 0.68; 2.6716 0.95; 2.6671 0.70; 2.5414 0.50; 2.5248 3.12; 2.5112 52.91; 2.5070 104.07; 2.5025 136.24; 2.4980 100.67; 2.4937 50.98; 2.3337 0.70; 2.3292 0.95; 2.3249 0.72; 2.0760 0.72; 1.6461 0.52; 1.6281 2.21; 1.6100 4.50; 1.5993 4.09; 1.5914 5.78; 1.5854 7.97; 1.5782 8.54; 1.5655 3.54; 1.2856 3.21; 1.2722 6.73; 1.2655 7.27; 1.2511 2.59; 0.7254 7.49; 0.7071 16.00; 0.6885 6.89; 0.0078 1.35; −0.0002 35.98; −0.0083 1.77
Compound No. 289 [DMSO] 9.5971 2.32; 9.5726 2.41; 9.1193 4.74; 8.1566 13.58; 7.7321 6.99; 7.4712 4.75; 7.3414 6.27; 6.3108 0.92; 6.2888 1.37; 6.2660 0.98; 4.5201 1.02; 4.5029 3.04; 4.4854 3.07; 4.4681 1.02; 4.0562 1.02; 4.0384 3.10; 4.0206 3.12; 4.0028 1.05; 3.3293 33.37; 2.6766 0.45; 2.6721 0.57; 2.6678 0.43; 2.5251 2.30; 2.5075 67.11; 2.5032 84.81; 2.4988 62.31; 2.4686 16.00; 2.3343 0.44; 2.3297 0.59; 2.3256 0.43; 1.9901 13.20; 1.5793 1.60; 1.5652 4.20; 1.5584 4.56; 1.5455 1.91; 1.2938 2.13; 1.2806 4.57; 1.2739 4.85; 1.2594 1.92; 1.2453 4.23; 1.2279 8.85; 1.2103 4.09; 1.1931 3.78; 1.1752 7.27; 1.1575 3.59; 0.0079 1.01; −0.0002 21.12; −0.0083 1.11
Compound No. 290 [DMSO] 9.5708 2.32; 9.5462 2.40; 9.1192 4.75; 8.1202 6.40; 8.1043 6.41; 7.7312 7.34; 7.7089 0.33; 7.4703 4.65; 7.3393 6.33; 6.2929 0.91; 6.2713 1.34; 6.2483 0.97; 4.5214 0.99; 4.5042 3.01; 4.4865 3.03; 4.4691 0.99; 4.0563 0.68; 4.0384 2.07; 4.0206 2.10; 4.0028 0.70; 3.3304 26.99; 2.6723 0.41; 2.5256 1.39; 2.5122 23.18; 2.5079 46.13; 2.5033 60.59; 2.4988 44.61; 2.4943 22.50; 2.4683 16.00; 2.3301 0.42; 1.9902 8.97; 1.5795 1.66; 1.5653 4.24; 1.5585 4.60; 1.5457 1.96; 1.2939 2.37; 1.2804 4.63; 1.2737 4.89; 1.2593 1.98; 1.2461 4.25; 1.2287 9.20; 1.2110 4.15; 1.1934 2.55; 1.1756 4.90; 1.1577 2.53; 1.1380 0.55; 1.1184 0.57; 0.0079 0.70; −0.0002 18.27; −0.0085 0.84
Compound No. 291 [DMSO] 9.6243 2.33; 9.6001 2.38; 9.1166 4.72; 8.1124 4.48; 7.7833 0.41; 7.7639 10.97; 7.7392 0.42; 7.7202 7.24; 7.7001 0.39; 7.4653 4.62; 7.3347 6.14; 6.2374 0.96; 6.2156 1.42; 6.1927 0.99; 4.5196 1.01; 4.5026 3.01; 4.4849 2.99; 4.4675 0.99; 4.0557 0.62; 4.0380 1.88; 4.0201 1.91; 4.0023 0.65; 3.3287 55.40; 2.6759 0.45; 2.6716 0.63; 2.6672 0.46; 2.5245 2.71; 2.5114 36.79; 2.5070 71.49; 2.5025 93.01; 2.4980 68.22; 2.4936 34.13; 2.4670 16.00; 2.3339 0.48; 2.3293 0.65; 2.3249 0.47; 1.9895 8.13; 1.5768 1.67; 1.5624 4.24; 1.5557 4.56; 1.5428 1.91; 1.2933 2.39; 1.2800 4.55; 1.2733 4.79; 1.2589 1.83; 1.2397 4.28; 1.2224 9.03; 1.2047 4.05; 1.1929 2.37; 1.1752 4.29; 1.1573 2.21; 1.1369 0.49; 1.1202 0.46; 1.1017 0.55; 0.0076 0.97; −0.0002 22.55; −0.0084 0.97
Compound No. 292 [DMSO] 9.5919 2.34; 9.5676 2.41; 9.1177 4.71; 9.0816 0.36; 7.9539 0.81; 7.9500 0.85; 7.9282 1.62; 7.9054 0.83; 7.9013 0.85; 7.7165 7.31; 7.6977 0.57; 7.6521 0.70; 7.6452 1.17; 7.6303 1.32; 7.6240 1.97; 7.5925 1.29; 7.5682 2.18; 7.5457 2.03; 7.5239 0.70; 7.4657 4.60; 7.3847 0.38; 7.3293 6.10; 6.2073 0.93; 6.1852 1.38; 6.1628 0.98; 4.5249 0.97; 4.5073 2.69; 4.4890 2.66; 4.4710 0.97; 4.0560 0.88; 4.0382 2.72; 4.0204 2.75; 4.0026 0.92; 3.3316 37.45; 2.6720 0.41; 2.5253 1.60; 2.5119 24.24; 2.5075 47.89; 2.5029 62.73; 2.4983 46.05; 2.4938 23.25; 2.4675 16.00; 2.3297 0.43; 1.9896 12.11; 1.5773 1.68; 1.5630 4.26; 1.5562 4.65; 1.5434 1.98; 1.2937 2.48; 1.2804 4.59; 1.2737 4.85; 1.2593 1.89; 1.2421 4.23; 1.2247 9.15; 1.2070 4.12; 1.1932 3.54; 1.1754 6.65; 1.1576 3.52; 1.1387 0.66; 1.1208 0.34; 1.1081 0.38; 1.0893 0.76; 1.0704 0.36; 0.0079 0.50; −0.0002 13.09; −0.0085 0.60
Compound No. 293 [DMSO] 9.5953 2.24; 9.5708 2.31; 9.1176 4.61; 8.3151 1.32; 7.7969 3.73; 7.7240 8.26; 7.6945 1.56; 7.5663 1.41; 7.5612 2.03; 7.5560 1.29; 7.5446 1.48; 7.5396 2.04; 7.5342 1.17; 7.4651 4.54; 7.3432 6.10; 6.2654 0.86; 6.2435 1.29; 6.2210 0.92; 4.5232 0.98; 4.5058 2.88; 4.4880 2.85; 4.4705 0.94; 4.0380 0.73; 4.0202 0.72; 3.8314 1.16; 3.3301 194.48; 2.6810 0.39; 2.6764 0.83; 2.6719 1.16; 2.6673 0.85; 2.6628 0.40; 2.5421 0.60; 2.5252 3.91; 2.5204 6.16; 2.5119 63.14; 2.5074 127.12; 2.5028 167.45; 2.4982 121.38; 2.4937 59.13; 2.4684 16.00; 2.3385 0.38; 2.3341 0.82; 2.3296 1.13; 2.3249 0.82; 2.3203 0.40; 1.9891 3.24; 1.5759 1.61; 1.5617 3.99; 1.5549 4.35; 1.5421 1.85; 1.2934 2.21; 1.2800 4.43; 1.2733 4.77; 1.2588 1.92; 1.2446 4.22; 1.2272 9.25; 1.2095 4.06; 1.1935 1.05; 1.1757 1.86; 1.1579 0.93; 0.0080 1.35; −0.0002 40.16; −0.0085 1.55
Compound No. 294 [DMSO] 9.9489 4.28; 9.9248 4.44; 9.3460 10.27; 8.2139 6.40; 8.0816 3.70; 8.0692 13.21; 7.9517 16.00; 7.8397 3.14; 7.8200 4.45; 7.7459 3.38; 7.7264 5.15; 7.7069 2.15; 7.6621 11.84; 6.3869 0.45; 6.3653 1.72; 6.3432 2.63; 6.3208 1.88; 6.2987 0.54; 5.7284 15.89; 3.3311 68.74; 2.6769 0.52; 2.6724 0.71; 2.6679 0.53; 2.5253 2.82; 2.5118 41.71; 2.5077 80.41; 2.5033 103.71; 2.4989 75.71; 2.3344 0.53; 2.3300 0.70; 2.3255 0.52; 2.0764 0.63; 1.6149 3.38; 1.6007 8.12; 1.5939 8.74; 1.5809 3.64; 1.5410 0.33; 1.3378 0.33; 1.2977 3.86; 1.2842 8.17; 1.2776 8.66; 1.2631 3.03; 0.0079 1.05; −0.0002 24.61; −0.0082 0.95
Compound No. 295 [DMSO] 9.5502 2.30; 9.5259 2.37; 8.2465 2.41; 8.2356 2.44; 7.9567 0.88; 7.9531 0.90; 7.9313 1.63; 7.9086 0.85; 7.9040 0.86; 7.6525 0.77; 7.6452 1.21; 7.6400 0.99; 7.6266 8.82; 7.6034 0.34; 7.5902 1.40; 7.5678 1.91; 7.5654 2.00; 7.5432 2.02; 7.5215 0.70; 7.4153 4.55; 7.3825 0.42; 7.3330 0.64; 7.3213 6.23; 6.2019 0.96; 6.1797 1.41; 6.1573 1.00; 4.5205 1.03; 4.5031 2.85; 4.4847 2.81; 4.4668 1.02; 4.0559 0.48; 4.0381 1.46; 4.0203 1.46; 4.0025 0.48; 3.3302 54.56; 2.8599 0.73; 2.8504 0.99; 2.8417 1.62; 2.8316 1.61; 2.8234 1.19; 2.8134 0.84; 2.8034 0.42; 2.6762 0.42; 2.6716 0.58; 2.6671 0.48; 2.6583 1.12; 2.5251 2.20; 2.5202 3.44; 2.5117 31.46; 2.5073 62.57; 2.5027 81.82; 2.4982 59.46; 2.4937 29.41; 2.4457 16.00; 2.3340 0.43; 2.3293 0.57; 2.3251 0.43; 1.9896 6.49; 1.3365 1.08; 1.2591 0.52; 1.2497 1.58; 1.2418 1.27; 1.2332 4.60; 1.2158 8.88; 1.1981 4.01; 1.1932 2.64; 1.1752 3.51; 1.1573 1.75; 1.1451 0.35; 1.1277 0.65; 1.0978 0.38; 1.0792 0.77; 1.0601 0.37; 0.7082 1.04; 0.6955 2.87; 0.6902 4.07; 0.6783 3.66; 0.6722 3.20; 0.6611 1.35; 0.5622 0.42; 0.5547 1.56; 0.5442 4.08; 0.5381 3.43; 0.5343 3.32; 0.5285 3.08; 0.5163 0.96; 0.0079 0.58; −0.0002 15.02; −0.0085 0.66
Compound No. 296 [DMSO] 9.5278 2.31; 9.5031 2.39; 8.3174 0.40; 8.2469 2.55; 8.2359 2.57; 8.1206 6.48; 8.1048 6.43; 8.0700 0.49; 8.0540 0.48; 7.6409 7.35; 7.6051 0.55; 7.4180 4.53; 7.3302 6.36; 6.2864 0.92; 6.2647 1.33; 6.2417 0.97; 5.7574 1.11; 4.5177 1.00; 4.5006 3.04; 4.4829 3.05; 4.4653 0.97; 4.0563 0.76; 4.0385 2.32; 4.0207 2.36; 4.0029 0.79; 3.3609 0.36; 3.3334 137.10; 2.86170.76; 2.8518 1.01; 2.8436 1.74; 2.8333 1.66; 2.8253 1.25; 2.8153 0.83; 2.8054 0.44; 2.6726 0.49; 2.6580 1.34; 2.5427 0.35; 2.5391 0.40; 2.5259 2.22; 2.5212 3.40; 2.5126 28.42; 2.5081 56.76; 2.5036 74.37; 2.4990 53.52; 2.4944 26.01; 2.4478 16.00; 2.3349 0.38; 2.3303 0.51; 2.3258 0.39; 1.9899 10.63; 1.2380 4.25; 1.2207 9.14; 1.2030 4.07; 1.1937 3.24; 1.1759 5.80; 1.1581 2.86; 1.1466 0.36; 1.1285 0.94; 1.1092 0.98; 1.0900 0.36; 0.7098 1.09; 0.6969 2.88; 0.6918 4.11; 0.6799 3.68; 0.6737 3.21; 0.6627 1.37; 0.5646 0.43; 0.5559 1.63; 0.5455 4.08; 0.5395 3.46; 0.5354 3.34; 0.5299 3.10; 0.5177 1.00; 0.0080 0.59; −0.0002 15.76; −0.0085 0.61
Compound No. 297 [DMSO] 9.5835 2.22; 9.5591 2.29; 8.3183 0.36; 8.2457 2.46; 8.2347 2.37; 8.1150 4.71; 7.79010.32; 7.7633 11.41; 7.7613 10.75; 7.7419 0.63; 7.6302 7.15; 7.5969 0.44; 7.5909 0.45; 7.4354 0.35; 7.4150 4.53; 7.3267 6.26; 7.1036 0.39; 6.2324 0.96; 6.2101 1.43; 6.1872 1.01; 5.7585 0.58; 4.5157 1.04; 4.4984 3.15; 4.4807 3.17; 4.4632 1.04; 4.0556 0.63; 4.0378 1.94; 4.0200 1.98; 4.0022 0.65; 3.3293 69.56; 2.8922 3.79; 2.8596 0.76; 2.8487 1.08; 2.8415 1.61; 2.8313 1.70; 2.8233 1.08; 2.8132 0.92; 2.6761 0.61; 2.6715 0.85; 2.6669 0.66; 2.6621 0.42; 2.6557 0.78; 2.5385 0.60; 2.5247 3.42; 2.5199 5.38; 2.5114 46.39; 2.5070 91.51; 2.5024 119.56; 2.4979 86.94; 2.4934 43.03; 2.4644 1.48; 2.4456 16.00; 2.3337 0.63; 2.3292 0.84; 2.3246 0.62; 1.9895 8.55; 1.3460 0.61; 1.3360 1.56; 1.24932.15; 1.2312 4.90; 1.2136 8.93; 1.1957 4.20; 1.1931 4.21; 1.1751 4.73; 1.1572 2.32; 1.1264 0.51; 1.1103 0.46; 1.0921 0.60; 0.7079 1.07; 0.6950 2.98; 0.6899 4.21; 0.6780 3.80; 0.6718 3.33; 0.6608 1.40; 0.5547 1.57; 0.5442 4.19; 0.5381 3.62; 0.5343 3.46; 0.5285 3.21; 0.5163 1.00; 0.0080 0.86; −0.0002 22.57; −0.0084 0.94

TABLE 1-continued
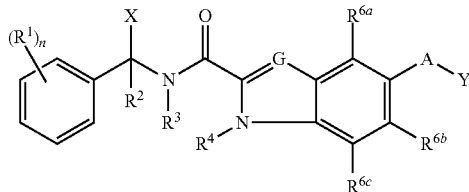
(I)
| No. | (R¹)ₙ | X | R² | R³ | R⁴ | G | R⁶ᵃ | R⁶ᵇ | R⁶ᶜ | A | Y | (M + H)⁺ᵃ⁾ | log p ᵃ⁾ |
|---|---|---|---|---|---|---|---|---|---|---|---|---|---|
Compound No. 298 [DMSO] 9.5565 2.34; 9.5319 2.40; 8.2467 2.55; 8.2358 2.48; 7.8023 4.22; 7.7238 1.80; 7.70041.79; 7.6358 7.11; 7.5698 1.54; 7.5648 2.26; 7.5596 1.35; 7.5481 1.65; 7.5431 2.31; 7.5379 1.27; 7.4708 0.33; 7.4180 4.68; 7.3953 0.61; 7.3357 6.56; 6.2633 0.98; 6.2415 1.44; 6.2187 1.05; 4.5193 1.14; 4.5017 3.36; 4.4840 3.32; 4.4667 1.09; 4.0557 0.71; 4.0379 2.14; 4.0201 2.17; 4.0023 0.74; 3.3291 72.08; 2.9091 0.71; 2.9032 1.42; 2.8605 0.73; 2.8509 1.02; 2.8422 1.52; 2.8323 1.54; 2.8242 1.00; 2.8141 0.74; 2.6756 0.84; 2.6716 1.05; 2.6671 0.82; 2.6581 1.65; 2.5246 4.26; 2.5112 51.04; 2.5070 97.20; 2.5025 124.58; 2.4981 90.33; 2.4939 44.60; 2.4645 0.97; 2.4467 16.00; 2.3335 0.63; 2.3292 0.86; 2.3249 0.63; 1.9895 9.33; 1.3474 0.38; 1.3361 3.13; 1.2593 0.92; 1.2494 4.17; 1.2431 2.16; 1.2348 5.86; 1.2175 8.94; 1.1999 4.10; 1.1929 3.11; 1.1750 4.99; 1.1572 2.47; 0.7083 1.01; 0.6955 2.88; 0.6904 3.94; 0.6783 3.58; 0.6724 3.13; 0.6614 1.27; 0.5546 1.37; 0.5442 4.05; 0.5380 3.60; 0.5286 3.18; 0.5164 0.94; 0.0079 0.91; −0.0002 19.97; −0.0077 0.85
Compound No. 299 [DMSO] 9.9273 3.75; 9.9032 3.91; 9.3024 8.90; 8.1830 5.51; 8.0574 2.97; 8.0381 3.30; 7.9526 0.86; 7.8756 10.33; 7.8375 16.00; 7.8102 3.87; 7.7327 2.97; 7.7132 4.53; 7.6937 1.90; 7.3185 10.82; 6.3272 0.42; 6.3065 1.49; 6.2835 2.24; 6.2610 1.59; 6.2391 0.46; 4.4126 0.93; 4.3939 1.09; 4.3770 2.72; 4.3585 3.16; 4.3525 3.23; 4.3333 2.77; 4.3178 1.09; 4.2985 0.97; 3.4037 0.39; 3.3326 880.92; 2.8905 6.85; 2.7307 5.55; 2.6756 2.67; 2.6711 3.67; 2.6666 2.73; 2.6621 1.35; 2.5244 14.21; 2.5111 213.88; 2.5067 428.19; 2.5021 560.62; 2.4976 408.56; 2.4931 204.67; 2.3378 1.21; 2.3333 2.58; 2.3289 3.56; 2.3243 2.66; 2.3200 1.31; 1.9273 0.72; 1.9105 1.44; 1.8934 1.82; 1.8765 1.48; 1.8590 0.76; 1.5975 3.04; 1.5834 7.27; 1.5766 7.97; 1.5637 3.43; 1.3355 2.93; 1.3232 0.46; 1.2978 1.91; 1.2825 3.64; 1.2690 7.50; 1.2623 8.31; 1.2488 6.33; 1.2354 1.14; 0.9990 0.32; 0.9821 0.32; 0.7562 0.35; 0.7381 0.74; 0.7173 13.64; 0.7007 13.29; 0.6666 13.48; 0.6500 13.15; 0.1460 0.99; 0.0079 8.68; −0.0002 234.15; −0.1498 1.03
Compound No. 300 [DMSO] 10.4523 2.00; 10.4281 2.10; 8.4559 2.21; 8.4450 2.21; 8.3588 1.43; 8.3448 1.39; 8.2008 0.79; 8.1943 0.86; 8.1865 1.00; 8.1792 0.90; 8.1733 0.86; 7.9255 7.27; 7.7383 7.63; 7.6943 1.25; 7.6686 1.62; 7.6460 1.18; 6.3936 0.79; 6.3719 1.17; 6.3493 0.84; 4.0564 1.21; 4.0386 3.68; 4.0208 3.72; 4.0030 1.25; 3.5783 0.36; 3.5688 0.79; 3.5602 1.06; 3.5513 1.47; 3.5422 1.07; 3.5339 0.77; 3.5240 0.38; 3.3336 31.59; 2.8511 0.60; 2.8418 0.86; 2.8329 1.33; 2.8229 1.38; 2.8146 0.86; 2.8048 0.63; 2.5258 1.28; 2.5123 17.74; 2.5080 34.99; 2.5036 45.56; 2.4990 33.48; 2.4948 16.85; 2.3303 0.34; 1.9902 16.00; 1.3371 0.55; 1.2995 0.47; 1.2592 0.67; 1.2499 0.75; 1.2351 0.61; 1.1934 4.34; 1.1756 8.61; 1.1578 4.34; 1.1457 0.50; 1.1362 0.70; 1.1260 0.85; 1.1194 1.02; 1.1127 0.93; 1.1045 1.32; 1.0954 1.38; 1.0885 0.92; 1.0824 0.96; 1.0759 0.94; 1.0652 0.73; 1.0565 0.47; 0.8647 0.34; 0.8533 0.60; 0.8375 0.80; 0.8267 1.13; 0.8136 1.17; 0.8045 0.61; 0.7917 0.59; 0.7825 1.13; 0.7689 1.06; 0.7580 0.77; 0.7471 0.46; 0.7422 0.50; 0.7282 0.95; 0.7150 2.29; 0.7101 3.31; 0.6981 2.98; 0.6920 2.65; 0.6809 1.10; 0.5833 1.14; 0.5729 3.34; 0.5664 3.03; 0.5574 2.64; 0.5450 0.84; −0.0002 1.38
Compound No. 301 [DMSO] 10.7140 2.01; 8.6376 1.15; 8.6264 1.16; 8.5370 4.38; 8.5259 4.41; 8.4752 3.01; 8.4630 2.87; 8.3178 0.93; 8.2604 1.86; 8.2550 2.00; 8.2483 2.29; 8.2378 2.47; 8.1843 13.71; 8.0901 3.43; 7.9851 3.51; 7.9495 0.64; 7.8515 14.05; 7.6658 2.87; 7.6401 3.72; 7.6172 2.73; 7.5925 0.37; 6.3961 1.26; 6.3760 1.76; 6.3569 1.22; 5.8181 2.18; 5.8048 16.00; 3.3276 362.33; 2.8863 0.50; 2.8761 1.38; 2.8663 1.92; 2.8580 2.79; 2.8478 2.85; 2.8394 1.76; 2.8297 1.28; 2.8193 0.50; 2.6757 2.66; 2.6712 3.57; 2.6668 2.69; 2.5412 3.95; 2.5384 3.34; 2.5244 16.00; 2.5109 206.69; 2.5066 402.55; 2.5022 521.64; 2.4977 377.76; 2.4934 185.73; 2.3334 2.61; 2.3289 3.52; 2.3245 2.64; 2.0753 2.61; 0.7538 0.54; 0.7402 2.76; 0.7361 2.29; 0.7223 7.71; 0.7100 6.19; 0.7042 5.41; 0.6930 2.06; 0.5716 2.42; 0.5608 7.71; 0.5550 7.31; 0.5510 6.82; 0.5460 5.91; 0.5335 1.73; 0.4661 0.37; 0.4578 0.33; 0.0079 0.58; −0.0002 15.23; −0.0083 0.68
Compound No. 302 cf. Synthesis Example 6
Compound No. 303 [CD3CN] 8.5834 3.10; 7.7549 6.64; 7.7516 7.02; 7.7435 7.02; 7.7401 7.17; 7.7251 7.12; 7.6719 11.14; 7.5778 3.42; 7.5740 3.82; 7.5707 4.09; 7.5639 4.55; 7.5597 4.39; 7.5565 4.39; 7.5527 3.75; 7.3401 9.39; 7.3253 16.00; 7.3105 8.32; 6.0652 0.97; 6.0564 1.96; 6.0478 2.13; 6.0384 2.95; 6.0281 3.53; 6.0190 3.32; 6.0104 3.56; 6.0021 2.61; 5.9884 1.53; 5.9791 1.47; 5.9444 3.38; 5.4286 3.76; 5.3234 3.05; 5.2847 12.72; 5.2767 12.73; 5.1999 3.28; 5.1832 3.39; 5.1694 8.58; 5.1521 7.98; 5.1508 7.88; 5.1018 0.71; 5.0312 8.23; 5.0296 8.01; 5.0025 7.71; 5.0009 7.56; 4.1637 4.24; 4.0824 0.72; 4.0706 1.84; 4.0587 1.84; 4.0468 0.70; 3.6943 0.52; 2.8012 0.38; 2.7963 0.38; 2.6862 2.87; 2.1017 0.34; 2.0989 0.37; 2.0962 0.43; 2.0909 0.79; 2.0859 0.64; 2.0819 0.74; 2.0763 0.87; 2.0741 1.26; 2.0476 2813.50; 2.0318 4.75; 2.0227 1.39; 2.0197 1.45; 2.0164 1.47; 2.0146 1.48; 2.0006 0.41; 1.9979 0.33; 1.9947 0.32; 1.9921 0.33; 1.9842 0.35; 1.9634 7.77; 1.9568 0.48; 1.9491 4.04; 1.9409 5.40; 1.9330 105.39; 1.9289 201.71; 1.9248 295.53; 1.9207 203.36; 1.9166 103.84; 1.8179 0.59; 1.8140 1.14; 1.8098 1.67; 1.8057 1.15; 1.8016 0.61; 1.2780 1.65; 1.2150 1.91; 1.2031 3.77; 1.1913 1.86; 0.8815 0.50; 0.8700 0.55; 0.8479 0.75; 0.7825 0.74; 0.5714 5.77; 0.3783 5.80; 0.3706 5.71; −0.0001 3.12
Compound No. 304 [DMSO] 9.6728 2.20; 9.6485 2.29; 8.4461 2.17; 8.4267 2.20; 8.3044 1.56; 8.2877 1.49; 8.1814 0.84; 8.1743 0.94; 8.1663 1.11; 8.1586 0.99; 8.1533 0.99; 7.6830 1.44; 7.6570 8.90; 7.6347 1.34; 7.6222 0.52; 7.4225 4.52; 7.3414 0.40; 7.3246 6.27; 6.3514 0.89; 6.3294 1.32; 6.3069 0.94; 4.5180 0.97; 4.5006 2.89; 4.4830 2.88; 4.4654 0.95; 4.4264 0.72; 4.4060 1.38; 4.3859 1.37; 4.3655 0.72; 4.0563 0.46; 4.0385 1.38; 4.0207 1.38; 4.0029 0.47; 3.4165 0.47; 3.3527 350.16; 2.6779 0.37; 2.6733 0.50; 2.6688 0.38; 2.5265 1.88; 2.5131 28.47; 2.5088 56.28; 2.5042 73.99; 2.4997 54.57; 2.4952 27.04; 2.4471 16.00; 2.3354 0.37; 2.3309 0.49; 2.3264 0.35; 2.2700 0.46; 2.2615 0.71; 2.2532 1.04; 2.2420 1.65; 2.2351 1.75; 2.2244 1.69; 2.2143 1.48; 2.1959 0.65; 2.0759 0.45; 2.0696 0.52; 2.0636 0.38; 2.0462 1.50; 2.0217 2.07; 2.0165 1.91; 1.9986 1.47; 1.9901 6.89; 1.9759 0.42; 1.9700 0.49; 1.7026 0.84; 1.6897 1.68; 1.6793 1.87; 1.6649 2.34; 1.6570 1.18; 1.6456 1.19; 1.6385 0.99; 1.6206 0.41; 1.2330 4.20; 1.2157 8.79; 1.1980 3.96; 1.1933 2.57; 1.1753 3.32; 1.1575 1.64; 1.1185 0.56; 1.1096 0.37; 1.0909 0.63; −0.0002 8.39
Compound No. 305 [DMSO] 9.6686 1.63; 9.6442 1.69; 8.3031 1.15; 8.2866 1.11; 8.1794 0.65; 8.1735 0.70; 8.1643 0.80; 8.1573 0.75; 8.1521 0.73; 8.0646 1.56; 8.0450 1.59; 7.6825 1.05; 7.6566 1.35; 7.6339 1.17; 7.6254 5.49; 7.5800 0.33; 7.4173 3.42; 7.3191 4.76; 6.3495 0.66; 6.3276 0.99; 6.3051 0.71; 4.5173 0.72; 4.5000 2.19; 4.4823 2.20; 4.4646 0.72; 4.0864 0.66; 4.0698 0.99; 4.0508 0.99; 4.0380 0.75; 4.0344 0.70; 4.0204 0.54; 3.3587 329.02; 2.6734 0.34; 2.5263 1.06; 2.5133 18.93; 2.5089 38.28; 2.5044 50.99; 2.4998 37.20; 2.4954 18.07; 2.4524 12.62; 2.3313 0.35; 2.0754 0.68; 1.9899 1.79; 1.2319 3.15; 1.2145 6.70; 1.1968 3.08; 1.1749 2.29; 1.1680 16.00; 1.1516 15.70; 1.1352 0.44; 1.1172 0.46; 1.0860 0.50; 0.0079 0.68; −0.0002 19.51; −0.0085 0.74
Compound No. 306 [DMSO] 9.6865 1.94; 9.6622 2.00; 8.5446 1.99; 8.5251 2.03; 8.3028 1.37; 8.2894 1.31; 8.2860 1.31; 8.1809 0.73; 8.1749 0.81; 8.1664 0.94; 8.1591 0.86; 8.1533 0.85; 7.7046 6.18; 7.6837 1.27; 7.6723 0.65; 7.6579 1.58; 7.6352 1.21; 7.4553 3.97; 7.3351 5.44; 6.3553 0.77; 6.3331 1.15; 6.3106 0.83; 5.7583 1.26; 4.6573 3.44; 4.6446 4.36; 4.5398 3.25; 4.5275 5.16; 4.5070 2.95; 4.4892 2.96; 4.4723 1.13; 4.4487 0.33; 4.0563 1.19; 4.0385 3.65; 4.0207 3.69; 4.0029 1.24; 3.6947 0.62; 3.3503 182.58; 3.3481 200.73; 2.6731 0.41; 2.6685 0.35; 2.5128 22.82; 2.5085 45.10; 2.5040 59.70; 2.4995 44.57; 2.4951 22.70; 2.4735 14.28; 2.3992 0.49; 2.3307 0.40; 2.0763 0.72; 1.9901 16.00; 1.2399 3.49; 1.2226 7.53; 1.2049 3.41; 1.1932 4.55; 1.1754 8.63; 1.1576 4.29; 1.1273 0.46; 1.0971 0.51; 0.0080 1.30; −0.0002 34.18; −0.0085 1.40
Compound No. 307 [DMSO] 9.5471 2.18; 9.5228 2.28; 8.2449 2.37; 8.2340 2.40; 7.8891 3.66; 7.8864 3.80; 7.8217 0.37; 7.6364

TABLE 1-continued (I)

| No. | (R¹)ₙ | X | R² | R³ | R⁴ | G | R⁶ᵃ | R⁶ᵇ | R⁶ᶜ | A | Y | (M + H)⁺ ᵃ⁾ | log p ᵃ⁾ |
|---|---|---|---|---|---|---|---|---|---|---|---|---|---|

1.66; 7.6329 1.74; 7.6219 7.32; 7.6158 2.71; 7.6121 2.45; 7.5933 0.71; 7.5432 0.51; 7.5251 5.34; 7.5041 3.72; 7.4139 4.33; 7.3315 0.55; 7.3189 6.00; 6.1999 0.86; 6.1779 1.27; 6.1551 0.92; 5.7580 6.51; 4.5196 0.88; 4.5019 2.40; 4.4830 2.34; 4.4648 0.87; 4.0559 1.17; 4.0381 3.60; 4.0203 3.66; 4.0025 1.22; 3.3276 76.24; 2.8595 0.69; 2.8500 0.91; 2.8413 1.56; 2.8310 1.52; 2.8232 1.13; 2.8129 0.79; 2.8031 0.40; 2.6760 0.53; 2.6716 0.71; 2.6670 0.52; 2.5249 1.78; 2.5201 2.90; 2.5116 37.27; 2.5071 74.63; 2.5025 97.70; 2.4979 70.56; 2.4934 33.50; 2.4444 15.20; 2.3338 0.50; 2.3292 0.67; 2.3246 0.50; 1.9895 16.00; 1.3530 1.24; 1.2335 4.48; 1.2161 8.61; 1.1983 3.93; 1.1930 5.14; 1.1752 8.98; 1.1574 4.40; 1.1465 0.38; 1.1288 0.72; 1.1111 0.35; 1.0973 0.43; 1.0787 0.89; 1.0599 0.41; 0.7078 1.01; 0.6952 2.74; 0.6899 3.89; 0.6779 3.49; 0.6718 3.01; 0.6608 1.27; 0.5616 0.44; 0.5537 1.54; 0.5433 3.86; 0.5372 3.18; 0.5332 3.06; 0.5276 2.84; 0.5154 0.91; 0.0080 2.60; −0.0002 76.07; −0.0085 2.39

Compound No. 308 [DMSO] 9.5898 1.72; 9.5655 1.78; 9.1167 3.56; 9.0801 0.33; 7.8834 3.01; 7.7118 5.39; 7.6966 0.50; 7.6366 1.26; 7.6335 1.24; 7.6155 1.88; 7.6123 1.81; 7.5453 0.40; 7.5274 4.02; 7.5065 2.79; 7.4644 3.46; 7.3830 0.35; 7.3273 4.58; 6.2055 0.70; 6.1834 1.02; 6.1609 0.73; 5.7578 1.65; 4.5239 0.70; 4.5064 1.74; 4.4879 1.87; 4.4697 0.68; 4.0563 1.21; 4.0385 3.71; 4.0207 3.76; 4.0029 1.26; 3.3284 38.82; 2.6719 0.38; 2.5254 1.01; 2.5119 21.92; 2.5075 43.33; 2.5030 56.60; 2.4984 41.46; 2.4940 20.19; 2.4666 11.90; 2.3297 0.40; 1.9897 16.00; 1.5769 1.20; 1.5627 3.13; 1.5559 3.40; 1.5431 1.42; 1.4542 0.35; 1.4470 0.34; 1.3535 0.45; 1.2932 1.88; 1.2799 3.40; 1.2733 3.54; 1.2588 1.40; 1.2428 3.17; 1.2254 6.76; 1.2077 3.05; 1.1934 4.59; 1.1756 8.91; 1.1578 4.82; 1.1400 0.64; 1.1081 0.34; 1.0895 0.68; 1.0705 0.33; 0.0080 1.33; −0.0002 38.57; −0.0085 1.37

Compound No. 309 [DMSO] 10.5019 1.42; 8.3280 7.72; 8.1088 4.37; 8.0893 4.81; 7.9759 15.51; 7.9628 1.98; 7.8699 16.00; 7.8587 1.28; 7.8273 4.22; 7.8076 5.83; 7.7805 1.62; 7.7194 3.92; 7.6999 6.23; 7.6804 2.71; 6.2912 2.04; 6.0479 0.77; 6.0347 1.83; 6.0216 1.76; 6.0088 2.37; 5.9918 3.07; 5.9890 2.85; 5.9779 2.90; 5.9657 2.94; 5.9631 3.20; 5.9523 1.77; 5.9457 2.64; 5.9323 1.66; 5.9198 2.11; 5.9057 0.97; 5.3285 4.19; 5.3249 4.31; 5.2854 4.34; 5.2817 4.57; 5.2515 5.70; 5.2145 4.87; 5.2112 4.70; 5.1888 4.25; 5.1855 4.10; 5.1247 5.18; 5.1221 5.31; 5.0986 4.90; 5.0962 5.23; 5.0713 0.37; 5.0031 4.17; 4.9602 4.00; 4.9572 3.85; 4.5640 0.35; 4.2802 0.72; 4.0558 0.81; 4.0380 1.95; 4.0201 2.04; 4.0024 1.10; 3.9730 0.73; 3.4961 0.34; 3.4817 0.45; 3.4280 0.49; 3.4158 0.54; 3.3267 127.16; 3.3031 2.43; 2.8094 0.37; 2.7994 0.52; 2.6760 1.11; 2.6715 1.55; 2.6669 1.32; 2.6620 1.17; 2.6507 1.60; 2.6429 2.17; 2.6340 2.83; 2.6252 2.23; 2.6171 1.64; 2.6073 0.84; 2.5418 0.90; 2.5248 3.45; 2.5113 72.48; 2.5070 149.29; 2.5024 201.19; 2.4979 149.02; 2.4936 73.09; 2.3381 0.48; 2.3337 1.03; 2.3292 1.39; 2.3247 1.03; 2.0963 1.20; 1.9896 7.03; 1.3514 0.40; 1.2337 0.97; 1.1925 1.95; 1.1747 3.84; 1.1569 1.89; 0.8541 0.46; 0.7395 1.34; 0.5507 5.70; 0.3608 4.53; 0.3455 4.37; 0.0080 2.08; −0.0002 63.47; −0.0085 2.22

Compound No. 310 [DMSO] 9.8316 2.59; 9.8077 2.64; 9.3012 6.28; 8.3173 0.55; 8.2865 1.55; 8.2680 2.70; 8.2495 1.46; 7.8654 11.49; 7.8601 7.49; 7.4131 7.32; 6.3725 1.08; 6.3510 1.52; 6.3290 1.11; 6.3079 0.33; 4.5438 1.22; 4.5263 3.39; 4.5086 3.34; 4.4911 1.10; 3.3296 122.91; 2.6767 0.55; 2.6721 0.74; 2.6676 0.53; 2.5253 4.79; 2.5121 43.87; 2.5076 84.02; 2.5031 108.33; 2.4985 77.28; 2.4940 36.71; 2.3344 0.56; 2.3298 0.73; 2.3252 0.51; 1.9897 0.53; 1.6032 2.21; 1.5891 4.97; 1.5822 5.28; 1.5693 2.30; 1.3975 16.00; 1.3362 2.06; 1.2989 0.55; 1.2864 2.63; 1.2729 5.13; 1.2663 5.48; 1.2501 4.07; 1.2373 5.40; 1.2200 10.55; 1.2023 4.69; 1.1756 0.42; 0.0079 1.76; −0.0002 39.91; −0.0085 1.41

Compound No. 311 [DMSO] 9.6912 3.15; 9.6668 3.27; 9.2980 7.62; 8.1170 8.88; 8.1012 8.89; 7.8562 14.76; 7.8517 9.31; 7.3879 8.83; 6.2991 1.16; 6.2772 1.71; 6.2545 1.26; 6.2333 0.38; 4.5447 1.29; 4.5273 3.99; 4.5096 3.99; 4.4922 1.28; 4.0567 0.70; 4.0389 2.16; 4.0211 2.18; 4.0033 0.73; 3.3306 41.75; 2.6777 0.34; 2.6731 0.47; 2.6684 0.34; 2.5266 1.26; 2.5219 1.83; 2.5131 25.28; 2.5086 52.16; 2.5040 69.32; 2.4994 49.74; 2.4949 23.45; 2.3353 0.34; 2.3308 0.47; 2.3264 0.34; 1.9905 9.68; 1.6041 2.52; 1.5900 5.80; 1.5831 6.33; 1.5702 2.74; 1.3968 16.00; 1.3369 1.27; 1.3291 0.34; 1.2992 0.39; 1.2890 3.04; 1.2755 5.94; 1.2688 6.44; 1.2543 2.72; 1.2500 2.26; 1.2368 6.29; 1.2195 12.99; 1.2018 5.71; 1.1939 3.24; 1.1761 5.52; 1.1583 2.68; 0.0080 0.81; −0.0002 27.85; −0.0085 0.88

Compound No. 312 cf. Synthesis Example 5

Compound No. 313 [DMSO] 10.4423 4.17; 10.4181 4.44; 9.6441 0.55; 9.6205 0.55; 8.4738 4.65; 8.4629 4.86; 8.3558 2.90; 8.3391 2.93; 8.3177 2.21; 8.1840 2.05; 8.1702 2.55; 8.0415 0.48; 8.0222 0.50; 7.8742 0.85; 7.8355 0.61; 7.8303 0.67; 7.8231 0.44; 7.8014 0.55; 7.7777 15.62; 7.7592 16.00; 7.7317 1.32; 7.7229 0.52; 7.6930 2.12; 7.6677 3.43; 7.6448 2.53; 7.1814 0.33; 6.4104 0.43; 6.3911 1.61; 6.3696 2.39; 6.3470 1.75; 6.3251 0.58; 6.2764 0.39; 4.0374 0.35; 4.0197 0.35; 3.5669 1.58; 3.5585 2.12; 3.5495 3.03; 3.5400 2.21; 3.5321 1.59; 3.5220 0.78; 3.3264 472.16; 2.8709 0.37; 2.8605 1.18; 2.8508 1.65; 2.8423 2.67; 2.8320 2.69; 2.8241 1.69; 2.8139 1.29; 2.8036 0.45; 2.6755 3.73; 2.6709 5.30; 2.6664 3.91; 2.5411 1.66; 2.5243 13.63; 2.5195 21.76; 2.5108 284.09; 2.5064 580.86; 2.5018 771.21; 2.4973 571.48; 2.4929 285.94; 2.4202 5.78; 2.3331 4.17; 2.3286 5.68; 2.3241 4.27; 1.9891 1.92; 1.6593 0.35; 1.6232 0.53; 1.3354 2.78; 1.2980 2.67; 1.2584 3.86; 1.2493 3.82; 1.2349 2.72; 1.1924 0.75; 1.1746 1.09; 1.1568 0.97; 1.1401 1.14; 1.1310 1.52; 1.1140 2.23; 1.0995 2.94; 1.0903 3.01; 1.0769 2.09; 1.0602 1.63; 1.0509 1.11; 1.0340 0.68; 0.8673 0.94; 0.8542 1.49; 0.8410 1.80; 0.8301 2.68; 0.8168 2.62; 0.8078 1.40; 0.7947 1.33; 0.7856 2.43; 0.7719 2.25; 0.7613 1.70; 0.7451 1.14; 0.7281 2.00; 0.7149 4.94; 0.7100 7.07; 0.6980 6.35; 0.6920 5.60; 0.6807 2.32; 0.6594 0.43; 0.6416 0.40; 0.6089 0.35; 0.5992 0.36; 0.5695 1.40; 0.5590 6.93; 0.5529 6.33; 0.5434 5.64; 0.5312 1.84; 0.4472 0.36; 0.1460 1.33; 0.0080 10.64; −0.0002 306.83; −0.0085 11.92; −0.0685 0.65; −0.1497 1.28

Compound No. 314 [DMSO] 10.3348 1.85; 10.3106 1.92; 8.4744 1.99; 8.4635 2.02; 8.0662 2.84; 7.8300 0.35; 7.8275 0.34; 7.7744 6.88; 7.7653 1.78; 7.7554 7.00; 7.7458 1.80; 7.6771 1.37; 7.6746 1.32; 7.6570 1.59; 7.6544 1.64; 7.4608 2.01; 7.4411 3.31; 7.4213 1.57; 6.1951 0.70; 6.1732 1.04; 6.1507 0.76; 4.0553 1.19; 4.0376 3.60; 4.0198 3.46; 4.0020 1.22; 3.5726 0.34; 3.5634 0.69; 3.5549 0.93; 3.5460 1.30; 3.5368 0.94; 3.5285 0.68; 3.5189 0.35; 3.3285 66.38; 2.8608 0.53; 2.8511 0.73; 2.8427 1.15; 2.8325 1.16; 2.8243 0.73; 2.8145 0.57; 2.6756 0.36; 2.6709 0.48; 2.6663 0.36; 2.5243 1.63; 2.5109 26.54; 2.5065 52.26; 2.5020 68.41; 2.4974 50.41; 2.4930 25.21; 2.3332 0.34; 2.3287 0.47; 2.3241 0.35; 1.9892 16.00; 1.6767 0.36; 1.6594 0.35; 1.3358 0.61; 1.2983 0.75; 1.2584 1.08; 1.2493 0.78; 1.2340 0.56; 1.1925 4.35; 1.1747 8.62; 1.1569 4.26; 1.1162 0.65; 1.1016 1.79; 1.0875 1.84; 1.0747 0.74; 0.8519 0.55; 0.8419 0.46; 0.8305 0.62; 0.8218 1.47; 0.8124 1.17; 0.7997 1.10; 0.7901 1.38; 0.7805 0.56; 0.7691 0.39; 0.7636 0.36; 0.7592 0.41; 0.7274 0.76; 0.7143 2.08; 0.7094 2.95; 0.6973 2.70; 0.6913 2.34; 0.6801 1.00; 0.5704 1.00; 0.5598 2.90; 0.5536 2.64; 0.5500 2.52; 0.5443 2.38; 0.5320 0.77; 0.0080 1.33; −0.0002 34.44; −0.0084 1.44

Compound No. 315 [DMSO] 9.7193 3.91; 9.6950 4.05; 9.2986 9.34; 7.9517 1.39; 7.9480 1.48; 7.9236 2.98; 7.9032 1.43; 7.8991 1.42; 7.8489 11.36; 7.8418 16.00; 7.6473 1.98; 7.6259 3.56; 7.5967 2.16; 7.5739 4.49; 7.5512 3.41; 7.5283 1.14; 7.3780 10.91; 6.2361 0.40; 6.2148 1.53; 6.1928 2.29; 6.1704 1.65; 6.1484 0.47; 4.5471 1.65; 4.5293 4.67; 4.5113 4.63; 4.4933 1.62; 4.0560 0.49; 4.0382 1.52; 4.0204 1.54; 4.0026 0.53; 3.3339 57.31; 2.6772 0.46; 2.6726 0.64; 2.6681 0.47; 2.5259 1.71; 2.5212 2.66; 2.5124 34.61; 2.5081 69.79; 2.5035 91.83; 2.4990 67.16; 2.4946 32.66; 2.3349 0.46; 2.3302 0.64; 2.3258 0.46; 1.9902 6.71; 1.6025 2.99; 1.5884 7.24; 1.5815 7.87; 1.5685 3.32; 1.3369 1.40; 1.2988 0.48; 1.2884 3.60; 1.2749 7.36; 1.2683 7.93; 1.2537 3.28; 1.2501 2.65; 1.2309 7.22; 1.2135 15.36; 1.1957 7.13; 1.1754 3.85;

TABLE 1-continued
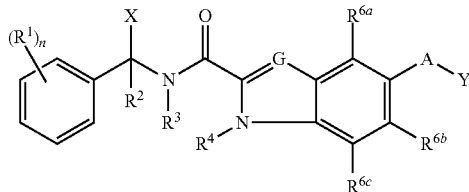
(I)
| No. | $(R^1)_n$ | X | $R^2$ | $R^3$ | $R^4$ | G | $R^{6a}$ | $R^{6b}$ | $R^{6c}$ | A | Y | (M + H)$^{+\ a)}$ | log p$^{a)}$ |
|---|---|---|---|---|---|---|---|---|---|---|---|---|---|
1.1576 1.89; 0.0080 1.27; −0.0002 39.65; −0.0085 1.28
Compound No. 316 [DMSO] 9.7524 2.29; 9.7282 2.38; 9.3010 5.43; 8.1132 4.28; 7.8490 16.00; 7.7870 0.46; 7.7669 10.52; 7.3860 6.28; 6.2483 0.88; 6.2264 1.33; 6.2039 0.96; 4.5448 0.93; 4.5276 2.82; 4.5099 2.83; 4.4925 0.94; 4.0570 0.67; 4.0392 2.05; 4.0214 2.08; 4.0036 0.70; 3.3370 23.15; 2.5271 0.61; 2.5223 0.98; 2.5137 11.94; 2.5093 23.97; 2.5048 31.51; 2.5003 23.22; 2.4959 11.43; 1.9912 9.04; 1.6043 1.70; 1.5901 4.10; 1.5833 4.47; 1.5703 1.89; 1.3960 5.72; 1.3378 0.94; 1.2908 2.03; 1.2773 4.17; 1.2706 4.47; 1.2561 1.77; 1.2498 1.43; 1.2315 4.16; 1.2140 8.61; 1.1944 4.89; 1.1763 4.99; 1.1584 2.46; 0.0080 0.43; −0.0002 12.94; −0.0085 0.47
Compound No. 317 [DMSO] 20.0019 0.38; 10.4337 1.44; 10.4089 1.62; 8.5558 1.24; 8.5447 1.33; 8.4884 1.21; 8.4770 1.24; 8.3189 3.23; 8.1255 0.51; 8.1045 0.51; 8.0334 7.87; 8.0200 4.32; 7.9597 0.53; 7.9323 0.63; 7.9079 4.56; 7.9008 4.42; 7.8892 0.67; 7.8289 0.58; 7.8078 0.73; 7.7976 0.49; 7.7835 4.11; 7.7288 2.66; 7.7242 4.89; 7.7195 2.65; 7.6761 0.41; 7.6564 0.61; 7.6378 0.48; 7.5533 0.47; 7.5262 0.41; 7.5057 0.58; 7.4394 0.36; 7.4241 0.51; 7.4044 0.45; 7.3900 0.44; 6.5403 0.36; 6.2814 0.87; 6.2592 1.27; 6.2378 0.92; 4.7859 0.46; 4.7714 0.45; 4.7675 0.53; 4.7533 1.22; 4.7351 1.21; 4.7170 0.38; 4.6385 0.92; 4.6213 2.64; 4.6038 2.70; 4.0460 0.47; 4.0284 0.55; 3.5720 0.32; 3.3307 448.75; 3.2332 3.89; 3.0191 3.60; 2.8908 1.91; 2.8592 0.85; 2.8495 1.23; 2.8401 1.25; 2.8316 0.88; 2.8221 0.63; 2.7316 1.38; 2.6802 2.37; 2.6758 5.09; 2.6712 7.06; 2.6667 5.08; 2.5415 1.73; 2.5246 17.74; 2.5199 27.38; 2.5112 362.24; 2.5067 738.28; 2.5022 973.29; 2.4976 705.38; 2.4931 337.44; 2.3335 5.52; 2.3289 7.29; 2.3244 5.38; 2.2759 0.70; 2.2573 0.85; 2.2390 0.62; 1.6210 0.74; 1.6026 1.17; 1.5844 0.69; 1.5319 1.61; 1.5137 3.06; 1.4954 1.76; 1.4084 0.81; 1.4017 0.81; 1.3840 1.22; 1.3664 1.09; 1.3506 2.92; 1.3330 6.77; 1.3145 6.50; 1.2976 5.59; 1.2584 6.70; 1.2343 16.00; 1.1857 1.63; 1.1679 1.91; 1.1504 1.38; 1.1255 1.07; 0.8535 3.65; 0.8360 2.42; 0.7410 0.86; 0.7287 1.92; 0.7234 2.51; 0.7122 3.39; 0.7050 2.19; 0.6946 2.20; 0.6839 0.78; 0.5798 0.84; 0.5693 2.22; 0.5547 3.30; 0.5406 1.91; 0.5273 0.84; 0.1460 1.75; 0.0080 14.09; −0.0002 409.80; −0.0085 12.46; −0.1496 1.69
Compound No. 318 [DMSO] 9.8544 4.12; 9.8302 4.28; 9.7781 4.66; 9.7581 4.72; 8.3185 3.23; 8.2056 6.31; 8.1508 0.36; 8.0700 3.39; 8.0506 3.69; 7.8975 15.98; 7.8601 11.43; 7.8464 1.00; 7.8347 3.09; 7.8146 4.65; 7.7851 0.86; 7.7381 3.28; 7.7189 5.00; 7.6992 2.14; 7.6232 0.32; 7.5946 6.91; 7.5763 9.89; 7.5132 3.33; 7.5099 4.80; 7.5053 2.04; 7.4924 10.59; 7.4884 4.79; 7.4735 6.54; 7.4516 4.62; 7.4397 1.72; 7.4337 5.15; 7.4267 1.39; 7.4154 1.54; 7.4118 1.19; 7.4017 11.52; 7.3767 0.33; 6.4289 5.72; 6.4089 5.73; 6.3441 0.58; 6.3233 1.80; 6.3014 2.52; 6.2784 1.78; 6.2572 0.48; 4.5435 1.95; 4.5265 5.38; 4.5086 5.23; 4.4914 1.76; 4.4705 0.36; 4.2313 0.34; 3.4006 0.38; 3.3307 830.52; 2.8185 0.34; 2.6758 5.42; 2.6712 7.32; 2.6667 5.41; 2.6330 0.46; 2.5415 4.03; 2.5246 21.80; 2.5198 33.33; 2.5111 370.43; 2.5067 740.94; 2.5022 970.57; 2.4976 705.98; 2.4932 339.25; 2.3380 2.38; 2.3335 5.03; 2.3289 6.85; 2.3244 4.88; 2.3200 2.26; 1.9894 0.57; 1.2587 0.54; 1.2262 7.63; 1.2088 16.00; 1.1912 7.37; 1.1748 0.66; 1.1357 0.40; 1.1190 0.82; 1.1018 0.40; 1.0883 0.38; 1.0673 0.68; 1.0485 0.39; 0.1459 1.32; 0.0080 11.06; −0.0002 331.07; −0.0085 11.56; −0.1496 1.39
Compound No. 319 [DMSO] 9.7261 2.55; 9.7019 2.64; 9.1876 5.70; 8.2147 3.58; 8.0727 1.90; 8.0532 2.12; 7.8321 1.72; 7.8125 2.50; 7.7387 1.93; 7.7191 2.97; 7.6996 1.25; 7.6193 8.92; 7.5118 5.74; 7.3353 6.83; 6.3225 0.97; 6.3001 1.46; 6.2777 1.05; 4.5709 1.01; 4.5536 3.10; 4.5359 3.11; 4.5185 1.01; 4.0559 0.51; 4.0381 1.59; 4.0203 1.61; 4.0025 0.54; 3.4161 0.50; 3.3990 1.34; 3.3819 1.91; 3.3649 1.46; 3.3472 0.68; 3.3324 40.94; 2.6768 0.35; 2.6722 0.48; 2.6675 0.34; 2.5256 1.24; 2.5208 1.98; 2.5121 26.10; 2.5076 52.84; 2.5031 69.96; 2.4985 51.38; 2.4940 25.07; 2.3344 0.37; 2.3298 0.49; 2.3253 0.36; 1.9898 7.14; 1.5799 1.83; 1.5657 4.44; 1.5590 4.91; 1.5461 2.07; 1.3533 0.65; 1.2821 11.44; 1.2717 12.69; 1.2652 16.00; 1.2549 12.09; 1.2448 2.82; 1.2307 4.88; 1.2133 9.65; 1.1955 4.55; 1.1934 4.50; 1.1753 4.11; 1.1575 2.02; 0.0080 0.87; −0.0002 27.03; −0.0085 0.95
Compound No. 321 [DMSO] 9.5524 1.51; 9.5281 1.57; 8.4084 1.48; 8.3878 1.51; 8.3200 0.33; 7.9558 0.59; 7.9344 1.06; 7.9072 0.56; 7.6742 4.44; 7.6564 0.52; 7.6488 0.76; 7.6342 0.93; 7.6279 1.25; 7.5940 0.79; 7.5696 1.30; 7.5471 1.26; 7.5254 0.44; 7.4371 3.14; 7.3352 3.72; 6.2074 0.62; 6.1855 0.91; 6.1630 0.64; 4.5273 0.64; 4.5096 1.74; 4.4911 1.74; 4.4737 0.65; 4.3756 0.70; 4.3585 2.94; 4.3481 2.46; 4.3387 0.73; 3.7921 0.50; 3.7815 0.51; 3.7768 0.68; 3.7663 0.64; 3.7616 0.52; 3.7511 0.49; 3.3337 87.26; 3.0339 0.60; 3.0158 0.62; 3.0023 1.35; 2.9840 1.27; 2.9588 1.31; 2.9417 1.38; 2.9273 0.68; 2.9100 0.58; 2.6762 0.83; 2.6718 1.11; 2.6673 0.88; 2.6446 16.00; 2.5822 0.49; 2.5607 0.42; 2.5402 1.16; 2.5249 3.44; 2.5071 116.69; 2.5027 151.65; 2.4984 112.68; 2.4698 10.91; 2.3338 0.75; 2.3294 1.04; 2.3252 0.77; 1.3048 5.13; 1.2881 5.08; 1.2395 2.77; 1.2223 5.74; 1.2046 2.67; 1.0444 14.60; 1.0291 14.52; 0.1463 0.42; 0.0080 3.58; −0.0002 93.99; −0.0085 4.69; −0.1491 0.42
Compound No. 322 [DMSO] 8.4003 0.39; 8.3191 0.47; 8.1238 0.32; 8.0590 0.33; 7.9324 0.34; 7.9089 0.39; 7.8280 0.32; 7.8078 0.41; 7.7821 0.38; 7.6970 0.34; 7.3902 0.37; 7.3351 0.69; 7.3310 0.69; 7.1819 1.39; 7.1766 0.81; 3.8408 1.01; 3.3330 151.86; 3.3146 0.35; 2.6805 0.42; 2.6760 0.86; 2.6716 1.19; 2.6671 0.89; 2.6625 0.45; 2.5248 3.66; 2.5200 5.39; 2.5114 59.74; 2.5070 120.85; 2.5025 159.67; 2.4979 116.98; 2.4935 57.70; 2.3383 0.34; 2.3338 0.77; 2.3292 1.07; 2.3247 0.78; 2.3203 0.37; 1.3506 1.02; 1.3356 12.64; 1.2979 5.37; 1.2799 0.43; 1.2584 7.89; 1.2491 16.00; 1.2345 4.67; 1.1868 0.49; 0.8535 0.61; 0.5544 0.44; 0.5490 0.49; 0.5393 0.49; 0.3864 0.37; 0.3708 0.34; 0.3323 0.34; 0.3231 0.36; 0.0080 0.32; −0.0002 9.87; −0.0085 0.39
Compound No. 323 [DMSO] 10.3305 3.35; 10.3169 3.02; 10.3060 3.55; 10.2925 2.69; 8.3192 1.55; 8.0683 8.71; 7.9544 11.87; 7.9130 8.79; 7.7838 3.16; 7.7643 7.07; 7.6334 4.13; 7.6139 5.61; 7.5344 2.16; 7.5188 2.86; 7.5141 4.02; 7.4989 3.91; 7.4946 2.93; 7.4791 1.92; 7.3136 2.09; 7.3082 2.24; 7.2923 3.69; 7.2870 3.83; 7.2708 1.78; 7.2655 1.77; 6.2099 0.61; 6.1891 2.22; 6.1671 3.31; 6.1448 2.35; 6.1229 0.67; 4.6398 1.61; 4.6225 5.26; 4.6049 6.87; 4.5879 4.01; 3.7663 0.65; 3.7491 0.89; 3.7328 0.97; 3.7149 0.87; 3.7069 0.61; 3.6882 1.16; 3.6708 1.48; 3.6541 1.69; 3.6367 1.40; 3.6194 0.49; 3.3832 0.75; 3.3956 2.02; 3.3327 315.73; 3.2721 0.89; 3.2548 1.02; 3.2375 0.93; 3.2201 0.73; 3.2046 0.44; 3.1894 0.78; 3.1718 1.34; 3.1533 1.81; 3.1399 1.96; 3.1228 1.70; 3.1057 0.88; 3.0271 1.25; 3.0091 1.93; 2.9917 1.90; 2.9768 1.42; 2.9597 0.87; 2.6763 2.61; 2.6718 3.57; 2.6673 2.69; 2.5422 33.92; 2.5249 12.51; 2.5114 186.54; 2.5072 368.37; 2.5027 489.26; 2.4982 370.51; 2.4940 191.66; 2.3339 2.55; 2.3295 3.49; 2.3250 2.61; 1.3565 3.29; 1.3387 7.19; 1.3304 7.00; 1.3128 11.58; 1.2949 5.26; 1.2342 1.25; 1.2142 6.97; 1.1967 16.00; 1.1831 12.70; 1.1657 5.15; 1.1501 0.72; 1.1327 0.36; 1.0257 2.97; 1.0086 8.66; 0.9931 10.38; 0.9759 6.76; 0.9582 1.77; 0.0079 0.63; −0.0002 18.08; −0.0083 0.93
Compound No. 324 [DMSO] 11.7911 0.42; 11.6226 0.35; 9.9330 5.41; 9.9169 5.59; 9.4987 0.36; 9.4824 0.37; 9.4639 0.37; 9.3343 10.85; 8.3016 9.95; 8.2426 0.39; 8.1962 7.30; 8.1844 0.85; 8.0600 4.10; 8.0469 4.47; 7.8646 1.59; 7.8620 1.37; 7.8497 10.85; 7.8470 13.46; 7.8445 13.30; 7.8365 4.13; 7.8297 2.67; 7.8233 4.93; 7.7379 3.67; 7.7248 6.23; 7.7181 2.81; 7.5057 5.24; 7.4908 6.10; 7.4853 16.00; 7.4791 6.23; 7.4642 5.43; 7.4115 0.32; 7.3967 0.39; 7.3922 0.37; 6.8597 0.86; 6.3060 0.54; 6.2920 1.78; 6.2774 2.67; 6.2625 1.96; 6.2477 0.64; 5.4132 6.28; 5.4114 6.60; 5.3866 6.40; 5.3849 6.34; 5.2388 6.08; 5.2371 6.54; 5.2239 6.66; 5.2224 5.92; 4.0360 0.35; 4.0241 0.36; 3.3249 329.04; 2.6211 0.43; 2.6181 0.90; 2.6151 1.25; 2.6120 0.92; 2.6090 0.44; 2.5241 2.40; 2.5210 2.93; 2.5179 2.94; 2.5091 68.04; 2.5061 147.03; 2.5030 203.36; 2.5000 146.37; 2.4970 67.05; 2.3930 0.39; 2.3900 0.86; 2.3869 1.20; 2.3839 0.85; 2.3809 0.38; 1.9896 1.56; 1.9103 0.35; 1.6147 0.69; 1.6093 0.48; 1.6050 0.72; 1.6006 0.90; 1.5899 4.41; 1.5806 9.68; 1.5761 10.87; 1.5673 4.42; 1.5406 0.41; 1.3971 2.45;

TABLE 1-continued (I)

[Structure of formula (I) showing a substituted phenyl group with (R¹)ₙ, X, R² substituents connected to a carbonyl-N(R³)-amide linked to a bicyclic heterocycle G containing N-R⁴, with substituents R⁶ᵃ, R⁶ᵇ, R⁶ᶜ, and A-Y]

| No. | (R¹)ₙ | X | R² | R³ | R⁴ | G | R⁶ᵃ | R⁶ᵇ | R⁶ᶜ | A | Y | (M+H)⁺ ᵃ⁾ | log p ᵃ⁾ |
|---|---|---|---|---|---|---|---|---|---|---|---|---|---|

1.3646 0.59; 1.3554 0.81; 1.3509 0.92; 1.3366 3.77; 1.3220 4.70; 1.3129 9.79; 1.3085 10.71; 1.2991 6.65; 1.2734 0.36; 1.2589 4.05; 1.2498 4.33; 1.2346 1.39; 1.2257 0.37; 1.1873 0.55; 1.1754 0.95; 1.1636 0.51; 0.0053 0.94; −0.0001 29.00; −0.0057 0.91

Compound No. 325 [CD3CN] 7.9665 0.74; 7.8926 0.39; 7.8753 0.73; 7.8533 1.87; 7.7888 0.39; 7.7688 0.56; 7.6950 0.46; 7.6753 0.68; 7.6426 1.44; 7.2503 1.61; 7.2041 0.51; 6.1353 0.41; 4.5139 0.35; 4.4961 1.11; 4.4783 1.13; 4.4606 0.37; 3.9111 1.77; 3.8872 2.56; 3.7840 2.49; 3.7601 1.78; 3.4253 16.00; 2.1629 194.88; 2.1614 222.97; 2.1199 0.52; 2.1137 0.58; 2.1075 0.72; 2.1013 0.54; 1.9644 5.02; 1.9583 4.33; 1.9524 35.91; 1.9463 66.77; 1.9401 92.87; 1.9339 64.22; 1.9277 33.22; 1.9149 0.54; 1.7747 0.39; 1.7685 0.55; 1.7624 0.38; 1.3089 1.49; 1.2911 3.15; 1.2733 1.51; −0.0002 10.36

Compound No. 326 [DMSO] 9.8219 1.59; 9.7977 1.65; 9.3268 3.91; 8.1999 2.28; 8.0626 1.22; 8.0429 1.36; 7.9311 4.44; 7.8860 6.43; 7.8273 1.11; 7.8076 1.59; 7.7315 1.20; 7.7120 1.86; 7.6924 0.77; 7.5722 4.40; 6.3012 0.62; 6.2790 0.93; 6.2563 0.68; 5.3453 5.56; 3.5942 16.00; 3.3290 61.17; 2.8906 0.33; 2.6892 0.41; 2.6757 0.34; 2.6712 0.46; 2.6667 0.34; 2.5245 1.48; 2.5112 26.22; 2.5068 52.24; 2.5022 68.57; 2.4976 49.87; 2.4932 24.69; 2.3334 0.35; 2.3289 0.46; 2.3244 0.34; 2.0756 1.18; 1.6051 1.23; 1.5909 2.94; 1.5841 3.21; 1.5712 1.37; 1.2913 1.43; 1.2778 2.95; 1.2712 3.17; 1.2567 1.15; 0.0080 0.70; −0.0002 18.53; −0.0085 0.76

Compound No. 327 [DMSO] 9.9448 0.75; 9.6959 0.52; 9.6708 0.81; 9.6606 4.11; 9.6361 4.24; 8.4262 0.74; 8.4121 4.85; 8.4011 4.74; 8.3210 0.44; 8.2015 0.68; 8.1289 1.92; 8.1210 11.60; 8.1052 11.60; 8.0472 0.50; 8.0311 0.49; 8.0163 0.65; 7.7976 11.32; 7.7723 16.00; 7.7193 0.43; 7.6502 0.64; 7.6288 0.72; 7.4893 1.41; 7.4137 0.49; 7.3916 0.82; 7.3761 11.23; 7.3356 1.22; 7.3142 1.02; 7.2736 0.42; 7.2676 0.37; 7.2522 0.35; 6.8880 1.63; 6.7206 1.13; 6.3185 0.57; 6.2969 1.81; 6.2752 2.49; 6.2526 1.74; 6.2309 0.52; 4.5628 0.76; 4.5385 1.94; 4.5210 5.41; 4.5034 5.40; 4.4858 1.78; 3.9913 0.73; 3.5733 0.47; 3.3373 92.66; 3.0318 1.00; 2.8681 0.60; 2.8580 1.43; 2.8485 1.92; 2.8398 2.97; 2.8295 2.84; 2.8213 1.83; 2.8114 1.35; 2.8012 0.52; 2.7725 0.84; 2.7189 0.52; 2.6990 0.34; 2.6821 0.38; 2.6776 0.73; 2.6731 1.00; 2.6685 0.73; 2.5685 0.46; 2.5491 0.76; 2.5434 0.76; 2.5265 2.95; 2.5217 4.32; 2.5129 51.41; 2.5085 104.97; 2.5040 139.87; 2.4994 104.73; 2.4950 52.90; 2.3400 0.40; 2.3352 0.75; 2.3309 1.02; 2.2924 0.76; 2.1806 0.42; 1.3538 1.97; 1.3360 15.62; 1.2989 8.90; 1.2810 1.02; 1.2588 13.81; 1.2494 5.13; 1.2415 5.38; 1.2332 11.93; 1.2286 10.75; 1.2107 15.95; 1.1930 7.32; 1.1786 0.97; 1.1647 0.68; 1.1490 0.38; 1.0915 0.78; 1.0571 0.38; 0.8695 0.64; 0.8658 0.59; 0.8531 1.51; 0.8355 0.74; 0.7210 2.08; 0.7081 5.75; 0.7030 7.15; 0.6909 6.77; 0.6849 5.51; 0.6737 2.27; 0.5570 3.26; 0.5465 7.41; 0.5404 6.56; 0.5367 5.94; 0.5307 5.60; 0.5187 1.71; 0.0080 0.78; −0.0002 24.43; −0.0084 0.99

Compound No. 328 [DMSO] 9.9556 1.15; 9.8212 0.42; 9.8051 4.00; 9.7812 4.19; 8.5288 0.32; 8.4167 4.66; 8.4056 4.63; 8.2949 2.49; 8.2764 4.60; 8.2579 2.54; 8.2040 1.03; 8.0618 0.33; 8.0169 0.98; 7.8078 11.56; 7.7837 15.80; 7.6593 0.38; 7.6375 0.44; 7.5099 0.85; 7.4172 0.62; 7.4035 11.68; 7.3434 0.62; 7.3220 0.56; 6.3929 0.63; 6.3729 1.92; 6.3516 2.64; 6.3294 1.90; 6.3085 0.57; 5.7611 6.64; 4.5635 0.45; 4.5389 1.95; 4.5214 5.58; 4.5037 5.59; 4.4862 1.91; 4.3621 0.41; 4.3435 0.42; 4.0565 0.44; 4.0387 1.38; 4.0208 1.40; 4.0031 0.47; 3.3369 57.37; 3.0325 0.71; 2.8683 0.56; 2.8583 1.41; 2.8489 1.94; 2.8401 2.98; 2.8299 2.92; 2.8214 1.88; 2.8118 1.38; 2.8015 0.51; 2.7739 0.54; 2.6779 0.47; 2.6734 0.66; 2.6689 0.50; 2.5267 1.80; 2.5131 36.45; 2.5088 73.85; 2.5044 98.26; 2.4999 74.32; 2.4958 38.99; 2.3354 0.53; 2.3311 0.76; 2.3268 0.55; 2.0784 2.48; 1.9910 6.11; 1.2903 0.58; 1.2726 1.28; 1.2612 1.00; 1.2529 1.09; 1.2439 1.87; 1.2304 7.68; 1.2131 16.00; 1.1949 8.13; 1.1761 3.45; 1.1583 1.68; 0.7217 2.28; 0.7088 5.89; 0.7037 7.49; 0.6916 6.90; 0.6858 5.75; 0.6746 2.35; 0.5571 3.17; 0.5465 7.60; 0.5403 6.75; 0.5369 6.40; 0.5308 5.92; 0.5188 1.83; 0.0080 0.69; −0.0002 27.97; −0.0081 1.41

Compound No. 329 [DMSO] 9.6827 4.06; 9.6583 4.18; 8.4059 4.57; 8.3948 4.62; 8.3193 0.60; 7.9532 1.39; 7.94931.46; 7.9287 2.83; 7.9259 2.79; 7.9044 1.39; 7.9002 1.38; 7.7917 11.17; 7.7557 15.91; 7.6459 1.96; 7.6245 3.49; 7.5939 2.16; 7.5708 4.65; 7.5481 3.53; 7.5255 1.16; 7.3657 10.86; 7.3362 0.36; 7.3317 0.34; 7.1824 0.63; 7.1773 0.36; 6.2306 0.41; 6.2089 1.54; 6.1870 2.29; 6.16441.65; 6.1422 0.47; 5.7597 0.78; 4.5401 1.66; 4.5224 4.69; 4.5041 4.60; 4.4860 1.02; 3.3238 194.54; 3.3119 0.42; 2.8654 0.45; 2.8554 1.20; 2.8458 1.58; 2.8373 2.59; 2.8269 2.62; 2.8189 1.59; 2.8087 1.26; 2.7987 0.50; 2.6805 0.50; 2.6763 1.07; 2.6717 1.46; 2.6672 1.07; 2.6628 0.51; 2.5419 0.67; 2.5252 4.14; 2.5204 6.30; 2.5117 76.26; 2.5072 154.81; 2.5027 203.53; 2.4981 147.60; 2.4936 70.27; 2.3384 0.51; 2.33401.04; 2.3294 1.47; 2.3248 1.05; 2.3203 0.53; 1.3974 0.46; 1.3360 6.09; 1.2985 0.98; 1.2822 0.39; 1.2586 1.66; 1.2493 8.11; 1.2343 2.10; 1.2220 7.36; 1.2046 16.00; 1.1869 7.20; 0.7189 1.85; 0.7061 4.74; 0.7009 6.88; 0.6889 6.19; 0.6827 5.31; 0.6715 2.22; 0.5553 2.31; 0.5448 6.66; 0.5387 5.93; 0.5347 5.58; 0.5292 5.39; 0.5170 1.70; 0.0080 2.10; −0.0002 67.40; −0.0085 2.11

Compound No. 330 [DMSO] 9.7163 2.35; 9.6922 2.46; 9.1309 5.11; 9.0990 0.68; 8.3053 1.35; 8.2867 2.46; 8.26821.36; 7.7399 7.36; 7.7160 0.96; 7.4800 4.74; 7.4004 0.69; 7.3680 6.42; 6.3796 0.93; 6.3585 1.38; 6.3363 1.09; 6.3153 0.42; 5.7611 0.49; 4.5219 0.99; 4.5046 2.98; 4.4868 3.00; 4.4693 1.02; 4.0565 0.52; 4.0387 1.60; 4.0209 1.62; 4.0031 0.55; 3.3373 28.73; 2.6904 0.67; 2.67350.33; 2.5268 1.05; 2.5132 18.11; 2.5089 36.45; 2.5044 48.54; 2.4998 36.71; 2.4955 18.84; 2.4762 3.44; 2.4475 16.00; 2.3311 0.34; 1.9909 7.16; 1.5819 1.72; 1.5676 4.43; 1.5609 4.89; 1.5481 2.07; 1.3145 0.34; 1.2941 2.67; 1.2807 4.67; 1.2740 4.83; 1.2595 2.03; 1.2482 4.23; 1.2308 9.13; 1.2132 4.09; 1.1939 2.03; 1.1761 3.84; 1.1583 2.19; 1.1467 0.81; 1.1381 1.22; 1.1279 1.42; 1.1203 0.67; 1.1090 0.64; 0.0080 0.76; −0.0002 22.55; −0.0084 0.98

Compound No. 331 [DMSO] 9.6945 1.79; 9.6701 1.86; 9.1242 3.79; 8.1264 2.88; 8.0751 1.18; 8.0520 1.18; 7.82891.24; 7.8076 1.25; 7.7369 5.67; 7.4724 3.59; 7.3469 4.82; 6.4119 0.68; 6.3898 1.01; 6.3672 0.74; 4.5224 0.75; 4.5050 2.26; 4.4873 2.27; 4.4697 0.75; 4.0566 1.19; 4.0388 3.65; 4.0210 3.69; 4.0032 1.23; 3.3375 19.95; 2.5270 0.74; 2.5223 1.14; 2.5135 13.66; 2.5091 27.73; 2.5046 36.84; 2.5000 27.61; 2.4956 13.91; 2.4710 11.98; 1.9909 16.00; 1.5804 1.24; 1.5662 3.09; 1.5594 3.38; 1.5466 1.43; 1.2956 1.64; 1.2822 3.37; 1.2756 3.62; 1.2611 1.38; 1.2413 3.18; 1.2239 6.91; 1.2063 3.10; 1.1938 4.60; 1.1760 8.89; 1.1582 4.35; 0.0080 0.62; −0.0002 18.74; −0.0085 0.73

Compound No. 332 [CD3CN] 10.5406 (1.19); 10.5161 (1.20); 8.4668 (1.47); 8.4555 (1.97); 8.4347 (0.95); 8.2445 (0.56); 8.2311 (0.69); 8.1627 (3.82); 7.7555 (4.17); 7.6680 (0.80); 7.6434 (1.04); 7.6195 (0.70); 6.3733 (0.54); 6.3511 (0.77); 6.3287 (0.54); 4.6394 (0.59); 4.6223 (1.71); 4.6045 (1.72); 4.5871 (0.57); 4.0562 (1.25); 4.0384 (3.75); 4.0206 (3.80); 4.0028 (1.28); 3.3353 (23.86); 2.8576 (0.37); 2.8486 (0.56); 2.8394 (0.83); 2.8295 (0.84); 2.8211 (0.58); 2.8115 (0.41); 2.6732 (0.32); 2.5083 (35.67); 2.5040 (46.25); 2.4997 (36.06); 1.9906 (16.00); 1.3430 (0.43); 1.3362 (0.64); 1.3260 (2.42); 1.3085 (4.74); 2.2993 (1.78); 1.2908 (2.36); 1.2590 (1.45); 1.2497 (0.76); 1.2334 (1.53); 1.1934 (4.37); 1.1756 (8.52); 1.1578 (4.37); 0.7301 (0.54); 0.7165 (1.53); 0.7122 (2.09); 0.7000 (1.89); 0.6943 (1.72); 0.6831 (0.69); 0.5800 (0.72); 0.5693 (2.10); 0.5630 (2.05); 0.5542 (1.75); 0.5416 (0.53); −0.0002 (1.92)

ᵃ⁾ The determination of the M⁺ by LC-MS in the acidic range is effected at pH 2.7, acetonitrile (contains 0.1% formic acid) and water as eluents; linear gradient from 10% acetonitrile to 95% acetonitrile, instrument: Agilent 1100 LC-System, Agilent MSD System, HTS PAL.
The log P values reported in the tables and Preparation Examples above were determined in accordance with EEC directive 79/831 Annex V.A8 by HPLC (High Performance Liquid Chromatography) using a reversed-phase column (C18). Temperature 43° C. The calibration is effected with unbranched alkan-2-ones (having 3 to 16 carbon atoms), for which the logP values are known.

TABLE 1-continued

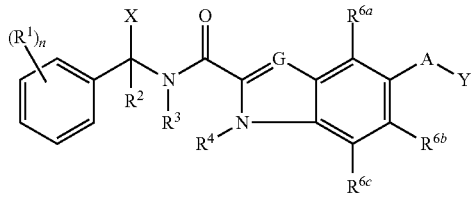

(I)

| No. | $(R^t)_n$ | X | $R^2$ | $R^3$ | $R^4$ | G | $R^{6a}$ | $R^{6b}$ | $R^{6c}$ | A | Y | (M+H)$^{+a)}$ | log p $^{a)}$ |
|---|---|---|---|---|---|---|---|---|---|---|---|---|---|

$^{b)}$ The $^1$H NMR data are determined with a Bruker Avance 400 equipped with a flow probe head (volume 60 μl), with tetramethylsilane as a reference (0.0) and the solvents CD$_3$CN, CDCl$_3$, D$_6$-DMSO.
The NMR data for selected examples are listed either in conventional form (δ values, multiplet splitting, number of hydrogen atoms) or as NMR peak lists.
NMR peak list method:
When the $^1$H NMR data for selected examples are noted in the form of $^1$H NMR peak lists, first the δ value in ppm and then the signal intensity is listed for each signal peak, separated by a space. The δ value-signal intensity number pairs for different signal peaks are listed with separation from one another by semicolons.
The peak list for one example therefore takes the form of: δ$_1$ intensity$_1$; δ$_2$ intensity$_2$; . . . ; δ$_i$ intensity$_i$; . . . ; δ$_n$ intensity$_n$
The solvent in which the NMR spectrum was recorded is listed in square brackets after the number of the example and before the NMR peak list or the conventional NMR interpretation list.

Use Examples

The examples which follow demonstrate the insecticidal and acaricidal action of the inventive compounds. These inventive compounds relate to the compounds listed in Table 1 with the corresponding reference numerals (No.):

*Amblyomma hebaraeum* Test (AMBYHE)

Solvent: dimethyl sulphoxide

To prepare an appropriate active ingredient formulation, 10 mg of active ingredient are mixed with 0.5 ml of dimethyl sulphoxide and the concentrate is diluted with water to the desired concentration.

Tick nymphs (*Amblyomma hebraeum*) are placed into perforated plastic beakers and immersed in the desired concentration for one minute. The ticks are transferred on filter paper into a Petri dish and stored in a climate-controlled cabinet.

After 42 days, the kill in % is determined 100% means that all of the ticks have been killed; 0% means that none of the ticks have been killed.

In this test, for example, the following compounds of the Preparation Examples show an efficacy of 100% at an application rate of 100 ppm: 14

*Boophilus microplus* Test (DIP)

Test animals: adult engorged *Boophilus microplus* females of the SP-resistant Parkhurst strain Solvent: dimethyl sulphoxide 10 mg of active ingredient are dissolved in 0.5 ml of dimethyl sulphoxide. For the purpose of preparing a suitable formulation, the active ingredient solution is diluted with water to the concentration desired in each case.

This active ingredient formulation is pipetted into tubes. 8-10 ticks are transferred into a further tube with holes. The tube is immersed into the active ingredient formulation, and all ticks are completely wetted. After the liquid has run out, the ticks are transferred onto filter discs in plastic dishes and stored in a climate-controlled room.

The activity is assessed after 7 days by laying of fertile eggs. Eggs whose fertility is not outwardly visible are stored in glass tubes in a climate-controlled cabinet until the larvae hatch. An efficacy of 100% means that none of the ticks has laid any fertile eggs.

In this test, for example, the following compounds of the Preparation Examples show an efficacy of 100% at an application rate of 100 ppm: 7

In this test, for example, the following compounds of the Preparation Examples show an efficacy of 80% at an application rate of 100 ppm: 18

*Boophilus microplus* Test (BOOPMI Injection)

Solvent: dimethyl sulphoxide

To prepare an appropriate active ingredient formulation, 10 mg of active ingredient are mixed with 0.5 ml of solvent and the concentrate is diluted with solvent to the desired concentration.

The active ingredient solution is injected into the abdomen (*Boophilus microplus*), and the animals are transferred into dishes and stored in a climate-controlled room.

After 7 days, the efficacy in % is determined. The activity is assessed by laying of fertile eggs. 100% means that none of the ticks has laid any fertile eggs.

In this test, for example, the following compounds of the Preparation Examples show an efficacy of 100% at an application rate of 20 μg/animal: 2, 3, 6, 7, 8, 10, 11, 12, 13, 14, 15, 16, 18, 19, 20, 22, 27, 28, 32, 36, 37, 38, 39, 40, 41, 42, 48, 49, 50, 52, 54, 57, 61, 62, 63, 97, 188, 190, 191, 192, 195, 275, 276, 282, 283, 285, 288

*Ctenocephalides felis* Oral (CTECFE)

Solvent: 1 part by weight of dimethyl sulphoxide

For the purpose of preparing an appropriate active ingredient formulation, 10 mg of active ingredient are mixed with 0.5 ml of dimethyl sulphoxide. A portion of the concentrate is diluted with citrated cattle blood, and the desired concentration is prepared.

About 20 unfed adult fleas (*Ctenocephalides felis*) are placed into a chamber which is closed at the top and bottom with gauze. A metal cylinder whose bottom end is closed with Parafilm is placed onto the chamber. The cylinder contains the blood/active ingredient formulation, which can be imbibed by the fleas through the Parafilm membrane.

After 2 days, the kill in % is determined 100% means that all of the fleas have been killed; 0% means that none of the fleas have been killed.

In this test, for example, the following compounds of the Preparation Examples show an efficacy of 100% at an application rate of 100 ppm: 3, 6, 7, 12, 13, 14, 15, 16, 18, 19, 20, 22, 32, 36, 37, 38, 39, 40, 41, 42, 48, 50, 52, 54, 57, 61, 62, 63, 188, 190, 191, 192, 195, 275, 276, 282, 283, 285, 288

In this test, for example, the following compounds of the Preparation Examples show an efficacy of 98% at an application rate of 100 ppm: 49

In this test, for example, the following compounds of the Preparation Examples show an efficacy of 95% at an application rate of 100 ppm: 2, 8, 10, 28, 97

In this test, for example, the following compounds of the Preparation Examples show an efficacy of 90% at an application rate of 100 ppm: 27

In this test, for example, the following compounds of the Preparation Examples show an efficacy of 80% at an application rate of 100 ppm: 11

*Lucilia cuprina* Test (LUCICU)

Solvent: dimethyl sulphoxide

To prepare an appropriate active ingredient formulation, 10 mg of active ingredient are mixed with 0.5 ml of dimethyl sulphoxide and the concentrate is diluted with water to the desired concentration.

Vessels containing horse meat treated with the active ingredient formulation of the desired concentration are populated with about 20 *Lucilia cuprina* larvae.

After 2 days, the kill in % is determined. 100% means that all of the larvae have been killed; 0% means that none of the larvae have been killed.

In this test, for example, the following compounds of the Preparation Examples show an efficacy of 100% at an application rate of 100 ppm: 2, 3, 6, 7, 8, 10, 11, 12, 13, 14, 15, 16, 18, 19, 20, 22, 27, 28, 32, 37, 38, 39, 40, 41, 42, 48, 49, 50, 52, 54, 57, 61, 62, 63, 97, 188, 190, 191, 192, 195, 275, 276, 282, 283, 285, 288

In this test, for example, the following compounds of the Preparation Examples show an efficacy of 95% at an application rate of 100 ppm: 36

*Musca domestica* Test (MUSCDO)

Solvent: dimethyl sulphoxide

To prepare an appropriate active ingredient formulation, 10 mg of active ingredient are mixed with 0.5 ml of dimethyl sulphoxide and the concentrate is diluted with water to the desired concentration.

Vessels containing a sponge treated with the active ingredient formulation of the desired concentration are populated with adult *Musca domestica*.

After 2 days, the kill in % is determined 100% means that all of the flies have been killed; 0% means that none of the flies have been killed.

In this test, for example, the following compounds of the Preparation Examples show an efficacy of 100% at an application rate of 100 ppm: 3, 6, 7, 10, 12, 13, 14, 15, 16, 18, 19, 20, 22, 27, 37, 38, 42, 49, 50, 52, 54, 57, 61, 63, 97, 188, 190, 192, 195, 275, 276, 288

In this test, for example, the following compounds of the Preparation Examples show an efficacy of 90% at an application rate of 100 ppm: 191, 282, 283, 285

In this test, for example, the following compounds of the Preparation Examples show an efficacy of 80% at an application rate of 100 ppm: 62

*Aulacophora femoralis* Spray Test (AUACFE)

Solvent: 3 parts by weight of dimethylformamide

Emulsifier: 1 part by weight of polyoxyethylene alkylphenyl ether

To produce an appropriate active ingredient formulation, 1 part by weight of active ingredient is mixed with the stated amounts of solvent and emulsifier, and the concentrate is diluted with emulsifier-containing water to the desired concentration. If required, ammonium salts or ammonium salts and penetrants are additionally added in a concentration of 1000 ppm.

Young cucumber plants (*Cucumis sativus*) at the cotyledonous leaf stage are sprayed with an active ingredient formulation of the desired concentration. After drying, the treated plant material is introduced into test vessels and each is infected with 5 L2 larvae of the cucurbit leaf beetle (*Aulacophora femoralis*).

After 6 days, the efficacy in % is determined. 100% means that all of the beetle larvae have been killed; 0% means that none of the beetle larvae have been killed.

In this test, for example, the following compounds of the Preparation Examples show an efficacy of 100% at an application rate of 20 ppm: 6, 7

*Myzus persicae* Spray Test (MYZUPE—OP/Carb-Resistant)

Solvent: 3 parts by weight of dimethylformamide

Emulsifier: 1 part by weight of polyoxyethylene alkylphenyl ether

To produce an appropriate active ingredient formulation, 1 part by weight of active ingredient is mixed with the stated amounts of solvent and emulsifier, and the concentrate is diluted with emulsifier-containing water to the desired concentration. If required, ammonium salts or ammonium salts and penetrants are additionally added in a concentration of 1000 ppm.

Aubergine plants (*Solanum melongena*) at the 2-leaf stage, which have been infested with a mixed population of the green peach aphid (*Myzus persicae*), are sprayed with an active ingredient formulation of the desired concentration.

After 6 days, the efficacy in % is determined. 100% means that all of the aphids have been killed; 0% means that none of the aphids have been killed.

In this test, for example, the following compounds of the Preparation Examples show an efficacy of 98% at an application rate of 100 ppm: 7

In this test, for example, the following compounds of the Preparation Examples show an efficacy of 90% at an application rate of 100 ppm: 6

*Spodoptera litura* Test (PRODLI)

Solvent: 3 parts by weight of dimethylformamide

Emulsifier: 1 part by weight of polyoxyethylene alkylphenyl ether

To produce an appropriate active ingredient formulation, 1 part by weight of active ingredient is mixed with the stated amounts of solvent and emulsifier, and the concentrate is diluted with emulsifier-containing water to the desired concentration.

The base of a PET vessel (diameter 7.5 cm, depth 4 cm) is covered with 2.3 g of a pulverulent synthetic feed mixture. Then 5 ml of the active ingredient formulation are added and mixed at the same time with the synthetic feed. After gelation, 5 L3 larvae of the cotton leafworm (*Spodoptera litura*) are placed into each vessel.

After 6 days, the efficacy in % is determined 100% means that all of the larvae have been killed; 0% means that none of the larvae have been killed.

In this test, for example, the following compounds of the Preparation Examples show an efficacy of 100% at an application rate of 20 ppm: 6, 7

Common Spider Mite Test (TETRUR)

Solvent: 3 parts by weight of dimethylformamide

Emulsifier: 1 part by weight of polyoxyethylene alkylphenyl ether

To produce an appropriate active ingredient formulation, 1 part by weight of active ingredient is mixed with the stated amounts of solvent and emulsifier, and the concentrate is diluted with emulsifier-containing water to the desired concentration. If required, ammonium salts or ammonium salts and penetrants are additionally added in a concentration of 1000 ppm.

Discs of bean leaves (*Phaseolus vulgaris*) infested by all stages of the red spider mite (*Tetranychus urticae*) are sprayed with an active ingredient formulation of the desired concentration.

After 6 days, the efficacy in % is determined. 100% means that all of the spider mites have been killed; 0% means that none of the spider mites have been killed.

In this test, for example, the following compounds of the Preparation Examples show an efficacy of 100% at an application rate of 100 ppm: 6, 7

*Thrips palmi* Spray Test (THRIPL)

Solvent: 3 parts by weight of dimethylformamide

Emulsifier: 1 part by weight of polyoxyethylene alkylphenyl ether

To produce an appropriate active ingredient formulation, 1 part by weight of active ingredient is mixed with the stated amounts of solvent and emulsifier, and the concentrate is diluted with emulsifier-containing water to the desired concentration. If required, ammonium salts or ammonium salts and penetrants are additionally added in a concentration of 1000 ppm.

Young cucumber plants (*Cucumis sativus*) are sprayed with an active ingredient formulation of the desired concentration. After drying, filter paper discs with about 100 thrips eggs (*Thrips palmi*) are placed onto the treated plants and, to give 100% air humidity, covered with housings.

After 6 days, the efficacy in % feeding damage is determined 100% means that there is no feeding damage; 0% means that there is no difference from the untreated control.

In this test, for example, the following compounds of the Preparation Examples show an efficacy of 98% at an application rate of 20 ppm: 7

In this test, for example, the following compounds of the Preparation Examples show an efficacy of 90% at an application rate of 20 ppm: 6

Myzus Test (MYZUPE Spray Treatment)

Solvent: 78 parts by weight of acetone 1.5 parts by weight of dimethylformamide

Emulsifier: 0.5 part by weight of alkylaryl polyglycol ether

To produce an appropriate active ingredient formulation, 1 part by weight of active ingredient is mixed with the stated amounts of solvent and emulsifier, and the concentrate is diluted with emulsifier-containing water to the desired concentration.

Leaf discs of Chinese cabbage (*Brassica pekinensis*) infested by all stages of the green peach aphid (*Myzus persicae*) are sprayed with an active ingredient formulation of the desired concentration.

After 6 days, the efficacy in % is determined. 100% means that all of the aphids have been killed; 0% means that none of the aphids have been killed.

In this test, for example, the following compounds of the Preparation Examples show an efficacy of 100% at an application rate of 500 g/ha: 289, 290, 312

In this test, for example, the following compounds of the Preparation Examples show an efficacy of 90% at an application rate of 500 g/ha: 5, 37, 38, 281, 301, 313

In this test, for example, the following compounds of the Preparation Examples show an efficacy of 100% at an application rate of 100 g/ha: 38, 54, 97, 281, 300, 312

In this test, for example, the following compounds of the Preparation Examples show an efficacy of 90% at an application rate of 100 g/ha: 7, 12, 40, 183, 191, 192, 193, 209, 276, 291, 295, 303, 311, 314, 315, 316

In this test, for example, the following compounds of the Preparation Examples show an efficacy of 80% at an application rate of 100 g/ha: 101, 282

Phaedon Test (PHAECO Spray Treatment)

Solvent: 78.0 parts by weight of acetone 1.5 parts by weight of dimethylformamide Emulsifier: 0.5 part by weight of alkylaryl polyglycol ether To produce an appropriate active ingredient formulation, 1 part by weight of active ingredient is mixed with the stated amounts of solvent and emulsifier, and the concentrate is diluted with emulsifier-containing water to the desired concentration.

Leaf discs of Chinese cabbage (*Brassica pekinensis*) are sprayed with an active ingredient formulation of the desired concentration and, after drying, populated with larvae of the mustard beetle (*Phaedon cochleariae*).

After 7 days, the efficacy in % is determined. 100% means that all of the beetle larvae have been killed; 0% means that none of the beetle larvae have been killed.

In this test, for example, the following compounds of the Preparation Examples show an efficacy of 100% at an application rate of 500 g/ha: 1, 4, 5, 13, 14, 37, 38, 97, 274, 281, 300, 301, 303, 312, 313, 317

In this test, for example, the following compounds of the Preparation Examples show an efficacy of 83% at an application rate of 500 g/ha: 309

In this test, for example, the following compounds of the Preparation Examples show an efficacy of 100% at an application rate of 100 g/ha: 2, 3, 6, 7, 8, 9, 10, 11, 12, 15, 16, 17, 18, 19, 20, 21, 22, 23, 24, 25, 26, 27, 28, 29, 30, 31, 32, 33, 34, 36, 39, 40, 42, 43, 44, 45, 46, 47, 48, 49, 50, 51, 52, 53, 54, 57, 58, 60, 61, 62, 63, 64, 66, 91, 101, 183, 184, 185, 188, 189, 190, 191, 192, 193, 195, 196, 209, 262, 263, 264, 266, 267, 268, 269, 270, 271, 272, 273, 275, 276, 277, 278, 279, 282, 283, 284, 285, 286, 287, 288, 289, 290, 291, 292, 293, 294, 295, 296, 297, 298, 299, 302, 304, 305, 306, 307, 308, 310, 311, 314, 315, 316, 318, 319, 320, 322, 325, 326

*Spodoptera frugiperda* Test (SPODFR Spray Treatment)

Solvent: 78.0 parts by weight of acetone 1.5 parts by weight of dimethylformamide To produce an appropriate active ingredient formulation, 1 part by weight of active ingredient is mixed with the stated amounts of solvent and emulsifier, and the concentrate is diluted with emulsifier-containing water to the desired concentration.

Leaf discs of maize (*Zea mays*) are sprayed with an active ingredient formulation of the desired concentration and, after drying, populated with caterpillars of the armyworm (*Spodoptera frugiperda*).

After 7 days, the efficacy in % is determined 100% means that all of the caterpillars have been killed; 0% means that none of the caterpillars have been killed.

In this test, for example, the following compounds of the Preparation Examples show an efficacy of 100% at an application rate of 500 g/ha: 1, 4, 5, 13, 14, 37, 38, 97, 274, 281, 300, 301, 303, 309, 312, 313, 317

In this test, for example, the following compounds of the Preparation Examples show an efficacy of 100% at an application rate of 100 g/ha: 2, 3, 6, 7, 8, 9, 12, 15, 16, 17, 18, 20, 24, 25, 27, 31, 36, 39, 40, 41, 42, 43, 44, 45, 48, 49, 50, 51, 52, 53, 54, 57, 58, 59, 60, 61, 62, 63, 64, 65, 66, 91, 101, 183, 184, 185, 188, 189, 190, 191, 192, 193, 195, 196, 209, 262, 263, 267, 268, 272, 273, 275, 276, 277, 278, 279, 282, 283, 284, 285, 287, 288, 289, 290, 291, 292, 293, 295, 296, 297, 298, 299, 302, 304, 305, 307, 308, 310, 311, 314, 315, 316, 319, 320, 322

In this test, for example, the following compounds of the Preparation Examples show an efficacy of 83% at an application rate of 100 g/ha: 10, 22, 28, 29, 30, 34, 306

*Tetranychus* Test, OP-Resistant (TETRUR Spray Treatment)

Solvent: 78.0 parts by weight of acetone 1.5 parts by weight of dimethylformamide Emulgator: 0.5 part by weight of alkylaryl polyglycol ether To produce an appropriate active ingredient formulation, 1 part by weight of active ingredient is mixed with the stated amounts of solvent and emulsifier, and the concentrate is diluted with emulsifier-containing water to the desired concentration.

Discs of bean leaves (*Phaseolus vulgaris*) infested by all stages of the red spider mite (*Tetranychus urticae*) are sprayed with an active ingredient formulation of the desired concentration.

After 6 days, the efficacy in % is determined. 100% means that all of the spider mites have been killed; 0% means that none of the spider mites have been killed.

In this test, for example, the following compounds of the Preparation Examples show an efficacy of 100% at an application rate of 500 g/ha: 2, 3, 4, 5, 14, 28, 37, 38, 97, 274, 281, 294, 300, 303, 304, 317

In this test, for example, the following compounds of the Preparation Examples show an efficacy of 90% at an application rate of 500 g/ha: 301, 313

In this test, for example, the following compounds of the Preparation Examples show an efficacy of 80% at an application rate of 500 g/ha: 13

In this test, for example, the following compounds of the Preparation Examples show an efficacy of 100% at an application rate of 100 g/ha: 7, 12, 16, 32, 36, 39, 40, 41, 42, 43, 46, 48, 49, 50, 51, 52, 53, 54, 57, 58, 59, 60, 61, 63, 64, 65, 66, 183, 184, 185, 188, 189, 190, 191, 192, 193, 195, 209, 263, 268, 272, 273, 275, 279, 282, 283, 284, 285, 286, 287, 288, 289, 290, 291, 292, 293, 295, 296, 297, 298, 302, 305, 310, 311, 315, 316, 320

In this test, for example, the following compounds of the Preparation Examples show an efficacy of 90% at an application rate of 100 g/ha: 9, 18, 47, 62, 276, 277, 278, 308, 314

In this test, for example, the following compounds of the Preparation Examples show an efficacy of 80% at an application rate of 100 g/ha: 6, 20, 22, 101

The invention claimed is:

1. A compound of formula (I), or a diastereomer, an enantiomer, an E/Z isomer, a N-oxide or a salt thereof,

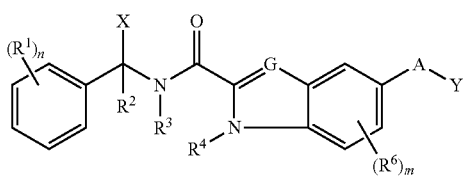

(I)

where
$R^1$ is the same or different and is cyano, fluorine, chlorine, bromine, iodine, difluoromethyl, dichlorofluoromethyl, chlorodifluoromethyl, trifluoromethyl, pentafluoroethyl, chlorotetrafluoroethyl, difluoromethoxy, trifluoromethoxy, trifluoromethylthio, trifluoromethylsulphinyl or trifluoromethylsulphonyl,
n is 1, 2, 3, 4 or 5,
or
$R^1$ is —OCF$_2$O—, and is bonded to two adjacent carbon atoms, in which case n is 1,
$R^2$ is hydrogen,
$R^3$ is hydrogen,
$R^4$ is methyl, ethyl, prop-1-yl, prop-2-en-1-yl, prop-2-yn-1-yl, ethenyl, but-2-yn-1-yl, cyclopropyl, cyclopropylmethyl, cyclobutyl, cyanomethyl, 2-methylprop-1-yl, ethoxymethyl, methoxycarbonylmethyl, phenylmethyl or benzyloxymethyl,
G is C($R^5$) or N,
$R^5$ is hydrogen, chlorine, bromine or cyano,
$R^6$ is cyano, fluorine, chlorine, bromine, methyl, ethyl, isopropyl or trifluoromethyl,
m is 0 or 1,
X is trifluoromethyl,
A is a bivalent chemical moiety which is the —C(=O)NR$^{13}$— moiety, where the first (left-hand) connection site in each case connects to the ring and the second (right-hand) connection site in each case connects to Y, and where
$R^{13}$ is hydrogen, methyl, ethyl or prop-2-en-1-yl, and
Y is 1-cyanocyclopropyl or 1-(aminothiocarbonyl)cyclopropyl.

2. A compound of formula (I), or a diastereomer, an enantiomer, an E/Z isomer, a N-oxide or a salt thereof, according to claim 1, where G is CH and A is
—C(=O)NH—.

3. A process for preparing a compound according to claim 1, in which
a) a carboxylic acid of formula (II)

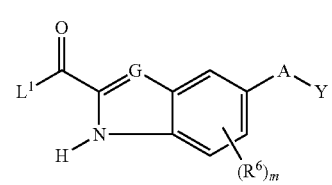

(II)

where
$L^1$ is hydroxyl or halogen,
is reacted with an amine of formula (III)

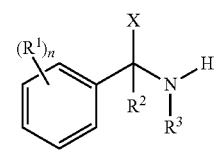

(III)

and
b) a compound of formula (IVa) thus obtained

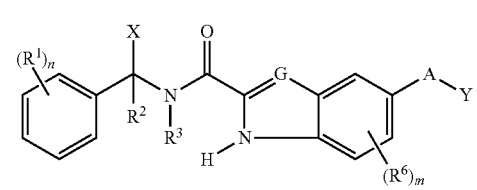

(IVa)

is then reacted with an alkylating agent of formula (V)

$R^4$-$L^2$ (V)

where
$L^2$ is halogen, a mesyl group or a tosyl group, in the presence of a base to give a compound of formula (I).

4. A process for producing a pesticide, in which a compound according to claim 1, is mixed with an extender and/or a surface-active substance.

5. A pesticide comprising a compound according to claim 1, in biologically effective contents of from 0.00000001 to 95% by weight, based on the weight of the pesticide.

6. The pesticide according to claim 5, additionally comprising a further active agrochemical ingredient.

7. A method for controlling an animal pest, comprising allowing a compound according to claim 1, to act on an animal pest and/or a habitat thereof, excluding methods for treatment of a human or animal body.

8. A compound of formula (I), or a diastereomer, an enantiomer, an E/Z isomer, a N-oxide, or a salt thereof, according to claim 1, where $R^1$ is trifluoromethyl.

9. A compound of formula (I), or a diastereomer, an enantiomer, an E/Z isomer, a N-oxide, or a salt thereof, according to claim 1, where G is $C(R^5)$.

10. A compound of formula (I), or a diastereomer, an enantiomer, an E/Z isomer, a N-oxide, or a salt thereof, according to claim 1, where G is N.

11. A compound of formula (I), or a diastereomer, an enantiomer, an E/Z isomer, a N-oxide, or a salt thereof, according to claim 1, where m is 1.

12. A compound of formula (I), or a diastereomer, an enantiomer, an E/Z isomer, a N-oxide, or a salt thereof, according to claim 1, where Y is 1-cyanocyclopropyl.

13. A compound of formula (I), or a diastereomer, an enantiomer, an E/Z isomer, a N-oxide, or a salt thereof, according to claim 1, where Y is 1-(aminothiocarbonyl)cyclopropyl.

14. A method for controlling an animal pest, comprising allowing a compound according to claim 1, to act on an animal pest and/or a habitat thereof.

* * * * *